(12) United States Patent
Cigan

(10) Patent No.: US 11,203,752 B2
(45) Date of Patent: Dec. 21, 2021

(54) COMPOSITIONS AND METHODS OF MODIFYING A PLANT GENOME TO PRODUCE A MS9, MS22, MS26, OR MS45 MALE-STERILE PLANT

(71) Applicant: PIONEER HI-BRED INTERNATIONAL, INC., Johnston, IA (US)

(72) Inventor: Andrew Mark Cigan, Madison, WI (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 16/214,897

(22) Filed: Dec. 10, 2018

(65) Prior Publication Data

US 2019/0177722 A1    Jun. 13, 2019

Related U.S. Application Data

(60) Provisional application No. 62/596,998, filed on Dec. 11, 2017.

(51) Int. Cl.
| | |
|---|---|
| *C12N 15/82* | (2006.01) |
| *C12N 15/11* | (2006.01) |
| *C12N 9/22* | (2006.01) |
| *C07K 14/415* | (2006.01) |

(52) U.S. Cl.
CPC ............ *C12N 15/11* (2013.01); *C07K 14/415* (2013.01); *C12N 9/22* (2013.01); *C12N 15/8213* (2013.01); *C12N 15/8289* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 9,499,837 B2* | 11/2016 | Bidney | C12N 15/8213 |
| 10,669,540 B2* | 6/2020 | Zhang | C12N 15/85 |
| 2012/0005781 A1 | 1/2012 | Alexandrov et al. | |
| 2015/0067913 A1 | 3/2015 | Fox et al. | |
| 2017/0058295 A1 | 3/2017 | Bidney et al. | |
| 2017/0298383 A1 | 10/2017 | Albertsen et al. | |

FOREIGN PATENT DOCUMENTS

| | | |
|---|---|---|
| WO | 1997/30581 A1 | 8/1997 |
| WO | 2017/079724 A1 | 5/2017 |

* cited by examiner

*Primary Examiner* — Brent T Page

(57) ABSTRACT

Compositions and methods are provided for genome modification of a nucleotide sequence located in or near a male fertility gene of MS9, MS22, MS26, or MS45 in the genome of a plant cell or plant to produce a male-sterile plant. In some examples, the methods and compositions employ a guide RNA/Cas endonuclease system for modifying or altering target sites located in or near a male fertility gene of MS9, MS22, MS26, or MS45 in the genome of a plant cell, plant or seed to produce a male-sterile plant. Also provided are compositions and methods employing a guide polynucleotide/Cas endonuclease system for genome modification a nucleotide sequence located in or near a male fertility gene of MS9, MS22, MS26, or MS45 in the genome of a plant cell to produce a male-sterile plant. Compositions and methods are also provided for restoring fertility to a Ms9, Ms22, Ms26, or Ms45 nucleotide sequence to a male-sterile Ms9, Ms22, Ms26, or Ms45 plant produced using the methods and compositions described herein.

8 Claims, 2 Drawing Sheets

Specification includes a Sequence Listing.

COMPOSITIONS AND METHODS OF MODIFYING A PLANT GENOME TO PRODUCE A MS9, MS22, MS26, OR MS45 MALE-STERILE PLANT

CROSS REFERENCE

This patent application claims the benefit of and priority to U.S. Provisional Application No. 62/596,998, filed Dec. 11, 2017, which is incorporated herein by reference in its entirety.

FIELD

The disclosure relates to the field of plant molecular biology, in particular, to compositions and methods of modifying a plant's genome to alter the male-fertility of a plant.

REFERENCE TO SEQUENCE LISTING SUBMITTED ELECTRONICALLY

The official copy of the sequence listing is submitted electronically via EFS-Web as an ASCII formatted sequence listing with a file named 7445USNP_SeqLst_ST25.txt, produced on Dec. 6, 2018, and having a size 227 kilobytes and is filed concurrently with the specification. The sequence listing contained in this ASCII formatted document is part of the specification and is herein incorporated by reference in its entirety.

BACKGROUND

Development of hybrid plant breeding has made possible considerable advances in quality and quantity of crops produced. Increased yield and combination of desirable characteristics, such as resistance to disease and insects, heat and drought tolerance, along with variations in plant composition are all possible because of hybridization procedures. These procedures frequently rely heavily on providing for a male parent contributing pollen to a female parent to produce the resulting hybrid.

Field crops are bred through techniques that take advantage of the plant's method of pollination. A plant is self-pollinating if pollen from one flower is transferred to the same or another flower of the same plant or a genetically identical plant. A plant is cross-pollinated if the pollen comes from a flower on a different plant.

In certain species, such as *Brassica campestris*, the plant is normally self-sterile and can only be cross-pollinated. In self-pollinating species, such as soybeans, cotton and wheat, the male and female plants are anatomically juxtaposed. During natural pollination, the male reproductive organs of a given flower pollinate the female reproductive organs of the same flower. Maize has male flowers, located on the tassel, and female flowers, located on the ear, on the same plant and can be bred by both self-pollination and cross-pollination techniques, The development of hybrids requires the crossing of homozygous inbred parents. A hybrid variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

During hybrid seed production, it is desirable to prevent self-pollination of the female inbred to avoid production and harvesting of female inbred seeds, since they exhibit less vigor than the hybrid seeds. To increase commercial quantities of the resulting hybrid seed, hybrid seed is often obtained using male-sterile female parents. Manual emasculation of the female can be labor intensive and/or impractical, depending on the crop. For example, in wheat, both male flowers and female flowers are located within the same floret on a spike making it challenging to prevent self-pollination. As a result, male-sterile female plants created from either chemical or genetic manipulations are often used in hybrid seed production.

SUMMARY

Provided herein are methods for producing male-sterile plants. In one embodiment, the method includes introducing a genetic modification into at least one or more endogenous MS9, MS22, MS26 or MS45 polynucleotide sequences in a plant cell, wherein the genetic modification confers male sterility to a plant obtained from the plant cell. In one aspect, the genetic modification is introduced using biotechnology approaches. Accordingly, also provided herein are male-sterile plants that contain a genetic modification in at least one or more endogenous MS9, MS22, MS26 or MS45 polynucleotide sequences. The genetic modification confers male sterility to a plant obtained from the plant cell.

In yet another aspect, the method includes providing to a plant cell a guide RNA and a Cas endonuclease. The RNA and Cas endonuclease are capable of forming a complex that enables the Cas endonuclease to introduce a double strand break at a target site located in or near a male fertility gene of MS9, MS22, MS26, or MS45. The method may additionally include identifying at least one plant cell that has the modification. The modification may be at least one deletion, insertion, or substitution of one or more nucleotides in said MS9, MS22, MS26, or MS45 gene that confers male-sterility to a plant. A male-sterile plant may be obtained from the plant cell.

A male-sterile plant may have at least one altered target site that confers male-sterility to the plant. The target site may originate from a corresponding target site that was recognized and cleaved by a guideRNA/Cas endonuclease system. The target site may be located in or near a male fertility gene of MS9, MS22, MS26, or MS45 and affect the expression level of the MS9, MS22, MS26, or MS45 gene so that the plant is male-sterile.

Also provided herein is a method for producing a male sterile plant that includes obtaining or providing a first plant comprising at least one Cas endonuclease capable of introducing a double strand break at a genomic target site located in a male fertility gene locus of MS9, MS22, MS26 or MS45 in the plant genome and a second plant comprising a guide RNA that is capable of forming a complex with the Cas endonuclease. In some aspects, the first and second plants may be crossed and the progeny evaluated for those that have an altered target site. Male-sterile progeny plants may be selected. Accordingly, also included herein are male-sterile progeny plants produced by any of the methods disclosed herein. The progeny plant may include at least one altered target site that originated from a corresponding target site that was recognized and cleaved by a guideRNA/Cas endonuclease system. The altered target site may be located in or near a male fertility gene of MS9, MS22, MS26, or MS45 and affects the expression level of the MS9, MS22, MS26, or MS45 gene so that the plant is male-sterile.

A method of modifying the male-fertility of a plant that includes introducing at least one guide RNA, at least one polynucleotide modification template and at least one Cas endonuclease into a plant cell is provided herein. The Cas endonuclease may introduce a double-strand break at a target site located in or near a MS9, MS22, MS26, or MS45 gene in the genome of the plant cell. The polynucleotide modification template includes at least one nucleotide modification of a nucleotide sequence at the target site, and the modification modifies the expression level of the MS9, MS22, MS26 or MS45 gene. A male-sterile plant may be obtained from the plant cell.

Also provided herein are methods for restoring male fertility in a male-sterile plant. A male sterile plant produced by any of the methods disclosed herein and having one or more endogenous MS9, MS22, MS26 or MS45 genes with a genetic modification that confers male-sterility to the plant may have fertility restored by introducing one or more polynucleotide sequences that encode a MS9, MS22, MS26 or MS45 polypeptide.

Also provided herein are isolated nucleic acids that impact male fertility of a plant. In some aspects, the nucleic acid has a polynucleotide sequence selected from the group consisting of: (a) a polynucleotide comprising the sequence set forth in SEQ ID NO1, 3, 5, 7, 9, 11, 13, 15, 17, or 19; (b) a polynucleotide having at least 85%, 90% or 95% sequence identity to SEQ ID NO1, 3, 5, 7, 9, 11, 13, 15, 17, or 19; (c) a polynucleotide that encodes a polypeptide having at least 85%, 90% or 95% sequence identity to SEQ ID NO: 4, 8, 12, 16, or 20; (d) a polynucleotide that encodes a polypeptide of SEQ ID NO: 4, 8, 12, 16, or 20; (e) a polynucleotide sequence comprising at least 500 consecutive nucleotides of SEQ ID NO: 1, 3, 5, 7, 9, 11, 13, 15, 17, or 19, wherein said polynucleotide encodes a polypeptide that impacts male fertility; and (f) a polynucleotide sequence which hybridizes to the full length of SEQ ID NO: 1, 3, 5, 7, 9, 11, 13, 15, 17, or 19 under highly stringent conditions of a wash of 0.1 SSC, 0.1% (w/v) SDS at 65 degrees Celsius. In some aspects, the nucleic acid is in an expression vector.

Also provided herein is an isolated polypeptide that impacts the male fertility of a plant. The polypeptide has an amino acid sequence selected from the group consisting of: (a) an amino acid sequence that has at least 85%, 90% or 95% sequence identity to the amino acid sequence set forth in SEQ ID NO: 4, 8, 12, 16, or 20, wherein said polypeptide impacts the male fertility of the plant, (b) an amino acid sequence comprising the amino acid sequence set forth in SEQ ID NO: 4, 8, 12, 16, or 20; (c) an amino acid sequence comprising at least 100 contiguous amino acids of the amino acid sequence set forth in SEQ ID NO: 4, 8, 12, 16, or 20, (d) an amino acid sequence encoded by a polynucleotide that has at least 85%, 90% or 95% sequence identity to SEQ ID NO: 1, 3, 5, 7, 9, 11, 13, 15, 17, or 19; and (e) an amino acid sequence encoded by a polynucleotide of SEQ ID NO: 1, 3, 5, 7, 9, 11, 13, 15, 17, or 19; and (f) a polynucleotide sequence which hybridizes to the full length of SEQ ID NO:1, 3, 5, 7, 9, 11, 13, 15, 17, or 19 under highly stringent conditions of a wash of 0.1 SSC, 0.1% (w/v) SDS at 65 degrees Celsius. Also provided herein are plant cells or plants having the nucleic acid and/or expressing the polypeptide.

In another aspect, disclosed herein is an isolated regulatory region driving male-tissue-preferred expression that includes the sequence of SEQ ID NO: 2, 6, 10, 14, and 18 and functional fragments thereof. Also disclosed herein are plant cells comprising the regulatory region. The regulatory region may be operably linked to a heterologous coding sequence. In some aspects, the regulatory region is included in a DNA construct to drive expression of a sequence of interest, for example, a heterologous polynucleotide. The regulatory region may be used to express a gene product in male tissue of a plant. In one aspect, the method includes introducing into the plant a polynucleotide comprising a polynucleotide sequence selected from the group consisting of SEQ ID NO:2, 6, 10, 14, and 18, and functional fragments thereof. The polynucleotide sequence may confer male-tissue-preferred expression of an operably linked sequence.

Also provided herein are methods of expressing a polynucleotide in a plant cell. In one aspect, the method includes introducing into a plant cell a polynucleotide of SEQ ID NO:451, 452 or 453, and functional fragments and variants thereof. The polynucleotide sequence may be used to drive expression of an operably linked heterologous polynucleotide sequence.

BRIEF DESCRIPTION OF THE FIGURES

FIG. 1A: Male fertile and male sterile wheat heads (white arrows mark extruded anthers). Insert at the bottom of the panel shows anthers from wild-type (left) and Tams45abd plants (right) at late uninucleate pollen stage. FIG. 1B-FIG. 1E: Cross sections of anthers from the following plants; wild-type (FIG. 1B), Tams45abd (FIG. 1C), Tams45 A/a,B/b,d/d (FIG. 1D) and Tams45a,b,d containing ZmMs45pro:OsMs45 (FIG. 1E).

DETAILED DESCRIPTION

Figure 1A:
FIG. 1A-FIG. 1E: Flower and anther phenotypes from wild-type and TaMs45 mutant wheat plants.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

Mutations that cause male sterility in plants have the potential to be useful in methods for hybrid seed production. For example, use of a male-sterile female inbred plant as a parent to produce hybrid seed can lower production costs by eliminating the need for the labor-intensive removal of male flowers and self-pollination of the female inbred. Emasculation of wheat can be especially challenging since the male flowers and female flowers are located within the same floret. This makes it difficult to prevent self-pollination of the female and fertilize it with pollen from another wheat plant. Self-pollination results in seed of the female inbred being harvested along with the hybrid seed which is normally produced. Female inbred seed does not exhibit heterosis and therefore is not as commercially desirable as F1 seed. Thus, use of a male-sterile female inbred prevents self-fertilization while maintaining the purity of hybrid seeds.

Mutations that cause male sterility in crop plants such as maize, wheat and rice have been produced by a variety of methods such as X-rays or UV-irradiations, chemical treatments, or transposable element insertions (ms23, ms25, ms26, ms32) (Chaubal et al. 2000) Am J Bot 87:1193-1201). However, such methods are random mutagenesis methods that induce mutations randomly throughout the genome and not just in the gene of interest. Typically, with such random mutagenesis methods, it requires considerable effort to identify a plant that contains a mutation in the gene of interest and it is by no means certain that such a plant will be identified. Furthermore, with random mutagenesis methods, each plant tested is likely to carry multiple mutations. Therefore, a plant that is identified with the mutation in the gene of interest must be backcrossed for several or more generations to eliminate the undesired mutations.

In contrast to such random mutagenesis methods, the described herein are methods for producing male sterile plants by introducing a genetic modification into at least one or more endogenous fertility genes, such as MS9, MS22, MS26 or MS45 polynucleotide sequences, in a plant cell. The introduced genetic modification confers male sterility to a plant arising from the plant cell. Preferably the plant is a crop plant.

U.S. Patent publication US 20150191743 A1, published Jul. 9, 2015, describes a male fertility gene referred to as "MS9" that is located on maize chromosome 1 and encodes a myb transcription factor critical to male fertility. The Ms9 phenotype was first identified in maize in 1932. Beadle, (1932) Genetics 17:413-431. It was found to be linked to the P1 gene on Chromosome 1. Breakdown of male reproductive tissue development occurs very early in premeiosis; tapetal cells may be affected as well. Greyson, et al., (1980) Can. J. Genet. Cytol. 22:153-166. Examples of genomic DNA and polypeptide sequences of maize Ms9 are disclosed in US patent publication 20150191743, published on Jul. 9, 2015.

U.S. Patent publication US 2009-0038026 A1, published Feb. 5, 2009, describes a male fertile gene referred to as "Msca1" or "MS22" that is located on maize chromosome 7 and encodes a protein critical to male fertility. Mutations referred to as ms22 or msca1 were first noted as phenotypically male sterile with anthers which did not extrude from the tassel and lacked sporogenous tissue. West and Albertsen (1985) Maize Newsletter 59:87; Neuffer et al. (1977) Mutants of maize. Cold Spring Harbor Laboratory Press, Cold Spring Harbor, N.Y. The mutant locus was originally referred to as ms22 but was later changed to msca1, or male sterile converted anther. See Chaubal et al. "The transformation of anthers in the msca1 mutant of maize" *Planta* (2003) 216:778-788. Examples of genomic DNA and polypeptide sequences of wheat Ms22 are disclosed in US patent publication 2014/007559, see for example U.S. Pat. No. 7,919,676).

U.S. Pat. No. 7,517,975, issued Apr. 14, 2009, describes a male fertile gene referred to as "MS26" (also known as SB200 or SBMu200) that is located on maize chromosome 1. MS26 can be used in the systems described above, and other systems impacting male fertility. The term "wheat Ms26 gene" or similar reference means a gene or sequence in wheat that is orthologous to Ms26 in maize or rice, e.g. as disclosed in U.S. Pat. No. 7,919,676 or 8,293,970. Examples of genomic DNA and polypeptide sequences of wheat Ms26 are disclosed in US patent publication 2014/0075597, U.S. Pat. Nos. 7,098,388, 7,517,975, 7,612,251 and described elsewhere herein.

U.S. Pat. No. 5,478,369 issued Dec. 26, 1995 describes a male fertile gene referred to as "MS45" cloned on maize chromosome 9. Examples of genomic DNA and polypeptide sequences of wheat Ms45 are disclosed in US patent publication 2014/0075597, see for example U.S. Pat. No. 6,265,640.

Additionally, the present disclosure includes the following MS9, MS22, MS26, and MS45 polynucleotides and polypeptides:

TABLE 1

Summary of SEQ ID NOs:

| SEQ ID NO: | Description |
| --- | --- |
| 1 | Wheat Ms9 4AS genomic (exon/intron) |
| 2 | Wheat Ms9 4AS promoter |
| 3 | Wheat Ms9 4AS coding |
| 4 | Wheat Ms9 4AS amino acid |
| 5 | Wheat Ms9 4BL genomic (exon/intron) |
| 6 | Wheat Ms9 4BL promoter |
| 7 | Wheat Ms9 4BL coding |
| 8 | Wheat Ms9 4BL amino acid |
| 9 | Wheat Ms9 4DL genomic (exon/intron) |
| 10 | Wheat Ms9 4DL promoter |
| 11 | Wheat Ms9 4DL coding |
| 12 | Wheat Ms9 4DL amino acid |
| 13 | Maize Ms9 genomic (exon/intron) |
| 14 | Maize Ms9 promoter |
| 15 | Maize Ms9 coding |
| 16 | Maize Ms9 amino acid |
| 17 | Rice Ms9 genomic (exon/intron) |
| 18 | Rice Ms9 promoter |
| 19 | Rice Ms9 coding |
| 20 | Rice Ms9 amino acid |
| 21 | Wheat Ms22 AL genomic (exon/intron) |
| 22 | Wheat Ms22 AL promoter |
| 23 | Wheat Ms22 AL coding |
| 24 | Wheat Ms22 AL amino acid |
| 25 | Wheat Ms22 BL genomic (exon/intron) |
| 26 | Wheat Ms22 BL promoter |
| 27 | Wheat Ms22 BL coding |
| 28 | Wheat Ms22 BL amino acid |
| 29 | Wheat Ms22 DL genomic (exon/intron) |
| 30 | Wheat Ms22 DL promoter |
| 31 | Wheat Ms22 DL coding |
| 32 | Wheat Ms22 DL amino acid |
| 33 | Maize Ms22 genomic (exon/intron) |
| 34 | Maize Ms22 promoter |
| 35 | Maize Ms22 coding |
| 36 | Maize Ms22 amino acid |
| 37 | Rice Ms22 genomic (exon/intron) |
| 38 | Rice Ms22 promoter |
| 39 | Rice Ms22 coding |
| 40 | Rice Ms22 amino acid |
| 41 | Wheat Ms26 4A5 genomic (exon/intron) |
| 42 | Wheat Ms26 4A5 promoter |
| 43 | Wheat Ms26 4A5 coding |
| 44 | Wheat Ms26 4A5 amino acid |
| 45 | Wheat Ms26 4BL genomic (exon/intron) |
| 46 | Wheat Ms26 4BL promoter |
| 47 | Wheat Ms26 4BL coding |
| 48 | Wheat Ms26 4BL amino acid |
| 49 | Wheat Ms26 4DL genomic (exon/intron) |
| 50 | Wheat Ms26 4DL promoter |
| 51 | Wheat Ms26 4DL coding |
| 52 | Wheat Ms26 4DL amino acid |
| 53 | Maize Ms26 genomic (exon/intron) |
| 54 | Maize Ms26 promoter |
| 55 | Maize Ms26 coding |

TABLE 1-continued

Summary of SEQ ID NOs:

| SEQ ID NO: | Description |
|---|---|
| 56 | Maize Ms26 amino acid |
| 57 | Rice Ms26 genomic (exon/intron) |
| 58 | Rice Ms26 promoter |
| 59 | Rice Ms26 coding |
| 60 | Rice Ms26 amino acid |
| 61 | Wheat Ms45 4AS genomic (exon/intron) |
| 62 | Wheat Ms45 4AS promoter |
| 63 | Wheat Ms45 4AS coding |
| 64 | Wheat Ms45 4A5 amino acid |
| 65 | Wheat Ms45 4BL genomic (exon/intron) |
| 66 | Wheat Ms45 4BL promoter |
| 67 | Wheat Ms45 4BL coding |
| 68 | Wheat Ms45 4BL amino acid |
| 69 | Wheat Ms45 4DL genomic (exon/intron) |
| 70 | Wheat Ms45 4DL promoter |
| 71 | Wheat Ms45 4DL coding |
| 72 | Wheat Ms45 4DL amino acid |
| 73 | Maize Ms45 genomic (exon/intron) |
| 74 | Maize Ms45 promoter |
| 75 | Maize Ms45 coding |
| 76 | Maize Ms45 amino acid |
| 77 | Rice Ms45 genomic (exon/intron) |
| 78 | Rice Ms45 promoter |
| 79 | Rice Ms45 coding |
| 80 | Rice Ms45 amino acid |
| 81 | Wheat Ms9 4BL CR1 target |
| 82 | Wheat Ms9 4BL CR2 target |
| 83 | Wheat Ms9 4BL CR3 target |
| 84 | Wheat Ms9 4BL CR4 target |
| 85 | Wheat Ms9 4BL CR5 target |
| 86 | Wheat Ms9 4BL CR6 target |
| 87 | Wheat Ms9 4BL CR7 target |
| 88 | Wheat Ms9 4BL CR8 target |
| 89 | Wheat Ms9 4BL CR9 target |
| 90 | Wheat Ms9 4BL CR10 target |
| 91 | Wheat Ms9 4BL CR11 target |
| 92 | Wheat Ms9 4BL CR12 target |
| 93 | Wheat Ms9 4BL CR13 target |
| 94 | Wheat Ms9 4BL CR14 target |
| 95 | Wheat Ms9 4BL CR15 target |
| 96 | Maize Ms9 CR1 target |
| 97 | Maize Ms9 CR2 target |
| 98 | Maize Ms9 CR3 target |
| 99 | Maize Ms9 CR4 target |
| 100 | Maize Ms9 CR5 target |
| 101 | Maize Ms9 CR6 target |
| 102 | Maize Ms9 CR7 target |
| 103 | Maize Ms9 CR8 target |
| 104 | Maize Ms9 CR9 target |
| 105 | Maize Ms9 CR10 target |
| 106 | Maize Ms9 CR11 target |
| 107 | Maize Ms9 CR12 target |
| 108 | Maize Ms9 CR13 target |
| 109 | Maize Ms9 CR14 target |
| 110 | Maize Ms9 CR15 target |
| 111 | Rice Ms9 CR1 target |
| 112 | Rice Ms9 CR2 target |
| 113 | Rice Ms9 CR3 target |
| 114 | Rice Ms9 CR4 target |
| 115 | Rice Ms9 CR5 target |
| 116 | Rice Ms9 CR6 target |
| 117 | Rice Ms9 CR7 target |
| 118 | Rice Ms9 CR8 target |
| 119 | Rice Ms9 CR9 target |
| 120 | Rice Ms9 CR10 target |
| 121 | Rice Ms9 CR11 target |
| 122 | Rice Ms9 CR12 target |
| 123 | Rice Ms9 CR13 target |
| 124 | Rice Ms9 CR14 target |
| 125 | Rice Ms9 CR15 target |
| 126 | Wheat Ms22CR1 target |
| 127 | Wheat Ms22CR2 target |
| 128 | Wheat Ms22CR3 target |
| 129 | Wheat Ms22CR4 target |
| 130 | Wheat Ms22CR5 target |
| 131 | Wheat Ms22CR6 target |
| 132 | Wheat Ms22CR7 target |
| 133 | Wheat Ms22CR8 target |
| 134 | Wheat Ms22CR9 target |
| 135 | Wheat Ms22CR10 target |
| 136 | Wheat Ms22CR11 target |
| 137 | Wheat Ms22CR12 target |
| 138 | Wheat Ms22CR13 target |
| 139 | Wheat Ms22CR14 target |
| 140 | Wheat Ms22CR15 target |
| 141 | Maize Ms22 CR1 target |
| 142 | Maize Ms22 CR2 target |
| 143 | Maize Ms22 CR3 target |
| 144 | Maize Ms22 CR4 target |
| 145 | Maize Ms22 CR5 target |
| 146 | Maize Ms22 CR6 target |
| 147 | Maize Ms22 CR7 target |
| 148 | Maize Ms22 CR8 target |
| 149 | Maize Ms22 CR9 target |
| 150 | Maize Ms22 CR10 target |
| 151 | Maize Ms22 CR11 target |
| 152 | Maize Ms22 CR12 target |
| 153 | Maize Ms22 CR13 target |
| 154 | Maize Ms22 CR14 target |
| 155 | Maize Ms22 CR15 target |
| 156 | Rice Ms22 CR1 target |
| 157 | Rice Ms22 CR2 target |
| 158 | Rice Ms22 CR3 target |
| 159 | Rice Ms22 CR4 target |
| 160 | Rice Ms22 CR5 target |
| 161 | Rice Ms22 CR6 target |
| 162 | Rice Ms22 CR7 target |
| 163 | Rice Ms22 CR8 target |
| 164 | Rice Ms22 CR9 target |
| 165 | Rice Ms22 CR10 target |
| 166 | Rice Ms22 CR11 target |
| 167 | Rice Ms22 CR12 target |
| 168 | Rice Ms22 CR13 target |
| 169 | Rice Ms22 CR14 target |
| 170 | Rice Ms22 CR15 target |
| 171 | Wheat Ms26 CR1 target |
| 172 | Wheat Ms26 CR2 target |
| 173 | Wheat Ms26 CR3 target |
| 174 | Wheat Ms26 CR4 target |
| 175 | Wheat Ms26 CR5 target |
| 176 | Wheat Ms26 CR6 target |
| 177 | Wheat Ms26 CR7 target |
| 178 | Wheat Ms26 CR8 target |
| 179 | Wheat Ms26 CR9 target |
| 180 | Wheat Ms26 CR10 target |
| 181 | Wheat Ms26 CR11 target |
| 182 | Wheat Ms26 CR12 target |
| 183 | Wheat Ms26 CR13 target |
| 184 | Wheat Ms26 CR14 target |
| 185 | Wheat Ms26 CR15 target |
| 186 | Maize Ms26 CR1 target |
| 187 | Maize Ms26 CR2 target |
| 188 | Maize Ms26 CR3 target |
| 189 | Maize Ms26 CR4 target |
| 190 | Maize Ms26 CR5 target |
| 191 | Maize Ms26 CR6 target |
| 192 | Maize Ms26 CR7 target |
| 193 | Maize Ms26 CR8 target |
| 194 | Maize Ms26 CR9 target |
| 195 | Maize Ms26 CR10 target |
| 196 | Maize Ms26 CR11 target |
| 197 | Maize Ms26 CR12 target |
| 198 | Maize Ms26 CR13 target |
| 199 | Maize Ms26 CR14 target |
| 200 | Maize Ms26 CR15 target |
| 201 | Maize Ms26 CR16 target |
| 202 | Maize Ms26 CR17 target |
| 203 | Maize Ms26 CR18 target |
| 204 | Rice Ms26 CR1 target |

TABLE 1-continued

Summary of SEQ ID NOs:

| SEQ ID NO: | Description |
| --- | --- |
| 205 | Rice Ms26 CR2 target |
| 206 | Rice Ms26 CR3 target |
| 207 | Rice Ms26 CR4 target |
| 208 | Rice Ms26 CR5 target |
| 209 | Rice Ms26 CR6 target |
| 210 | Rice Ms26 CR7 target |
| 211 | Rice Ms26 CR8 target |
| 212 | Rice Ms26 CR9 target |
| 213 | Rice Ms26 CR10 target |
| 214 | Rice Ms26 CR11 target |
| 215 | Rice Ms26 CR12 target |
| 216 | Wheat Ms45 CR1 target |
| 217 | Wheat Ms45 CR2 target |
| 218 | Wheat Ms45 CR3 target |
| 219 | Wheat Ms45 CR4 target |
| 220 | Wheat Ms45 CR5 target |
| 221 | Wheat Ms45 CR6 target |
| 222 | Wheat Ms45 CR7 target |
| 223 | Wheat Ms45 CR8 target |
| 224 | Wheat Ms45 CR9 target |
| 225 | Wheat Ms45 CR10 target |
| 226 | Wheat Ms45 CR11 target |
| 227 | Wheat Ms45 CR12 target |
| 228 | Wheat Ms45 CR13 target |
| 229 | Wheat Ms45 CR14 target |
| 230 | Wheat Ms45 CR15 target |
| 231 | Wheat Ms45 CR16 target |
| 232 | Maize Ms45 CR1 target |
| 233 | Maize Ms45 CR2 target |
| 234 | Maize Ms45 CR3 target |
| 235 | Maize Ms45 CR4 target |
| 236 | Maize Ms45 CR5 target |
| 237 | Maize Ms45 CR6 target |
| 238 | Maize Ms45 CR7 target |
| 239 | Maize Ms45 CR8 target |
| 240 | Maize Ms45 CR9 target |
| 241 | Maize Ms45 CR10 target |
| 242 | Maize Ms45 CR11 target |
| 243 | Maize Ms45 CR12 target |
| 244 | Maize Ms45 CR13 target |
| 245 | Maize Ms45 CR14 target |
| 246 | Maize Ms45 CR15 target |
| 247 | Maize Ms45 CR16 target |
| 248 | Maize Ms45 CR17 target |
| 249 | Maize Ms45 CR18 target |
| 250 | Rice Ms45 CR1 target |
| 251 | Rice Ms45 CR2 target |
| 252 | Rice Ms45 CR3 target |
| 253 | Rice Ms45 CR4 target |
| 254 | Rice Ms45 CR5 target |
| 255 | Rice Ms45 CR6 target |
| 256 | Rice Ms45 CR7 target |
| 257 | Rice Ms45 CR8 target |
| 258 | Rice Ms45 CR9 target |
| 259 | Rice Ms45 CR10 target |
| 260 | Rice Ms45 CR11 target |
| 261 | Rice Ms45 CR12 target |
| 262 | Rice Ms45 CR13 target |
| 263 | Rice Ms45 CR14 target |
| 264 | Rice Ms45 CR15 target |
| 265 | Wheat MS45 wildtype |
| 266 | Wheat MS45 A genome mutation |
| 267 | Wheat Ms9 4BL CR1 guide |
| 268 | Wheat Ms9 4BL CR2 guide |
| 269 | Wheat Ms9 4BL CR3 guide |
| 270 | Wheat Ms9 4BL CR4 guide |
| 271 | Wheat Ms9 4BL CR5 guide |
| 272 | Wheat Ms9 4BL CR6 guide |
| 273 | Wheat Ms9 4BL CR7 guide |
| 274 | Wheat Ms9 4BL CR8 guide |
| 275 | Wheat Ms9 4BL CR9 guide |
| 276 | Wheat Ms9 4BL CR10 guide |
| 277 | Wheat Ms9 4BL CR11 guide |
| 278 | Wheat Ms9 4BL CR12 guide |
| 279 | Wheat Ms9 4BL CR13 guide |
| 280 | Wheat Ms9 4BL CR14 guide |
| 281 | Wheat Ms9 4BL CR15 guide |
| 282 | Maize Ms9 CR1 guide |
| 283 | Maize Ms9 CR2 guide |
| 284 | Maize Ms9 CR3 guide |
| 285 | Maize Ms9 CR4 guide |
| 286 | Maize Ms9 CR5 guide |
| 287 | Maize Ms9 CR6 guide |
| 288 | Maize Ms9 CR7 guide |
| 289 | Maize Ms9 CR8 guide |
| 290 | Maize Ms9 CR9 guide |
| 291 | Maize Ms9 CR10 guide |
| 292 | Maize Ms9 CR11 guide |
| 293 | Maize Ms9 CR12 guide |
| 294 | Maize Ms9 CR13 guide |
| 295 | Maize Ms9 CR14 guide |
| 296 | Maize Ms9 CR15 guide |
| 297 | Rice Ms9 CR1 guide |
| 298 | Rice Ms9 CR2 guide |
| 299 | Rice Ms9 CR3 guide |
| 300 | Rice Ms9 CR4 guide |
| 301 | Rice Ms9 CR5 guide |
| 302 | Rice Ms9 CR6 guide |
| 303 | Rice Ms9 CR7 guide |
| 304 | Rice Ms9 CR8 guide |
| 305 | Rice Ms9 CR9 guide |
| 306 | Rice Ms9 CR10 guide |
| 307 | Rice Ms9 CR11 guide |
| 308 | Rice Ms9 CR12 guide |
| 309 | Rice Ms9 CR13 guide |
| 310 | Rice Ms9 CR14 guide |
| 311 | Rice Ms9 CR15 guide |
| 312 | Wheat Ms22CR1 guide |
| 313 | Wheat Ms22CR2 guide |
| 314 | Wheat Ms22CR3 guide |
| 315 | Wheat Ms22CR4 guide |
| 316 | Wheat Ms22CR5 guide |
| 317 | Wheat Ms22CR6 guide |
| 318 | Wheat Ms22CR7 guide |
| 319 | Wheat Ms22CR8 guide |
| 320 | Wheat Ms22CR9 guide |
| 321 | Wheat Ms22CR10 guide |
| 322 | Wheat Ms22CR11 guide |
| 323 | Wheat Ms22CR12 guide |
| 324 | Wheat Ms22CR13 guide |
| 325 | Wheat Ms22CR14 guide |
| 326 | Wheat Ms22CR15 guide |
| 327 | Maize Ms22 CR1 guide |
| 328 | Maize Ms22 CR2 guide |
| 329 | Maize Ms22 CR3 guide |
| 330 | Maize Ms22 CR4 guide |
| 331 | Maize Ms22 CR5 guide |
| 332 | Maize Ms22 CR6 guide |
| 333 | Maize Ms22 CR7 guide |
| 334 | Maize Ms22 CR8 guide |
| 335 | Maize Ms22 CR9 guide |
| 336 | Maize Ms22 CR10 guide |
| 337 | Maize Ms22 CR11 guide |
| 338 | Maize Ms22 CR12 guide |
| 339 | Maize Ms22 CR13 guide |
| 340 | Maize Ms22 CR14 guide |
| 341 | Maize Ms22 CR15 guide |
| 342 | Rice Ms22 CR1 guide |
| 343 | Rice Ms22 CR2 guide |
| 344 | Rice Ms22 CR3 guide |
| 345 | Rice Ms22 CR4 guide |
| 346 | Rice Ms22 CR5 guide |
| 347 | Rice Ms22 CR6 guide |
| 348 | Rice Ms22 CR7 guide |
| 349 | Rice Ms22 CR8 guide |
| 350 | Rice Ms22 CR9 guide |
| 351 | Rice Ms22 CR10 guide |
| 352 | Rice Ms22 CR11 guide |
| 353 | Rice Ms22 CR12 guide |
| 354 | Rice Ms22 CR13 guide |
| 355 | Rice Ms22 CR14 guide |
| 356 | Rice Ms22 CR15 guide |

TABLE 1-continued

Summary of SEQ ID NOs:

| SEQ ID NO: | Description |
|---|---|
| 357 | Wheat Ms26 CR1 guide |
| 358 | Wheat Ms26 CR2 guide |
| 359 | Wheat Ms26 CR3 guide |
| 360 | Wheat Ms26 CR4 guide |
| 361 | Wheat Ms26 CR5 guide |
| 362 | Wheat Ms26 CR6 guide |
| 363 | Wheat Ms26 CR7 guide |
| 364 | Wheat Ms26 CR8 guide |
| 365 | Wheat Ms26 CR9 guide |
| 366 | Wheat Ms26 CR10 guide |
| 367 | Wheat Ms26 CR11 guide |
| 368 | Wheat Ms26 CR12 guide |
| 369 | Wheat Ms26 CR13 guide |
| 370 | Wheat Ms26 CR14 guide |
| 371 | Wheat Ms26 CR15 guide |
| 372 | Maize Ms26 CR1 guide |
| 373 | Maize Ms26 CR2 guide |
| 374 | Maize Ms26 CR3 guide |
| 375 | Maize Ms26 CR4 guide |
| 376 | Maize Ms26 CR5 guide |
| 377 | Maize Ms26 CR6 guide |
| 378 | Maize Ms26 CR7 guide |
| 379 | Maize Ms26 CR8 guide |
| 380 | Maize Ms26 CR9 guide |
| 381 | Maize Ms26 CR10 guide |
| 382 | Maize Ms26 CR11 guide |
| 383 | Maize Ms26 CR12 guide |
| 384 | Maize Ms26 CR13 guide |
| 385 | Maize Ms26 CR14 guide |
| 386 | Maize Ms26 CR15 guide |
| 387 | Maize Ms26 CR16 guide |
| 388 | Maize Ms26 CR17 guide |
| 389 | Maize Ms26 CR18 guide |
| 390 | Rice Ms26 CR1 guide |
| 391 | Rice Ms26 CR2 guide |
| 392 | Rice Ms26 CR3 guide |
| 393 | Rice Ms26 CR4 guide |
| 394 | Rice Ms26 CR5 guide |
| 395 | Rice Ms26 CR6 guide |
| 396 | Rice Ms26 CR7 guide |
| 397 | Rice Ms26 CR8 guide |
| 398 | Rice Ms26 CR9 guide |
| 399 | Rice Ms26 CR10 guide |
| 400 | Rice Ms26 CR11 guide |
| 401 | Rice Ms26 CR12 guide |
| 402 | Wheat Ms45 CR1 guide |
| 403 | Wheat Ms45 CR2 guide |
| 404 | Wheat Ms45 CR3 guide |
| 405 | Wheat Ms45 CR4 guide |
| 406 | Wheat Ms45 CR5 guide |
| 407 | Wheat Ms45 CR6 guide |
| 408 | Wheat Ms45 CR7 guide |
| 409 | Wheat Ms45 CR8 guide |
| 410 | Wheat Ms45 CR9 guide |
| 411 | Wheat Ms45 CR10 guide |
| 412 | Wheat Ms45 CR11 guide |
| 413 | Wheat Ms45 CR12 guide |
| 414 | Wheat Ms45 CR13 guide |
| 415 | Wheat Ms45 CR14 guide |
| 416 | Wheat Ms45 CR15 guide |
| 417 | Wheat Ms45 CR16 guide |
| 418 | Maize Ms45 CR1 guide |
| 419 | Maize Ms45 CR2 guide |
| 420 | Maize Ms45 CR3 guide |
| 421 | Maize Ms45 CR4 guide |
| 422 | Maize Ms45 CR5 guide |
| 423 | Maize Ms45 CR6 guide |
| 424 | Maize Ms45 CR7 guide |
| 425 | Maize Ms45 CR8 guide |
| 426 | Maize Ms45 CR9 guide |
| 427 | Maize Ms45 CR10 guide |
| 428 | Maize Ms45 CR11 guide |
| 429 | Maize Ms45 CR12 guide |
| 430 | Maize Ms45 CR13 guide |
| 431 | Maize Ms45 CR14 guide |
| 432 | Maize Ms45 CR15 guide |
| 433 | Maize Ms45 CR16 guide |
| 434 | Maize Ms45 CR17 guide |
| 435 | Maize Ms45 CR18 guide |
| 436 | Rice Ms45 CR1 guide |
| 437 | Rice Ms45 CR2 guide |
| 438 | Rice Ms45 CR3 guide |
| 439 | Rice Ms45 CR4 guide |
| 440 | Rice Ms45 CR5 guide |
| 441 | Rice Ms45 CR6 guide |
| 442 | Rice Ms45 CR7 guide |
| 443 | Rice Ms45 CR8 guide |
| 444 | Rice Ms45 CR9 guide |
| 445 | Rice Ms45 CR10 guide |
| 446 | Rice Ms45 CR11 guide |
| 447 | Rice Ms45 CR12 guide |
| 448 | Rice Ms45 CR13 guide |
| 449 | Rice Ms45 CR14 guide |
| 450 | Rice Ms45 CR15 guide |
| 451 | Wheat U6 RNA polymerase III promoter |
| 452 | Wheat U6 RNA polymerase III promoter |
| 453 | Wheat U6 RNA polymerase III promoter |

An isolated Ms9 polynucleotide comprising: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO: 4, 8, 12, 16, or 20; or (ii) a full complement of the nucleic acid sequence of (i), wherein the full complement and the nucleic acid sequence of (i) consist of the same number of nucleotides and are 100% complementary.

An isolated Ms9 polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO: 4, 8, 12, 16, or 20.

An isolated Ms9 polynucleotide comprising (i) a nucleic acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO: 1-3, 5-7, 9-11, 13-15, or 17-19 and combinations thereof; or (ii) a full complement of the nucleic acid sequence of (i).

An isolated Ms9 polynucleotide comprising a nucleotide sequence, wherein the nucleotide sequence is hybridizable under stringent conditions with a DNA molecule comprising the full complement of SEQ ID NO: 1-3, 5-7, 9-11, 13-15, or 17-19. The isolated MS9 protein of the present disclosure may also be a protein which is encoded by a nucleic acid comprising a nucleotide sequence hybridizable under stringent conditions with the complementary strand of the nucleotide sequence of SEQ ID NO: 1, 3, 5, 7, 9, 11, 13, 15, 17, or 19.

An isolated Ms9 polynucleotide comprising a nucleotide sequence, wherein the nucleotide sequence is derived from SEQ ID NO: 1-3, 5-7, 9-11, 13-15, or 17-19 by alteration of one or more nucleotides by at least one method selected from the group consisting of: deletion, substitution, addition and insertion.

An isolated Ms9 polynucleotide comprising a nucleotide sequence, wherein the nucleotide sequence corresponds to an allele of SEQ ID NO: 1, 5, 9, 13, or 17.

An isolated Ms22 polynucleotide comprising: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO: 24, 28, 32, 36, or 40; or (ii) a full complement of the nucleic acid sequence of (i), wherein the full complement and the nucleic acid sequence of (i) consist of the same number of nucleotides and are 100% complementary.

An isolated Ms22 polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO: 24, 28, 32, 36, or 40.

An isolated Ms22 polynucleotide comprising (i) a nucleic acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO: 21-23, 25-27, 29-31, 33-35, or 37-39 and combinations thereof; or (ii) a full complement of the nucleic acid sequence of (i).

An isolated Ms22 polynucleotide comprising a nucleotide sequence, wherein the nucleotide sequence is hybridizable under stringent conditions with a DNA molecule comprising the full complement of SEQ ID NO: 21-23, 25-27, 29-31, 33-35, or 37-39. The isolated MS22 protein of the present disclosure may also be a protein which is encoded by a nucleic acid comprising a nucleotide sequence hybridizable under stringent conditions with the complementary strand of the nucleotide sequence of SEQ ID NO: 21, 23, 25, 27, 29, 31, 33, 35, 37, or 39.

An isolated Ms22 polynucleotide comprising a nucleotide sequence, wherein the nucleotide sequence is derived from SEQ ID NO: 21-23, 25-27, 29-31, 33-35, or 37-39 by alteration of one or more nucleotides by at least one method selected from the group consisting of: deletion, substitution, addition and insertion.

An isolated Ms22 polynucleotide comprising a nucleotide sequence, wherein the nucleotide sequence corresponds to an allele of SEQ ID NO: 21, 25, 29, 33, or 37.

An isolated MS26 polynucleotide comprising: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO: 44, 48, 52, 56, or 60; or (ii) a full complement of the nucleic acid sequence of (i), wherein the full complement and the nucleic acid sequence of (i) consist of the same number of nucleotides and are 100% complementary.

An isolated MS26 polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO: 44, 48, 52, 56, or 60.

An isolated MS26 polynucleotide comprising (i) a nucleic acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO: 41-43, 45-47, 49-51, 53-55, or 57-59 and combinations thereof; or (ii) a full complement of the nucleic acid sequence of (i).

An isolated MS26 polynucleotide comprising a nucleotide sequence, wherein the nucleotide sequence is hybridizable under stringent conditions with a DNA molecule comprising the full complement of SEQ ID NO: 41-43, 45-47, 49-51, 53-55, or 57-59. The isolated MS26 protein of the present disclosure may also be a protein which is encoded by a nucleic acid comprising a nucleotide sequence hybridizable under stringent conditions with the complementary strand of the nucleotide sequence of SEQ ID NO: 41, 43 45, 47, 49, 51, 53, 55, 57, or 59.

An isolated MS26 polynucleotide comprising a nucleotide sequence, wherein the nucleotide sequence is derived from SEQ ID NO: 41-43, 45-47, 49-51, 53-55, or 57-59 by alteration of one or more nucleotides by at least one method selected from the group consisting of: deletion, substitution, addition and insertion.

An isolated MS26 polynucleotide comprising a nucleotide sequence, wherein the nucleotide sequence corresponds to an allele of SEQ ID NO: 41, 45, 49, 53, or 57.

An isolated MS45 polynucleotide comprising: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO: 64, 68, 72, 76 or 80; or (ii) a full complement of the nucleic acid sequence of (i), wherein the full complement and the nucleic acid sequence of (i) consist of the same number of nucleotides and are 100% complementary.

An isolated MS45 polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO: 64, 68, 72, 76 or 80.

An isolated MS45 polynucleotide comprising (i) a nucleic acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO: 61-63, 65-67, 69-71, 73-75, or 77-79 and combinations thereof; or (ii) a full complement of the nucleic acid sequence of (i).

An isolated MS45 polynucleotide comprising a nucleotide sequence, wherein the nucleotide sequence is hybridizable under stringent conditions with a DNA molecule comprising the full complement of SEQ ID NO: 61-63, 65-67, 69-71, 73-75, or 77-79. The isolated MS45 protein of the present disclosure may also be a protein which is encoded by a nucleic acid comprising a nucleotide sequence hybridizable under stringent conditions with the complementary strand of the nucleotide sequence of SEQ ID NO: 61, 63, 65, 67, 69, 71, 73, 75, 77, or 79.

An isolated MS45 polynucleotide comprising a nucleotide sequence, wherein the nucleotide sequence is derived from SEQ ID NO: 61-63, 65-67, 69-71, 73-75, or 77-79 by alteration of one or more nucleotides by at least one method selected from the group consisting of: deletion, substitution, addition and insertion.

An isolated MS45 polynucleotide comprising a nucleotide sequence, wherein the nucleotide sequence corresponds to an allele of SEQ ID NO: 61, 65, 69, 73, or 77.

Any of the Ms9, Ms22, Ms26, or Ms45 polynucleotides and polypeptide described herein and known in the art may be utilized in any methods and compositions of the present disclosure.

Because the genetic modification is introduced at a target site located in or near a male fertility gene of MS9, MS22, MS26, or MS45, it is not necessary to screen a population of thousands of plants carrying random mutations, such as those resulting from chemical mutagenesis, in order to identify a plant with the introduced genetic modification. Therefore, the need to backcross a plant to remove undesired mutations that are not the introduced genetic modification is eliminated or at least reduced.

Described herein are compositions and methods for producing male-sterile plants that introduce a genetic modification into a male fertility gene locus of MS9, MS22, MS26 or MS45 in the plant genome in a plant cell and obtaining a plant from that plant cell. The methods may employ a guide RNA/Cas endonuclease system, wherein the Cas endonuclease is guided by the guide RNA to recognize and optionally introduce a double strand break at a specific target site into the genome of a cell. The guide RNA/Cas endonuclease system provides for an effective system for modifying target sites within the genome of a plant, plant cell or seed. The target site recognized by a Cas endonuclease may be located within or outside the MS9, MS22, MS26 or MS45 polynucleotide sequence, for example, within or outside the MS9, MS22, MS26 or MS45 gene locus.

In one embodiment, the method comprises a method for producing a male-sterile plant, the method comprising: a) obtaining a first plant comprising at least one Cas endonuclease capable of introducing a double strand break at a genomic target site located in a male fertility gene locus of MS9, MS22, MS26 or MS45 in the plant genome; b) obtaining a second plant comprising a guide RNA that is capable of forming a complex with the Cas endonuclease of (a),c) crossing the first plant of (a) with the second plant of (b); d) evaluating the progeny of (c) for an alteration in the target site; and e) selecting a progeny plant that is male-sterile.

Compositions and methods are also provided for editing a nucleotide sequence in the genome of a cell. In one embodiment, the disclosure describes a method for editing a nucleotide sequence located in or near a male fertility gene of MS9, MS22, MS26, or MS45 in the genome of a plant cell, the method comprising providing a guide RNA, a polynucleotide modification template, and at least one maize optimized Cas9 endonuclease to a plant cell, wherein the maize optimized Cas9 endonuclease is capable of introducing a double-strand break at a target site in the plant genome, wherein said polynucleotide modification template includes at least one nucleotide modification of said nucleotide sequence. The nucleotide to be edited (the nucleotide sequence of interest) can be located within or outside a target site located in or near a male fertility gene of MS9, MS22, MS26, or MS45 that is recognized and cleaved by a Cas endonuclease. Cells include, but are not limited to, plant cells as well as plants and seeds produced by the methods described herein.

Compositions and methods are also provided for methods of modifying the male-fertility of a plant, the method comprising introducing at least one guide RNA, at least one polynucleotide modification template and at least one Cas endonuclease into a cell. The Cas endonuclease introduces a double-strand break at a target site located in or near a MS9, MS22, MS26, or MS45 gene in the genome of said plant cell and the polynucleotide modification template comprises at least one nucleotide modification of a nucleotide sequence at the target site located in or near a male fertility gene of MS9, MS22, MS26, or MS45 that decreases the expression level of the MS9, MS22, MS26 or MS45 gene, to produce a male-sterile plant.

In another embodiment, the methods include selecting a male-sterile plant, the method comprising selecting at least one male-sterile plant that comprises the introduced genetic modification(s) in at least one or more of the endogenous MS9, MS22, MS26 or MS45 polynucleotide sequences or MS9, MS22, MS26 or MS45 gene locus. Also provided is a plant cell or plant or seed obtained or produced from the methods described herein.

The plant in the embodiments described herein is a monocot or a dicot. More specifically, the monocot is selected from the group consisting of maize, rice, sorghum, rye, barley, wheat, millet, oats, sugarcane, turfgrass, or switchgrass. The dicot is selected from the group consisting of soybean, canola, alfalfa, sunflower, cotton, tobacco, peanut, potato, tobacco, *Arabidopsis*, or safflower.

CRISPR loci (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

A Cas gene includes a gene that is generally coupled, associated or close to or in the vicinity of flanking CRISPR loci. The terms "Cas gene", "CRISPR-associated (Cas) gene" are used interchangeably herein. A comprehensive review of the Cas protein family is presented in Haft et al. (2005) Computational Biology, PLoS Comput Biol 1(6): e60. doi:10.1371/joumal.pcbi.0010060.

Cas endonuclease relates to a Cas protein encoded by a Cas gene, wherein said Cas protein is capable of introducing a double strand break into a DNA target sequence. The Cas endonuclease is guided by the guide polynucleotide to recognize and optionally introduce a double strand break at a specific target site into the genome of a cell. As used herein, the term "guide polynucleotide/Cas endonuclease system" includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA, but only if the correct protospacer-adjacent motif (PAM) is approximately oriented at the 3' end of the target sequence.

In one embodiment, the Cas endonuclease gene is a Cas9 endonuclease, such as but not limited to, Cas9 genes listed in SEQ ID NOs: 462, 474, 489, 494, 499, 505, and 518 of WO2007/025097 published Mar. 1, 2007, and incorporated herein by reference. In another embodiment, the Cas endonuclease gene is plant optimized Cas9 endonuclease, for example, codon-optimized for expression in maize, wheat, or soybean. In another embodiment, the Cas endonuclease gene is operably linked to a SV40 nuclear targeting signal upstream of the Cas codon region and a bipartite VirD2 nuclear localization signal (Tinland et al. (1992) Proc. Natl. Acad. Sci. USA 89:7442-6) downstream of the Cas codon region. As used to herein, "operably linked" is intended to mean a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. When used to refer to the joining of two protein coding regions, operably linked means that the coding regions are in the same reading frame. In one embodiment, the Cas endonuclease gene is a Cas9 endonuclease gene of SEQ ID NO:1, 124, 212, 213, 214, 215, 216, 193 or nucleotides 2037-6329 of SEQ ID NO:5, or any functional fragment or variant thereof of US publication number 20160208272, published Jul. 26, 2016, and incorporated herein by reference.

The terms "functional fragment", "fragment that is functionally equivalent" and "functionally equivalent fragment" are used interchangeably herein. These terms refer to a portion or subsequence of the polypeptide sequence of the present disclosure in which the polypeptide's native function is retained.

The terms "functional variant", "Variant that is functionally equivalent" and "functionally equivalent variant" are used interchangeably herein. These terms refer to a variant of a polypeptide of the present disclosure in which which the polypeptide's native function is retained. Fragments and variants can be obtained via methods such as site-directed mutagenesis and synthetic construction.

The Cas endonuclease gene may be a plant codon optimized *Streptococcus Pyogenes* Cas9 gene that can recognize any genomic sequence of the form N(12-30) NGG can in principle be targeted.

The Cas endonuclease may be introduced directly into a cell by any method known in the art, for example, but not limited to transient introduction methods, transfection and/ or topical application, including those described in US publication number 20160208272, published Jul. 26, 2016, and incorporated herein by reference. The type II CRISPR/ Cas system from bacteria employs a crRNA and tracrRNA to guide the Cas endonuclease to its DNA target. The crRNA (CRISPR RNA) contains the region complementary to one strand of the double strand DNA target and base pairs with the tracrRNA (trans-activating CRISPR RNA) forming a RNA duplex that directs the Cas endonuclease to cleave the DNA target.

As used herein, the term "guide RNA" relates to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

As used herein, the term "guide polynucleotide", relates to a polynucleotide sequence that can form a complex with a Cas endonuclease and enables the Cas endonuclease to recognize and optionally cleave a DNA target site. The guide polynucleotide can be a single molecule or a double molecule. The guide polynucleotide sequence can be a RNA sequence, a DNA sequence, or a combination thereof (a RNA-DNA combination sequence). A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In one embodiment, the size of the fragment of the cRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In one example, the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides. In one example, the RNA that guides the RNA/Cas9 endonuclease complex, is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some examples, the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide RNA may comprise a cRNA or cRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some examples, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one example, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another example, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

The guide RNA and Cas endonuclease are capable of forming a complex that enables the Cas endonuclease to introduce in the plant genome a double strand break at a DNA target site, for example, in a male fertility gene locus of MS9, MS22, MS26 or MS45 or within MS9, MS22, MS26 or MS45 polynucleotides themselves. The variable target domain may be 12, 13, 14, 15, 16, 17, 18, 19, 20, 21, 22, 23, 24, 25, 26, 27, 28, 29 or 30 nucleotides in length.

In some approaches, the guide RNA comprises a cRNA (or cRNA fragment) and a tracrRNA (or tracrRNA fragment) of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site.

The guide RNA can be introduced into a plant or plant cell directly using any method known in the art such as, but not limited to, particle bombardment or topical applications, for example, as described in US publication number 20160208272, published Jul. 26, 2016, and incorporated herein by reference.

The guide RNA may be introduced indirectly by introducing a recombinant DNA molecule comprising the corresponding guide DNA sequence operably linked to a plant specific promoter that is capable of transcribing the guide RNA in said plant cell. The term "corresponding guide DNA" includes a DNA molecule that is identical to the RNA molecule but has a "T" substituted for each "U" of the RNA molecule. The guide RNA may be introduced via particle bombardment or *Agrobacterium* transformation of a recombinant DNA construct comprising the corresponding guide DNA operably linked to a plant U6 polymerase III promoter. Some embodiments of the disclosure relate to identified wheat U6 RNA polymerase III promoters, for example, wheat U6 RNA polymerase III promoter (SEQ ID NO: 451), wheat U6 RNA polymerase III promoter (SEQ ID NO: 452), and wheat U6 RNA polymerase III promoter (SEQ ID NO: 453). See, for example, Example 4 as described herein.

The RNA that guides the RNA/Cas9 endonuclease complex, may be a duplexed RNA comprising a duplex crRNA-tracrRNA. One advantage of using a guide RNA versus a duplexed crRNA-tracrRNA is that only one expression cassette needs to be made to express the fused guide RNA.

The terms "target site", "target sequence", "target DNA", "target locus", "genomic target site", "genomic target sequence", and "genomic target locus" are used interchangeably herein and refer to a polynucleotide sequence in the genome (including choloroplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature. As used herein, terms "endogenous target sequence" and "native target sequence" are used interchangeable herein to refer to a target sequence that is endogenous or native to the genome of a plant and is at the endogenous or native position of that target sequence in the genome of the plant.

The target site may be similar to a DNA recognition site or target site that that is specifically recognized and/or bound by a double-strand break inducing agent such as a LIG3-4 endonuclease (US patent publication 2009-0133152 A1 (published May 21, 2009) or a MS26++ meganuclease (U.S. patent publication 20150184194 published Jul. 2, 2015).

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii). For example, the methods and compositions described herein may be used to produce a Ms9, Ms22, Ms26, or Ms45 modified target site which confers male-sterility to the plant containing the modified Ms9, Ms22, Ms26, or Ms45 target site or introduced genetic modification.

Methods for modifying a plant genomic target site are disclosed herein.

In another embodiment, the method includes modifying a target site located in or near a MS9, MS22, MS26, or MS45 gene in the genome of a plant cell, the method comprising introducing a guide RNA into a plant cell having a Cas endonuclease, wherein said guide RNA and Cas endonuclease are capable of forming a complex that enables the Cas endonuclease to introduce a double strand break at said target site.

Also provided is a method for modifying a target site in the genome of a plant cell, the method comprising introducing a guide RNA and a Cas endonuclease into said plant, wherein said guide RNA and Cas endonuclease are capable of forming a complex that enables the Cas endonuclease to introduce a double strand break at said target site. In some embodiments, the guideRNA can simultaneously modify the same target site in multiple genomes in the plant cell or plant. See, for example, Example 2, demonstrating the generation of ms45 mutations in the a-, b- and d-genomes in wheat using the same guideRNA. Table 2 provided herein shows exemplary wheat guideRNAs and target sequences for making Ms9, Ms22, Ms26, or Ms45 mutations in wheat, maize, or rice genomes to confer male-sterility to a plant. Additionally, the target sequences listed for wheat are consensus sequences so that each genome can be modified simultaneously using the same guideRNA to produce the genetic modification.

Further provided is a method for modifying a target site in or near a MS9, MS22, MS26, or MS45 gene in the genome of a plant cell, the method comprising: a) introducing into a plant cell a guide RNA comprising a variable targeting domain and a Cas endonuclease, wherein said guide RNA and Cas endonuclease are capable of forming a complex that enables the Cas endonuclease to introduce a double strand break at said target site; and, b) identifying at least one plant cell that has a modification at said target, wherein the modification includes at least one deletion or substitution of one or more nucleotides in said target site. A plant derived the modified plant cell is male-sterile.

Further provided, a method for modifying a target DNA sequence in or near a MS9, MS22, MS26, or MS45 gene in the genome of a plant cell, the method comprising: a) introducing into a plant cell a first recombinant DNA construct capable of expressing a guide RNA and a second recombinant DNA construct capable of expressing a Cas endonuclease, wherein said guide RNA and Cas endonuclease are capable of forming a complex that enables the Cas endonuclease to introduce a double strand break at said target site; and, b) identifying at least one plant cell that has a modification at said target, wherein the modification includes at least one deletion or substitution of one or more nucleotides in said target site and the modification confers male-sterility to a plant derived from the modified plant cell.

The length of the target site can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs.

In some embodiment, the genomic target site capable of being cleaved by a Cas endonuclease comprises a 12 to 30 nucleotide fragment of a male fertility gene. Exemplary male fertility genes for use in the compositions and methods described here include but are not limited to MS9, MS22, MS26, and MS45. In some embodiments, the MS9, MS22, MS26, and MS45 fertility genes or gene loci to be targeted are from wheat, barley, maize, rice, sorghum, rye, millet, oats, sugarcane, turfgrass, switchgrass, soybean, canola, alfalfa, sunflower, cotton, tobacco, peanut, potato, tobacco, *Arabidopsis*, or safflower.

TABLE 2

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
|---|---|---|---|---|---|---|---|
| Wheat Ms9 4BL CR1 | GCGGCCGCCGTGCTGCG ACAAGG- Sense (SEQ ID NO: 81) | 6 | 28 | Positions relative to ATG in SEQ ID NO: 5 | AGG | GCGGCCGC CGTGCTGC GACA (SEQ ID NO: 267) | Exon1 |
| Wheat Ms9 4BL CR2 | GCGTCCTCCTCCGCCGTC CACGG- Complementary (SEQ ID NO: 82) | 46 | 68 | Positions relative to ATG in SEQ ID NO: 5 | CGG | GCGTCCTC CTCCGCC GTCCA (SEQ ID NO: 268) | Exon1 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
| --- | --- | --- | --- | --- | --- | --- | --- |
| Wheat Ms9 4BL CR3 | GAAGAAGGGGCCGTGG ACGGCGG-Sense (SEQ ID NO: 83) | 36 | 58 | Positions ATG in SEQ relative to ID NO: 5 | CGG | GAAGAAG GGGCCGT GGACGG (SEQ ID NO: 269) | Exon1 |
| Wheat Ms9 4BL CR4 | GAAGGGGCCGTGGACG GCGGAGG-Sense (SEQ ID NO: 84) | 39 | 61 | Positions relative to ATG in SEQ ID NO: 5 | AGG | GAAGGGG CCGTGGA CGGCGG (SEQ ID NO: 270) | Exon1 |
| Wheat Ms9 4BL CR5 | GGGGCCGTGGACGGCG GAGGAGG-Sense (SEQ ID NO: 85) | 42 | 64 | Positions relative to ATG in SEQ ID NO: 5 | AGG | GGGGCCG TGGACGG CGGAGG (SEQ ID NO: 271) | Exon1 |
| Wheat Ms9 4BL CR6 | GGTGCCATGGTTGGAGG TGTAGG- Complementary (SEQ ID NO: 86) | 80 | 102 | Positions relative to ATG in SEQ ID NO: 5 | AGG | GGTGCCA TGGTTGG AGGTGT (SEQ ID NO: 272) | Exon 1 |
| Wheat Ms9 4BL CR7 | GTTGCCGGTGCCATGGT TGGAGG- Complementary (SEQ ID NO: 87) | 86 | 108 | Positions relative to ATG in SEQ ID NO: 5 | AGG | GTTGCCG GTGCCAT GGTTGG (SEQ ID NO: 273) | Exon1 |
| Wheat Ms9 4BL CR8 | GGGAACAGAGGTCCAGT TGCCGG- Complementary (SEQ ID NO: 88) | 101 | 123 | Positions relative to ATG in SEQ ID NO: 5 | CGG | GGGAACA GAGGTCC AGTTGC (SEQ ID NO: 274 | Exon 1 |
| Wheat Ms9 4BL CR9 | GCACGAGAACTTCACGC AGGAGG-Sense (SEQ ID NO: 89) | 309 | 331 | Positions relative to ATG in SEQ ID NO: 5 | AGG | GCACGAG AACTTCAC GCAGG (SEQ ID NO: 275) | Exon2 |
| Wheat Ms9 4BL CR10 | GAACTTCACGCAGGAGG AGGAGG-Sense (SEQ ID NO: 90) | 315 | 337 | Positions relative to ATG in SEQ ID NO: 5 | AGG | GAACTTC ACGCAGG AGGAGG (SEQ ID NO: 276) | Exon2 |
| Wheat Ms9 4BL CR11 | GCTTCCCAGCATGGCAT GGAGGG- Complementary (SEQ ID NO: 91) | 350 | 372 | Positions relative to ATG in SEQ ID NO: 5 | GGG | GCTTCCCA GCATGGC ATGGA (SEQ ID NO: 277) | Exon2 |
| Wheat Ms9 4BL CR12 | GTCACCCTCCATGCCATG CTGGG-Sense (SEQ ID NO: 92) | 346 | 368 | Positions relative to ATG in SEQ ID NO: 5 | GGG | GTCACCCT CCATGCC ATGCT (SEQ ID NO: 278 | Exon2 |
| Wheat Ms9 4BL CR13 | GAACCAGCTGCCGGGGC GGACGG-Sense (SEQ ID NO: 93) | 882 | 904 | Positions relative to ATG in SEQ ID NO: 5 | CGG | GAACCAG CTGCCGG GGCGGA (SEQ ID NO: 279) | Exon3 |
| Wheat Ms9 4BL CR14 | TGAGGTACACCAACTAC CTGAGG-Sense (SEQ ID NO: 94) | 275 | 297 | Positions relative to ATG in SEQ ID NO: 5 | AGG | TGAGGTAC ACCAACTA CCTG (SEQ ID NO: 280) | Exon2 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
|---|---|---|---|---|---|---|---|
| Wheat Ms9 4BL CR15 | GCCAGGGGCGGCGGCG TCCCCGG-Sense (SEQ ID NO: 95) | 1185 | 1207 | Positions relative to ATG in SEQ ID NO: 5 | CGG | GCCAGGG GCGGCGG CGTCCC (SEQ ID NO: 281) | Exon3 |
| Maize Ms9 CR1 | GGTGCCATGGGTGGAG GTGTAGG-Complementary (SEQ ID NO: 96) | 80 | 102 | Positions relative to ATG in SEQ ID NO: 13 | AGG | GGTGCCAT GGGTGGA GGTGT (SEQ ID NO: 282) | Exon1 |
| Maize Ms9 CR2 | GTTGCCGGTGCCATGGG TGGAGG-Complementary (SEQ ID NO: 97) | 86 | 108 | Positions relative to ATG in SEQ ID NO: 13 | AGG | GTTGCCG GTGCCAT GGGTGG (SEQ ID NO: 283) | Exon1 |
| Maize Ms9 CR3 | GGTCCAGTTGCCGGTGC CATGGG-Complementary (SEQ ID NO: 98) | 92 | 114 | Positions relative to ATG in SEQ ID NO: 13 | GGG | GGTCCAG TTGCCGG TGCCAT (SEQ ID NO: 284) | Exon1 |
| Maize Ms9 CR4 | GGGCACGTTGGTCCAGT TGCCGG-Complementary (SEQ ID NO: 99) | 101 | 123 | Positions relative to ATG in SEQ ID NO: 13 | CGG | GGGCACG TTGGTCCA GTTGC (SEQ ID NO: 285) | Exon1 |
| Maize Ms9 CR5 | GCGGCAAGAGCTGCAG GCTGAGG-Sense (SEQ ID NO: 100) | 244 | 266 | Positions relative to ATG in SEQ ID NO: 13 | AGG | GCGGCAA GAGCTGC AGGCTG (SEQ ID NO: 286) | Exon2 |
| Maize Ms9 CR6 | GAAGTTCTCGTGCTTCA GGTTGG-Complementary (SEQ ID NO: 101) | 286 | 308 | Positions relative to ATG in SEQ ID NO: 13 | TGG | GAAGTTC TCGTGCTT CAGGT (SEQ ID NO: 287) | Exon2 |
| Maize Ms9 CR7 | GGGTGAAGTTCTCGTGC TTCAGG-Complementary (SEQ ID NO: 102) | 290 | 312 | Positions relative to ATG in SEQ ID NO: 13 | AGG | GGGTGAA GTTCTCGT GCTTC (SEQ ID NO: 288) | Exon2 |
| Maize Ms9 CR8 | GATGAGGTCTTCCTCCTC CTGGG-Complementary (SEQ ID NO: 103) | 310 | 332 | Positions relative to ATG in SEQ ID NO: 13 | GGG | GATGAGG TCTTCCTC CTCCT (SEQ ID NO: 289) | Exon2 |
| Maize Ms9 CR9 | GAAGCACGAGAACTTCA CCCAGG-Sense (SEQ ID NO: 104) | 293 | 315 | Positions relative to ATG in SEQ ID NO: 13 | AGG | GAAGCAC GAGAACT TCACCC (SEQ ID NO: 290) | Exon2 |
| Maize Ms9 CR10 | GCACGAGAACTTCACCC AGGAGG-Sense (SEQ ID NO: 105) | 296 | 315 | Positions relative to ATG in SEQ ID NO: 13 | AGG | GCACGAG AACTTCAC CCAGG (SEQ ID NO: 291) | Exon2 |
| Maize Ms9 CR11 | GCTTCCGAGCATGGCGT GGAGGG-Complementary (SEQ ID NO: 106) | 337 | 359 | Positions relative to ATG in SEQ ID NO: 13 | GGG | GCTTCCG AGCATGG CGTGGA (SEQ ID NO: 292) | Exon2 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
|---|---|---|---|---|---|---|---|
| Maize Ms9 CR12 | GTCACCCTCCACGCCATG CTCGG-Sense (SEQ ID NO: 107) | 333 | 355 | Positions relative to ATG in SEQ ID NO: 13 | CGG | GTCACCCT CCACGCC ATGCT (SEQ ID NO: 293) | Exon2 |
| Maize Ms9 CR13 | GAACCAGCTGCCGGGAA GGACGG-Sense (SEQ ID NO: 108) | 1284 | 1306 | Positions relative to ATG in SEQ ID NO: 13 | CGG | GAACCAG CTGCCGG GAAGGA (SEQ ID NO: 294) | Exon3 |
| Maize Ms9 CR14 | GCAAGAAGCTGCGGCA GCGCGGG-Sense (SEQ ID NO: 109) | 1343 | 1365 | Positions relative to ATG in SEQ ID NO: 13 | GGG | GCAAGAA GCTGCGG CAGCGC (SEQ ID NO: 295) | Exon3 |
| Maize Ms9 CR15 | GCGATGGGGCGGTGGG TGAGGGG-Complementary (SEQ ID NO: 110) | 1372 | 1394 | Positions relative to ATG in SEQ ID NO: 13 | GGG | GCGATGG GGCGGTG GGTGAG (SEQ ID NO: 296) | Exon3 |
| Rice Ms9 CR1 | GCTGCGACAAGGCGAAC GTGAAGAAGG-Sense (SEQ ID NO: 111) | 17 | 43 | Positions relative to ATG in SEQ ID NO: 17 | AGG | GCTGCGA CAAGGCG AACGTGA AGA (SEQ ID NO: 297 | Exon1 |
| Rice Ms9 CR2 | GCTGCGACAAGGCGAAC GTGAAGAAGGG-Sense (SEQ ID NO: 112) | 17 | 44 | Positions relative to ATG in SEQ ID NO: 17 | GGG | GCTGCGAC AAGGCGAA CGTGAAGA A (SEQ ID NO: 298) | Exon1 |
| Rice Ms9 CR3 | GGCGTACACCTCCACCC ACGGCACCGG-Sense (SEQ ID NO: 113) | 78 | 104 | Positions relative to ATG in SEQ ID NO: 17 | CGG | GGCGTACA CCTCCACCC ACGGCAC (SEQ ID NO: 299) | Exon1 |
| Rice Ms9 CR4 | GCGCCGGCGCCGCAGGC TGCTCTCGG-Sense (SEQ ID NO: 114) | 1981 | 2006 | Positions relative to ATG in SEQ ID NO: 17 | CGG | GCGCCGGC GCCGCAGG CTGCTCT (SEQ ID NO: 300) | Exon3 |
| Rice Ms9 CR5 | GCAGGCTGCTCTCGGCC AGTATCAGG-Sense (SEQ ID NO: 115) | 1992 | 2017 | Positions relative to ATG in SEQ ID NO: 17 | AGG | GCAGGCTG CTCTCGGC CAGTATC (SEQ ID NO: 301) | Exon3 |
| Rice Ms9 CR6 | GGCTGAGGTACACCAAC TACCTGAGG-Sense (SEQ ID NO: 116) | 339 | 364 | Positions relative to ATG in SEQ ID NO: 17 | AGG | GGCTGAGG TACACCAA CTACCTG (SEQ ID NO: 302) | Exon2 |
| Rice Ms9 CR7 | GAAGCACGAGAACTTCA CGCAGG-Sense (SEQ ID NO: 117) | 373 | 395 | Positions relative to ATG in SEQ ID NO: 17 | AGG | GAAGCACG AGAACTTC ACGC (SEQ ID NO: 303) | Exon2 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
|---|---|---|---|---|---|---|---|
| Rice Ms9 CR8 | GAAGCACGAGAACTTCA CGCAGGAGG-Sense (SEQ ID NO: 118) | 373 | 398 | Positions relative to ATG in SEQ ID NO: 17 | AGG | GAAGCACG AGAACTTC ACGCAGG (SEQ ID NO: 304) | Exon2 |
| Rice Ms9 CR9 | GCACGAGAACTTCACGC AGGAGGAGG-Sense (SEQ ID NO: 119) | 376 | 401 | Positions relative to ATG in SEQ ID NO: 17 | AGG | GCACGAGA ACTTCACG CAGGAGG (SEQ ID NO: 305) | Exon2 |
| Rice Ms9 CR10 | GTCACCCTCCACGCCATG CTGG-Sense (SEQ ID NO: 120) | 413 | 434 | Positions relative to ATG in SEQ ID NO: 17 | TGG | GTCACCCT CCACGCCA TGC (SEQ ID NO: 306) | Exon2 |
| Rice Ms9 CR11 | GTCACCCTCCACGCCATG CTGGG-Sense (SEQ ID NO: 121) | 413 | 435 | Positions relative to ATG in SEQ ID NO: 17 | GGG | GTCACCCT CCACGCCA TGCT (SEQ ID NO: 307) | Exon2 |
| Rice Ms9 CR12 | GGCTGCTCTCGGCCAGT ATCAGGAGG-Sense (SEQ ID NO: 122) | 1995 | 2020 | Positions relative to ATG in SEQ ID NO: 17 | AGG | GGCTGCTC TCGGCCAG TATCAGG (SEQ ID NO: 308) | Exon3 |
| Rice Ms9 CR13 | GGTCGCTGATCGCGAAC CAGCTGCCGG-Sense (SEQ ID NO: 123) | 1613 | 1640 | Positions relative to ATG in SEQ ID NO: 17 | CGG | GGTCGCTG ATCGCGAA CCAGCTGC (SEQ ID NO: 309) | Exon3 |
| Rice Ms9 CR14 | GACTCGCAGCATCTGCA GCTCAACTGG-Sense (SEQ ID NO: 124) | 1912 | 1938 | Positions relative to ATG in SEQ ID NO: 17 | TGG | GACTCGCA GCATCTGC AGCTCAAC (SEQ ID NO: 310) | Exon3 |
| Rice Ms9 CR15 | GCCGACCTCATGCAGAG CATCGG-Sense (SEQ ID NO: 125) | 1735 | 1757 | Positions relative to ATG in SEQ ID NO: 17 | CGG | GCCGACCT CATGCAGA GCAT (SEQ ID NO: 311) | Exon3 |
| Wheat Ms22CR1 | GTTGAGGATGCAGCAGC AGGTGG-Sense (SEQ ID NO: 126) | 3 | 25 | Positions relative to ATG in SEQ ID NO: 21 | TGG | GTTGAGG ATGCAGC AGCAGG (SEQ ID NO: 312) | Exon 1 |
| Wheat Ms22CR2 | GAGGATGCAGCAGCAG GTGGAGG-Sense (SEQ ID NO: 127) | 6 | 28 | Positions relative to ATG in SEQ ID NO: 21 | AGG | GAGGATG CAGCAGC AGGTGG (SEQ ID NO: 313) | Exon 1 |
| Wheat Ms22CR3 | GCAGCAGCAGGTGGAG GGCGTGG-Sense (SEQ ID NO: 128) | 12 | 34 | Positions relative to ATG in SEQ ID NO: 21 | TGG | GCAGCAG CAGGTGG AGGGCG (SEQ ID NO: 314) | Exon 1 |
| Wheat Ms22CR4 | GCAGCAGGTGGAGGGC GTGGTGG-Sense (SEQ ID NO: 129) | 15 | 37 | Positions relative to ATG in SEQ ID NO: 21 | TGG | GCAGCAG GTGGAGG GCGTGG (SEQ ID NO: 315) | Exon1 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
| --- | --- | --- | --- | --- | --- | --- | --- |
| Wheat Ms22CR5 | GTGGAGGGCGTGGTGG GCGGCGG-Sense (SEQ ID NO: 130) | 22 | 44 | Positions relative to ATG in SEQ ID NO: 21 | CGG | GTGGAGG GCGTGGT GGGCGG (SEQ ID NO: 316) | Exon1 |
| Wheat Ms22CR6 | TGG-Complementary (SEQ ID NO: 131) | 128 | 150 | Positions relative to ATG in SEQ ID NO: 21 | TGG | GTGGCAC ATGCAGC AGCCGC (SEQ ID NO: 317) | Exon1 |
| Wheat Ms22CR7 | GTGGTCGTCTTCAGCGC CAGCGG-Sense (SEQ ID NO: 132) | 112 | 134 | Positions relative to ATG in SEQ ID NO: 21 | CGG | GTGGTCG TCTTCAGC GCCAG (SEQ ID NO: 318) | Exon1 |
| Wheat Ms22CR8 | GCAGGAGGCGCTTGACG ACGTGG-Complementary (SEQ ID NO: 133) | 147 | 169 | Positions relative to ATG in SEQ ID NO: 21 | TGG | GCAGGAG GCGCTTG ACGACG (SEQ ID NO: 319) | Exon1 |
| Wheat Ms22CR9 | GTCGTCAAGCGCCTCCT GCTTGG-Sense (SEQ ID NO: 134) | 151 | 173 | Positions relative to ATG in SEQ ID NO: 21 | TGG | GTCGTCA AGCGCCT CCTGCT (SEQ ID NO: 320) | Exon1 |
| Wheat Ms22CR10 | GTGGCCGGCGCCGGGTC CGGGGG-Complementary (SEQ ID NO: 135) | 260 | 282 | Positions relative to ATG in SEQ ID NO: 21 | GGG | GTGGCCG GCGCCGG GTCCGG (SEQ ID NO: 321) | Exon1 |
| Wheat Ms22CR11 | GGTGGCCGGCGCCGGG TCCGGGG-Complementary (SEQ ID NO: 136) | 261 | 283 | Positions relative to ATG in SEQ ID NO: 21 | GGG | GGTGGCC GGCGCCG GGTCCG (SEQ ID NO: 322) | Exon1 |
| Wheat Ms22CR12 | GTGGTGGCCGGCGCCG GGTCCGG-Complementary (SEQ ID NO: 137) | 263 | 285 | Positions relative to ATG in SEQ ID NO: 21 | CGG | GTGGTGG CCGGCGC CGGGTC (SEQ ID NO: 323) | Exon1 |
| Wheat Ms22CR13 | GGACGAGCGTGCCGTTG ATGTGG-Complementary (SEQ ID NO: 138) | 357 | 379 | Positions relative to ATG in SEQ ID NO: 21 | TGG | GGACGAG CGTGCCG TTGATG (SEQ ID NO: 324) | Exon1 |
| Wheat Ms22CR14 | GTGATGGCGTGCCACAT CAACGG-Sense (SEQ ID NO: 139) | 346 | 368 | Positions relative to ATG in SEQ ID NO: 21 | CGG | GTGATGG CGTGCCA CATCAA (SEQ ID NO: 325) | Exon1 |
| Wheat Ms22CR15 | GCGCCGGCGTCCTTGAG GAGCGG-Complementary (SEQ ID NO: 140) | 379 | 402 | Positions relative to ATG in SEQ ID NO: 21 | CGG | GCGCCGG CGTCCTTG AGGAG (SEQ ID NO: 326) | Exon1 |
| Maize Ms22 CR1 | GTCGGGAGTGAGCGGC GGCGTGG-Sense (SEQ ID NO: 141) | 36 | 58 | Positions relative to ATG in SEQ ID NO: 33 | TGG | GTCGGGA GTGAGCG GCGGCG (SEQ ID NO: 327) | Exon1 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
| --- | --- | --- | --- | --- | --- | --- | --- |
| Maize Ms22 CR2 | GGGAGTGAGCGGCGGC GTGGTGG-Sense (SEQ ID NO: 142) | 39 | 61 | Positions relative to ATG in SEQ ID NO: 33 | TGG | GGGAGTG AGCGGCG GCGTGG (SEQ ID NO: 328) | Exon1 |
| Maize Ms22 CR3 | GCGGACGCGGCGGCGG CATCCGG-Sense (SEQ ID NO: 143) | 61 | 83 | Positions relative to ATG in SEQ ID NO: 33 | CGG | GCGGACG CGGCGGC GGCATC (SEQ ID NO: 329) | Exon1 |
| Maize Ms22 CR4 | GGACGCGGCGGCGGCA TCCGGGG-Sense (SEQ ID NO: 144) | 63 | 85 | Positions relative to ATG in SEQ ID NO: 33 | GGG | GGACGCG GCGGCGG CATCCG (SEQ ID NO: 330) | Exon1 |
| Maize Ms22 CR5 | GCCACCATCGTCGTCGTC GTCGG-Complementary (SEQ ID NO: 145) | 119 | 97 | Positions relative to ATG in SEQ ID NO: 33 | CGG | GCCACCA TCGTCGTC GTCGT (SEQ ID NO: 331 | Exon1 |
| Maize Ms22 CR6 | GCCGACGACGACGACGA TGGTGG-Sense (SEQ ID NO: 146) | 96 | 118 | Positions relative to ATG in SEQ ID NO: 33 | TGG | GCCGACG ACGACGA CGATGG (SEQ ID NO: 332) | Exon1 |
| Maize Ms22 CR7 | GACGACGACGATGGTG GCCGCGG-Sense (SEQ ID NO: 147) | 102 | 124 | Positions relative to ATG in SEQ ID NO: 33 | CGG | GACGACG ACGATGG TGGCCG (SEQ ID NO: 333) | Exon1 |
| Maize Ms22 CR8 | GCCAGCGCCGACGCCGA GTGCGG-Complementary (SEQ ID NO: 148) | 149 | 127 | Positions relative to ATG in SEQ ID NO: 33 | CGG | GCCAGCG CCGACGC CGAGTG (SEQ ID NO: 334) | Exon1 |
| Maize Ms22 CR9 | GGTGGCCGCGGCGCCGC ACTCGG-Sense (SEQ ID NO: 149) | 114 | 136 | Positions relative to ATG in SEQ ID NO: 33 | CGG | GGTGGCC GCGGCGC CGCACT (SEQ ID NO: 335) | Exon1 |
| Maize Ms22 CR10 | GCCGCACTCGGCGTCGG CGCTGG-Sense (SEQ ID NO: 150) | 126 | 148 | Positions relative to ATG in SEQ ID NO: 33 | TGG | GCCGCAC TCGGCGT CGGCGC (SEQ ID NO: 336) | Exon1 |
| Maize Ms22 CR11 | GCACTCGGCGTCGGCGC TGGCGG-Sense (SEQ ID NO: 151) | 129 | 151 | Positions relative to ATG in SEQ ID NO: 33 | CGG | GCACTCG GCGTCGG CGCTGG (SEQ ID NO: 337) | Exon1 |
| Maize Ms22 CR12 | GGCGCTGGCGGTGTACG AGCGGG-Sense (SEQ ID NO: 152) | 141 | 163 | Positions relative to ATG in SEQ ID NO: 33 | GGG | GGCGCTG GCGGTGT ACGAGC (SEQ ID NO: 338) | Exon1 |
| Maize Ms22 CR13 | GCTGGCGGTGTACGAGC GGGTGG-Sense (SEQ ID NO: 153) | 144 | 166 | Positions relative to ATG in SEQ ID NO: 33 | TGG | GCTGGCG GTGTACG AGCGGG (SEQ ID NO: 339) | Exon1 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
| --- | --- | --- | --- | --- | --- | --- | --- |
| Maize Ms22 CR14 | GTACGAGCGGGTGGCG CGCATGG-Sense (SEQ ID NO: 154) | 153 | 175 | Positions relative to ATG in SEQ ID NO: 33 | TGG | GTACGAG CGGGTGG CGCGCA (SEQ ID NO: 340) | Exon1 |
| Maize Ms22 CR15 | GAGCGGGTGGCGCGCA TGGCGGG-Sense (SEQ ID NO: 155) | 157 | 179 | Positions relative to ATG in SEQ ID NO: 33 | GGG | GAGCGGG TGGCGCG CATGGC (SEQ ID NO: 341) | Exon1 |
| Rice Ms22 CR1 | GCGATGATGTCGGTGTA CGAGAGGGTGG-Sense (SEQ ID NO: 156) | 55 | 82 | Positions relative to ATG in SEQ ID NO: 37 | TGG | GCGATGAT GTCGGTGT ACGAGAGG G (SEQ ID NO: 342) | Exon1 |
| Rice Ms22 CR2 | GCGGTGGTGGTGTTCAG CGCGAGCGG-Sense (SEQ ID NO: 157) | 103 | 128 | Positions relative to ATG in SEQ ID NO: 37 | CGG | GCGGTGGT GGTGTTCA GCGCGAG (SEQ ID NO: 343) | Exon1 |
| Rice Ms22 CR3 | GCGGTGGTGGTGTTCAG CGCGAGCGGG-Sense (SEQ ID NO: 158) | 103 | 129 | Positions relative to ATG in SEQ ID NO: 37 | GGG | GCGGTGGT GGTGTTCA GCGCGAGC (SEQ ID NO: 344) | Exon1 |
| Rice Ms22 CR4 | GCTCGCCGCCGCCGCCG ACATCCAGG-Sense (SEQ ID NO: 159) | 204 | 229 | Positions relative to ATG in SEQ ID NO: 37 | AGG | GCTCGCCG CCGCCGCC GACATCC (SEQ ID NO: 345) | Exon1 |
| Rice Ms22 CR5 | GCGCTGTCGCAGCTCCT CCCGCCGGG-Sense (SEQ ID NO: 160) | 232 | 257 | Positions relative to ATG in SEQ ID NO: 37 | GGG | GCGCTGTC GCAGCTCC TCCCGCC (SEQ ID NO: 346) | Exon1 |
| Rice Ms22 CR6 | GTTCGTCGGCGGCAGGC TCCTCGGCGG-Sense (SEQ ID NO: 161) | 279 | 305 | Positions relative to ATG in SEQ ID NO: 37 | CGG | GTTCGTCG GCGGCAGG CTCCTCGG (SEQ ID NO: 347) | Exon1 |
| Rice Ms22 CR7 | GAAGGTGATGGCGTGCC ACATCAATGG-Sense ((SEQ ID NO: 162) | 312 | 338 | Positions relative to ATG in SEQ ID NO: 37 | TGG | GAAGGTGA TGGCGTGC CACATCAA (SEQ ID NO: 348) | Exon1 |
| Rice Ms22 CR8 | GGCACCCTCGTCCCCCTC CTCAAGCAGG-Sense (SEQ ID NO: 163)) | 337 | 364 | Positions relative to ATG in SEQ ID NO: 37 | AGG | GGCACCCT CGTCCCCCT CCTCAAGC (SEQ ID NO: 349) | Exon1 |
| Rice Ms22 CR9 | GTCCCCCTCCTCAAGCAG GCCGG-Sense (SEQ ID NO: 164) | 346 | 368 | Positions relative to ATG in SEQ ID NO: 37 | CGG | GTCCCCCTC CTCAAGCA GGC (SEQ ID NO: 350) | Exon1 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
|---|---|---|---|---|---|---|---|
| Rice Ms22 CR10 | GAGGGGGGTCAAAGGA GTGG-Complementary (SEQ ID NO: 165) | 1379 | 1398 | Positions in SEQ ID NO: 38 | TGG | GAGGGGG GTCAAAGG AG (SEQ ID NO: 351) | Exon1 |
| Rice Ms22 CR11 | GGTGCGAGGGGGTCA AAGG-Complementary (SEQ ID NO: 166) | 1384 | 1403 | Positions in SEQ ID NO: 38 | AGG | GGTGCGAG GGGGTCA A (SEQ ID NO: 352) | Exon1 |
| Rice Ms22 CR12 | GAATTGGTGTGGTGCGA GGGGGG- Complementary (SEQ ID NO: 167) | 1391 | 1413 | Positions in SEQ ID NO: 38 | GGG | GAATTGGT GTGGTGCG AGGG (SEQ ID NO: 353) | Exon1 |
| Rice Ms22 CR13 | GAATTGGTGTGGTGCGA GGGG-Complementary (SEQ ID NO: 168) | 1393 | 1413 | Positions in SEQ ID NO: 38 | GGG | GAATTGGT GTGGTGCG AG (SEQ ID NO: 354) | Exon1 |
| Rice Ms22 CR14 | GTCGAGCTCGTAGACGG CGGG-Complementary (SEQ ID NO: 169) | 181 | 201 | Positions relative to ATG in SEQ ID NO: 37 | GGG | GTCGAGCT CGTAGACG GC (SEQ ID NO: 355) | Exon1 |
| Rice Ms22 CR15 | GTCGAGCTCGTAGACGG CGG-Complementary (SEQ ID NO: 170) | 182 | 201 | Positions relative to ATG in SEQ ID NO: 37 | CGG | GTCGAGCT CGTAGACG G (SEQ ID NO: 356) | Exon1 |
| Wheat Ms26 CR1 | GGCAGGGCTCCACAAGT TCATGG-Sense (SEQ ID NO: 171) | 66 | 88 | Positions relative to ATG in SEQ ID NO: 41 | TGG | GGCAGGG CTCCACAA GTTCA (SEQ ID NO: 357) | Exon 1 |
| Wheat Ms26 CR2 | GCTTCCTCAGGCTCCACC AGTGG- Complementary (SEQ ID NO: 172) | 123 | 145 | Positions relative to ATG in SEQ ID NO: 41 | TGG | GCTTCCTC AGGCTCC ACCAG (SEQ ID NO: 358) | Exon 1 |
| Wheat Ms26 CR3 | GTGGAGCCTGAGGAAG CAGAAGG-Sense (SEQ ID NO: 173) | 129 | 151 | Positions relative to ATG in SEQ ID NO: 41 | AGG | GTGGAGC CTGAGGA AGCAGA (SEQ ID NO: 359) | Exon 1 |
| Wheat Ms26 CR4 | GGAGCCTGAGGAAGCA GAAGGGG-Sense (SEQ ID NO: 174) | 131 | 153 | Positions relative to ATG in SEQ ID NO: 41 | GGG | GGAGCCT GAGGAAG CAGAAG (SEQ ID NO: 360) | Exon 1 |
| Wheat Ms26 CR5 | GCCGGTCATCGGCGCGA CGCTGG-Sense (SEQ ID NO: 175) | 165 | 187 | Positions relative to ATG in SEQ ID NO: 41 | TGG | GCCGGTC ATCGGCG CGACGC (SEQ ID NO: 361) | Exon 1 |
| Wheat Ms26 CR6 | GCGCGACGCTGGAGCA GCTGAGG-Sense (SEQ ID NO: 176) | 176 | 198 | Positions relative to ATG in SEQ ID NO: 41 | AGG | GCGCGAC GCTGGAG CAGCTG (SEQ ID NO: 362) | Exon 1 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
|---|---|---|---|---|---|---|---|
| Wheat Ms26 CR7 | GTACCTGTCCAAGCACC GGACGG-Sense (SEQ ID NO: 177) | 231 | 253 | Positions relative to ATG in SEQ ID NO: 41 | CGG | GTACCTGT CCAAGCA CCGGA (SEQ ID NO: 363) | Exon 1 |
| Wheat Ms26 CR8 | GGAGGTGAAGGGCATG TCGACGG-Complementary (SEQ ID NO: 178) | 257 | 279 | Positions relative to ATG in SEQ ID NO: 41 | CGG | GGAGGTG AAGGGCA TGTCGA (SEQ ID NO: 364) | Exon 1 |
| Wheat Ms26 CR9 | GATGTAGGTGTAGGAG GTGAAGG-Complementary (SEQ ID NO: 179) | 269 | 291 | Positions relative to ATG in SEQ ID NO: 41 | AGG | GATGTAG GTGTAGG AGGTGA (SEQ ID NO: 365) | Exon 1 |
| Wheat Ms26 CR10 | GTCGGCGATGTAGGTGT AGGAGG-Complementary (SEQ ID NO: 180) | 275 | 297 | Positions relative to ATG in SEQ ID NO: 41 | AGG | GTCGGCG ATGTAGG TGTAGG (SEQ ID NO: 366) | Exon 1 |
| Wheat Ms26 CR11 | GTTCACCGGGTCGGCGA TGTAGG-Complementary (SEQ ID NO: 181) | 284 | 306 | Positions relative to ATG in SEQ ID NO: 41 | AGG | GTTCACC GGGTCGG CGATGT (SEQ ID NO: 367) | Exon 1 |
| Wheat Ms26 CR12 | GCCGAGCAGCACGTCCA TGTAGG-Complementary (SEQ ID NO: 182) | 456 | 478 | Positions relative to ATG in SEQ ID NO: 41 | AGG | GCCGAGC AGCACGT CCATGT (SEQ ID NO: 368) | Exon 2 |
| Wheat Ms26 CR13 | GGAGGTGTACAGGTCCT ACATGG-Sense (SEQ ID NO: 183) | 442 | 464 | Positions relative to ATG in SEQ ID NO: 41 | TGG | GGAGGTG TACAGGT CCTACA (SEQ ID NO: 369) | Exon 2 |
| Wheat Ms26 CR14 | GCGAGCTCTGGAGGAA GCAGAGG-Sense (SEQ ID NO: 184) | 501 | 523 | Positions relative to ATG in SEQ ID NO: 41 | AGG | GCGAGCT CTGGAGG AAGCAG (SEQ ID NO: 370) | Exon 2 |
| Wheat Ms26 CR15 | GCCTGCGCGAAGCTGTT CTCCGG-Complementary (SEQ ID NO: 185) | 821 | 843 | Positions relative to ATG in SEQ ID NO: 41 | CGG | GCCTGCG CGAAGCT GTTCTC (SEQ ID NO: 371) | Exon 3 |
| Maize Ms26 CR1 | GCGATGGCGTCGCCGGC GTGAGG-Complementary (SEQ ID NO: 186) | 15 | 37 | Positions relative to ATG in SEQ ID NO: 53 | AGG | GCGATGG CGTCGCC GGCGTG (SEQ ID NO: 372) | Exon 1 |
| Maize Ms26 CR2 | GGAGGAAGCTCACCTCA CGCCGG-Sense (SEQ ID NO: 187) | 3 | 25 | Positions relative to ATG in SEQ ID NO: 53 | CGG | GGAGGAA GCTCACCT CACGC (SEQ ID NO: 373) | Exon 1 |
| Maize Ms26 CR3 | GCTAGTGGGAAGAATG GCGATGG-Complementary (SEQ ID NO: 188) | 31 | 53 | Positions relative to ATG in SEQ ID NO: 53 | TGG | GCTAGTG GGAAGAA TGGCGA (SEQ ID NO: 374) | Exon 1 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
|---|---|---|---|---|---|---|---|
| Maize Ms26 CR4 | GGCCCTGCTAGTGGGAA GAATGG- Complementary (SEQ ID NO: 189) | 37 | 59 | Positions relative to ATG in SEQ ID NO: 53 | TGG | GGCCCTG CTAGTGG GAAGAA (SEQ ID NO: 375) | Exon 1 |
| Maize Ms26 CR5 | GGTTGTCCTCTCATGGAT CCTGG-Sense (SEQ ID NO: 190) | 84 | 106 | Positions relative to ATG in SEQ ID NO: 53 | TGG | GGTTGTC CTCTCATG GATCC (SEQ ID NO: 376) | Exon 1 |
| Maize Ms26 CR6 | GCTTCCTCAGGCTCCACC TCTGG-Complementary (SEQ ID NO: 191) | 108 | 130 | Positions relative to ATG in SEQ ID NO: 53 | TGG | GCTTCCTC AGGCTCC ACCTC (SEQ ID NO: 377) | Exon 1 |
| Maize Ms26 CR7 | GCCAGTCATCGGCGCAA CGGTGG-Sense (SEQ ID NO: 192) | 150 | 172 | Positions relative to ATG in SEQ ID NO: 53 | TGG | GCCAGTC ATCGGCG CAACGG (SEQ ID NO: 378) | Exon 1 |
| Maize Ms26 CR8 | GCGCAACGGTGGAGCA GCTGAGG-Sense (SEQ ID NO: 193) | 161 | 183 | Positions relative to ATG in SEQ ID NO: 53 | AGG | GCGCAAC GGTGGAG CAGCTG (SEQ ID NO: 379) | Exon 1 |
| Maize Ms26 CR9 | GGATGCACGACTGGCTT GTCGGG-Sense (SEQ ID NO: 194) | 194 | 216 | Positions relative to ATG in SEQ ID NO: 53 | GGG | GGATGCA CGACTGG CTTGTC (SEQ ID NO: 380) | Exon 1 |
| Maize Ms26 CR10 | GGCTTGTCGGGTACCTG TCACGG-Sense (SEQ ID NO: 195) | 206 | 228 | Positions relative to ATG in SEQ ID NO: 53 | CGG | GGCTTGT CGGGTAC CTGTCA (SEQ ID NO: 381) | Exon 1 |
| Maize Ms26 CR11 | GGAAGTGAACGGCATGT CGACGG- Complementary (SEQ ID NO: 196) | 242 | 264 | Positions relative to ATG in SEQ ID NO: 53 | CGG | GGAAGTG AACGGCA TGTCGA (SEQ ID NO: 382) | Exon 1 |
| Maize Ms26 CR12 | GGACATGCTCGACATTC ACCGGG- Complementary (SEQ ID NO: 197) | 282 | 304 | Positions relative to ATG in SEQ ID NO: 53 | GGG | GGACATG CTCGACAT TCACC (SEQ ID NO: 383) | Exon 1 |
| Maize Ms26 CR13 | GACGGCATCTTCAACGC CGACGG-Sense (SEQ ID NO: 198) | 455 | 477 | Positions relative to ATG in SEQ ID NO: 53 | CGG | GACGGCA TCTTCAAC GCCGA (SEQ ID NO: 384) | Exon 2 |
| Maize Ms26 CR14 | GCGAGCTGTGGAGGAA GCAGAGG-Sense (SEQ ID NO: 199) | 477 | 499 | Positions relative to ATG in SEQ ID NO: 53 | AGG | GCGAGCT GTGGAGG AAGCAG (SEQ ID NO: 385) | Exon 2 |
| Maize Ms26 CR15 | GTGGAGGAAGCAGAGG AAGACGG-Sense (SEQ ID NO: 200) | 484 | 506 | Positions relative to ATG in SEQ ID NO: 53 | CGG | GTGGAGG AAGCAGA GGAAGA (SEQ ID NO: 386) | Exon 2 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
|---|---|---|---|---|---|---|---|
| Maize Ms26 CR16 | GTACTCCATCCGCCCCAT CGAGTAGGG- Complementary (SEQ ID NO: 201) | 1724 | 1747 | Positions relative to ATG in SEQ ID NO: 53 | GGG | GTACTCCA TCCGCCCC ATCGAGTA (SEQ ID NO: 387) | EXON 4 |
| Maize Ms26 CR17 | GCACGTACGTCACCATC CCGCCGG- Complementary (SEQ ID NO: 202) | 1698 | 1721 | Positions relative to ATG in SEQ ID NO: 53 | CGG | GCACGTAC GTCACCAT CCCGC (SEQ ID NO: 388) | EXON 4 |
| Maize Ms26 CR18 | GACGTACGTGCCCTACT CGATGGG- Sense (SEQ ID NO: 203) | 1711 | 1731 | Positions relative to ATG in SEQ ID NO: 53 | GGG | GACGTACG TGCCCTACT CGAT (SEQ ID NO: 389) | EXON 4 |
| Rice Ms26 CR1 | GTGGATTCCTGCTACTG GGAAGAAT- Complementary (SEQ ID NO: 204) | 45 | 69 | Positions relative to ATG in SEQ ID NO: 57 | GAAGAAT | GTGGATT CCTGCTAC TGG (SEQ ID NO: 390) | Exon 1 |
| Rice Ms26 CR2 | GGCCTTGCATGCTTGGC TCAGAAT- Complementary (SEQ ID NO: 205) | 599 | 622 | Positions relative to ATG in SEQ ID NO: 57 | TCAGAAT | GGCCTTG CATGCTTG GC (SEQ ID NO: 391) | Exon 1 |
| Rice Ms26 CR3 | GTCCTGAAGACCAACTT CACCAATTACCCCAA- Sense (SEQ ID NO: 206) | 307 | 388 | Positions relative to ATG in SEQ ID NO: 57 | TACCCCA A | GTCCTGA AGACCAA CTTCACCA AT (SEQ ID NO: 392) | Exon 1 |
| Rice Ms26 CR4 | GGAAGACGGCGAGCTTC GAGTTTGCCTCCAA- Sense (SEQ ID NO: 207) | 510 | 540 | Positions relative to ATG in SEQ ID NO: 57 | GCCTCCA A | GGAAGAC GGCGAGC TTCGAGTT T (SEQ ID NO: 393) | Exon 2 |
| Rice Ms26 CR5 | GCCTCTACCCGGCGGTG CCGCAGGACCCCAA- Sense (SEQ ID NO: 208) | 1521 | 1551 | Positions relative to ATG in SEQ ID NO: 57 | GACCCCA A | GCCTCTAC CCGGCGG TGCCGCA G (SEQ ID NO: 394) | Exon 4 |
| Rice Ms26 CR6 | GACATCATTCTTCCCAGT AGCAGGAATCCAC- Sense (SEQ ID NO: 209) | 39 | 69 | Positions relative to ATG in SEQ ID NO: 57 | AATCCAC | GACATCA TTCTTCCC AGTAGCA GG (SEQ ID NO: 395) | Exon 1 |
| Rice Ms26 CR7 | GTTGTCCTCTCATGGATC TTGGTCCAC-Sense (SEQ ID NO: 210) | 91 | 117 | Positions relative to ATG in SEQ ID NO: 57 | GGTCCAC | GTTGTCCT CTCATGG ATCTT (SEQ ID NO: 396) | Exon 1 |
| Rice Ms26 CR8 | GCGCGACAGTGGAGCA ACTGAAGAACTACCAC- Sense (SEQ ID NO: 211) | 167 | 198 | Positions relative to ATG in SEQ ID NO: 57 | CTACCAC | GCGCGAC AGTGGAG CAACTGA AGAA (SEQ ID NO: 397) | Exon 1 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
|---|---|---|---|---|---|---|---|
| Rice Ms26 CR9 | GGCGGGATGGTGACGT ACGTGCCCTACTCCAT- Sense (SEQ ID NO: 212) | 1601 | 1632 | Positions relative to ATG in SEQ ID NO: 57 | ACTCCAT | GGCGGGA TGGTGAC GTACGTG CCCT (SEQ ID NO: 398) | Exon 4 |
| Rice Ms26 CR10 | GCCTACCTCCAGATGAA GATGGCGCTCGCCAT- Sense (SEQ ID NO: 213) | 1784 | 1815 | Positions relative to ATG in SEQ ID NO: 57 | TCGCCAT | GCCTACCT CCAGATG AAGATGG CGC (SEQ ID NO: 399) | Exon 4 |
| Rice Ms26 CR11 | GACCACCCCGTCAAGTA CCGGATGATGACCAT- Sense (SEQ ID NO: 214) | 1849 | 1882 | Positions relative to ATG in SEQ ID NO: 57 | TGACCAT | GACCACC CCGTCAA GTACCGG ATGA (SEQ ID NO: 400) | Exon 4 |
| Rice Ms26 CR12 | ACGTACGTGCCCTACTCC AT-Sense (SEQ ID NO: 215) | 1613 | 1632 | Positions relative to ATG in SEQ ID NO: 57 | | ACGTACGT GCCCTACT CCAT (SEQ ID NO: 401) | Exon 2 |
| Wheat Ms45 CR1 | GGGCCGCGATGAAGAG GTGCGGG Complementary (SEQ ID NO: 216) | 60 | 82 | Positions relative to ATG in SEQ ID NO: 61 | GGG | GGGCCGC GATGAAG AGGTGC (SEQ ID NO: 402) | Exon 1 |
| Wheat Ms45 CR2 | GCGCCAGGGCCGCGATG AAGAGG- Complementary (SEQ ID NO: 217) | 66 | 88 | Positions relative to ATG in SEQ ID NO: 61 | AGG | GCGCCAG GGCCGCG ATGAAG (SEQ ID NO: 403) | Exon 1 |
| Wheat Ms45 CR3 | GTACCCGCACCTCTTCAT CGCGG-Sense (SEQ ID NO: 218) | 57 | 79 | Positions relative to ATG in SEQ ID NO: 61 | CGG | GTACCCG CACCTCTT CATCG (SEQ ID NO: 404) | Exon 1 |
| Wheat Ms45 CR4 | GCACCTCTTCATCGCGGC CCTGG-Sense (SEQ ID NO: 219) | 63 | 85 | Positions relative to ATG in SEQ ID NO: 61 | TGG | GCACCTCT TCATCGC GGCCC (SEQ ID NO: 405) | Exon 1 |
| Wheat Ms45 CR5 | GCCAGCGGGCCGAGGT GGAAGGG- Complementary (SEQ ID NO: 220) | 109 | 131 | Positions relative to ATG in SEQ ID NO: 61 | GGG | GCCAGCG GGCCGAG GTGGAA (SEQ ID NO: 406) | Exon 1 |
| Wheat Ms45 CR6 | GGCGCCAGCTCGTGCTT CACCGG- Complementary (SEQ ID NO: 221) | 148 | 170 | Positions relative to ATG in SEQ ID NO: 61 | CGG | GGCGCCA GCTCGTG CTTCAC (SEQ ID NO: 407) | Exon 1 |
| Wheat Ms45 CR7 | GGTCATGCAGCGCTGGC CGAGGG-Sense (SEQ ID NO: 222) | 180 | 202 | Positions relative to ATG in SEQ ID NO: 61 | GGG | GGTCATG CAGCGCT GGCCGA (SEQ ID NO: 408) | Exon 1 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
|---|---|---|---|---|---|---|---|
| Wheat Ms45 CR8 | GCAGCGCTGGCCGAGG GACAACGG-Sense (SEQ ID NO: 223) | 186 | 209 | Positions relative to ATG in SEQ ID NO: 61 | CGG | GCAGCGC TGGCCGA GGGACAA (SEQ ID NO: 409) | Exon 1 |
| Wheat Ms45 CR9 | GGGACAACGGCAGCCG CCTCAGG-Sense (SEQ ID NO: 224) | 200 | 222 | Positions relative to ATG in SEQ ID NO: 61 | AGG | GGGACAA CGGCAGC CGCCTC (SEQ ID NO: 410) | Exon 1 |
| Wheat Ms45 CR10 | GCAGCCGCCTCAGGCTC GGCAGG-Sense (SEQ ID NO: 225) | 209 | 231 | Positions relative to ATG in SEQ ID NO: 61 | AGG | GCAGCCG CCTCAGG CTCGGC (SEQ ID NO: 411) | Exon 1 |
| Wheat Ms45 CR11 | GAGTTCGTCAACGAGGT GTTCGG-Sense (SEQ ID NO: 226) | 235 | 257 | Positions relative to ATG in SEQ ID NO: 61 | CGG | GAGTTCG TCAACGA GGTGTT (SEQ ID NO: 412) | Exon 1 |
| Wheat Ms45 CR12 | GACGCGGCCGTCGGCGA GCCCGG- Complementary (SEQ ID NO: 227) | 302 | 324 | Positions relative to ATG in SEQ ID NO: 61 | CGG | GACGCGG CCGTCGG CGAGCC (SEQ ID NO: 413) | Exon 1 |
| Wheat Ms45 CR13 | GGCCGCGTCGTGCGGTG GATGGG-Sense (SEQ ID NO: 228) | 316 | 338 | Positions relative to ATG in SEQ ID NO: 61 | GGG | GGCCGCG TCGTGCG GTGGAT (SEQ ID NO: 414) | Exon 1 |
| Wheat Ms45 CR14 | GCCGCGTCGTGCGGTGG ATGGGG-Sense (SEQ ID NO: 229) | 317 | 339 | Positions relative to ATG in SEQ ID NO: 61 | GGG | GCCGCGT CGTGCGG TGGATG (SEQ ID NO: 415) | Exon 1 |
| Wheat Ms45 CR15 | GACGGCGAACGTCTCCC ACCCGG- Complementary (SEQ ID NO: 230) | 347 | 369 | Positions relative to ATG in SEQ ID NO: 61 | CGG | GACGGCG AACGTCTC CCACC (SEQ ID NO: 416) | Exon 1 |
| Wheat Ms45 CR16 | GAAAGTTTGTGCTAACG GAGTGG-Sense (SEQ ID NO: 231) | 466 | 488 | Positions relative to ATG in SEQ ID NO: 61 | TGG | GAAAGTT TGTGCTA ACGGAG (SEQ ID NO: 417) | Exon 2 |
| Maize Ms45 CR1 | GGAACCTGCAGTGGCGG CGAGGG-Sense (SEQ ID NO: 232) | 11 | 33 | Positions relative to ATG in SEQ ID NO: 73 | GGG | GGAACCT GCAGTGG CGGCGA (SEQ ID NO: 418) | Exon 1 |
| Maize Ms45 CR2 | GGGCCGCGAAGAAGAG GTGAGGG- Complementary (SEQ ID NO: 233) | 54 | 76 | Positions relative to ATG in SEQ ID NO: 73 | GGG | GGGCCGC GAAGAAG AGGTGA (SEQ ID NO: 419) | Exon 1 |
| Maize Ms45 CR3 | GCGCCAGGGCCGCGAA GAAGAGG- Complementary (SEQ ID NO: 234) | 60 | 82 | Positions relative to ATG in SEQ ID NO: 73 | AGG | GCGCCAG GGCCGCG AAGAAG (SEQ ID NO: 420) | Exon 1 ID |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
|---|---|---|---|---|---|---|---|
| Maize Ms45 CR4 | GTACCCTCACCTCTTCTT CGCGG-Sense (SEQ ID NO: 235) | 51 | 73 | Positions relative to ATG in SEQ ID NO: 73 | CGG | GTACCCTC ACCTCTTC TTCG (SEQ ID NO: 421) | Exon 1 |
| Maize Ms45 CR5 | GACTAGGAGGGCCAGC GCCAGGG-Complementary (SEQ ID NO: 236) | 74 | 96 | Positions relative to ATG in SEQ ID NO: 73 | GGG | GACTAGG AGGGCCA GCGCCA (SEQ ID NO: 422) | Exon 1 |
| Maize Ms45 CR6 | GAACGGGTCCGCGACTA GGAGGG-Complementary (SEQ ID NO: 237) | 86 | 108 | Positions relative to ATG in SEQ ID NO: 73 | GGG | GAACGGG TCCGCGA CTAGGA (SEQ ID NO: 423 | Exon 1 |
| Maize Ms45 CR7 | GGCCGAACGGGTCCGCG ACTAGG-Complementary (SEQ ID NO: 238) | 90 | 112 | Positions relative to ATG in SEQ ID NO: 73 | AGG | GGCCGAA CGGGTCC GCGACT (SEQ ID NO: 424) | Exon 1 |
| Maize Ms45 CR8 | GGCGCTGGCCCTCCTAG TCGCGG-Sense (SEQ ID NO: 239) | 78 | 100 | Positions relative to ATG in SEQ ID NO: 73 | CGG | GGCGCTG GCCCTCCT AGTCG (SEQ ID NO: 425) | Exon 1 |
| Maize Ms45 CR9 | GCCAGCGGACTGAGGCC GAACGG-Complementary (SEQ ID NO: 240) | 103 | 125 | Positions relative to ATG in SEQ ID NO: 73 | CGG | GCCAGCG GACTGAG GCCGAA (SEQ ID NO: 426) | Exon 1 |
| Maize Ms45 CR10 | GGCGCGAGCTCGTGCTT CACCGG-Complementary (SEQ ID NO: 241) | 142 | 164 | Positions relative to ATG in SEQ ID NO: 73 | CGG | GGCGCGA GCTCGTG CTTCAC (SEQ ID NO: 427) | Exon 1 |
| Maize Ms45 CR11 | GGCCGAGGTCGACTACC GGCCGG-Sense (SEQ ID NO: 242) | 123 | 145 | Positions relative to ATG in SEQ ID NO: 73 | CGG | GGCCGAG GTCGACT ACCGGC (SEQ ID NO: 428) | Exon 1 |
| Maize Ms45 CR12 | GCACGAGCTCGCGCCGT ACGGGG-Sense (SEQ ID NO: 243) | 150 | 172 | Positions relative to ATG in SEQ ID NO: 73 | GGG | GCACGAG CTCGCGC CGTACG (SEQ ID NO: 429) | Exon 1 |
| Maize Ms45 CR13 | GCGCCGTACGGGGAGG TCATGGG-Sense (SEQ ID NO: 244) | 160 | 182 | Positions relative to ATG in SEQ ID NO: 73 | GGG | GCGCCGT ACGGGGA GGTCAT (SEQ ID NO: 430) | Exon 1 |
| Maize Ms45 CR14 | GAGCCGGCTGGCATTGT CTCTGG-Complementary (SEQ ID NO: 245) | 191 | 213 | Positions relative to ATG in SEQ ID NO: 73 | TGG | GAGCCGG CTGGCATT GTCTC (SEQ ID NO: 431) | Exon 1 |
| Maize Ms45 CR15 | GGCCCAGAGACAATGCC AGCCGG-Sense (SEQ ID NO: 246) | 188 | 210 | Positions relative to ATG in SEQ ID NO: 73 | CGG | GGCCCAG AGACAAT GCCAGC (SEQ ID NO: 432) | Exon 1 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
|---|---|---|---|---|---|---|---|
| Maize Ms45 CR16 | GCTGGCCGAGGTCGACT ACCGG-Sense (SEQ ID NO: 247) | 120 | 141 | Positions relative to ATG in SEQ ID NO: 73 | CGG | GCTGGCCG AGGTCGAC TAC (SEQ ID NO: 433) | Exon 1 |
| Maize Ms45 CR17 | GGCCGAGGTCGACTACC GGCCGG-Sense (SEQ ID NO: 248) | 123 | 142 | Positions relative to ATG in SEQ ID NO: 73 | CGG | GGCCGAGG TCGACTAC CGGC (SEQ ID NO: 434) | Exon 1 |
| Maize Ms45 CR18 | GGCGCGAGCTCGTGCTT CACCGG-Complementary (SEQ ID NO: 249) | 145 | 164 | Positions relative to ATG in SEQ ID NO: 73 | CGG | GGCGCGAG CTCGTGCTT CAC (SEQ ID NO: 435) | Exon 1 |
| Rice Ms45 CR1 | GCGTACTACGGGCTCAT GTCCGTCGGTCCGAA-Sense (SEQ ID NO: 250) | 608 | 639 | Positions relative to ATG in SEQ ID NO: 77 | GGTCCGA A | GCGTACT ACGGGCT CATGTCC GTC (SEQ ID NO: 436) | Exon 2 |
| Rice Ms45 CR2 | GGGAGGCTGCTCAGATA TGACCCAGAAACCAAA-Sense (SEQ ID NO: 251) | 894 | 926 | Positions relative to ATG in SEQ ID NO: 77 | AAACCAA A | GGGAGGC TGCTCAG ATATGAC CCAG (SEQ ID NO: 437) | Exon 3 |
| Rice Ms45 CR3 | GTCGTGCTGAGCGGGCT GGTCTTCCCGAA-Sense (SEQ ID NO: 252) | 936 | 964 | Positions relative to ATG in SEQ ID NO: 77 | TTCCCGA A | GTCGTGC TGAGCGG GCTGGTC (SEQ ID NO: 438) | Exon 3 |
| Rice Ms45 CR4 | GCTGGCCCTGCTCCTCAC CGACCCGTTCCAC-Sense (SEQ ID NO: 253) | 90 | 120 | Positions relative to ATG in SEQ ID NO: 77 | GTTCCAC | GCTGGCC CTGCTCCT CACCGAC CC (SEQ ID NO: 439) | Exon 1 |
| Rice Ms45 CR5 | GTCGGAGAGGTGTTCGG GCCGGAGTCCAT-Sense (SEQ ID NO: 254) | 244 | 272 | Positions relative to ATG in SEQ ID NO: 77 | AGTCCAT | GTCGGAG AGGTGTT CGGGCCG G (SEQ ID NO: 440) | Exon 1 |
| Rice Ms45 CR6 | GTGCCTCACCGGCCGGT AGTCCAC-Complementary (SEQ ID NO: 255) | 139 | 162 | Positions relative to ATG in SEQ ID NO: 77 | AGTCCAC | GTGCCTC ACCGGCC GGT (SEQ ID NO: 441) | Exon 1 |
| Rice Ms45 CR7 | GCCGGCTGCCGTTGTCC CGCGGCCAC-Complementary (SEQ ID NO: 256) | 195 | 220 | Positions relative to ATG in SEQ ID NO: 77 | CGGCCAC | GCCGGCT GCCGTTG TCCCG (SEQ ID NO: 442) | Exon 1 |
| Rice Ms45 CR8 | GTCTCCCACCCGGCGTCC TCCCCCAT-Complementary (SEQ ID NO: 257) | 337 | 362 | Positions relative to ATG in SEQ ID NO: 77 | CCCCCAT | GTCTCCCA CCCGGCG TCCT (SEQ ID NO: 443) | exon 1 |

TABLE 2-continued

Exemplary Guide RNAs and Target Sequence Description

| Target Sequence Designation | Target Sequence (5'-3') and target strand | Start Position (bp) | End Position (bp) | Start and End Positions of Target Sequence | PAM Sequence | DNA version of Guide RNA | Target Site |
|---|---|---|---|---|---|---|---|
| Rice Ms45 CR9 | GCTCATGACGGCGAACG TCTCCCAC- Complementary (SEQ ID NO: 258) | 354 | 378 | Positions relative to ATG in SEQ ID NO: 77 | CTCCCAC | GCTCATG ACGGCGA ACGT (SEQ ID NO: 444) | Exon 1 |
| Rice Ms45 CR10 | GCTTCTTCGTCGTCGACT CCACCCCAT- Complementary (SEQ ID NO: 259) | 501 | 527 | Positions relative to ATG in SEQ ID NO: 77 | ACCCCAT | GCTTCTTC GTCGTCG ACTCC (SEQ ID NO: 445) | Exon 2 |
| Rice Ms45 CR11 | GACTTCTCTCGCGAGAG AGGTCGCCAC- Complementary (SEQ ID NO: 260) | 647 | 673 | Positions relative to ATG in SEQ ID NO: 77 | TCGCCAC | GACTTCTC TCGCGAG AGAGG (SEQ ID NO: 446) | Exon 2 |
| Rice Ms45 CR12 | GGTCGTCAGAAATCTGC ACGCCAT- Complementary (SEQ ID NO: 261) | 964 | 987 | Positions relative to ATG in SEQ ID NO: 77 | ACGCCAT | GGTCGTC AGAAATC TGC (SEQ ID NO: 447) | Exon 3 |
| Rice Ms45 CR13 | GAACCCCGGCAGGTCGG CGAACACCTCCAC- Complementary (SEQ ID NO: 262) | 1157 | 1186 | Positions relative to ATG in SEQ ID NO: 77 | CCTCCAC | GAACCCC GGCAGGT CGGCGAA CA (SEQ ID NO: 448) | Exon 4 |
| Rice Ms45 CR14 | GCTTGAAGTAGAGCGTT CGCAGCCAC- Complementary (SEQ ID NO: 263) | 1288 | 1313 | Positions relative to ATG in SEQ ID NO: 77 | CAGCCAC | GCTTGAA GTAGAGC GTTCG (SEQ ID NO: 449) | Exon 4 |
| Rice Ms45 CR15 | GGTGTGCATCCGCATGC TGACCAT- Complementary (SEQ ID NO: 264) | 1343 | 1366 | Positions relative to ATG in SEQ ID NO: 77 | TGACCAT | GGTGTGC ATCCGCAT GC (SEQ ID NO: 450) | Exon 4 |

Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by a Cas endonuclease. Assays to measure the double-strand break of a target site by an endonuclease are known in the art and generally measure the overall activity and specificity of the agent on DNA substrates containing recognition sites.

As used herein, a "genomic region" is a segment of a chromosome in the genome of a plant cell. The genomic region may be present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the plant genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology. Homology-directed repair (HDR) is a mechanism in cells to repair double-stranded and single stranded DNA breaks. Homology-directed repair includes homologous recombination (HR) and single-strand annealing (SSA) (Lieber. 2010 Annu. Rev. Biochem 79:181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. PNAS (0027-8424), 111 (10), p. E924-E932.

Alteration of the genome of a plant cell, for example, through homologous recombination (HR), is a powerful tool for genetic engineering. Despite the low frequency of homologous recombination in higher plants, there are a few examples of successful homologous recombination of plant endogenous genes. The parameters for homologous recombination in plants have primarily been investigated by rescuing introduced truncated selectable marker genes. In these experiments, the homologous DNA fragments were typically between 0.3 kb to 2 kb. Observed frequencies for homologous recombination were on the order of $10^{-4}$ to $10^{-5}$. See, for example, Halfter et al., (1992) Mol Gen Genet 231:186-93; Offringa et al., (1990) EMBO J 9:3077-84; Offringa et al., (1993) Proc. Natl. Acad. Sci. USA 90:7346-50; Paszkowski et al., (1988) EMBO J 7:4021-6; Hourda and Paszkowski, (1994) Mol Gen Genet 243:106-11; and Risseeuw et al., (1995) Plant J 7:109-19.

Once a double-strand break is induced in the DNA, the cell's DNA repair mechanism is activated to repair the break. Error-prone DNA repair mechanisms can produce mutations at double-strand break sites. The most common repair mechanism to bring the broken ends together is the nonhomologous end-joining (NHEJ) pathway (Bleuyard et al., (2006) DNA Repair 5:1-12). The structural integrity of chromosomes is typically preserved by the repair, but deletions, insertions, or other rearrangements are possible (Siebert and Puchta, (2002) Plant Cell 14:1121-31; Pacher et al., (2007) Genetics 175:21-9).

Alternatively, the double-strand break can be repaired by homologous recombination between homologous DNA sequences.

Genome Editing Using the Guide RNA/Cas Endonuclease System

Further provided is a method for modifying a target site at or near a Ms9, Ms22, Ms26, or Ms45 gene in the genome of a plant cell, the method comprising introducing a guide RNA and a donor DNA into a plant cell having a Cas endonuclease, wherein said guide RNA and Cas endonuclease are capable of forming a complex that enables the Cas endonuclease to introduce a double strand break at said target site, wherein said donor DNA comprises a polynucleotide of interest that when inserted confers male-sterility to a plant obtained from the modified plant cell.

As described herein, the guide RNA/Cas endonuclease system can be used in combination with a co-delivered polynucleotide modification template to allow for editing of a genomic nucleotide sequence of interest, MS9, MS22, MS26, or MS45, to confer male-sterility to a plant. Also, as described herein, for each embodiment that uses a guide RNA/Cas endonuclease system, a similar guide polynucleotide/Cas endonuclease system can be deployed where the guide polynucleotide does not solely comprise ribonucleic acids but wherein the guide polynucleotide comprises a combination of RNA-DNA molecules or solely comprise DNA molecules.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

In one embodiment provided herein, the method comprises contacting a plant cell with the donor DNA and the endonuclease. Once a double-strand break is introduced in the target site by the endonuclease, the first and second regions of homology of the donor DNA can undergo homologous recombination with their corresponding genomic regions of homology resulting in exchange of DNA between the donor and the genome. As such, the provided methods result in the integration of the polynucleotide of interest of the donor DNA into the double-strand break in the target site in the plant genome so that the endogenous male fertility gene of MS9, MS22, MS26, or MS45 is disrupted, thereby altering the original target site and producing an altered genomic target site that confers male sterility to the plant.

The donor DNA may be introduced by any means known in the art. For example, a plant having a target site is provided. The donor DNA may be provided by any transformation method known in the art including, for example, *Agrobacterium*-mediated transformation or biolistic particle bombardment. The donor DNA may be present transiently in the cell or it could be introduced via a viral replicon. In the presence of the Cas endonuclease and the target site, the donor DNA is inserted into the transformed plant's genome to disrupt an endogenous male fertility gene of MS9, MS22, MS26, or MS45.

In one embodiment, the disclosure describes a method for editing a nucleotide sequence in the genome of a cell, the method comprising providing a guide RNA, a polynucleotide modification template, and at least one Cas endonuclease to a cell, wherein the Cas endonuclease is capable of introducing a double-strand break at a target sequence in the genome of said cell to confer male-sterility, wherein said polynucleotide modification template includes at least one nucleotide modification of said nucleotide sequence. The nucleotide to be edited can be located within or outside a target site of one or more MS9, MS22, MS26 or MS45 genes recognized and cleaved by a Cas endonuclease. In one embodiment, the at least one nucleotide modification is not a modification at a target site recognized and cleaved by a Cas endonuclease. In another embodiment, there are at least 1, 2, 3, 4, 5, 6, 7, 8, 9, 10, 11, 12, 13, 14, 15, 16, 17, 18, 19, 20, 21, 22, 23, 24, 25, 26, 27, 30, 40, 50, 100, 200, 300, 400, 500, 600, 700, 900 or 1000 nucleotides between the at least one nucleotide to be edited and the genomic target site.

In another embodiment of genome editing, editing of an endogenous MS9, MS22, MS26, and MS45 gene in a plant cell or plant is disclosed herein. In some embodiments, the polynucleotide modification template (male fertility gene polynucleotide modification template) includes a partial fragment of the MS9, MS22, MS26 or MS45 gene (and therefore does not encode a fully functional MS9, MS22, MS26 or MS45 polypeptide by itself).

In one embodiment of the disclosure, a wheat Ms9, Ms22, Ms26, or Ms45 mutant plant is produced by the method described herein, said method comprising: a) providing a guide RNA, a polynucleotide modification template and at least one Cas endonuclease to a plant cell, wherein the Cas endonuclease introduces a double strand break at a target site within a wheat Ms9, Ms22, Ms26, or Ms45 (male sterility 45) genomic sequence in the plant genome, wherein said polynucleotide modification template comprises at least one nucleotide modification of the Ms9, Ms22, Ms26, or Ms45 genomic sequence; b) obtaining a plant from the plant cell of (a); c) evaluating the plant of (b) for the presence of said at least one nucleotide modification and d) selecting a progeny plant exhibiting male sterility from the modification of the endogenous Ms9, Ms22, Ms26, or Ms45 gene. The nucleotide sequence to be edited may be a sequence that is endogenous to the cell that is being edited.

Regulatory Sequence Modifications Using the Guide Polynucleotide/Cas Endonuclease System In one example, the nucleotide sequence to be modified can be a regulatory sequence such as a promoter, for example, for an endogenous MS9, MS22, MS26, and MS45 gene in a plant cell or plant. In some examples, the promoter may be modified to include or remove an element in the promoter. In one embodiment, the guide polynucleotide/Cas endonuclease system can be used to allow for the deletion of a promoter or promoter element, wherein the promoter deletion (or promoter element deletion) results in any one of the following or any one combination of the following: a permanently inactivated gene locus, a decreased promoter activity, a decreased promoter tissue specificity, a modification of the timing or developmental progress of gene expression, a mutation of DNA binding elements and/or an addition of DNA binding elements. Promoter elements to be deleted can be, but are not limited to, promoter core elements, such as, but not limited to, a CAAT box, a CCAAT box, a Pribnow box, TATA box, and/or translational regulation sequences, promoter enhancer elements. The promoter or promoter fragment to be deleted may be endogenous to the cell that is being edited, for example, the promoter of an endogenous MS9, MS22, MS26, and MS45 fertility gene.

Additional Regulatory Sequence Modifications Using the Guide Polynucleotide/Cas Endonuclease System The guide polynucleotide/Cas endonuclease system may be used to modify or replace a regulatory sequence in the genome of a cell. A regulatory sequence is a segment of a nucleic acid molecule which is capable of increasing or decreasing the expression of specific genes within an organism and/or is capable of altering tissue specific expression of genes within an organism. Examples of regulatory sequences include, but are not limited to, 3' UTR (untranslated region) region, 5' UTR region, transcription activators, transcriptional enhancers transcriptions repressors, translational repressors, splicing factors, miRNAs, siRNA, artificial miRNAs, promoter elements, polyadenylation signals, and polyubiquitination sites. In one example, the editing (modification) or replacement of a regulatory element results in altered protein translation, RNA cleavage, RNA splicing, transcriptional termination or post translational modification that confers male-sterility to a plant. In one embodiment, regulatory elements can be identified within a promoter and these regulatory elements can be edited or modified do to optimize these regulatory elements for down regulation of the promoter to create a male sterile plant.

In one embodiment, the genomic sequence of interest to be modified is an intron or UTR site, wherein the modification consists of inserting at least one microRNA into said intron or UTR site, wherein expression of the gene comprising the intron or UTR site also results in expression of said microRNA, which in turn can silence any gene targeted by the microRNA without disrupting the gene expression of the native/transgene comprising said intron.

Modifications of Splicing Sites and/or Introducing Alternate Splicing Sites Using the Guide Polynucleotide/Cas Endonuclease System The guide polynucleotide/Cas endonuclease system can be used in combination with a co-delivered polynucleotide modification template to edit an endogenous MS9, MS22, MS26, or MS45 gene to introduce a canonical splice site at a described junction or any variant of a splicing site that disrupts the splicing pattern of pre-mRNA molecules so that the plant with the introduced genetic modification is male-sterile.

Modifications of Nucleotide Sequences Encoding a Protein of Interest Using the Guide Polynucleotide/Cas Endonuclease System In one embodiment, the guide polynucleotide/Cas endonuclease system can be used to modify or replace a coding sequence in the fertility gene locus of MS9, MS22, MS26 or MS45 in the genome of a plant cell, wherein the modification or replacement results in conferring male-sterility to the plant. In one embodiment, the protein knockout is due to the introduction of a stop codon into the coding sequence of interest. In one embodiment, the protein knockout is due to the deletion of a start codon into the coding sequence of interest.

Gene Silencing by Expressing an Inverted Repeat or Antisense Using the Guide Polynucleotide/Cas Endonuclease System In one embodiment, the guide polynucleotide/Cas endonuclease system can be used in combination with a co-delivered polynucleotide sequence to insert an inverted gene fragment into a gene of interest in the genome of an organism, wherein the insertion of the inverted gene fragment can allow for an in-vivo creation of an inverted repeat (hairpin) and results in the silencing of said endogenous gene of MS9, MS22, MS26 or MS45, for example, a hairpin promoter inverted repeat (pIR) directed to MS9, MS22, MS26 or MS45.

In one embodiment, the insertion of the inverted gene fragment can result in the formation of an in-vivo created inverted repeat (hairpin) in a native (or modified) promoter of a gene and/or in a native 5' end of the native gene. The inverted gene fragment can further comprise an intron which can result in an enhanced silencing of the targeted endogenous MS9, MS22, MS26 or MS45 gene.

In one embodiment, the region of interest can be flanked by two independent guide polynucleotide/CAS endonuclease target sequences. Cutting would be done concurrently. The deletion event would be the repair of the two chromosomal ends without the region of interest. Alternative results would include inversions of the region of interest, mutations at the cut sites and duplication of the region of interest. Furthermore, the introduced genetic modification may also comprise antisense sequences complementary to at least a portion of the messenger RNA (mRNA) for MS9, MS22, MS26 or MS45. Modifications of the antisense sequences may be made as long as the sequences hybridize to and interfere with expression of the corresponding mRNA. In this manner, antisense constructs having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the introduced genetic modification may also be a polynucleotide arranged in the sense orientation to suppress the expression of endogenous MS9, MS22, MS26, or MS45 genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

Protocols for introducing polynucleotides and polypeptides into plants may vary depending on the type of plant or plant cell targeted for transformation, such as monocot or dicot. Suitable methods of introducing polynucleotides and polypeptides into plant cells include but are not limited to *Agrobacterium*-meditated transformation (U.S. Pat. Nos. 5,563,055 and 5,981,840), direct gene transfer (Paszkowski et al., (1984) EMBO J 3:2717-22), and ballistic particle acceleration (U.S. Pat. Nos. 4,945,050; 5,879,918; 5,886,244; 5,932,782; Tomes et al., (1995) "Direct DNA Transfer into Intact Plant Cells via Microprojectile Bombardment" in Plant Cell, Tissue, and Organ Culture: Fundamental Methods, ed. Gamborg & Phillips (Springer-Verlag, Berlin). Wheat transformation may be carried out by any suitable technique known to one skilled in the art, including those described in published patent application no. 20140173781 published on Jun. 19, 2014.

Methods for Identifying at Least One Plant Cell Comprising in its Genome the Introduced Genetic Modification at the Target Site.

Further provided are methods for identifying at least one plant cell, comprising in its genome, the introduced genetic modification at the target site. A variety of methods are available for identifying those plant cells with the introduced genetic modification into the genome at or near to the target site without using a screenable marker phenotype. Such methods can be viewed as directly analyzing a target sequence to detect any change in the target sequence, including but not limited to PCR methods, sequencing methods, nuclease digestion, Southern blots, and any combination thereof. See, for example, U.S. patent application Ser. No. 12/147,834, herein incorporated by reference. The method also comprises recovering a male-sterile plant from the plant cell having the introduced genetic modification in its genome.

The present disclosure further provides expression constructs for expressing in a plant, plant cell, or plant part a guide RNA/Cas system that is capable of binding to and creating a double strand break in a target site of the fertility gene locus of MS9, MS22, MS26 or MS45. In one embodiment, the expression constructs of the disclosure comprise a promoter operably linked to a nucleotide sequence encoding a Cas gene and a promoter operably linked to a guide RNA of the present disclosure. The promoter is capable of driving expression of an operably linked nucleotide sequence in a plant cell.

A promoter is a region of DNA involved in recognition and binding of RNA polymerase and other proteins to initiate transcription. A plant promoter is a promoter capable of initiating transcription in a plant cell, for a review of plant promoters, see, Potenza et al., (2004) *In Vitro Cell Dev Biol* 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell et al., (1985) *Nature* 313:810-2); rice actin (McElroy et al., (1990) *Plant Cell* 2:163-71); ubiquitin (Christensen et al., (1989) *Plant Mol Biol* 12:619-32; Christensen et al., (1992) *Plant Mol Biol* 18:675-89); pEMU (Last et al., (1991) *Theor Appl Genet* 81:581-8); MAS (Velten et al., (1984) *EMBO J* 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142 and 6,177,611. In some examples, an inducible promoter may be used. Pathogen-inducible promoters induced following infection by a pathogen include, but are not limited to those regulating expression of PR proteins, SAR proteins, beta-1, 3-glucanase, chitinase, etc.

Marker Assisted Selection and Breeding of Plants

Use of markers, and/or genetically-linked nucleic acids is an effective method for selecting plant having the desired traits in breeding programs. For example, one advantage of marker-assisted selection over field evaluations is that MAS can be done at any time of year regardless of the growing season. Moreover, environmental effects are irrelevant to marker-assisted selection.

A plant breeder can advantageously use molecular markers to identify individuals containing any of the targeted genome edits by identifying marker alleles that show a statistically significant probability of co-segregation with male sterility, manifested as linkage disequilibrium. This is referred to as marker assisted selection (MAS). Thus, methods for the selection of mutant wheat plants that are homozygous or heterozygous for a mutation in the Ms9, Ms 22, Ms 26, Ms 45 gene, are also provided.

To perform MAS, a nucleic acid corresponding to the marker nucleic acid allele is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, DNA sequencing of a PCR amplification product, or the like. For any of the marker sequences described herein, one of ordinary skill in the art would understand how to obtain the allele at a marker locus in a particular wheat line or variety using known DNA amplification and sequencing techniques. For the purposes described herein, the lines or varieties that were used were publicly available. Hence, DNA could be obtained, and one of ordinary skill in the art could either use the provided primers or develop primers from the provided reference sequence to amplify and obtain the sequence at each marker locus from each line or variety.

After the presence (or absence) of a particular marker allele in the biological sample is verified, the plant is selected and is crossed to a second plant, optionally a wheat plant from an elite line. The progeny plants produced by the cross can be evaluated for that specific marker allele, and only those progeny plants that have the desired marker allele will be chosen.

Through marker assisted selection, a plant breeder can follow the presence of the male sterility trait through controlled crosses to obtain, when desired, a new plant containing a Ms9, Ms 22, Ms 26, Ms 45 gene mutation in either the homozygous or heterozygous state, thus maintaining the Ms9, Ms 22, Ms 26, Ms 45 gene mutations. In addition, marker assisted selection can be used to produce mutant male sterile seed parents that would be used as female, i.e. plants that need pollination by a pollen donor plant, to produce seeds of commercial interest. Alternatively, marker assisted selection could be used to produce F1 hybrids containing a Ms9, Ms 22, Ms 26, Ms 45 gene mutation in the heterozygous state.

Any of the markers provided herein, as well as any marker linked to and associated with any of those markers, can be used for marker assisted selection of the male sterility trait.

Compositions and methods for restoring male fertility to a male-sterile plant are provided. In some examples, the male-sterile plants are homozygous recessive for the fertility gene of Ms9, Ms22, Ms26 or Ms45. In some embodiments, the male-sterile phenotype is caused by the introduction of genetic modification of a target site located in a male fertility gene locus of Ms9, Ms22, Ms26 or Ms45 in a plant cell's genome. In some examples, the wheat genomes (A, B, and D) contain homologous genes that have similar gene structure and function, requiring triple mutants to result in a male-sterile phenotype. Male-sterile plants may be created using the methods and compositions described herein and those known to one skilled in the art. In some embodiments, provided herein are compositions and methods to complement and restore male fertility to wheat plants containing mutations or introduced genetic modifications in MS9, MS22, MS26 or MS45 genes or MS9, MS22, MS26 or MS45 locus.

Male-sterile plants may be restored to male fertility when a functional copy of the Ms9, Ms22, Ms26 or Ms45 fertility gene, from the same or different species, is used to complement the Ms9, Ms22, Ms26 or Ms45 mutation or introduced genetic modification. See, for example, Example 3 which demonstrates that a single copy of a rice ms45 gene can restore fertility and maintain tams45-abd triple homozygous wheat mutants.

When the male-fertility MS9, MS22, MS26 or MS45 polynucleotide, fragment or variant is expressed, the plant is able to successfully produce mature pollen grains because the male-fertility polynucleotide restores the plant to a fertile condition. In some examples, the MS9, MS22, MS26 or MS45 polynucleotide, fragment, or variant thereof is maintained in a hemizygous state in a plant, so that only certain daughter cells will inherit the MS9, MS22, MS26 or MS45 polynucleotide, fragment, or variant in the process of pollen grain formation. Hemizygosity is a genetic condition existing when there is only one copy of a gene (or set of genes) with no allelic counterpart.

In some embodiments, the male-fertility MS9, MS22, MS26 or MS45 polynucleotide, fragment, or variants thereof, is operably linked to a promoter, to express the MS9, MS22, MS26 or MS45 polynucleotide, fragment, or variant and modulate, e.g., restore, the male fertility of a plant. In some examples, the MS9, MS22, MS26 or MS45 polynucleotide, fragment, or variant are expressed from an expression cassette. In some embodiments, the male-fertility MS9, MS22, MS26 or MS45 polynucleotides or expression cassette disclosed herein are maintained in a hemizygous state in a plant.

In particular embodiments, the male-fertility MS9, MS22, MS26 or MS45 polynucleotide, or fragment or variant thereof, is operably linked to a promoter. In certain embodiments, plant promoters can preferentially initiate transcription in certain tissues, such as stamen, anther, filament, and pollen, or developmental growth stages, such as sporogenous tissue, microspores, and microgametophyte. Such plant promoters are referred to as "tissue-preferred," "cell-type-preferred," or "growth-stage preferred." Promoters which initiate transcription only in certain tissue are referred to as "tissue-specific." Likewise, promoters which initiate transcription only at certain growth stages are referred to as "growth-stage-specific." A "cell-type-specific" promoter drives expression only in certain cell types in one or more organs, for example, stamen cells, or individual cell types within the stamen such as anther, filament, or pollen cells.

A "male-fertility promoter" may initiate transcription exclusively or preferentially in a cell or tissue involved in the process of microsporogenesis or microgametogenesis. Male-fertility polynucleotides disclosed herein, and active fragments and variants thereof, can be operably linked to male-tissue-specific or male-tissue-preferred promoters including, for example, stamen-specific or stamen-preferred promoters, anther-specific or anther-preferred promoters, pollen-specific or pollen-preferred promoters, tapetum-specific promoters or tapetum-preferred promoters, and the like. Promoters can be selected based on the desired outcome. For example, the Ms9, Ms22, Ms26, or Ms45 polynucleotides can be operably linked to constitutive, tissue-preferred, growth stage-preferred, or other promoters for expression in plants.

In one embodiment, the promoters may be those which express an operably-linked Ms9, Ms22, Ms26, or Ms45 polynucleotide exclusively or preferentially in the male tissues of the plant. Any suitable male-fertility tissue-preferred or tissue-specific promoter may be used in the process; and any of the many such promoters known to one skilled in the art may be employed. One such promoter is the 5126 promoter, which preferentially directs expression of the polynucleotide to which it is linked to male tissue of the plants, as described in U.S. Pat. Nos. 5,837,851 and 5,689,051. Other exemplary promoters include the native promoter of Ms9, Ms22, Ms26, or Ms45, including those known and disclosed herein in SEQ ID NO:2, 6, 10, 14, 18, 22, 26, 30, 34, 38, 42, 46, 50, 54, 58, 62, 66, 70, 74, and 78.

In some examples, a termination region is operably linked to the male-fertility MS9, MS22, MS26 or MS45 polynucleotide, fragment or variant. In some examples, the terminator region is the native terminator of Ms9, Ms22, Ms26, or Ms45, including those known and disclosed herein.

Where appropriate, the MS9, MS22, MS26 or MS45 polynucleotides may be optimized for increased expression in the plant. That is, the MS9, MS22, MS26 or MS45 polynucleotides can be synthesized or altered to use plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

A male-fertility MS9, MS22, MS26 or MS45 polynucleotide disclosed herein can be provided in an expression cassette for expression in a plant of interest. The cassette can include 5' and 3' regulatory sequences operably linked to a male-fertility polynucleotide as disclosed herein. In some examples, the expression cassette includes in addition to the polynucleotide encoding the Ms9, Ms22, Ms26, or Ms45 polypeptide a male-gamete-disruptive polynucleotide, that is, a polynucleotide which interferes with the function, formation, or dispersal of male gametes. A male-gamete-disruptive polynucleotide can operate to prevent function, formation, or dispersal of male gametes by any of a variety of methods. By way of example but not limitation, this can include use of polynucleotides which encode a gene product such as DAM-methylase or bamase (See, for example, U.S. Pat. Nos. 5,792,853 and 5,689,049; PCT/EP89/00495); encode a gene product which interferes with the accumulation of starch, degrades starch, or affects osmotic balance in pollen, such as alpha-amylase (See, for example, U.S. Pat. Nos. 7,875,764; 8,013,218; 7,696,405, 8,614,367); inhibit formation of a gene product important to male gamete function, formation, or dispersal (See, for example, U.S. Pat. Nos. 5,859,341; 6,297,426). In some examples, the male-gamete-disruptive polynucleotide is operably linked to a male-tissue-preferred promoter.

When the expression cassette is introduced into the plant in a hemizygous condition, only certain daughter cells will inherit the expression cassette in the process of pollen grain formation. The daughter cells that inherit the expression cassette containing the male-fertility MS9, MS22, MS26 or MS45 polynucleotide will not develop into mature pollen grains due to the male-tissue-preferred expression of the stacked encoded male-gamete-disruptive gene product. Those pollen grains that do not inherit the expression cassette will continue to develop into mature pollen grains and be functional, but will not contain the male-fertility polynucleotide of the expression cassette and therefore will not transmit the male-fertility polynucleotide to progeny through pollen. See, for example, U.S. Pat. Nos. 7,875,764; 8,013,218; 7,696,405, 8,614,367, herein incorporated by reference in its entirety.

In one embodiment, the homozygous recessive condition of a male-sterile plant produced using methods described herein is maintained. A method of maintaining the homozygous recessive condition of a male-sterile plant may include fertilizing the homozygous recessive male-sterile plant with pollen from a plant expressing (1) a MS9, MS22, MS26, or MS45 fertility gene that when the gene is expressed in the plant restores male fertility to the male-sterile plant and (2) a polynucleotide sequence that inhibits the function or formation of viable male gametes, which are driven by promoters that preferentially expresses the sequence in male plant cells, such as male gametes. See, for example, U.S. Pat. No. 8,614,367. The progeny produced will continue to be male sterile as a result of maintaining homozygosity for the fertility gene, e.g. MS9, MS22, MS26, and MS45. The progeny will not contain the introduced restoring fertility gene-male gamete inhibition construct. The plant having the restorer nucleotide sequence may be self-fertilized, that is pollen from the plant transferred to the flower of the same plant to achieve the propagation of the restorer plants. Note that in referring to "self fertilization", it includes the situation where the plant producing the pollen is fertilized with that same pollen, and the situation where two or more identical inbred plants are planted together and pollen from the identical inbred plant pollinate a different identical inbred plant. The pollen will not have the restoring transgene construct but it will be contained in 50% of the ovules (the female gamete). The seed resulting from the self-fertilization can be planted, and selection made for the seed having the restoring fertility gene-male gamete inhibition construct. Selection will allow for the identification of those plants produced from the seed having the restoring fertility gene-male gamete inhibition construct.

Also provided herein are wheat U6 promoters. As used herein, the terms "wheat U6 promoter", "wheat U6 RNA polymerase III promoter", and "wheat U6 snRNA polymerase III promoter" are used interchangeably herein. The term "wheat U6 promoter" includes a native wheat promoter (or a functional fragment thereof) and an engineered sequence comprising at least a fragment of the native wheat promoter with a DNA linker attached to facilitate cloning. A DNA linker may comprise a restriction enzyme site.

In some aspects, the wheat U6 promoter may be used to express a coding sequence or functional RNA. Functional RNA includes, but is not limited to, crRNA, tracerRNA, guide RNA, transfer RNA (tRNA) and ribosomal RNA (rRNA). The promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene or functional RNA in different tissues or cell types, or at different stages of development, or in response to different environmental conditions. New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation of the promoter may also have promoter activity.

"Promoter functional in a plant" is a promoter capable of controlling transcription in plant cells whether or not its origin is from a plant cell.

"Constitutive promoter" refers to promoters active in all or most tissues or cell types of a plant at all or most developing stages. As with other promoters classified as "constitutive" (e.g., ubiquitin), some variation in absolute levels of expression can exist among different tissues or stages.

The wheat U6 promoter nucleotide sequences and methods disclosed herein are useful in regulating constitutive expression of any heterologous nucleotide sequences (such as but not limited to RNA sequences) in a host plant in order to alter the phenotype of a plant. In one embodiment, this disclosure concerns a recombinant DNA construct comprising a nucleotide sequence comprising any of the sequences set forth in SEQ ID NOs: 451, 452, or 453, or a functional fragment thereof, operably linked to at least one heterologous sequence, wherein said nucleotide sequence is a constitutive promoter.

While this nucleotide sequence is heterologous to the promoter sequence, it may be homologous, or native, or heterologous, or foreign, to the plant host. However, it is recognized that the instant wheat U6 promoters may be used with their native coding sequences to increase or decrease expression resulting in a change in phenotype in a transformed seed. The terms "heterologous nucleotide sequence", "heterologous polynucleotide sequence", "heterologous sequence", "heterologous nucleic acid fragment", and "heterologous nucleic acid sequence" are used interchangeably herein.

The present disclosure encompasses recombinant DNA constructs comprising functional fragments of the wheat U6 promoter sequences or Ms9, MS22, MS26, or MS45 promoter sequences disclosed herein.

With regard to promoters, the term a "functional fragment" refer to a portion or subsequence of the promoter sequence of the present disclosure in which the ability to initiate transcription or drive gene expression (such as to produce a certain phenotype) of a polynucleotide. For example, a "functional fragment" of a wheat U6 promoter would retain the ability to express a functional RNA.

Fragments can be obtained via methods such as site-directed mutagenesis and synthetic construction. As with the provided promoter sequences described herein, the functional fragments operate to promote the expression of an operably linked heterologous polynucleotide sequence, forming a recombinant DNA construct (also, a chimeric gene). For example, the wheat U6 promoter fragment can be used in the design of recombinant DNA constructs to produce guide RNAs capable of interacting with Cas enducleases and forming a guideRNA/Cas endonuclease complex. Recombinant DNA constructs can be designed for use in co-suppression or antisense by linking a promoter fragment in the appropriate orientation relative to a heterologous polynucleotide sequence.

In an embodiment of the present disclosure, the promoters disclosed herein can be modified. Those skilled in the art can create promoters that have variations in the polynucleotide sequence. The polynucleotide sequence of the promoters of SEQ ID NO: 2, 6, 10, 14, 18, 22, 26, 30, 34, 38, 42, 46, 50, 54, 58, 62, 66, 70, 74, 78, 451, 452, or 453 may be modified or altered to enhance their control characteristics. As one of ordinary skill in the art will appreciate, modification or alteration of the promoter sequence can also be made without substantially affecting to the promoter function. The methods are well known to those of skill in the art. Sequences can be modified, for example by insertion, deletion, or replacement of template sequences in a PCR-based DNA modification approach.

A "variant promoter", as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

The promoter sequences disclosed herein may be comprised in a recombinant DNA construct.

Moreover, the skilled artisan recognizes that substantially similar nucleic acid sequences encompassed by this disclosure are also defined by their ability to hybridize, under moderately stringent conditions (for example, 0.5×SSC, 0.1% SDS, 60 degree C.) with the sequences exemplified herein, or to any portion of the nucleotide sequences reported herein and which are functionally equivalent to the promoter of the disclosure. Estimates of such homology are provided by either DNA-DNA or DNA-RNA hybridization under conditions of stringency as is well understood by those skilled in the art (Hames and Higgins, Eds.; In Nucleic Acid Hybridization; IRL Press: Oxford, U K, 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6.times.SSC, 0.5% SDS at room temperature for 15 min, then repeated with 2×SSC, 0.5% SDS at 45 degree C. for 30 min, and then repeated twice with 0.2×SSC, 0.5% SDS at 50 degree C. for 30 min. Another set of stringent conditions uses higher temperatures in which the washes are identical to those above except for the temperature of the final two 30 min washes in 0.2×SSC, 0.5% SDS was increased to 60 degree C. Another set of highly stringent conditions uses two final washes in 0.1× SSC, 0.1% SDS at 65 degree C.

Preferred substantially similar nucleic acid sequences encompassed by this disclosure are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 71% to 100%, such as 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%. Also included herein are promoter that may comprise a polynucleotide having at least 85%, 90%, 95%, 96%, 97%, 98%, or 99% sequence identity to SEQ ID NO: 2, 6, 10, 14, 18, 22, 26, 30, 34, 38, 42, 46, 50, 54, 58, 62, 66, 70, 74, 78, 451, 452, or 453. In some aspects, the % sequence identity is determined over the entire length of the nucleotide sequence, for example, over the full-length.

A "substantially homologous sequence" refers to variants of the disclosed sequences such as those that result from site-directed mutagenesis, as well as synthetically derived sequences. A substantially homologous sequence of the present disclosure also refers to those fragments of a particular promoter nucleotide sequence disclosed herein that operate to promote the expression of an operably linked heterologous nucleic acid fragment. These promoter fragments may comprise at least about 100 contiguous nucleotides, 150 contiguous nucleotides, 200 contiguous nucleotides, 250 contiguous nucleotides, 300 contiguous nucleotides, 350 contiguous nucleotides, 400 contiguous nucleotides, 450 contiguous nucleotides, 500 contiguous nucleotides, 550 contiguous nucleotides, 600 contiguous nucleotides, 650 contiguous nucleotides, 700 contiguous nucleotides, 750 contiguous nucleotides, 800 contiguous nucleotides, 850 contiguous nucleotides, 900 contiguous nucleotides, 950 contiguous nucleotides, or 1000 contiguous nucleotides of the particular promoter nucleotide sequence disclosed herein, for example, of SEQ ID NO: 2, 6, 10, 14, 18, 22, 26, 30, 34, 38, 42, 46, 50, 54, 58, 62, 66, 70, 74, 78, 451, 452, or 453. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis, et al., (1987) Methods Enzymol. 155:335-350, and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present disclosure.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Also included herein is a recombinant DNA construct comprising a MS9, MS22, MS26, or MS45 or wheat U6 promoter. This disclosure also concerns a recombinant DNA construct comprising a promoter wherein said promoter consists essentially of the nucleotide sequence set forth in SEQ ID NOS: 2, 6, 10, 14, 18, 22, 26, 30, 34, 38, 42, 46, 50, 54, 58, 62, 66, 70, 74, 78, 451, 452, or 453 or a functional fragment of SEQ ID NOS: 2, 6, 10, 14, 18, 22, 26, 30, 34, 38, 42, 46, 50, 54, 58, 62, 66, 70, 74, 78, 451, 452, or 453. This disclosure also concerns an isolated polynucleotide comprising a promoter wherein said promoter comprises the nucleotide sequence set forth in SEQ ID NOS: 2, 6, 10, 14, 18, 22, 26, 30, 34, 38, 42, 46, 50, 54, 58, 62, 66, 70, 74, 78, 451, 452, or 453, or a functional fragment of SEQ ID NOS: 2, 6, 10, 14, 18, 22, 26, 30, 34, 38, 42, 46, 50, 54, 58, 62, 66, 70, 74, 78, 451, 452, or 453.

In some aspects, one of the wheat U6 promoters disclosed herein is operably linked to a nucleotide sequence encoding a suitable functional RNA such as but not limited to a crRNA, a tracerRNA or a single guide RNA. This expression cassette may be transformed into an appropriate plant for expression of the promoter. There are a variety of appropriate plants which can be used as a host for transformation that are well known to those skilled in the art, including the dicots, Arabidopsis, tobacco, soybean, oilseed rape, peanut, sunflower, safflower, cotton, tomato, potato, cocoa and the monocots, corn, wheat, rice, barley and palm. The cassette may be tested for expression of the wheat U6 promoter in various cell types of transgenic plant tissues, e.g., leaves, roots, flowers, seeds, transformed with the chimeric U6 promoter-reporter gene expression cassette by assaying for expression of the reporter gene product.

In another embodiment, this disclosure concerns host cells comprising either the recombinant DNA constructs of the disclosure as described herein or isolated polynucleotides of the disclosure as described herein. Examples of host cells which can be used to practice the disclosure include, but are not limited to, yeast, bacteria, and plants. Plasmid vectors comprising the instant recombinant DNA construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

Non-limiting examples of methods and compositions disclosed herein are as follows:

1. A recombinant DNA construct comprising a nucleotide sequence comprising any one of the sequence set forth in SEQ ID NO: 451, 452, or 453, or a functional fragment thereof, operably linked to at least one heterologous sequence, wherein said nucleotide sequence is a promoter.

2. The recombinant DNA construct of embodiment 1, wherein said nucleotide sequence has at least 95% identity, based on the Clustal V method of alignment with pairwise alignment default parameters (KTUPLE=2, GAP PENALTY=5, WINDOW=4 and DIAGONALS SAVED=4), when compared to any one of the sequence set forth in SEQ ID NO: 451, 452, or 453.

3. A vector comprising the recombinant DNA construct of embodiment 1.

4. A cell comprising the recombinant DNA construct of embodiment 1.

5. The cell of embodiment 4, wherein the cell is a plant cell.

6. A transgenic plant having stably incorporated into its genome the recombinant DNA construct of embodiment 1.

7. The transgenic plant of embodiment 6 wherein said plant is a monocot plant.

8. The transgenic plant of embodiment 7 wherein the plant is wheat.

9. A transgenic seed produced by the transgenic plant of embodiment 7, wherein the transgenic seed comprises the recombinant DNA construct.

10. The recombinant DNA construct of embodiment 1 wherein the at least one heterologous sequence codes for a functional RNA molecule selected from the group consisting of crRNA, tracrRNA and guide-RNA.

11. The recombinant DNA construct of embodiment 1, wherein the at least one heterologous sequence encodes a single guide RNA that is capable of forming a guide RNA/Cas endonuclease complex, wherein said guide-RNA hybridizes to a DNA target site.

12. A method of expressing a functional RNA in a plant comprising:
a) introducing the recombinant DNA construct of embodiment 1 into the plant, wherein the at least one heterologous sequence encodes a functional RNA;
b) growing the plant of step a); and
c) selecting a plant displaying expression of the functional RNA of the recombinant DNA construct.

13. The method of Embodiment 12 wherein the plant is a monocot plant.

14. The method of Embodiment 12 wherein the plant is a wheat plant.

15. A plant stably transformed with a recombinant DNA construct comprising a wheat U6 polymerase III promoter and a heterologous nucleic acid fragment operably linked to said U6 polymerase III promoter, wherein said U6 polymerase III promoter is a capable of controlling expression of said heterologous nucleic acid fragment in a plant cell, and further wherein said U6 polymerase III promoter comprises any of the sequences set forth in SEQ ID NO: 451, 452, or 453.

16. A recombinant DNA construct comprising a wheat U6 polymerase III promoter driving a heterologous nucleic acid fragment encoding a guide polynucleotide, a crRNA, or a tracrRNA, wherein said promoter comprises any of the sequences set forth in SEQ ID NO: 451, 452, or 453, or a functional fragment thereof.

17. A method for modifying a target site in the genome of a plant cell, the method comprising introducing a guide RNA and a Cas endonuclease into said plant cell, wherein said guide RNA and Cas endonuclease are capable of forming a complex that enables the Cas endonuclease to introduce a double strand break at said target site, wherein said guide RNA is expressed by a recombinant DNA construct comprising a promoter comprising any of the sequences set forth in SEQ ID NO451, 452, or 453, or a functional fragment thereof.

18. A recombinant DNA construct comprising a wheat U6 polymerase III promoter driving a heterologous nucleic acid fragment encoding a guide polynucleotide comprising: (i) a first nucleotide sequence domain that is complementary to a nucleotide sequence in a target DNA; and, (ii) a second nucleotide sequence domain that interacts with a Cas endonuclease, wherein the first nucleotide sequence domain and the second nucleotide sequence domain are composed of deoxyribonucleic acids (DNA), ribonucleic acids (RNA), or a combination thereof, wherein the guide polynucleotide does not solely comprises ribonucleic acids.

1. A recombinant DNA construct comprising a nucleotide sequence comprising any one of the sequence set forth in SEQ ID NO: 2, 6, 10, 14, 18, 22, 26, 30, 34, 38, 42, 46, 50, 54, 58, 62, 66, 70, 74, or 78, or a functional fragment thereof, operably linked to at least one heterologous sequence, wherein said nucleotide sequence is a promoter.

2. The recombinant DNA construct of embodiment 1, wherein said nucleotide sequence has at least 95% identity, based on the Clustal V method of alignment with pairwise alignment default parameters (KTUPLE=2, GAP PENALTY=5, WINDOW=4 and DIAGONALS SAVED=4), when compared to any one of the sequence set forth in SEQ ID NO: 2, 6, 10, 14, 18, 22, 26, 30, 34, 38, 42, 46, 50, 54, 58, 62, 66, 70, 74, or 78.

3. A vector comprising the recombinant DNA construct of embodiment 1.

4. A cell comprising the recombinant DNA construct of embodiment 1.

5. The cell of embodiment 4, wherein the cell is a plant cell.

6. A transgenic plant having stably incorporated into its genome the recombinant DNA construct of embodiment 1.

7. The transgenic plant of embodiment 6 wherein said plant is a monocot plant.

8. The transgenic plant of embodiment 7 wherein the plant is wheat.

9. A transgenic seed produced by the transgenic plant of embodiment 7, wherein the transgenic seed comprises the recombinant DNA construct.

10. The recombinant vector where the promoter is a male-tissue preferred or male-tissue specific promoter.

Definitions

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

"Coding region" generally refers to the portion of a messenger RNA (or the corresponding portion of another nucleic acid molecule such as a DNA molecule) which encodes a protein or polypeptide. "Non-coding region" generally refers to all portions of a messenger RNA or other nucleic acid molecule that are not a coding region, including but not limited to, for example, the promoter region, 5' untranslated region ("UTR"), 3' UTR, intron and terminator. The terms "coding region" and "coding sequence" are used interchangeably herein. The terms "non-coding region" and "non-coding sequence" are used interchangeably herein.

"Cosuppression" generally refers to the production of sense RNA transcripts capable of suppressing the expression of the target gene or gene product. "Sense" RNA generally refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

The term "crossed" or "cross" or "crossing" in the context of this disclosure means the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

"Expression" generally refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

The terms "full complement" and "full-length complement" are used interchangeably herein, and refer to a complement of a given nucleotide sequence, wherein the complement and the nucleotide sequence consist of the same number of nucleotides and are 100% complementary.

"Gamete" refers to a reproductive cell having the 1 n set (haploid number) of chromosomes that can fuse with another gamete of the opposite sex during fertilization in organisms undergoing sexual reproduction. As used herein, a gamete in organisms undergoing asexual reproduction refers to a cell having a 2n number (an unreduced number) of chromosomes.

The term "gene" as used herein refers to a polynucleotide that is expressed by at least one of transcription and translation. An example of a gene is a nucleic acid fragment capable of being transcribed into mRNA or translated into a protein. A "gene" may or may not include a coding region or a regulatory sequence of a 5'-non coding sequence and a 3'-non coding sequence in addition to the coding region. For example, a Ms9 gene refers to a Ms9 polynucleotide that is expressed by at least one of transcription and translation.

As used herein, the term "gene locus" refers to the position of a gene on a genome. For example, Ms9 gene locus refers to the position of a Ms9 gene on genome.

The term "genome" refers to the entire complement of genetic material (genes and non-coding sequences) that is present in each cell of an organism, or virus or organelle; and/or a complete set of chromosomes inherited as a (haploid) unit from one parent.

"Heterologous" with respect to sequence means a sequence that originates from a foreign species, or, if from the same species, is substantially modified from its native form in composition and/or genomic locus by deliberate human intervention.

The term "introduced" in the context of inserting a nucleic acid into a cell," and includes reference to the incorporation of a nucleic acid or nucleic acid fragment into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA).

"Isolated" generally refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. The term also embraces recombinant polynucleotides and chemically synthesized polynucleotides.

As used herein, a "male sterile plant" is a plant that does not produce male gametes that are viable or otherwise capable of fertilization.

The term "miRNA* sequence" refers to a sequence in the miRNA precursor that is highly complementary to the miRNA sequence. The miRNA and miRNA* sequences form part of the stem region of the miRNA precursor hairpin structure.

The terms "monocot" and "monocotyledonous plant" are used interchangeably herein. A monocot of the current disclosure includes the Gramineae.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. In certain embodiments, sequence identity may be based on the Clustal V or Clustal W method of alignment. The term "about" when used herein in context with percent sequence identity means+/−1.0%.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollen, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

"Polypeptide", "peptide", "amino acid sequence" and "protein" are used interchangeably herein to refer to a polymer of amino acid residues.

"Progeny" comprises any subsequent generation of a plant.

"Promoter functional in a plant" is a promoter capable of controlling transcription in plant cells whether or not its origin is from a plant cell.

As used herein "promoter" includes reference to a region of DNA upstream from the start of transcription and involved in recognition and binding of RNA polymerase and other proteins to initiate transcription.

A "plant promoter" is a promoter capable of initiating transcription in plant cells.

"Recombinant" generally refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" generally refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct" and "recombinant construct" are used interchangeably herein.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other.

The terms "stringent conditions" or "stringent hybridization conditions" means conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence. The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

The terms "suppress", "suppressed", "suppression", "suppressing" and "silencing", are used interchangeably herein and include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches and the like.

"Transcription terminator", "termination sequences", or "terminator" refer to DNA sequences located downstream of a protein-coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al., Plant Cell 1:671-680 (1989). A polynucleotide sequence with "terminator activity" generally refers to a polynucleotide sequence that, when operably linked to the 3' end of a second polynucleotide sequence that is to be expressed, is capable of terminating transcription from the second polynucleotide sequence and facilitating efficient 3' end processing of the messenger RNA resulting in addition of poly A tail. Transcription termination is the process by which RNA synthesis by RNA polymerase is stopped and both the processed messenger RNA and the enzyme are released from the DNA template.

The term "under stringent conditions" means that two sequences hybridize under moderately or highly stringent conditions.

As used herein, the term "wheat" refers to any species of the genus Triticum, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes T. aestivum, T. spelta, T. mocha, T. compactum, T. sphaerococcum, T. vavilovii, and interspecies cross thereof. Tetraploid wheat includes T. durum (also referred to as durum wheat or Triticum turgidum ssp. durum), T. dicoccoides, T. dicoccum, T. polonicum, and interspecies cross thereof. In addition, the term "wheat" includes possible progenitors of hexaploid or tetraploid Triticum sp. such as T. uartu, T. monococcum or T. boeoticum for the A genome, Aegilops speltoides for the B genome, and T. tauschii (also known as Aegilops squarrosa or Aegilops tauschii) for the D genome. A wheat cultivar for use in the present disclosure may belong to, but is not limited to, any of the above-listed species. Also encompassed are plants that are produced by conventional techniques using Triticum sp. as a parent in a sexual cross with a non-Triticum species, such as rye (Secale cereale), including but not limited to Triticale. In some embodiments, the wheat plant is suitable for commercial production of grain, such as commercial varieties of hexaploid wheat or durum wheat, having suitable agronomic characteristics which are known to those skilled in the art.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram (s), "μg" means microgram(s), "ng" means nanogram(s), "U" means unit(s), "bp" means base pair(s) and "kb" means kilobase(s).

Also, as described herein, for each example or embodiment that cites a guide RNA, a similar guide polynucleotide can be designed wherein the guide polynucleotide does not solely comprise ribonucleic acids but wherein the guide polynucleotide comprises a combination of RNA-DNA molecules or solely comprises DNA molecules.

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Example 1: Maize Optimized Expression Cassettes for Guide RNA/Cas Endonuclease Based Genome Modification in Wheat Plants For genome engineering applications, the type II CRISPR/Cas system minimally requires the Cas9 protein and a duplexed crRNA/tracrRNA molecule or a synthetically fused crRNA and tracrRNA (guide RNA) molecule for DNA target site recognition and cleavage (See, published PCT application, WO2015026883 published on Feb. 26, 201). Described herein is a guideRNA/Cas endonuclease system that is based on the type II CRISPR/Cas system and consists of a Cas endonuclease and a guide RNA (or duplexed crRNA and tracrRNA) that together can form a complex that recognizes a genomic target site in a wheat plant and introduces a double-strand-break into said target site.

To test the guide RNA/Cas endonuclease system in wheat, the CRISPR/Cas system for maize as described by Cigan et al. was used (See, published PCT application, WO2015026883 published on Feb. 26, 2015). Briefly, this system consists of a maize codon optimized Cas9 gene from Streptococcus pyogenes M1 GAS (SF370) and the potato ST-LS1 intron was introduced in order to eliminate its expression in E. coli and Agrobacterium. To facilitate nuclear localization of the Cas9 protein in cells, monopartite amino terminal nuclear localization signal from Simian virus 40 (SV40), and bipartite VirD2 T-DNA border endonuclease carboxyl terminal nuclear localization signal from Agrobacterium tumefaciens were incorporated at the amino and carboxyl-termini of the Cas9 open reading frame, respectively. The maize optimized Cas9 gene was operably linked to a constitutive promoter from maize by standard molecular biological techniques.

The second component necessary to form a functional guide RNA/Cas endonuclease system for genome engineering applications is a duplex of the crRNA and tracrRNA molecules or a synthetic fusing of the crRNA and tracrRNA molecules, a guide RNA. To confer efficient guide RNA expression (or expression of the duplexed crRNA and tracrRNA), the maize U6 polymerase III promoter and maize U6 polymerase III terminator were operably fused to the termini of a guide RNA using standard molecular biology techniques.

Two crRNAs, a 20 nucleotide molecule (GGT-CATGCAGCGCTGGCCGA SEQ ID: 222) and a 21 nucleotide molecule (GCAGCGCTGGCCGAGGGACAA SEQ ID:223), containing a region complementary to one strand of the double strand DNA target (referred to as the variable targeting domain) was designed upstream of a PAM sequence (GGG) and (CGG) respectively. Guide RNA (gRNA) also consisted of a 77 nucleotide tracrRNA fusion transcripts used to direct Cas9 to cleave sequence of interest. The construct also included a DsRed2 gene under control of the maize Ubiquitin promoter (see, e.g., U.S. Pat. No. 5,525,716) and PINII terminator for selection during transformation. This construct was transformed directly into wheat by Agrobacterium-mediated transformation methods as described in Cigan A M et al. (2017), yielding several independent T-DNA insertion events for construct evaluation. See Cigan et al, Targeted mutagenesis of a conserved anther-expressed P450 gene confers male sterility in monocots. Plant Biotechnology Journal In Press: (2017) 15:379-389.

T0 wheat plants containing variable number of transgenes were grown to maturity and seed harvested. T1 plants were grown and examined for the presence of NHEJ mutations by deep sequencing. A total of 28 T1 plants were identified with different mutations, including three plants with mutations in two different genomes and two plants with a mutation in each of three genomes (Table 3).

TABLE 3

CRISPR-CAS induced NHEJ mutations in wheat Ms45 gene

| Plant ID | Genotype | CRISPR | A-genome | B-genome | D-genome | Cas9 TDNA Copy # |
|---|---|---|---|---|---|---|
| 1 | Fielder | MS45-CR1 | | | 20 bp del | 3 |
| 2 | Fielder | MS45-CR1 | | G ins | | 5 |
| 3 | Fielder | MS45-CR2 | 23 bp del | | | 4 |
| 4 | Fielder | MS45-CR1 | | 27 bp indel | | 1 |
| 5 | Fielder | MS45-CR1 | | | C ins | 3 |
| 6 | Fielder | MS45-CR1 | | | T ins | >5 |
| 7 | Fielder | MS45-CR1 | T ins | | | 2 |
| 8 | Fielder | MS45-CR1 | 18 bp indel | | | 5 |
| 9 | Fielder | MS45-CR1 | 20 bp del | A ins | | 2 |
| 10 | Fielder | MS45-CR2 | 18 bp del | | | 7 |
| 11 | Fielder | MS45-CR1 | 7 bp del | A ins | A ins | 5 |
| 12 | Fielder | MS45-CR1 | | | 20 bp del | 2 |
| 13 | Fielder | MS45-CR1 | | | A ins | 1 |
| 14 | Fielder | MS45-CR1 | | | A ins | 2 |
| 15 | Fielder | MS45-CR1 | | | A ins | 8 |
| 16 | Fielder | MS45-CR2 | | | 10 bp ins/subst | 2 |
| 17 | Fielder | MS45-CR2 | GA del | | | 1 |
| 18 | Fielder | MS45-CR1 | A ins* (A or D) | | | 4 |
| 19 | Fielder | MS45-CR1 | | | T ins | 2 |
| 20 | Fielder | MS45-CR1 | | G ins | | 4 |
| 21 | Fielder | MS45-CR2 | 23 bp del | | | 2 |
| 22 | Fielder | MS45-CR2 | | 23 bp del | | 1 |
| 23 | SBC0456D* | MS45-CR1 | T ins (A or D) | | | 4 |
| 24 | SBC0456D | MS45-CR1 | A ins (A or D) | A ins | | 2 |
| 25 | SBC0456D | MS45-CR1 | AA ins (A or D) | A ins | T ins (A or D) | 1 |
| 26 | SBC0456D | MS45-CR1 | | 20 bp del | | 1 |
| 27 | SBC0456D | MS45-CR1 | T ins (A or D) | | | 1 |
| 28 | SBC0456D | MS45-CR1 | T ins (A or D) | | G ins (a or D) | 1 |

*SBC0456D is a pioneer elite spring wheat variety, see US published patent application no. 20140173781

Example 2: Simultaneous Tams45 Mutations in A-, B- and D-Genomes with CRISPR-Cas9 Results in Male Sterile Wheat This example shows that triple homozygous mutant plants of TaMs45 gene derived from CRISPR-Cas9 induced mutations in the A, B, and D-genomes result in male sterile phenotype.

The genetic nature of TaMs45 mutant alleles in hexaploid wheat is denoted as follows:

Homozygous wild-type TaMs45 alleles in the genome A, B, and D are designated as TaMs45-ABD.

Homozygous mutant alleles are designated by a small letter; for example A-genome homozygous mutations are designated as TaMs-aBD.

Heterozygous mutant alleles are designated by a double letter; for example A-genome heterozygous mutations are designated as TaMs-AaBD.

Triple homozygous mutant alleles are designated as Tams-abd.

Triple heterozygous mutant alleles are designated as TaMs-AaBbDd.

Two plants with heterozygous mutations in all three homeologs (TaMs-AaBbDd), plant #11 and plant #25 in Table 3, were identified and allowed to self-pollinate to produce T2-T4 generations. Progeny from these generations was screened by deep sequencing and 17 triple homozygous mutant plants were identified (Tams45-abd; Table 4). Four plants were identified in the T4 progeny of plant #25 which were homozygous for all three mutations but without Cas9-sgRNA T-DNA (Table 5).

TABLE 4

Mutations and deep sequencing read counts from the three TaMs45 homeologs of Plant #11 and Plant #25. Bold text represents insertions, (-) represents a deletion mutation or a gap in the WT sequence due to insertion mutations
Triple homozygous mutants (Tams45-abd) were similar to wild-type plants in vegetative growth and flowering characteristics. However, the anthers in Tams45-abd plants were shrunken in shape and did not extrude or dehisce like anthers from a fertile wild-type plant (See FIG. 1).

| Plant #11 | Mutation | Read Count | % of counts | Zygosity in T1 |
|---|---|---|---|---|
| WT | TACAGGGAGGTCATGCAGCGCTGGCCGAGGGACAACGGCAGCCG (SEQ ID NO: 265) | 172,654 | 47.4 | |

TABLE 4-continued

Mutations and deep sequencing read counts from the three TaMs45 homeologs of Plant #11 and Plant #25. Bold text represents insertions, (-) represents a deletion mutation or a gap in the WT sequence due to insertion mutations
Triple homozygous mutants (Tams45-abd) were similar to wild-type plants in vegetative growth and flowering characteristics. However, the anthers in Tams45-abd plants were shrunken in shape and did not extrude or dehisce like anthers from a fertile wild-type plant (See FIG. 1).

| | | | | |
|---|---|---|---|---|
| A-genome | TACAGGGAGGTCATGCAG-------CGAGGGACAACGGCAGCCG (SEQ ID NO: 266) | 59,842 | 16.4 | HET |
| B-genome | TACAGGGAGGTCATGCAGCGCTGGCACGAGGGACAACGGCAGCCG (SEQ ID NO: 454) | 45,578 | 12.5 | HET |
| D-genome | TACAGGGAGGTCATGCAGCGCTGGCACGAGGGACAACGGCAGCCG (SEQ ID NO: 455 | 73,592 | 20.2 | HET |
| Plant #25 | | | | |
| WT | TACAGGGAGGTCATGCAGCGCTGGC-CGAGGGACAACGGCAGCCG (SEQ ID NO: 456) | 363,042 | 48.6 | |
| A-/D-genome | TACAGGGAGGTCATGCAGCGCTGGCAACGAGGGACAACGGCAGCCG (SEQ ID NO: 457) | 134,946 | 18.1 | HET |
| B-genome | TACAGGGAGGTCATGCAGCGCTGGCACGAGGGACAACGGCAGCCG (SEQ ID NO: 458) | 94,464 | 12.6 | HET |
| A-/D-genome | TACAGGGAGGTCATGCAGCGCTGGCTCGAGGGACAACGGCAGCCG (SEQ ID NO: 459) | 124,340 | 16.6 | HET |

Seed from Tams45-abd individual plants was pooled and counted as a qualitative measure of male fertility. As shown in Table 5, at maturity plants containing triple homozygous ms45 mutations (tams45-abd), were male sterile did not set self-seed. (Note, seed observed in two of these plants was likely to due to open fertilization as these heads were not bagged prior to anthesis).

Figure 1B:
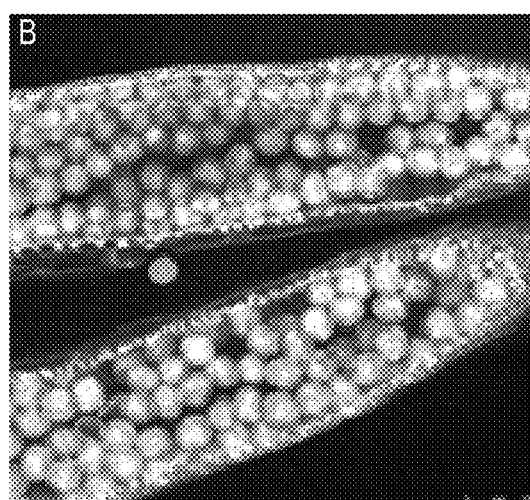
Figure 1C:
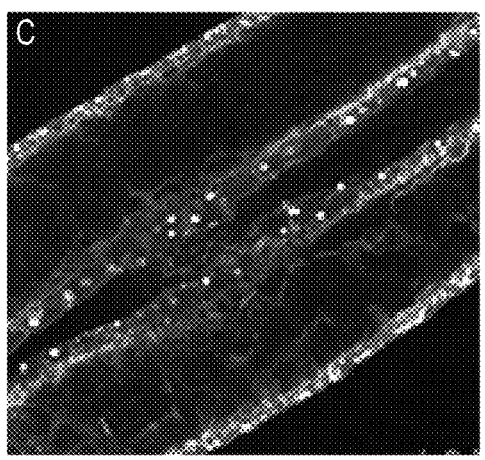
Figure 1D:
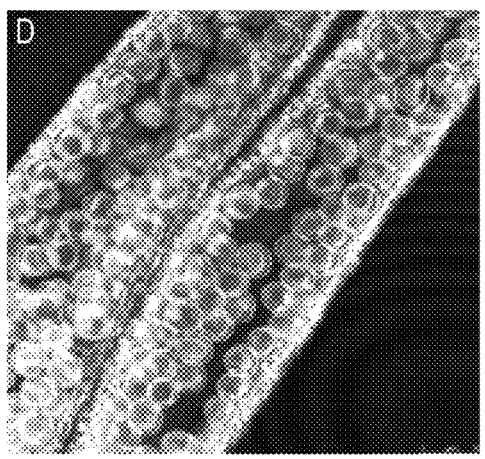

Previous studies of ms45 mutants in maize de<onstrated that the breakdown of microspores occurred shortly after tetrad release (Cigan et al., 2001). To determine whether plants containing mutations in the wheat Ms45 gene conferred a similar phenotype, anthers at the vacuolate stage of microspore development were examined for the presence of microspores using confocal microscopy. As shown in FIG. 1B and FIG. 1C, anthers from a wild-type plant contained many developing microspores, while anthers from a Tams45-abd plant contained only a few vestigial microspores.

Anther phenotype and microspore development observed in double homozygote-single heterozygote plants were normal and comparable to wild-type plants (FIG. 1D) and at maturity, the double homozygote-single heterozygotes showed seed set comparable to the wild-type plants (Table 5).

TABLE 5

Male fertility as indicated by seed set in TaMs45 mutants (T1, T2 and T3 generations).

| Genotype of TaMs45 homeologs[1] | Seed Set-Fertility | | |
|---|---|---|---|
| | Plants | Total Seed | Seed per Plant |
| Tams45-abd (T2; Plant #11) | 2 | 2 | ~0 |
| Tams45-abd (T3; Plant #25) | 11 | 0 | 0 |
| Tams45-abd (T4; Plant #25; No Cas9-sgRNA) | 4 | 0 | 0 |
| Total Tams45-abd plants | 17 | 2 | ~0 |
| Tams45-Aabd or -aBbd or -abDd (Plant #11) | 2 | 235 | 118 |
| Tams45-Aabd or -aBbd or -abDd (Plant #25) | 9 | 1249 | 139 |
| TaMs45-ABD | 5 | 855 | 171 |

[1](plant generation, T0 plant ID, No TDNA indicates the absence of Cas9-gRNA TDNA insertion).

Example 3: A Single Copy of Monocot Ms45 Gene can Restore Fertility and Maintain Tams45-abd Triple Homozygous Mutants To propagate the Tams45-abd male sterile plants, it would be advantageous to generate a maintainer line. The main component required for maintaining a male sterile plant is the ability of an introduced wild-type copy of the gene to complement the mutations and render the plant fertile. To accomplish this, the rice Ms45 gene under control of the maize Ms45 promoter was linked to a DsRed2 gene under control of the maize ubiquitin promoter and also carrying a PINII terminator sequence (OsMs45-DsRED). This construct was transformed directly into wheat by Agrobacterium-mediated transformation methods as referenced elsewhere herein, yielding several independent T-DNA insertion events for evaluation. Wheat plants containing single-copy OsMs45-DsRED cassette were used as male plants to pollinate Tams45-abd plants. Seeds were harvested, planted, and progeny screened by PCR to confirm the presence of OsMs45-DsRED and TaMS45-A, -B and -D mutations and allowed to self-pollinate.

Figure 1E:
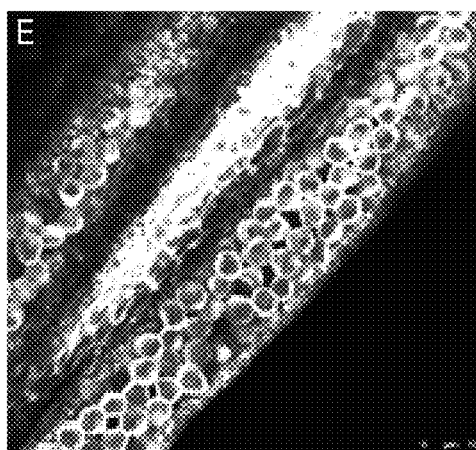

F2 seed were planted and progeny were genotyped for the OsMs45 gene and TaMs45 mutant alleles. Triple homozygous mutant plants with and without the complementation OsMs45-DsRED T-DNA were identified and analyzed for male fertility through microscopy of anthers and determination of seed set on individual plants. In total, six triple homozygous Tams45-abd mutant plants were analyzed, four with one copy of OsMs45-DsRED T-DNA and two lacking the T-DNA (Table 6). Pollen development in the anthers of plants with OsMs45 was similar to wild-type plants (FIG. 1E). All four Tams45-abd plants that carried OsMs45 were male fertile with seed set comparable to wild-type plants while the two plants without the OsMs45 showed negligible seed-set (Table 6; Note, seed observed in two of these plants was likely to due to open fertilization as these heads were not bagged prior to anthesis). This data exhibits that the male sterility observed in Tams45-abd plants is due to mutations in the TaMs45 gene and a single, transformed copy of Ms45 gene can complement and restore fertility and maintain the triple homozygous mutants.

TABLE 6

Complementation of TaMs45 triple homozygous mutants.

| Genotype of TaMs45 homeologs[1] | Plants | Seed Set-Fertility | | | |
|---|---|---|---|---|---|
| | | Total Seed | Seed per Plant | Male fertile | Male sterile |
| Tams45-abd/OsMs45 | 4 | 565 | 141.5 | 4 | 0 |
| Tams45-abd | 2 | 3 | 1.5 | 0 | 2 |
| TaMs45-ABD | 5 | 855 | 171 | 5 | 0 |

Example 4: Wheat U6 RNA Polymerase III Promoters

Wheat U6 RNA polymerase III promoter sequences were identified for use in expressing guide RNA to direct Cas9 nuclease (or other endonuclease) to a designated genomic site, see, for example, SEQ ID NOs: 451-453 identified on *Triticum aestivum* Chromosome 2, Chromosome 4 and Chromosome 5 respectively. The first nucleotide of a 20 bp variable targeting domain may contain a G residue for use by a RNA polymerase III for transcription see, for example, the target site sequences shown in Table 2. The wheat U6 snRNA polymerase III promoters may be synthesized and/or then cloned with an appropriate DNA sequence that encodes a guide RNA into an appropriate vector to make, for example, a DNA construct. This U6 RNA polymerase III promoter may be used to express other Cas endonuclease components, including but not limited to a Cas9 endonuclease.

That which is claimed:

1. A method of expressing a heterologous polynucleotide sequence in a wheat plant cell comprising:
    introducing into the wheat plant cell a polynucleotide comprising a polynucleotide sequence selected from the group consisting of:
    (a) SEQ ID NO:451, 452, or 453; and
    (b) a fragment of at least 200 contiguous nucleotides of SEQ ID NO:451, 452, or 453,
wherein said polynucleotide sequence drives expression of an operably linked heterologous polynucleotide sequence.

2. The method of claim 1, wherein the heterologous polynucleotide sequence encodes an RNA sequence.

3. The method of claim 2, wherein the heterologous polynucleotide sequence encodes a guideRNA.

4. The method of claim 1, wherein a recombinant DNA construct comprises the polynucleotide sequence operably linked to the heterologous polynucleotide sequence.

5. The method of claim 1, wherein the polynucleotide is introduced into the wheat plant cell via particle bombardment or *Agrobacterium* transformation.

6. A wheat plant cell comprising a polynucleotide sequence selected from the group consisting of: (a) SEQ ID NO:451, 452, or 453, and (b) a fragment of at least 200 contiguous nucleotides of SEQ ID NO:451, 452, or 453, wherein said polynucleotide sequence is operably linked to a heterologous polynucleotide sequence.

7. The wheat plant cell of claim 6, wherein the heterologous polynucleotide sequence encodes an RNA sequence.

8. The wheat plant cell of claim 6, wherein the heterologous polynucleotide sequence encodes a guideRNA.

* * * * *

SEQUENCE LISTING

<160> NUMBER OF SEQ ID NOS: 459

<210> SEQ ID NO 1
<211> LENGTH: 1525
<212> TYPE: DNA
<213> ORGANISM: Triticum aestivum

<400> SEQUENCE: 1

```
atgggcggc cgccgtgctg cgacaaggcc aacgtgaaga aggggccgtg gacggcggag        60
gaggacgcca agctgctggc ctacacctcc aaccatggca ccggcaactg gacctctgtt       120
ccccagaggg caggtcggaa ccctctcccc cggccggccg gatcggcgtc tggcatcgaa       180
atggtgttgg ttttgcatgg tttctggctg atgtgtgttg cgtcatggat gggtgcgtgc       240
tgcagggctg aagcggtgcg ggaagagctg caggctgagg tacaccaact acctgaggcc       300
caacctcaag cacgagaact tcacgcagga ggaggaggag ctcatcgtca ccctccatgc       360
catgctggga agcaggtgca tctctgtaca tgcatgtcat ccatcggtta ctttctcgat       420
tttgtcatca agttttcggt gaatgcgaaa ctttgctatg gacagactac tgtttctgtc       480
atcattcctg ctataaactt tgcatccata tactctagcg tacgttcaga tcttatagat       540
ttatggaagt tctaaaaacc tcacgttggt gtatcattca gacaattgct catacaccgg       600
aaatcacgtc ctacttctat tcaagaattt actttagccg ttcattcata aagtagaaac       660
aaatgtagtt taatccagta accagtctcg tgtctacggt tcttctgaat atattctgtt       720
tcctggtaga atgtagtgaa aagctgaata ttgggtgaag aacagatctg aatagctgtc       780
ttaaattgat agtgtttgac agaaaatact ccacactgag cgtaatataa catgaaagta       840
cgtgtacgtg ttgggtgcat gcaggtggtc tctgatcgcg aaccagctgc cggggcggac       900
ggacaacgac gtcaagaatt actggaacac caagctgagc aagaagctgc ggcagcgggg       960
```

| | |
|---|---|
| catcgacccc atcacccatc gccccatcgc cgacctcatg cagagcatcg gcaccctccc | 1020 |
| catccgcccg ccgcccagcg ccgcgggtgc ctcctcgtcc tcctacatcc ccgtgaaccc | 1080 |
| agcggcggcg ccggggctcc agccgctgca cgacgacgtc aaataccacg cagtcctgaa | 1140 |
| ccaccaccag cagcaggtca tcacgctcct cgaccccgac gcgccagggg cggcggcgtc | 1200 |
| cccggaccac cagctcaagt ggagcgactt ccttgccgac gacgccgccg ccttcgaggc | 1260 |
| ggcgccgcag gtggttcttg gtcagtacca ggaggccgcg gtggctggtg gcggagcagc | 1320 |
| gtatggagac actgatagta ttgcagccga tggtgtcggc gggggcgggg aggatagcgc | 1380 |
| agcgtcagcg ttcatcgacg cgatgctgga cagcgacaaa aagatgggcg tggaccagct | 1440 |
| catcgccgac ctgctcgccg acccggcata ctactacggc ggaggctctt cctcttcgac | 1500 |
| gtcggagctg gggcggggcg gttga | 1525 |

<210> SEQ ID NO 2
<211> LENGTH: 1751
<212> TYPE: DNA
<213> ORGANISM: Triticum aestivum

<400> SEQUENCE: 2

| | |
|---|---|
| gcgacgtgcc cagggcgcgg tggccggtgg atcgcagggg ctgtcggttg ggatgcatgg | 60 |
| gacggagagt ggagcgtcca aactatactt tactccatgg gagggaactg ggcgtcgggg | 120 |
| tcggtcggtc ttcacgtgtc ccgggaatgg gaagtgcaac tctgtgtggt gctgcatctg | 180 |
| atgctcgtat tgctgatgcc atgtgtatcc acaggagaga tgctgcagcg tagctgcttt | 240 |
| ggaagcattt ctcggttctc agcgttggaa gcataagata agtaacgcac ggaagtaagt | 300 |
| tgaacacaaa atcagagtgg cgcagcgaaa gtgtggtggg cccataaccc ataggtccca | 360 |
| ggatcgaaac ttggctctaa tttgattttt tgaatttttc ttttgaattt gatatttcta | 420 |
| tctctttatt ttcttggatt aaacttcgtt tctttttttct cttcgcgaat ggcttactct | 480 |
| actttctgtt ctccttcaaa tattgatcat ctacacactt tcctttacat gaagcttttt | 540 |
| acctgacgaa ctataagaac aagtagtaca aactgttaac gccacaccag aaatgctcgg | 600 |
| tgcttcttct ctgaaaccaa cacgagacgc tgaaaaaggc attccaaaaa aaaaaacacg | 660 |
| agacgctgaa aacagcatgc atttttctcct tgtaataccaa caactcgaaa cctggctctg | 720 |
| atatgatttt ttgaattttt cttttggatt tgatatttct atctgtttat ttcctggat | 780 |
| cgaaacttgg ctctgatatg attttttgaa ttttctttt ggatttgata tttctatctg | 840 |
| tttattttcc tggattaaac ttcgtttctt ttttctcttc gcgaatggct tactctactt | 900 |
| tctgttctcc tccaaatatt gatcatctac acactttcct ttacacgaag cttttttacct | 960 |
| gacgaaccat aagaacaagt agtacaaact gttaacgcca caccagaaat gctcggtgct | 1020 |
| tcttctctga aaccaacacg agacgctgaa aaaggcatta aaaaaaacac gagacgctga | 1080 |
| aaacagcatg cattttctcc ttgtaatacc acaactgtta aggatcacat gtgcggcgcc | 1140 |
| aacacaactg tcaagacgat cgtacaaacg cgatgagcag aggcgcctgt gatatgatcg | 1200 |
| catcgccagc tcccaggtga aaaccgattc cgcggcgctg atgtcgtgaa aatcatcatg | 1260 |
| tccaactcgt gaaatatttt gaaacagccc ccggcccctc caccctcaca cacggcgttt | 1320 |
| gattagatta gatcggattg tattaaccca ccaacccgca tctgcataca tatttgatcc | 1380 |
| ctccctgatt aagcggttga tttgccggag ggaaacagtt gcaggcgtgc cataaactag | 1440 |
| ggttaaagaa gcgtttccat cggatcgtca ctaacccatg ccatgccatc actagttaaa | 1500 |

```
tgaggagggg ggaggtcatg cttccgtcgc gtgcccctcc accatctgga catgttgttg       1560
ccgtgcagtg cccctctctc tctcgccgga gcgccccgcc ccctatatgt acgccggtgc       1620
caccctgcag tgtgatctcg tcgggggggca ccggaggttg gtgcggtgct ggggttctcg      1680
agctatatta tctatcaccg tttggctgct tgttgtagaa ggggaggggg aggagggtgg       1740
tgccggccgg g                                                            1751

<210> SEQ ID NO 3
<211> LENGTH: 923
<212> TYPE: DNA
<213> ORGANISM: Triticum aestivum

<400> SEQUENCE: 3
atggggcggc cgccgtgctg cgacaaggcc aacgtgaaga aggggccgtg gacggcggag         60
gaggacgcca agctgctggc ctacacctcc aaccatggcc ccggcaactg gacctctgtt       120
ccccagaggg cagggctgaa gcggtgcggg aagagctgca ggctgaggta caccaactac       180
ctgaggccca acctcaagca cgagaacttc acgcaggagg aggaggagct catcgtcacc       240
ctccatgcca tgctgggaag caggtggtct ctgatcgcga accagctgcc ggggcggacg       300
gacaacgacg tcaagaatta ctggaacacc aagctgagca gaagctgcg gcagcggggc        360 atcgacccca tcacccatcg ccccatcgcc gacctcatgc agagcatcgg caccctcccc       420
atccgcccgc cgcccagcgc cgcgggtgcc tcctcgtcct cctacatccc cgtgaaccca       480
gcggcggcgc cggggctcca gccgctgcac gacgacgtca ataccacgc agtcctgaac        540 caccaccagc agcaggtcat cacgctcctc gaccccgacg cgccaggggc ggcggcgtcc       600
ccggaccacc agctcaagtg gagcgacttc cttgccgacg acgccgccgc cttcgaggcg       660
gcgccgcagg tggttcttgg tcagtaccag gaggccgcgg tggctggtgg cggagcagcg       720
tatggagaca ctgatagtat tgcagccgat ggtgtcggcg ggggcgggga ggatagcgca       780
gcgtcagcgt tcatcgacgc gatgctggac agcgacaaaa agatgggcgt ggaccagctc       840
atcgccgacc tgctcgccga cccggcatac tactacggcg gaggctcttc ctcttcgacg       900
tcggagctgg ggcggggcgg ttg                                               923

<210> SEQ ID NO 4
<211> LENGTH: 307
<212> TYPE: PRT
<213> ORGANISM: Triticum aestivum

<400> SEQUENCE: 4

Met Gly Arg Pro Pro Cys Cys Asp Lys Ala Asn Val Lys Lys Gly Pro
1               5                  10                  15

Trp Thr Ala Glu Glu Asp Ala Lys Leu Leu Ala Tyr Thr Ser Asn His
                20                  25                  30

Gly Thr Gly Asn Trp Thr Ser Val Pro Gln Arg Ala Gly Leu Lys Arg
            35                  40                  45

Cys Gly Lys Ser Cys Arg Leu Arg Tyr Thr Asn Tyr Leu Arg Pro Asn
        50                  55                  60

Leu Lys His Glu Asn Phe Thr Gln Glu Glu Glu Leu Ile Val Thr
65                  70                  75                  80

Leu His Ala Met Leu Gly Ser Arg Trp Ser Leu Ile Ala Asn Gln Leu
                85                  90                  95

Pro Gly Arg Thr Asp Asn Asp Val Lys Asn Tyr Trp Asn Thr Lys Leu
            100                 105                 110
```

```
Ser Lys Lys Leu Arg Gln Arg Gly Ile Asp Pro Ile Thr His Arg Pro
        115                 120                 125
Ile Ala Asp Leu Met Gln Ser Ile Gly Thr Leu Pro Ile Arg Pro Pro
    130                 135                 140
Pro Ser Ala Ala Gly Ala Ser Ser Ser Tyr Ile Pro Val Asn Pro
145                 150                 155                 160
Ala Ala Ala Pro Gly Leu Gln Pro Leu His Asp Asp Val Lys Tyr His
                165                 170                 175
Ala Val Leu Asn His His Gln Gln Val Ile Thr Leu Leu Asp Pro
            180                 185                 190
Asp Ala Pro Gly Ala Ala Ala Ser Pro Asp His Gln Leu Lys Trp Ser
        195                 200                 205
Asp Phe Leu Ala Asp Asp Ala Ala Phe Glu Ala Ala Pro Gln Val
    210                 215                 220
Val Leu Gly Gln Tyr Gln Glu Ala Ala Val Ala Gly Gly Gly Ala Ala
225                 230                 235                 240
Tyr Gly Asp Thr Asp Ser Ile Ala Ala Asp Gly Val Gly Gly Gly
                245                 250                 255
Glu Asp Ser Ala Ala Ser Ala Phe Ile Asp Ala Met Leu Asp Ser Asp
                260                 265                 270
Lys Lys Met Gly Val Asp Gln Leu Ile Ala Asp Leu Leu Ala Asp Pro
        275                 280                 285
Ala Tyr Tyr Tyr Gly Gly Gly Ser Ser Ser Ser Thr Ser Glu Leu Gly
        290                 295                 300
Arg Gly Gly
305

<210> SEQ ID NO 5
<211> LENGTH: 1530
<212> TYPE: DNA
<213> ORGANISM: Triticum aestivum

<400> SEQUENCE: 5 atgggggcggc cgccgtgctg cgacaaggcc aacgtgaaga aggggccgtg gacggcggag      60
gaggacgcca agctgctcgc ctacacctcc aaccatggcc ccggcaactg gacctctgtt     120
ccccagaggg caggtcggaa ccctccccccc ggccggccgg atcgacgtcc gtcatggaaa     180
tggtgttggt cttgcatggt ttctggctga tgtgtgttgc atcatggatg cgtgcgtgct     240
gcagggctga agcggtgcgg gaagagctgc aggctgaggt acaccaacta cctgaggccc     300
aacctcaagc acgagaactt cacgcaggag gaggaggagc tcatcgtcac cctccatgcc     360
atgctgggaa gcaggtgcgt ctctctgtgt agtacatgca tgtttctgcc atcagttact     420
ttctcgattt tgtcatcaag ttttcggtga atgcgaaact tgctatggca cgactgctg      480 tttctgtcat cattcctgct ataaaccttg catccatata ctctagcgtt cagatcttat     540
agatttatgg aagttctgaa tatctcacgt tggtgtatca gacaattgct catataccgg     600
aaatcacgtc ctacttctat tcaagaattt acttcagtcg ttcgttcaaa aatagaaaga     660
aatgtagttt agtccagtga ccagtctcgt gtctacgtac ggttcttctg aatatatata     720
ttctgtttcc tggtagaatg tagtgaaaag ctgaaaattc ggtgaagaac atatctgaat     780
agctgtctta aattgatagt gtttgacaga aaatactcca cactgagcgt aacgtgaaag     840
tgcgtgtacg tgttgggtgc atgcaggtgg tctctgatcg cgaaccagct gccggggcgg     900
acggacaacg acgtcaagaa ctactggaac accaagctga gcaagaagct gaggcagcgg     960
```

| | |
|---|---|
| ggcatcgacc ccatcaccca ccgccccatc gccgatctca tgcagagcat cggcaccctc | 1020 |
| gccatccgcc cgccaccgag cgccgcgggt gcctcctcct cctcctacct ccccgtgaac | 1080 |
| ccaccggcgg cgccggggct ccagccgctg cacgacgacg tcaaatacca cacagtcctg | 1140 |
| aaccagcagc agcagcaggt catcacgctc ctcgaccccg acgcccagg ggcggcggcg | 1200 |
| tccccggagc accagctcaa gtggagcgac ttcctcgcgg acgacgccgc ggccctcgag | 1260 |
| gcggcgccgc aggtcgttct tggtcagtac caggaggccg cggtcgctgg tggcggagca | 1320 |
| cacgcgtatg gcgacactga cagtactgca gccgatggtg tcggcggggg cggggacgat | 1380 |
| agcgcagcgt cagcgttcat cgacgcgatg ctggacagcg acaagaagat gggcgtggac | 1440 |
| cagctcatcg ccgacctgct cgccgacccg gcatactact acggcggagg ctcttcctct | 1500 |
| tcgacgtcgg agctggggtg gggctgttga | 1530 |

<210> SEQ ID NO 6
<211> LENGTH: 1212
<212> TYPE: DNA
<213> ORGANISM: Triticum aestivum

<400> SEQUENCE: 6

| | |
|---|---|
| gcgacgtgcc cacggcgcgg tggccagtgg atcgcagggg ttgtctgtgg ggatgcccgg | 60 |
| gacggcgagt gccgaaacta tactttactc catgggaatt gagcgtcggg gtcggtcggt | 120 |
| cttcacgtgt cccgggaatg ggaagtgcaa ctctgtgagc aacgggcggg tggggtgct | 180 |
| gcatctgagg ctcgtaatgc tggtgccatg tctatccaca cgagagaagc tgcagcgtac | 240 |
| agtgtgaagc ctgataggtt ggttgcgatg cttagcgttg aagagaaac tactactagt | 300 |
| accgtacggg tctacgttag acacaaaaat cagagtggcg cagcggaagc gtggtgggcc | 360 |
| cataacccac aggtcccagg atcgaaacct ggctctgata tgattatttt tttgaatttt | 420 |
| tcttgattag atttgatact tctatctgtt tcttttccct ggattgagct tcgttttttt | 480 |
| ccctctctgc ccgaatggct tgctcggtgc ttcttcttcc ttcttctcta aaaccaacac | 540 |
| gagacgctga gacagcatgc atgcattttc tcctcgtaat actacaaact gtcaaggatc | 600 |
| acatgtgcgc cgccaacaca actgtcaaga cgatcgtaca aacgcgatga gcagaggcgc | 660 |
| ctgcgatatg atcgcatcgc cagctcccag gtgaaaaccg attccgcggc gctgatgtcg | 720 |
| tgaaaatcat catgtacaac tcgtgaaaat atttgaaaca gccccggcc ctccaccctc | 780 |
| acacacagcg tttgattaga ttagattaga ttaacccacc aacccgcatc tgaatatttg | 840 |
| atccctccct gattaagctg ttgatttgcc ggagggaaac agttgcaggc gtgccataaa | 900 |
| ctagggttaa agaagcgttt ccatcggatc gtcactaacc catgccatca ctagttaaat | 960 |
| gaggaggggg gaggtcatgc ttccgtcgcg tgccctcca ccatctggac atgttgttgc | 1020 |
| cgtgccccca tctctctcgc cggagcgccc cggcccctta tatgtacacc ggtgccaccc | 1080 |
| tgcagtgtgc gatctcgtcg gggggcaccg gaggttggtg cagtgctggt tctcgagcta | 1140 |
| tacatatata tatatctatc accgtttggc tgcttgtaga aggggagggg aaggagggtg | 1200 |
| gcgccggcct gg | 1212 |

<210> SEQ ID NO 7
<211> LENGTH: 927
<212> TYPE: DNA
<213> ORGANISM: Triticum aestivum

<400> SEQUENCE: 7

| | |
|---|---|
| tcgttcttgg tcagtaccag gatgccgcgg tcgctggtgg cggagcacac gcgtatggcg | 60 |

```
acactgacag tactgcagcc gatggtgtcg gcgtgggcgg ggaggatagc gcagcgtcag    120
cgttcatcga cgcgatgctg gacagcgaca agaagatggg cgtggaccag ctcatcgccg    180
acctgctcgc cgacccggca tactactacg gcggggctc ttcctcttcg acgtcggatc    240
tggggtgggg ctgttgaatg gggcggccgc cgtgctgcga caaggcgaac gtgaagaagg    300
ggccgtggac ggcggaggag gacgccaagc tgctcgccta cacctccaac catggcaccg    360
gcaactggac ctctgttccc cagagggcag ggctgaagcg gtgcgggaag agctgcaggc    420
tgaggtacac caactacctg aggcccaatc tcaagcacga gaacttcacg caggaggagg    480
aggagctcat cgtcaccctc catgccatgc tgggaagcag gtggtctctg atcgcgaacc    540
agctgccggg gcggacggac aacgacgtca agaactactg gaacaccaag ctgagcaaga    600
agctgcggca gcggggcatc gaccccatca cccaccgccc catcgccgac ctcatgcaga    660
gcatcggcac cctcgccatc cgcccgccac cgagcgccgc gggtgcctcc tcctcctcct    720
acctccccgt gaacccagcg gcggcgccgg ggctccagcc gctgcacgac gacgtcaaat    780
accacgcagt cctgaaccag cagcagcagc aggtcatcac gctcctcgac gccgacgcgc    840 cagggggcggc ggcgtccccg gaccaccgc tcaagtggag cgacttcctc gccgacgacg    900
ccgccgcctt cgaggcggcg ccgcagg                                       927
```

<210> SEQ ID NO 8
<211> LENGTH: 308
<212> TYPE: PRT
<213> ORGANISM: Triticum aestivum

<400> SEQUENCE: 8

```
Met Gly Arg Pro Pro Cys Cys Asp Lys Ala Asn Val Lys Lys Gly Pro
1               5                   10                  15

Trp Thr Ala Glu Glu Asp Ala Lys Leu Leu Ala Tyr Thr Ser Asn His
                20                  25                  30

Gly Thr Gly Asn Trp Thr Ser Val Pro Gln Arg Ala Gly Leu Lys Arg
            35                  40                  45

Cys Gly Lys Ser Cys Arg Leu Arg Tyr Thr Asn Tyr Leu Arg Pro Asn
        50                  55                  60

Leu Lys His Glu Asn Phe Thr Gln Glu Glu Glu Leu Ile Val Thr
65                  70                  75                  80

Leu His Ala Met Leu Gly Ser Arg Trp Ser Leu Ile Ala Asn Gln Leu
                85                  90                  95

Pro Gly Arg Thr Asp Asn Asp Val Lys Asn Tyr Trp Asn Thr Lys Leu
            100                 105                 110

Ser Lys Lys Leu Arg Gln Arg Gly Ile Asp Pro Ile Thr His Arg Pro
        115                 120                 125

Ile Ala Asp Leu Met Gln Ser Ile Gly Thr Leu Ala Ile Arg Pro Pro
    130                 135                 140

Pro Ser Ala Ala Gly Ala Ser Ser Ser Tyr Leu Pro Val Asn Pro
145                 150                 155                 160

Ala Ala Ala Pro Gly Leu Gln Pro Leu His Asp Asp Val Lys Tyr His
                165                 170                 175

Ala Val Leu Asn Gln Gln Gln Gln Val Ile Thr Leu Leu Asp Ala
            180                 185                 190

Asp Ala Pro Gly Ala Ala Ala Ser Pro Asp His Pro Leu Lys Trp Ser
        195                 200                 205

Asp Phe Leu Ala Asp Asp Ala Ala Ala Phe Glu Ala Ala Pro Gln Val
```

```
                210                 215                 220
Val Leu Gly Gln Tyr Gln Asp Ala Ala Val Ala Gly Gly Ala His
225                 230                 235                 240

Ala Tyr Gly Asp Thr Asp Ser Thr Ala Ala Asp Gly Val Gly Val Gly
                245                 250                 255

Gly Glu Asp Ser Ala Ala Ser Ala Phe Ile Asp Ala Met Leu Asp Ser
            260                 265                 270

Asp Lys Lys Met Gly Val Asp Gln Leu Ile Ala Asp Leu Leu Ala Asp
        275                 280                 285

Pro Ala Tyr Tyr Tyr Gly Gly Gly Ser Ser Ser Ser Thr Ser Asp Leu
        290                 295                 300

Gly Trp Gly Cys
305
```

<210> SEQ ID NO 9
<211> LENGTH: 1530
<212> TYPE: DNA
<213> ORGANISM: Triticum aestivum

<400> SEQUENCE: 9

```
atggggcggc cgccgtgctg cgacaaggcc aacgtgaaga aggggccgtg gacggcggag      60
gaggacgcca agctgctcgc ctacacctcc aaccatggca ccggcaactg gacctctgtt     120
ccccagaggg caggtcggaa ccctccccccc ggccggccgg atcgacgtcc gtcatggaaa    180
tggtgttggt cttgcatggt ttctggctga tgtgtgttgc atcatggatg cgtgcgtgct     240
gcagggctga agcggtgcgg gaagagctgc aggctgaggt acaccaacta cctgaggccc     300
aacctcaagc acgagaactt cacgcaggag gaggaggagc tcatcgtcac cctccatgcc     360
atgctgggaa gcaggtgcgt ctctctgtgt agtacatgca tgtttctgcc atcagttact     420
ttctcgattt tgtcatcaag ttttcggtga atgcgaaact ttgctatgga ccgactgctg     480
tttctgtcat cattcctgct ataaaccttg catccatata ctctagcgtt cagatcttat     540
agatttatgg aagttctgaa tatctcacgt tggtgtatca gacaattgct catataccgg     600
aaatcacgtc ctacttctat tcaagaattt acttcagtcg ttcgttcaaa aatagaaaga     660
aatgtagttt agtccagtga ccagtctcgt gtctacgtac ggttcttctg aatatatata     720
ttctgttttcc tggtagaatg tagtgaaaag ctgaaaattc ggtgaagaac atatctgaat    780
agctgtctta aattgatagt gtttgacaga aaatactcca cactgagcgt aacgtgaaag     840
tgcgtgtacg tgttgggtgc atgcaggtgg tctctgatcg cgaaccagct gccggggcgg     900
acggacaacg acgtcaagaa ctactggaac accaagctga gcaagaagct gaggcagcgg     960
ggcatcgacc ccatcaccca ccgcccatc gccgatctca tgcagagcat cggcacccctc   1020
gccatccgcc cgccaccgag cgccgcgggt gcctcctcct cctcctacct ccccgtgaac    1080
ccaccggcgg cgccgggct ccagccgctg cacgacgacg tcaaatacca cacagtcctg    1140
aaccagcagc agcagcaggt catcacgctc ctcgaccccg acgcgccagg ggcggcggcg    1200
tccccggagc accagctcaa gtggagcgac ttcctcgcgg acgacgccgc ggccctcgag    1260
gcggcgccgc aggtcgttct tggtcagtac caggaggccg cggtcgctgg tggcggagca    1320
cacgcgtatg gcgacactga cagtactgca gccgatggtg tcggcggggg cggggacgat    1380
agcgcagcgt cagcgttcat cgacgcgatg ctggacagcg acaagaagat gggcgtggac    1440
cagctcatcg ccgacctgct cgccgacccg gcatactact acggcggagg ctcttcctct    1500
tcgacgtcgg agctggggtg gggctgttga                                     1530
```

<210> SEQ ID NO 10
<211> LENGTH: 1102
<212> TYPE: DNA
<213> ORGANISM: Triticum aestivum

<400> SEQUENCE: 10

| | | | | | |
|---|---|---|---|---|---|
| cgacgtgccc | acggcgcggt | ggccggtgga | tcgcaggggt | tgtcggtggg | aatgcctggg | 60 |
| acggagagcg | tccaaactgt | agtagtagta | ctttactcca | tgggaactgg | gcgtcggggt | 120 |
| cggtcggtct | tcacgtgtcc | cggggatggg | aagtgcaact | ctgtgtgctg | catctgatgc | 180 |
| tcgtattgct | ggtgccatgt | gtatccacag | gagagatgc | gctttgggag | tctagagtgt | 240 |
| gtgtcaagcg | gcattgctcg | gtgctcagcg | ttggaagcat | aagacaagta | ccgcacgaga | 300 |
| gatgctgttt | cttttcctgg | atttaacttc | gtatcttccc | aagtggctta | ctgactcagt | 360 |
| agtacaaaac | gttacacgcc | aaaccacaaa | atgctcggtg | cttcttctcc | cttcttctct | 420 |
| gaaaccaaca | cgagacgctg | agacagcatg | cattttctcc | tcgtaatact | gcaactgtca | 480 |
| agcatcacat | ctccggcgcc | aacgcaactg | tcaatacgat | cgtacaaaag | cgatgagcag | 540 |
| aggcgcctgc | gatatgatcg | catcgccagc | tcccaggtga | aaaccgattc | cgcggcgctg | 600 |
| atgtcgtgaa | aatcatcatg | tccaactcgt | gaaaatattt | gaaacagccc | ccggcccctc | 660 |
| caccctcaca | cacagcgttt | gattagatta | gatcggatta | acccaccaac | ccgcatctga | 720 |
| atatttgatc | cctccctgat | taagcggttg | atttgccgga | gggaaacagt | tgcaggcgtg | 780 |
| ccataaacta | gggttaaaga | agcgtttcca | tcggatcgtc | actaacccat | gcatgccatc | 840 |
| acttgttaaa | tgaggagggg | ggaggtcatg | cttccgtcgc | gtgcccctcc | accatctgga | 900 |
| catgttgttg | ccgtgcagtg | cccctctctc | tctcgccgga | gcgccccggc | ccctatatgt | 960 |
| acaccggtgc | caccctgcag | tgcgatctcg | tcgggggca | ccgcaccgga | ggttggtgca | 1020 |
| gtgcgggggt | tctcgagcta | tatatctatc | accgtttggc | tgcttgtaga | aggggagggg | 1080 |
| aaggagggtg | gcgccggccg | gg | | | | 1102 |

<210> SEQ ID NO 11
<211> LENGTH: 927
<212> TYPE: DNA
<213> ORGANISM: Triticum aestivum

<400> SEQUENCE: 11

| | | | | | |
|---|---|---|---|---|---|
| atggggcggc | cgccgtgctg | cgacaaggcc | aacgtgaaga | aggggccgtg | gacggcggag | 60 |
| gaggacgcca | agctgctcgc | ctacacctcc | aaccatggca | ccggcaactg | gacctctgtt | 120 |
| ccccagaggg | cagggctgaa | gcggtgcggg | aagagctgca | ggctgaggta | caccaactac | 180 |
| ctgaggccca | acctcaagca | cgagaacttc | acgcaggagg | aggaggagct | catcgtcacc | 240 |
| ctccatgcca | tgctgggaag | caggtggtct | ctgatcgcga | accagctgcc | ggggcggacg | 300 |
| gacaacgacg | tcaagaacta | ctggaacacc | aagctgagca | agaagctgag | gcagcggggc | 360 |
| atcgacccca | tcacccaccg | ccccatcgcc | gatctcatgc | agagcatcgg | caccctcgcc | 420 |
| atccgcccgc | caccgagcgc | cgcgggtgcc | tcctcctcct | cctacctccc | cgtgaaccca | 480 |
| ccggcggcgc | cggggctcca | gccgctgcac | gacgacgtca | ataccacac | agtcctgaac | 540 |
| cagcagcagc | agcaggtcat | cacgctcctc | gaccccgacg | cgccagggc | ggcggcgtcc | 600 |
| ccggagcacc | agctcaagtg | gagcgacttc | ctcgcggacg | acgccgcggc | cctcgaggcg | 660 |
| gcgccgcagg | tcgttcttgg | tcagtaccag | gaggccgcgg | tcgctggtgg | cggagcacac | 720 |

```
gcgtatggcg acactgacag tactgcagcc gatggtgtcg gcgggggcgg ggacgatagc    780
gcagcgtcag cgttcatcga cgcgatgctg gacagcgaca agaagatggg cgtggaccag    840
ctcatcgccg acctgctcgc cgacccggca tactactacg gcggaggctc ttcctcttcg    900
acgtcggagc tggggtgggg ctgttga                                        927
```

<210> SEQ ID NO 12
<211> LENGTH: 308
<212> TYPE: PRT
<213> ORGANISM: Triticum aestivum
<400> SEQUENCE: 12

```
Met Gly Arg Pro Pro Cys Cys Asp Lys Ala Asn Val Lys Lys Gly Pro
1               5                   10                  15

Trp Thr Ala Glu Glu Asp Ala Lys Leu Leu Ala Tyr Thr Ser Asn His
            20                  25                  30

Gly Thr Gly Asn Trp Thr Ser Val Pro Gln Arg Ala Gly Leu Lys Arg
        35                  40                  45

Cys Gly Lys Ser Cys Arg Leu Arg Tyr Thr Asn Tyr Leu Arg Pro Asn
    50                  55                  60

Leu Lys His Glu Asn Phe Thr Gln Glu Glu Glu Leu Ile Val Thr
65                  70                  75                  80

Leu His Ala Met Leu Gly Ser Arg Trp Ser Leu Ile Ala Asn Gln Leu
                85                  90                  95

Pro Gly Arg Thr Asp Asn Asp Val Lys Asn Tyr Trp Asn Thr Lys Leu
            100                 105                 110

Ser Lys Lys Leu Arg Gln Arg Gly Ile Asp Pro Ile Thr His Arg Pro
        115                 120                 125

Ile Ala Asp Leu Met Gln Ser Ile Gly Thr Leu Ala Ile Arg Pro Pro
    130                 135                 140

Pro Ser Ala Ala Gly Ala Ser Ser Ser Tyr Leu Pro Val Asn Pro
145                 150                 155                 160

Pro Ala Ala Pro Gly Leu Gln Pro Leu His Asp Asp Val Lys Tyr His
            165                 170                 175

Thr Val Leu Asn Gln Gln Gln Gln Val Ile Thr Leu Leu Asp Pro
        180                 185                 190

Asp Ala Pro Gly Ala Ala Ala Ser Pro Glu His Gln Leu Lys Trp Ser
    195                 200                 205

Asp Phe Leu Ala Asp Asp Ala Ala Leu Glu Ala Pro Gln Val
    210                 215                 220

Val Leu Gly Gln Tyr Gln Glu Ala Ala Val Ala Gly Gly Gly Ala His
225                 230                 235                 240

Ala Tyr Gly Asp Thr Asp Ser Thr Ala Ala Asp Gly Val Gly Gly Gly
            245                 250                 255

Gly Asp Asp Ser Ala Ala Ser Ala Phe Ile Asp Ala Met Leu Asp Ser
        260                 265                 270

Asp Lys Lys Met Gly Val Asp Gln Leu Ile Ala Asp Leu Leu Ala Asp
    275                 280                 285

Pro Ala Tyr Tyr Tyr Gly Gly Gly Ser Ser Ser Thr Ser Glu Leu
    290                 295                 300

Gly Trp Gly Cys
305
```

<210> SEQ ID NO 13
<211> LENGTH: 1965

<212> TYPE: DNA
<213> ORGANISM: Zea mays

<400> SEQUENCE: 13

```
atggggaggc cgccgtgctg cgacaaggcg aacgtgaaga aggggccgtg gacgccggag      60
gaggacgcca agctgctggc ctacacctcc acccatggca ccggcaactg gaccaacgtg     120
ccccaacgag caggtgatcg tgccgccgtg caccatgcat tttgttgttt tgtttgtggc     180
tcatgacgag gcgctggcgg acggtgcggc atgatgtgat atgatgcgca gggctcaaga     240
ggtgcggcaa gagctgcagg ctgaggtaca ccaactacct gcgtcccaac ctgaagcacg     300
agaacttcac ccaggaggag gaagacctca tcgtcaccct ccacgccatg ctcggaagca     360
ggtacgcagt acagcgctgc agaatcatgt tcatggccgt ttgctttgat taattccaca     420
caacatgcat gcatgcattc gcatcatcct tcagcttcct cacctaggaa ccggatagat     480
ccttcgtagt gctgcagata atccgattt atcttctatc tcaatgcggt tttgaaacta     540
agtatatcac attagatagt gttaattgct gaactgaaga agatctgaat tatgaaagac     600
acgtccgatc ctgcagctct tacaaaggtt ttctcttttt ttaagaaaaa aaatctgcct     660
ccatttaccg taggtgattc ttcctggaca tttttgttcc gcggcaaatt aaatagtaat     720
tgaacctatg tttcacatga gaaaattgct agtaatcggg tgtttggaaa tgattctgaa     780
tcttgcggac ttaaatctga aaccaatcgt cccaatgcaa ttcgctagag caattgatct     840
gttcatttcc aatcagtcaa tcaccaagcc ctagaaaacg gacagctagt tcagtagttc     900
ccgcatcagc gccattgctg atggatcgaa cagctgacgc gaatgaaaac gacatgacac     960
cgtcggggag atcgttggat gagttccgag cgataacgaa ctgtacgggc agtgacatac    1020
acaatgcgtg cgcgcatgca aagttgattg gaatccaatg cgtccagctg ataggagtat    1080
ttacactaca gatacactca tagttgctag ggtaggtgat cttgagatgc atcttgatcc    1140
ctcgctagtt agtactattc atgctatttg ctgcagttaa ttaacgggtc cggcctgcaa    1200
tggaaattgt agtgcgctag accgcgcgct gctgatctgg gccacgaact gcgcgcgttt    1260
gcatgcaggt ggtctctgat cgcgaaccag ctgccgggaa ggacggacaa cgacgtgaag    1320
aactactgga acacgaagct gagcaagaag ctgcggcagc gcgggatcga ccccctcacc    1380
caccgcccca tcgccgacct catgcacagc atcggcgcgc tggccatccg cccgccgcag    1440
ccggcgacct cccctaacgg ctccgccgcc taccttcctg cgccggcgct cccgctcgtc    1500
cacgacgtcg cgtaccacgc cgccggaatg ctgccgccga cgccggcgcc gccccggcag    1560
gtcgtcatcg cgcgcgtgga agcggacgcg cccgcgtcgc cgacgagca cgggcacgag    1620
ctcaagtgga gcgacttcct cgccgacgac gccgccgccg cggcggcggc cgcggccgag    1680
gcgcagcagc agctggccgt tgttgggcag taccaccacg aggccaacgc cgggagcagc    1740
agcgctgcgg ccggcggtaa cgacggttgt ggcattgccg tcgcggcga cgacggcgca    1800
gcggcgttca tcgacgccat cctggactgc gacaaggaga cgggggtgga ccagctcatc    1860
gccgagctgc tggccgaccc ggcctactac gcgggctcct cctcctcctc ctcctcctcg    1920
tccgggatgg gctgggccgg catgggcctg ctgaacgctg attaa                    1965
```

<210> SEQ ID NO 14
<211> LENGTH: 966
<212> TYPE: DNA
<213> ORGANISM: Zea mays

<400> SEQUENCE: 14

| | |
|---|---|
| tccatccgga aacgaaaccg ctagagctaa ggtctcaatc aacacagtgt cgagtgtgga | 60 |
| caagttggtg ctgctggact gctggcacat atacgaaaac gaaagcaggt caggtggaga | 120 |
| gcagaggagg agccgtgccg caggcagcta ttttatagct gctcgacgcg ggtgctacac | 180 |
| gcgtccagtg ggaacggctg cctttctcgg agcgcgtagc ctggcgcgcg ctggttggct | 240 |
| ccactctgcg gcgttttttc aatttgtttt tttactcctc tttctgcggg gaggcggcga | 300 |
| gatgtcgggt ggacggtgga tcggcaaacg aggggcctgt cggtgtggac ggtgagatg | 360 |
| cactaagcct tctttgagca ggtcacatct tttgcaagtt catggtgccc agtacgtagt | 420 |
| ggacagcaga gaagctccgg gcggggccaa tgcaaaaccg atctggcggc gtcgatgtcg | 480 |
| tgaaaaccgt catgcccaac tcgtgaaaat tttaaacccc agcatcacca ggccgctagc | 540 |
| tccgtctctc aacgataaga ttacccacac caacccgcgc tcgccctaat gagctgttga | 600 |
| tttgccggag ggaagcagtt gcgcgcgcgc tctactatac tgtcgccgcc gccataaaca | 660 |
| aagagggaac cagcgtctct tccctaatct aaccatctcc tgcgtgattg acactaacca | 720 |
| tgccgtggct agttaaatga cggggggcggg gtcacgcctt cgttgcgtgc ctccacctcc | 780 |
| cccctcggc gccccaacg acatgttgtt accgtggctg tggcagccgg ccggtctcct | 840 |
| tctccatcca tatgtaccgg cagcatcgta tcaccttttt ttctgcagcg gtgatctcat | 900 |
| ctaggcgtcg gtcagagctc tctcgagctc gccagcggtg gttggtcgtc gtcgtcgtcg | 960 |
| tcgtcg | 966 |

<210> SEQ ID NO 15
<211> LENGTH: 959
<212> TYPE: DNA
<213> ORGANISM: Zea mays

<400> SEQUENCE: 15

| | |
|---|---|
| atggggaggc cgccgtgctg cgacaaggcg aacgtgaaga aggggccgtg gacgccggag | 60 |
| gaggacgcca agctgctggc ctacacctcc acccatggca ccggcaactg gaccaacgtg | 120 |
| ccccaacgag cagggctcaa gaggtgcggc aagagctgca ggctgaggta caccaactac | 180 |
| ctgcgtccca acctgaagca cgagaacttc acccaggagg aggaagacct catcgtcacc | 240 |
| ctccacgcca tgctcggaag caggtggtct ctgatcgcga accagctgcc gggaaggacg | 300 |
| gacaacgacg tgaagaacta ctggaacacg aagctgagca agaagctgcg gcagcgcggg | 360 |
| atcgaccccc tcacccaccg ccccatcgcc gacctcatgc acagcatcgg cgcgctggcc | 420 |
| atcgcccgc cgcagccggc gacctcccct aacggctccg ccgcctacct tcctgcgccg | 480 |
| gcgctcccgc tcgtccacga cgtcgcgtac cacgccgccg gaatgctgcc gccgacgccg | 540 |
| gcgccgcccc ggcaggtcgt catcgcgcgc gtggaagcgg acgcgcccgc gtcgccgacg | 600 |
| gagcacgggc acgagctcaa gtggagcgac ttcctcgccg acgacgccgc cgccgcggcg | 660 |
| gcggccgcgg ccgaggcgca gcagcagctg ccgttgttg ggcagtacca ccacgaggcc | 720 |
| aacgccggga gcagcagcgc tgcggccggc ggtaacgacg gttgtggcat tgccgtcggc | 780 |
| ggcgacgacg gcgcagcggc gttcatcgac gccatcctgg actgcgacaa ggagacgggg | 840 |
| gtggaccagc tcatcgccga gctgctggcc gacccggcct actacgcggg ctcctcctcc | 900 |
| tcctcctcct cctcgtccgg gatgggctgg gccggcatgg gcctgctgaa cgctgatta | 959 |

<210> SEQ ID NO 16
<211> LENGTH: 319
<212> TYPE: PRT
<213> ORGANISM: Zea mays

<400> SEQUENCE: 16

```
Met Gly Arg Pro Pro Cys Cys Asp Lys Ala Asn Val Lys Lys Gly Pro
1               5                   10                  15

Trp Thr Pro Glu Glu Asp Ala Lys Leu Leu Ala Tyr Thr Ser Thr His
            20                  25                  30

Gly Thr Gly Asn Trp Thr Asn Val Pro Gln Arg Ala Gly Leu Lys Arg
        35                  40                  45

Cys Gly Lys Ser Cys Arg Leu Arg Tyr Thr Asn Tyr Leu Arg Pro Asn
    50                  55                  60

Leu Lys His Glu Asn Phe Thr Gln Glu Glu Asp Leu Ile Val Thr
65                  70                  75                  80

Leu His Ala Met Leu Gly Ser Arg Trp Ser Leu Ile Ala Asn Gln Leu
                85                  90                  95

Pro Gly Arg Thr Asp Asn Asp Val Lys Asn Tyr Trp Asn Thr Lys Leu
            100                 105                 110

Ser Lys Lys Leu Arg Gln Arg Gly Ile Asp Pro Leu Thr His Arg Pro
        115                 120                 125

Ile Ala Asp Leu Met His Ser Ile Gly Ala Leu Ala Ile Arg Pro Pro
130                 135                 140

Gln Pro Ala Thr Ser Pro Asn Gly Ser Ala Ala Tyr Leu Pro Ala Pro
145                 150                 155                 160

Ala Leu Pro Leu Val His Asp Val Ala Tyr His Ala Ala Gly Met Leu
                165                 170                 175

Pro Pro Thr Pro Ala Pro Pro Arg Gln Val Val Ile Ala Arg Val Glu
            180                 185                 190

Ala Asp Ala Pro Ala Ser Pro Thr Glu His Gly His Glu Leu Lys Trp
        195                 200                 205

Ser Asp Phe Leu Ala Asp Ala Ala Ala Ala Ala Ala Ala Ala Ala Ala
210                 215                 220

Glu Ala Gln Gln Gln Leu Ala Val Val Gly Gln Tyr His His Glu Ala
225                 230                 235                 240

Asn Ala Gly Ser Ser Ser Ala Ala Ala Gly Gly Asn Asp Gly Cys Gly
                245                 250                 255

Ile Ala Val Gly Gly Asp Asp Gly Ala Ala Ala Phe Ile Asp Ala Ile
            260                 265                 270

Leu Asp Cys Asp Lys Glu Thr Gly Val Asp Gln Leu Ile Ala Glu Leu
        275                 280                 285

Leu Ala Asp Pro Ala Tyr Tyr Ala Gly Ser Ser Ser Ser Ser Ser
    290                 295                 300

Ser Ser Gly Met Gly Trp Ala Gly Met Gly Leu Leu Asn Ala Asp
305                 310                 315
```

<210> SEQ ID NO 17
<211> LENGTH: 2268
<212> TYPE: DNA
<213> ORGANISM: Oryza sativa

<400> SEQUENCE: 17

```
atgggcggc  cgccgtgctg  cgacaaggcg  aacgtgaaga  aggggccgtg  gacggcggag    60
gaggacgcca  agctgctggc  gtacacctcc  acccacggca  ccggcaactg  gacctccgtt   120
cctcagcgag  caggtcgtga  aaatcaacga  tatcgatcgc  cgttgctgct  gctgccgatg   180
ggatcgagat  tgcaattaga  gacgcatttg  atcacatcag  atcagatcaa  aatatggtgt   240
```

-continued

```
cattgtttat cacttttttt tccctttgt tttgttctgt aaaaattgca tgggggtga      300 tgtgggtgca ggtttgaaga ggtgcgggaa gagctgcagg ctgaggtaca ccaactacct    360
gaggcccaac ctgaagcacg agaacttcac gcaggaggag aagagctca tcgtcaccct     420 ccacgccatg ctgggcagca ggtatatcat cgtgttacgc tcagcttgtc ccgttatctc    480
gtcatttcag acgtcaccat gcttttgcat gtgtggtgag tggtgtaata cactccgtcc    540
gttggaccct cctgcttgat tgatctgtcg ttgctgtttt cgaattgata atccacgtgc    600
tagtttgtca tcgactcaga tttggcgaat cggtgttcgt gatttgtatc tgatttctgc    660
gtgtaatgct aagcatgttg cgaactacct tgatcctata ataagcgtaa ttataggttt    720
cagtgtccaa ctttatctaa caatcttatt taaaatattt taatgattag tattttttt    780 attgttatta gatgataaaa tatgaacagt actttatgcg tgtcttaact tttaaaaaaa    840
attcataaac ttttaaata agacggacaa ttaaatgttg ggcacgtaaa cttatagctg     900
cacgtataat aagacggagg gagtaattcc cttgaatcct aacatgagat aaatagctag    960
tgcacataat tggctgctct aatgtacttt ggcagtatga tgctgatgca attagcattt    1020
acatttaatg ttctaaaaat tttatggaat caacctagat gtgaacgaaa atggcatgac    1080
aaaataatca agatccctga gcggtaacaa actgatacac acacaatgca tgtaacgcca    1140
ctattcacag ttaattagta ctgtactact aattaactta gttaatacta gcactagtta    1200
ttttacactc taaacaaatg ctgcgagatc atctctaccc tcaatcagaa atgggagcta    1260
gtttgacaca tcaacacaca atttggactg agatcattga gcatgcatgt aatttctact    1320
ccatccgttt cagattataa gatattttaa ctttgatcaa agttaaactg ttttaaattt    1380
gactaagttt atagacaaat atagtaatat ttacattacc aaattagttt tattaaatta    1440
ataataaaat atattttat aataaattta tcttaagtca aaaatattat tatttttct      1500 atcaaattaa tcaaacttga agcagtttaa cttttatcta agtcaaaaac atccgaggga    1560
gtataaccaa agttgtgcgc gtgcatcaat caaatgcgcg tgattggcag gtggtcgctg    1620
atcgcgaacc agctgccggg gaggacggac aacgacgtga agaactactg gaacaccaag    1680
ctgagcaaga agctgcggca gcgtggcatc gaccccatca cccaccgccc catcgccgac    1740
ctcatgcaga gcatcggcac gctcgccatc cgcccccctc ccgccgccgg cgccgcgccg    1800
ccgccctgcc tcccggtgtt ccacgacgcg ccgtacttcg ccgccctgca gcatcagcat    1860
cagcagcagc aggtcgtcac gcacgtcgac gccgacgcgc ccgcgtcgcc cgactcgcag    1920
catctgcagc tcaactggag cgacttcctc gccgacgacg ccgcggggca cggcgccgac    1980
gcgccggcgc cgcaggctgc tctcggccag tatcaggagg ggtcagcacc ggcggcgact    2040
gccgtcgtgg gcggaggccg cgcgttcggt gacgtcgacg gtgcatcagc tggcgtcggc    2100
gccggcacgg acgacggcgc cggggctgcg tcggcgttca ttgacgcgat cctcgactgc    2160
gacaaggaga tggggtgga ccagctcatc gccgagatgc tcgccgaccc ggcatactac     2220
ggcggcggtg gcggctcctc ctcgtcggag ctcggctggg gttgctaa                 2268
```

<210> SEQ ID NO 18
<211> LENGTH: 1316
<212> TYPE: DNA
<213> ORGANISM: Oryza sativa

<400> SEQUENCE: 18

```
tggaacgcat ggcaagaagg gtagtagtac gccgtacgat cagacggtta cgcgtgatgt    60
aacgtgtcga cgatccatga tccatcgact aggaggtcat caccggggcc cacctgcccc    120
```

```
ccgggaggga ggttgcgttg gtgggcccgg gggagtcaaa cgacggcgga gatgagacgg      180
agagggcccc gccgttatgc tgtcgggctg tcggcgcttc acacagtggc cgtccgtacg      240
tgatgtcgcc tcctccagcc gtctccaagt acagctatac tagtagagta gtatactact      300
gctcctatac tgtacagtat accccgtact gtactagtgg caatatcact caaaacacat      360
ggagcattat gtatacatac aaccatcatg aatatatatt cttctagaaa cgaaaaaagc      420
atgcacatcg cccctatttt ggggagttag ttaattagaa tattcagctg ataggaatct      480
ttaaaagaat cggataatta attaaccata atttctgtca tgcagggtat caaatgtacc      540
acattaaatt tttctagcaa tgtaaaatct atgcatgcac cacactggac agcgaaatat      600
atactccctt cgtactcata aagggaatcg ttttggacag tgacacggtc tccaaaacac      660
aactttgact ttttgtttct ataaaaatat ttattgaaaa gtgatatatg tatacttttta     720 tgaaagtatt tttcaagaca aatctattca tatattttt atattttcaa attcaataat       780
ttaaaaatta ttcatgattt atattctcaa ggtttgactt aaatattatc ctaaacgatt      840
ttctttatga gtacggaggg agtatactta caattttgta cctctcgagt acgataaaat      900
ctctctccag attttgcgcg agaatatctg aacggtttgt agctgcatta tctagaagat      960
ctcttgaaaa tgaacatagt tcatatatta cctcatgtat gtggtgctat atatatatat     1020
gtttcactgg atggttaatt acttctggga aactgttta acatgcaaca tgtactagct     1080
agctagctcc atttctcttc attccattcc agagagctcc tctatttctt ttactaatct     1140 ttttcccta tcaaaaagcc accagctttc tagtaagcaa cactagtcac tttaacctcc      1200
tcccttgctt ttgcttacta caccttgcat ctctctctgg taaccgtatc gtggtggaag     1260
gaaaggaaga aaggagtgta ctgggtagct cagctcagct cagctaggca gtggcc         1316
```

<210> SEQ ID NO 19
<211> LENGTH: 579
<212> TYPE: DNA
<213> ORGANISM: Oryza sativa

<400> SEQUENCE: 19

```
atgtcagagc gtgtgttcgc cgagctcgcg accatccact accaaaaaag ccttccatgt       60
cgccactcct ttgaccccc tcgcaccaca ccaattctcc atctatatat catccacctt      120
cttcttcctc ctctcattgc cattgtgtgt ttgtgttaca ttgcaatcgt gccatttgaa      180
gaagaggagg agaggatgag gatgcaggtg gtggagacgg cggcggtgga ggaggaggag      240
gcggcggcgc cgatgatgtc ggtgtacgag agggtggcga ggatggcgag cgggaacgcg      300
gtggtggtgt tcagcgcgag cgggtgctgc atgtgccacg tcgtcaagcg cctcctcctc      360
ggcctcggcg tcgccccgc cgtctacgag ctcgaccagc tcgccgccgc cgccgacatc      420
caggccgcgc tgtcgcagct cctcccgccg ggccagccgc cggtgcccgt cgtgttcgtc      480
ggcggcaggc tcctcggcgg cgtcgagaag gtgatggcgt gccacatcaa tggcacccttc     540 gtccccctcc tcaagcaggc cggcgccctc tggctctga                             579
```

<210> SEQ ID NO 20
<211> LENGTH: 306
<212> TYPE: PRT
<213> ORGANISM: Oryza sativa

<400> SEQUENCE: 20

```
Met Gly Arg Pro Pro Cys Cys Asp Lys Ala Asn Val Lys Lys Gly Pro
1               5                   10                  15
```

```
Trp Thr Pro Glu Glu Asp Ala Lys Leu Leu Ala Tyr Thr Ser Thr His
             20                  25                  30
Gly Thr Gly Asn Trp Thr Ser Val Pro Gln Arg Ala Gly Leu Lys Arg
         35                  40                  45
Cys Gly Lys Ser Cys Arg Leu Arg Tyr Thr Asn Tyr Leu Arg Pro Asn
 50                  55                  60
Leu Lys His Glu Asn Phe Thr Gln Glu Glu Glu Leu Ile Val Thr
65                  70                  75                  80
Leu His Ala Met Leu Gly Ser Arg Trp Ser Leu Ile Ala Asn Gln Leu
                 85                  90                  95
Pro Gly Arg Thr Asp Asn Asp Val Lys Asn Tyr Trp Asn Thr Lys Leu
            100                 105                 110
Ser Lys Lys Leu Arg Gln Arg Gly Ile Asp Pro Ile Thr His Arg Pro
        115                 120                 125
Ile Ala Asp Leu Met Gln Ser Ile Gly Thr Leu Ala Ile Arg Pro Pro
130                 135                 140
Pro Ala Gly Ala Ala Pro Pro Cys Leu Pro Val Phe His Asp
145                 150                 155                 160
Ala Pro Tyr Phe Ala Ala Leu Gln His Gln His Gln Gln Gln Val
                165                 170                 175
Val Thr His Val Asp Ala Asp Ala Pro Ala Ser Pro Asp Ser Gln His
            180                 185                 190
Leu Gln Leu Asn Trp Ser Asp Phe Leu Ala Asp Ala Ala Gly His
        195                 200                 205
Gly Ala Asp Ala Pro Ala Pro Gln Ala Ala Leu Gly Gln Tyr Gln Glu
    210                 215                 220
Gly Ser Ala Pro Ala Ala Thr Ala Val Val Gly Gly Arg Ala Phe
225                 230                 235                 240
Gly Asp Val Asp Gly Ala Ser Ala Gly Val Gly Ala Gly Thr Asp Asp
                245                 250                 255
Gly Ala Gly Ala Ala Ser Ala Phe Ile Asp Ala Ile Leu Asp Cys Asp
            260                 265                 270
Lys Glu Met Gly Val Asp Gln Leu Ile Ala Glu Met Leu Ala Asp Pro
        275                 280                 285
Ala Tyr Tyr Gly Gly Gly Gly Ser Ser Ser Glu Leu Gly Trp
    290                 295                 300
Gly Cys
305
```

<210> SEQ ID NO 21
<211> LENGTH: 414
<212> TYPE: DNA
<213> ORGANISM: Triticum aestivum

<400> SEQUENCE: 21

```
atgttgagga tgcagcagca ggtggagggc gtggtgggcg gcggcatcgt ggccgaggcg      60
gaggaggcgg cggtgtacga gcgggtggct cgcatggcca gcggcaacgc cgtggtcgtc     120
ttcagcgcca gcggctgctg catgtgccac gtcgtcaagc gcctcctgct ggcctgggga    180
gtcggcccca ccgtctacga gttggaccag atgggcggcg ccgggcggga gatccaggcg    240
gccctggcgc agctgctgcc ccccggaccc ggcgccggcc accaccagca gccgccggtg    300
cccgtggtgt cgtcggcgg gaggctcctg ggaggcgtgg agaaggtgat ggcgtgccac    360
atcaacggca cgctcgtccc gctcctcaag gacgccggcg cgctctggct ctga          414
```

<210> SEQ ID NO 22
<211> LENGTH: 1052
<212> TYPE: DNA
<213> ORGANISM: Triticum aestivum

<400> SEQUENCE: 22

```
gttatgcatg cggccggggt ctggtggggg aatcgctcac gtgaaggcaa tgtgggacgt      60
gaaggaggtg acgatgggcg tgacggcgtt tggtggcagt ggggccgagg agtcaaacgg     120
cggctgaggg ggacgtcgtg ctgtcggctt gtcggctgcc gtgacgatcg acgcttgtct     180
tgtcacgtcg tgtccatgct tcgttccctt cctccctccc tccctccgta tagtcggcgt     240
tcaaattctt ggcctgcaga tacatgtaaa ttcctaagtt tgaaggcaca ttggttcatt     300
ataaagaaaa tagttttgct gaccgagact tcgttatatc tcagttgatg ttattttttct     360
ttaattttgc atgaagattc gtacaaaaaa tatattttca gttttttttc tcttttttctt     420
cttacatact actgtatatc atttgagtga gacttggtta agtctcagtc gactgagacc     480
taaccacacc ctaaaagaaa agagtactat taattgattt tgctgatgtg ccacaacatg     540
agtagattag gcggccgtgc atgcatgcta ggatcggctc gccatgccat gcatccatcc     600
atctttcggc catcccttg ctttttttcct tctcctcgtc tacggacaaa agctactacc     660
gcatagctct ttagcttgct cctcgcttta ctctctatct catctcttgt aaccgtagtg     720
gaatggggtg gagtagtggt ggtcagagtg tgccgggttc gttgcggagc tcgcgacagg     780
ctctgccaaa agcgatccat gtctctttga ctccccacac cccaccccg tatactccct     840
tcccttctcc catcacactt ccattcgaga gacacacaca cacacccttc gacctgtccg     900
cctctcctat ataaacgcac gtccaccgct ccctgttttc ttcatcctcg ttcccttgca     960
ctgcgccaac aaacaattaa ctacactctc actagctagc taggcgaggc taggccggcg    1020
agggagaagg agaaggagaa gtaggcgcca ag                                   1052
```

<210> SEQ ID NO 23
<211> LENGTH: 414
<212> TYPE: DNA
<213> ORGANISM: Triticum aestivum

<400> SEQUENCE: 23

```
atgttgagga tgcagcagca ggtggagggc gtggtgggcg gcggcatcgt ggccgaggcg      60
gaggaggcgg cggtgtacga gcgggtggct cgcatggcca gcggcaacgc cgtggtcgtc     120
ttcagcgcca gcggctgctg catgtgccac gtcgtcaagc gcctcctgct tggcctggga     180
gtcggcccca ccgtctacga gttggaccag atgggcggcg ccgggcggga gatccaggcg     240
gccctggcgc agctgctgcc ccccggaccc ggcgccggcc accaccagca gccgccggtg     300
cccgtggtgt tcgtcggcgg gaggctcctg ggaggcgtgg agaaggtgat ggcgtgccac     360
atcaacggca cgctcgtccc gctcctcaag gacgccggcg cgctctggct ctga           414
```

<210> SEQ ID NO 24
<211> LENGTH: 137
<212> TYPE: PRT
<213> ORGANISM: Triticum aestivum

<400> SEQUENCE: 24

```
Met Leu Arg Met Gln Gln Gln Val Glu Gly Val Val Gly Gly Gly Ile
1               5                   10                  15

Val Ala Glu Ala Glu Glu Ala Ala Val Tyr Glu Arg Val Ala Arg Met
```

```
                    20                  25                  30
Ala Ser Gly Asn Ala Val Val Phe Ser Ala Ser Gly Cys Cys Met
        35                  40                  45

Cys His Val Val Lys Arg Leu Leu Gly Leu Gly Val Gly Pro Thr
    50                  55                  60

Val Tyr Glu Leu Asp Gln Met Gly Gly Ala Gly Arg Glu Ile Gln Ala
65                  70                  75                  80

Ala Leu Ala Gln Leu Leu Pro Pro Gly Pro Gly Ala Gly His His Gln
                85                  90                  95

Gln Pro Pro Val Pro Val Val Phe Val Gly Gly Arg Leu Leu Gly Gly
            100                 105                 110

Val Glu Lys Val Met Ala Cys His Ile Asn Gly Thr Leu Val Pro Leu
        115                 120                 125

Leu Lys Asp Ala Gly Ala Leu Trp Leu
        130                 135
```

<210> SEQ ID NO 25
<211> LENGTH: 414
<212> TYPE: DNA
<213> ORGANISM: Triticum aestivum

<400> SEQUENCE: 25

```
atgttgagga tgcagcagca ggtggagggc gtggtgggcg gcggcatcgt ggcggaggcg      60
gaggaggcgg cggtgtacga gagggtggct cgcatggcca gcggcaacgc ggtggtcgtc     120
ttcagcgcca gcggctgctg catgtgccac gtcgtcaagc gcctcctgct tggcctggga     180
gtcggcccca ccgtgtacga gttggaccag atgggcggcg ccgggcggga gatccaggcg     240
gccctggcgc agctgctgcc ccccggaccc ggcgccggcc accaccagca gccgccggtg     300
cccgtggtgt tcgttggcgg gaggctcctg ggcggcgtgg agaaggtgat ggcgtgccac     360
atcaacggca cgctcgtccc gctcctcaag gacgccggcg cgctctggct ctga           414
```

<210> SEQ ID NO 26
<211> LENGTH: 1044
<212> TYPE: DNA
<213> ORGANISM: Triticum aestivum

<400> SEQUENCE: 26

```
acacgctcta catgcataca tacatacata catacatacg gaggctgtca atacggggac      60
tctattaccg ttgctctact gcccgcaacc gactatggcc cgttgtgctg atctattggt     120
tggttgtgtc gtgttaggcg ttggtgacga agacccaaga gcgatggacg ttatgcatg     180
ccgccggggc ctggtggggg gaatcgatca cgtgaaggca atgtgggacg tgaaggaggt     240
gacgatgggc gtgacggcgt ttggtggctg tggggccgag gagtcaaacg gcggctgagg     300
gggacgtcgt gctgtcggct tgtcggctgc cgtgacgatc gacgcttgtc ttgtcacgcc     360
gtgtccatgc tccgttccct ccctccgtat agtcggcgtt caaattcttg tcctgcagat     420
acatgtaaat tcctacagta gtactactac tttagaattc gcctgtaaat caagatggac     480
attattttct gagagcgttg aacgcccatt ggttcattat attataggag tataaagaaa     540
agggtaatt gattttgctg atgtgccacg acaggagtag attaggcggc tgtgcatgca     600
tgcatgctag gatcgcctcg ccatgccatg ccatgccatg catccatcca tctttcggcc     660
atcccttcgc ttttccttc tcctcgtcta cgcacaaaag ctaccgcata gctctttaac     720
ttgctcctcg ctttactctc atctcttgta accgtagtgg aatggggtgg agtactagtg     780
```

```
gtcagagtgt gccgggttcg ttgcggagct cgcgaccggc tctgccaaaa gcgatccatg    840
tctctttgac tccccacacc ccaccccttc ccttctccca tcacacttcc gttcgagaca    900
cacacacaca ccctgtccgc ttctcctatc ctatataaac gcacgtccac cgctccctgt    960
tttcttcatc ctcgttccct tgcactgcgc caacaaacaa ttaactacac tctcactctc   1020
actagctagc taggctaggc caag                                          1044

<210> SEQ ID NO 27
<211> LENGTH: 414
<212> TYPE: DNA
<213> ORGANISM: Triticum aestivum

<400> SEQUENCE: 27
atgttgagga tgcagcagca ggtggagggc gtggtgggcg gcggcatcgt ggcggaggcg     60
gaggaggcgg cggtgtacga gagggtggct cgcatggcca gcggcaacgc ggtggtcgtc    120
ttcagcgcca gcggctgctg catgtgccac gtcgtcaagc gcctcctgct tggcctggga    180
gtcggcccca ccgtgtacga gttggaccag atgggcgggg ccgggcggga gatccaggcg    240
gccctggcgc agctgctgcc ccccggaccc ggcgccggcc accaccagca gccgccggtg    300
cccgtggtgt tcgttggcgg gaggctcctg ggcggcgtgg agaaggtgat ggcgtgccac    360
atcaacggca cgctcgtccc gctcctcaag gacgccggcg cgctctggct ctga          414

<210> SEQ ID NO 28
<211> LENGTH: 137
<212> TYPE: PRT
<213> ORGANISM: Triticum aestivum

<400> SEQUENCE: 28

Met Leu Arg Met Gln Gln Gln Val Glu Gly Val Val Gly Gly Gly Ile
1               5                   10                  15

Val Ala Glu Ala Glu Glu Ala Ala Val Tyr Glu Arg Val Ala Arg Met
            20                  25                  30

Ala Ser Gly Asn Ala Val Val Val Phe Ser Ala Ser Gly Cys Cys Met
        35                  40                  45

Cys His Val Val Lys Arg Leu Leu Leu Gly Leu Gly Val Gly Pro Thr
    50                  55                  60

Val Tyr Glu Leu Asp Gln Met Gly Gly Ala Gly Arg Glu Ile Gln Ala
65                  70                  75                  80

Ala Leu Ala Gln Leu Leu Pro Pro Gly Pro Gly Ala Gly His His Gln
                85                  90                  95

Gln Pro Pro Val Pro Val Val Phe Val Gly Gly Arg Leu Leu Gly Gly
            100                 105                 110

Val Glu Lys Val Met Ala Cys His Ile Asn Gly Thr Leu Val Pro Leu
        115                 120                 125

Leu Lys Asp Ala Gly Ala Leu Trp Leu
    130                 135

<210> SEQ ID NO 29
<211> LENGTH: 414
<212> TYPE: DNA
<213> ORGANISM: Triticum aestivum

<400> SEQUENCE: 29
atgttgagga tgcagcagca ggtggagggc gtggtgggcg gcggcatcat ggcggaggcg     60
gaggaggcgg cggtgtacga gcgggtggct cgcatggcca gcggcaacgc ggtggtcgtc    120
```

-continued

| | |
|---|---|
| ttcagcgcca gcggctgctg catgtgccac gtcgtcaagc gcctcctgct tggcctgggg | 180 |
| gtcggcccca ccgtctacga gttggaccag atgggcggcg ccgggcgaga gatccaggcg | 240 |
| gcgctggcgc agctgctgcc ccccggaccc ggcgccggcc accaccagca gccgccagtg | 300 |
| cccgtggtgt tcgtcggcgg gaggctcctg ggcggcgtgg agaaggtgat ggcgtgccac | 360 |
| atcaacggca cgctcgtccc gctcctcaag gacgccggcg cgctctggct ctga | 414 |

<210> SEQ ID NO 30
<211> LENGTH: 1071
<212> TYPE: DNA
<213> ORGANISM: Triticum aestivum

<400> SEQUENCE: 30

| | |
|---|---|
| aagattggga caaactttt cgctcggagg aagtatgata gacgctctac atacatatat | 60 |
| acgtacggag gctgtcaata cggggactat taccgttgct ctactgcgcg caaccgacta | 120 |
| tggcccgttg tgctgatcta ttggttggtt gtgtggtgtg agccgttggt gaggaagacc | 180 |
| caagagcgat ggacggttat gcatgccgcg ggggcctggt gggggaatcg atcacgtgaa | 240 |
| ggcaatgtgg gacgtgaagg aggtgacgat gggcgtgacg gcgtttggtg gcagtggggc | 300 |
| cgaggagtca aacggcggct gaggggggacg tcgtgctgtc ggcttgtcgg ctgccgtgac | 360 |
| gatcgacgat tgtcttgtca cgccgtgtcc atgctccgtt ccctccctcc ctccctccgt | 420 |
| atagtcggcg ttcaaattct tggcctgcag atacatgtaa attcctagta cttagaattc | 480 |
| gcctgtaaat cgagatggac aatattttct gagagcgtta aaggcccatt ggttcattat | 540 |
| aaagaaaagg agtaactgat tttgctgatg tgccacaaca taagtagatt aggcggccgt | 600 |
| gcatgcatgc atgctacgga gtaggatcgg ctcgccatgc catgcattgc atccatcttt | 660 |
| cggccatccc tttgcttttt ccttctcctc gtctacgcac aaaagctacc gcatagctct | 720 |
| ttaacttgct cctcgcttta ctctcatctc ttgtaaccgt agtggaatgg ggtggagtag | 780 |
| tggtggctag agtgtgccgg gttcgttgcg gagctcgcga ccagctctgc caaaagcgat | 840 |
| ccatgtctct ttgaccccc acaccccacc ccgtatact cccttccctt ctcccatcac | 900 |
| acttccattc gagacacact caccctccga cctgtccgcc tctcctatat aaacgcacgt | 960 |
| ccaccgctcc ctgttcctca tcctcgttcc cttgcactgc gccaacaaac aattaactac | 1020 |
| actctcacta gctagctagg ctaggccggg gagggagaag gaggcgccaa g | 1071 |

<210> SEQ ID NO 31
<211> LENGTH: 414
<212> TYPE: DNA
<213> ORGANISM: Triticum aestivum

<400> SEQUENCE: 31

| | |
|---|---|
| atgttgagga tgcagcagca ggtggagggc gtggtgggcg gcggcatcat ggcggaggcg | 60 |
| gaggaggcgg cggtgtacga gcgggtggct cgcatggcca gcgcaacgc ggtggtcgtc | 120 |
| ttcagcgcca gcggctgctg catgtgccac gtcgtcaagc gcctcctgct tggcctgggg | 180 |
| gtcggcccca ccgtctacga gttggaccag atgggcggcg ccgggcgaga gatccaggcg | 240 |
| gcgctggcgc agctgctgcc ccccggaccc ggcgccggcc accaccagca gccgccagtg | 300 |
| cccgtggtgt tcgtcggcgg gaggctcctg ggcggcgtgg agaaggtgat ggcgtgccac | 360 |
| atcaacggca cgctcgtccc gctcctcaag gacgccggcg cgctctggct ctga | 414 |

<210> SEQ ID NO 32
<211> LENGTH: 137

<212> TYPE: PRT
<213> ORGANISM: Triticum aestivum

<400> SEQUENCE: 32

Met Leu Arg Met Gln Gln Val Glu Gly Val Val Gly Gly Gly Ile
1               5                   10                  15

Met Ala Glu Ala Glu Ala Ala Val Tyr Glu Arg Val Ala Arg Met
            20                  25                  30

Ala Ser Gly Asn Ala Val Val Val Phe Ser Ala Ser Gly Cys Cys Met
        35                  40                  45

Cys His Val Val Lys Arg Leu Leu Gly Leu Gly Val Gly Pro Thr
    50                  55                  60

Val Tyr Glu Leu Asp Gln Met Gly Gly Ala Gly Arg Glu Ile Gln Ala
65              70                  75                  80

Ala Leu Ala Gln Leu Leu Pro Pro Gly Pro Ala Gly His His Gln
            85                  90                  95

Gln Pro Pro Val Pro Val Val Phe Val Gly Gly Arg Leu Leu Gly Gly
            100                 105                 110

Val Glu Lys Val Met Ala Cys His Ile Asn Gly Thr Leu Val Pro Leu
            115                 120                 125

Leu Lys Asp Ala Gly Ala Leu Trp Leu
    130                 135

<210> SEQ ID NO 33
<211> LENGTH: 480
<212> TYPE: DNA
<213> ORGANISM: Zea mays

<400> SEQUENCE: 33
atgctgcgga tggaggtgca gcagcagcag caggagtcgg gagtgagcgg cggcgtggtg      60
gcggacgcgg cggcggcatc cggggcggat ccgcgccga cgacgacgac gatggtggcc     120
gcggcgccgc actcggcgtc ggcgctggcg gtgtacgagc gggtggcgcg catggcgggc     180
gggaacgcgg tggtggtgtt cagcgccagc ggctgctgca tgtgccacgt cgtcaagcgc     240
ctgctgctgg gcctcggcgt cggccccacc gtgtacgagc tcgaccagat ggccgccggc     300
ggcggcgggg gcagggagat ccaggcggcg ctggcgcagc tgctgccgcc gggccagccg     360
cccctgcccg tcgtcttcgt gggcggacgc ctcctcggcg gcgtcgagaa ggtcatggcg     420
tgccacatca acggcaccct cgtcccgctc ctcaagcagg ccggcgcgct ctggctctga     480

<210> SEQ ID NO 34
<211> LENGTH: 1132
<212> TYPE: DNA
<213> ORGANISM: Zea mays

<400> SEQUENCE: 34
aattcgcggg acgtggcgtt gtcggctccg tgtcggcggc cgaaccacca cgaatcactg      60
acgtatctcg tctcctctct cctctagact cccacgatac ggccaacgaa gtgtatgtac     120
atatataccc atggtcatat ggcaacaaac gccaacgcca gcagagcact gcccggcggc     180 cttttttccca tctctctctc tctctctgat ggggtgtgca tgcctgactg actgatagat     240
agatagatgg tcaggtccgt ctgatcctca tcggcctagc tcaccccacg cgaaaaaagc     300
cactgctggc tggcgcccag ttgcgcttgc aacagtcact ttaacgagct ccgtccttgc     360
gtttgccctc ctcgctctgc ccctgccgcc gctgccgctg cgtggtggtg ctggtgcatg     420
aggcaggcag gcgtactagt gcatgcaatt gcaatgcaac cgtaggagtg cgttgcgtac     480

```
cctggtctgt ccctgcggcc tggcctgccc ttgttcgttg cggatgcggg gggtgccggg      540
tgggtactgt actgtactac tgggtagaga gatactacta gatagagaga gagagaggtc      600
ggtcaccccg ggcgcgggac acagcctctg cgaaaaagcg atccatgtcg cgcctagctt      660
tgacccggaa cggatccccc aaccaggaac cagcagagca ggagggccag gccaccacct      720
ctcgccattc cattcccggt cctagctagt cctgttctgt tcctgtagca gtagcagtag      780
ctacggtact acgagtcctc ctcgacgtcc caggcactac tccactccac gcagcagcag      840
gcagcgagca tctctcgacc agatgcatac aagctacacc ctcctcggct ccgatcctac      900
ccatgccggc ccaggcggcc tataaaagcg caccccggc ccgtcttcct cccactgcat       960
gcccattgcc cctcccccgg ccttcgccgt gccaacgaca cacctcatca ccggccggaa     1020
cattccacga ccgaagaaac cagtccctag ctagtccacg cacgaccaac aaggcaggcg     1080
agcgacgaca gtccaagcct ccaagaagaa gaagaagaag aagaagaaga ag            1132
```

<210> SEQ ID NO 35
<211> LENGTH: 480
<212> TYPE: DNA
<213> ORGANISM: Zea mays

<400> SEQUENCE: 35

```
atgctgcgga tggaggtgca gcagcagcag caggagtcgg gagtgagcgg cggcgtggtg       60
gcggacgcgg cggcggcatc cggggcggat gccgcgccga cgacgacgac gatggtggcc      120
gcggcgccgc actcggcgtc ggcgctggcg gtgtacgagc gggtggcgcg catggcgggc      180
gggaacgcgg tggtggtgtt cagcgccagc ggctgctgca tgtgccacgt cgtcaagcgc      240
ctgctgctgg gcctcggcgt cggccccacc gtgtacgagc tcgaccagat ggccgccggc      300
ggcggcgggg gcagggagat ccaggcggcg ctggcgcagc tgctgccgcc gggccagccg      360
cccctgcccg tcgtcttcgt gggcggacgc ctcctcggcg gcgtcgagaa ggtcatggcg      420
tgccacatca acggcaccct cgtcccgctc ctcaagcagg ccggcgcgct ctggctctga      480
```

<210> SEQ ID NO 36
<211> LENGTH: 155
<212> TYPE: PRT
<213> ORGANISM: Zea mays

<400> SEQUENCE: 36

```
Met Leu Arg Met Glu Val Gln Gln Gln Glu Ser Gly Val Ser Gly Gly
1               5                   10                  15

Val Val Ala Asp Ala Ala Ala Ala Gly Ser Val Ala Glu Ala Ala Thr
                20                  25                  30

Thr Thr Met Val Ala Ala Ala Pro His Ser Ala Ser Ala Leu Ala Val
            35                  40                  45

Tyr Glu Arg Val Ala Arg Met Ala Gly Gly Asn Ala Val Val Val Phe
        50                  55                  60

Ser Ala Ser Gly Cys Cys Met Cys His Val Val Lys Arg Leu Leu Leu
65                  70                  75                  80

Gly Leu Gly Val Gly Pro Thr Val Tyr Glu Leu Asp Gln Met Ala Gly
                85                  90                  95

Gly Gly Gly Gly Arg Glu Ile Gln Ala Ala Leu Ala Gln Leu Leu Pro
                100                 105                 110

Pro Gly Gln Pro Pro Leu Pro Val Val Phe Val Gly Gly Arg Leu Leu
        115                 120                 125
```

Gly Gly Val Glu Lys Val Met Ala Cys His Ile Asn Gly Thr Leu Val
    130                 135                 140

Pro Leu Leu Lys Gln Ala Gly Ala Leu Trp Leu
145                 150                 155

<210> SEQ ID NO 37
<211> LENGTH: 384
<212> TYPE: DNA
<213> ORGANISM: Oryza sativa

<400> SEQUENCE: 37

| | | | | | | |
|---|---|---|---|---|---|---|
| atgaggatgc | aggtggtgga | gacggcggcg | gtggaggagg | aggaggcggc | ggcggcgatg | 60 |
| atgtcggtgt | acgagagggt | ggcgaggatg | gcgagcggga | acgcggtggt | ggtgttcagc | 120 |
| gcgagcgggt | gctgcatgtg | ccacgtcgtc | aagcgcctcc | tcctcggcct | cggcgtcggc | 180 |
| cccgccgtct | acgagctcga | ccagctcgcc | gccgccgccg | acatccaggc | cgcgctgtcg | 240 |
| cagctcctcc | cgccgggcca | gccgccggtg | cccgtcgtgt | cgtcggcgg | caggctcctc | 300 |
| ggcggcgtcg | agaaggtgat | ggcgtgccac | atcaatggca | ccctcgtccc | cctcctcaag | 360 |
| caggccggcg | ccctctggct | ctga | | | | 384 |

<210> SEQ ID NO 38
<211> LENGTH: 1511
<212> TYPE: DNA
<213> ORGANISM: Oryza sativa

<400> SEQUENCE: 38

| | | | | | | |
|---|---|---|---|---|---|---|
| tggaacgcat | ggcaagaagg | gtagtagtac | gccgtacgat | cagacggtta | cgcgtgatgt | 60 |
| aacgtgtcga | cgatccatga | tccatcgact | aggaggtcat | caccggggcc | cacctgcccc | 120 |
| ccgggaggga | ggttgcgttg | gtgggcccgg | gggagtcaaa | cgacggcgga | gatgagacgg | 180 |
| agagggcccc | gccgttatgc | tgtcgggctg | tcggcgcttc | acacagtggc | cgtccgtacg | 240 |
| tgatgtcgcc | tcctccagcc | gtctccaagt | acagctatac | tagtagagta | gtatactact | 300 |
| gctcctatac | tgtacagtat | accccgtact | gtactagtgg | caatatcact | caaaacacat | 360 |
| ggagcattat | gtatacatac | aaccatcatg | aatatatatt | cttctagaaa | cgaaaaaagc | 420 |
| atgcacatcg | cccctatttt | ggggagttag | ttaattagaa | tattcagctg | ataggaatct | 480 |
| ttaaaagaat | cggataatta | attaaccata | atttctgtca | tgcagggtat | caaatgtacc | 540 |
| acattaaatt | tttctagcaa | tgtaaaatct | atgcatgcac | cacactggac | agcgaaatat | 600 |
| atactccctt | cgtactcata | aagggaatcg | ttttggacag | tgacacggtc | tccaaaacac | 660 |
| aactttgact | ttttgtttct | ataaaaatat | ttattgaaaa | gtgatatatg | tatacttta | 720 |
| tgaaagtatt | tttcaagaca | aatctattca | tatatttttt | atattttcaa | attcaataat | 780 |
| ttaaaaatta | ttcatgattt | atattctcaa | ggtttgactt | aaatattatc | ctaaacgatt | 840 |
| ttctttatga | gtacggaggg | agtatactta | caattttgta | cctctcgagt | acgataaaat | 900 |
| ctctctccag | attttgcgcg | agaatatctg | aacggtttgt | agctgcatta | tctagaagat | 960 |
| ctcttgaaaa | tgaacatagt | tcatatatta | cctcatgtat | gtggtgctat | atatatatat | 1020 |
| gtttcactgg | atggttaatt | acttctggga | aactgttta | acatgcaaca | tgtactagct | 1080 |
| agctagctcc | atttctcttc | attccattcc | agagagctcc | tctatttctt | ttactaatct | 1140 |
| ttttccccta | tcaaaaagcc | accagctttc | tagtaagcaa | cactagtcac | tttaacctcc | 1200 |
| tcccttgctt | tgcttactac | accttgcat | ctctctctgg | taaccgtatc | gtggtggaag | 1260 |
| gaaaggaaga | aaggagtgta | ctgggtagct | cagctcagct | cagctaggca | gtggccatgt | 1320 |

```
cagagcgtgt gttcgccgag ctcgcgacca tccactacca aaaaagcctt ccatgtcgcc   1380
actcctttga ccccctcgc accacaccaa ttctccatct atatatcatc caccttcttc   1440
ttcctcctct cattgccatt gtgtgtttgt gttacattgc aatcgtgcca tttgaagaag   1500
aggaggagag g                                                       1511

<210> SEQ ID NO 39
<211> LENGTH: 384
<212> TYPE: DNA
<213> ORGANISM: Oryza sativa

<400> SEQUENCE: 39
atgaggatgc aggtggtgga cggcggcg gtggaggagg aggaggcggc ggcggcgatg   60
atgtcggtgt acgagagggt ggcgaggatg gcgagcggga acgcggtggt ggtgttcagc   120
gcgagcgggt gctgcatgtg ccacgtcgtc aagcgcctcc tcctcggcct cggcgtcggc   180
cccgccgtct acgagctcga ccagctcgcc gccgccgccg acatccaggc cgcgctgtcg   240
cagctcctcc cgccgggcca gccgccggtg cccgtcgtgt tcgtcggcgg caggctcctc   300
ggcggcgtcg agaaggtgat ggcgtgccac atcaatggca ccctcgtccc cctcctcaag   360
caggccggcg ccctctggct ctga                                         384

<210> SEQ ID NO 40
<211> LENGTH: 127
<212> TYPE: PRT
<213> ORGANISM: Oryza sativa

<400> SEQUENCE: 40

Met Arg Met Gln Val Val Glu Thr Ala Ala Val Glu Glu Glu Glu Ala
1               5                   10                  15

Ala Ala Ala Met Met Ser Val Tyr Glu Arg Val Ala Arg Met Ala Ser
            20                  25                  30

Gly Asn Ala Val Val Val Phe Ser Ala Ser Gly Cys Cys Met Cys His
        35                  40                  45

Val Val Lys Arg Leu Leu Leu Gly Leu Gly Val Gly Pro Ala Val Tyr
    50                  55                  60

Glu Leu Asp Gln Leu Ala Ala Ala Ala Asp Ile Gln Ala Ala Leu Ser
65                  70                  75                  80

Gln Leu Leu Pro Pro Gly Gln Pro Pro Val Pro Val Val Phe Val Gly
                85                  90                  95

Gly Arg Leu Leu Gly Gly Val Glu Lys Val Met Ala Cys His Ile Asn
            100                 105                 110

Gly Thr Leu Val Pro Leu Leu Lys Gln Ala Gly Ala Leu Trp Leu
        115                 120                 125

<210> SEQ ID NO 41
<211> LENGTH: 1926
<212> TYPE: DNA
<213> ORGANISM: Triticum aestivum

<400> SEQUENCE: 41
atgagcagcc ccatggagga agctcaccat ggcatgccgt cgacgacgac ggcgttcttc   60
ccgctggcag ggctccacaa gttcatggcc atcttcctcg tgttcctctc gtggatcttg   120
gtccactggt ggagcctgag gaagcagaag gggccgaggt catggccggt catcggcgcg   180
acgctggagc agctgaggaa ctactaccgg atgcacgact ggctcgtgga gtacctgtcc   240
```

```
aagcaccgga cggtcaccgt cgacatgccc ttcacctcct acacctacat cgccgacccg    300
gtgaacgtcg agcatgtgct caagaccaac ttcaacaatt accccaaggt gaaactgaaa    360
gaacccctca gccttgtgaa ttttttttgcc aaggttcaga agtttacact gacacaaatg   420
tctgaaattg tacgtgtagg gggaggtgta caggtcctac atggacgtgc tgctcggcga    480
cggcatcttc aacgccgacg cgagctctg gaggaagcag aggaagacgg cgagcttcga     540
gttcgcttcc aagaacctga gagactttag cacgatcgtg ttcagggagt actccctgaa    600
gctgcgcagc atcctgagcc aggcttgcaa ggccggcaaa gtcgtggaca tgcaggtaac    660
cgaactcagt cccttggtca tctgaacatt gatttcttgg acaaaatttc aagattctga    720
cgcgagcgag cgaattcagg agctgtacat gaggatgacg ctggactcga tctgcaaggt    780
ggggttcggg gtcgagatcg gcacgctgtc gccggagctg ccggagaaca gcttcgcgca    840
ggcgttcgac gccgccaaca tcatcgtgac gctgcggttc atcgacccgc tgtggcgcgt    900
gaagaagttc ctgcacgtcg gctcggaggc gctgctggag cagagcatca agctcgtcga    960
cgagttcacc tacagcgtca tccgccggcg caaggccgag atcgtgcagg cccgggccag   1020
cggcaagcag gagaaggtgc gtacgtgatc gtcgtcgtca agctccggat cgctggtttg   1080
tgtaggtgcc attgatcact gacacactag ctgggtgcgc agatcaagca cgacatactg   1140
tcgcggttca tcgagctggg cgaggccggc ggggacgacg cggcagcct gttcggggac    1200 gacaagggcc tccgcgacgt ggtgctcaac ttcgtgatcg ccgggcggga caccacggcc   1260
acgacgctct cctggttcac ctacatggcc atgacgcacc cggccgtggc cgagaagctc   1320
cgccgcgagc tggccgcctt cgaggcggac cgcgcccgcg aggatggcgt cgcgctggtc   1380
ccctgcagcg actcagacgg cgacggctcc gacgaggcct tcgccgcccg cgtggcgcag   1440
ttcgcggggc tgctgagcta cgacgggctc gggaagctgg tgtacctcca cgcgtgcgtg   1500
acggagacgc tgcgcctgta cccggcggtg ccgcaggacc ccaagggcat cgcggaggac   1560
gacgtgctcc cggacggcac caaggtgcgc gccggcggga tggtgacgta cgtgccctac   1620
tccatggggc ggatggagta caactggggc cccgacgccg ccagcttccg gccggagcgg   1680
tggatcggcg acgacggcgc gttccgcaac gcgtcgccgt tcaagttcac ggcgttccag   1740
gcggggccgc ggatctgcct cggcaaggac tcggcgtacc tgcagatgaa gatggcgctg   1800
gccatcctgt gcaggttctt caggttcgag ctcgtggagg gccacccgt caagtaccgc    1860 atgatgacca tcctctccat ggcgcacggc ctcaaggtcc gcgtctccag ggcgccgctc   1920
gcctga                                                              1926

<210> SEQ ID NO 42
<211> LENGTH: 1000
<212> TYPE: DNA
<213> ORGANISM: Triticum aestivum

<400> SEQUENCE: 42
ctgttcggtt attctttcat tgtttgccat ggagacatga attatcttca tctgatactt     60
gtcaaattag aagtgatctt cattagttgt acatcatcca cagctgctac ggtagtacca    120
acagaaaacg gccagcttga aagttttgga atgcaatgtt agggagtact atttagtaga    180
gcatatatat gataaaagtg ttctcatctg tggaacatat ttatttggca gcactagatg    240
cctcggcata ttgcaaggtt tttaatattt gcgatctttt ctgttcaag cttctaataa     300 atagaaggtg accactttca tcaaaatttt cttctgttta gcttctgcta caaatttcta    360
ataaatatag aagggggaac tttcagcaag atttttata tttgtgattt tcaggctttt     420
```

```
tccatttagg gagaacatca gagcacccct tgacagttga caccccttca ttcgaaattt      480
ctcaacttgt tctgctttga cttcaaaaac tgtttcactg aaagatgcac tttgtattgg      540
ttagtgcggg ttcaataaag accagatgga ccataaccat ggctccatgg ctccaactgt      600
gaagatgaca taatcacaac gctaactgtc atcaaacgca tcacctacat cccccgcaaa      660
acgaaataaa aatgcatcag tgcatcacct acatttatag taaaacagaa ggaaaatgca      720
gaatccatga cctagcttag caccaagcac atactaacat acctagttat gcatataaaa      780
atgagtgttt tcttggtcag cagatcacaa aaaggacaca aacggtaggt tccatctagt      840 caggggtta ggtagggac gccatgtgga tgaggcaatc ttaattctcg gccacaccaa        900
gattgtttgg tgctcggcgc cactaatgcc caatatatta cctaaccgag ccatccaaat     960
gctacataga attaatcctc ctgtagactg aacccacttg                          1000

<210> SEQ ID NO 43
<211> LENGTH: 1665
<212> TYPE: DNA
<213> ORGANISM: Triticum aestivum

<400> SEQUENCE: 43
atgagcagcc ccatggagga agctcaccat ggcatgccgt cgacgacgac ggcgttcttc       60
ccgctggcag ggctccacaa gttcatggcc atcttcctcg tgttcctctc gtggatcttg      120
gtccactggt ggagcctgag gaagcagaag gggccgaggt catggccggt catcggcgcg      180
acgctggagc agctgaggaa ctactaccgg atgcacgact ggctcgtgga gtacctgtcc      240
aagcaccgga cggtcaccgt cgacatgccc ttcacctcct acacctacat cgccgacccg      300
gtgaacgtcg agcatgtgct caagaccaac ttcaacaatt accccaaggg ggaggtgtac      360
aggtcctaca tggacgtgct gctcggcgac ggcatcttca cgccgacgg cgagctctgg       420 aggaagcaga ggaagacggc gagcttcgag ttcgcttcca agaacctgag agactttagc      480
acgatcgtgt tcagggagta ctccctgaag ctgcgcagca tcctgagcca ggcttgcaag      540
gccggcaaag tcgtggacat gcaggagctg tacatgagga tgacgctgga ctcgatctgc      600
aaggtggggt tcgggtcga gatcggcacg ctgtcgccgg agctgccgga aacagcttc       660 gcgcaggcgt tcgacgccgc caacatcatc gtgacgctgc ggttcatcga cccgctgtgg      720
cgcgtgaaga agttcctgca cgtcggctcg gaggcgctgc tggagcagag catcaagctc      780
gtcgacgagt tcacctacag cgtcatccgc cggcgcaagg ccgagatcgt gcaggcccgg      840
gccagcggca agcaggagaa gatcaagcac gacatactgt cgcggttcat cgagctgggc      900
gaggccggcg ggacgacgg cggcagcctg ttcgggacg acaagggcct ccgcgacgtg        960
gtgctcaact tcgtgatcgc cgggcggac accacggcca cgacgctctc ctggttcacc      1020
tacatggcca tgacgcaccc ggccgtggcc gagaagctcc gccgcgagct ggccgccttc      1080
gaggcggacc gcgcccgcga ggatggcgtc gcgctggtcc cctgcagcga ctcagacggc      1140
gacggctccg acgaggcctt cgccgcccgc gtggcgcagt cgcgggggct gctgagctac      1200
gacgggctcg ggaagctggt gtacctccac gcgtgcgtga cggagacgct gcgcctgtac      1260
ccggcggtgc cgcaggaccc caagggcatc gcggaggacg acgtgctccc ggacggcacc      1320
aaggtgcgcg ccggcgggat ggtgacgtac gtgccctact ccatggggcg gatggagtac      1380 aactgggggcc ccgacgccgc cagcttccgg ccggagcggt ggatcggcga cgacggcgcg      1440
ttccgcaacg cgtcgccgtt caagttcacg gcgttccagg cggggccgcg gatctgcctc      1500
```

-continued

```
ggcaaggact cggcgtacct gcagatgaag atggcgctgg ccatcctgtg caggttcttc    1560
aggttcgagc tcgtggaggg ccaccccgtc aagtaccgca tgatgaccat cctctccatg    1620
gcgcacggcc tcaaggtccg cgtctccagg gcgccgctcg cctga                    1665
```

<210> SEQ ID NO 44
<211> LENGTH: 554
<212> TYPE: PRT
<213> ORGANISM: Triticum aestivum

<400> SEQUENCE: 44

```
Met Ser Ser Pro Met Glu Glu Ala His His Gly Met Pro Ser Thr Thr
1               5                   10                  15

Thr Ala Phe Phe Pro Leu Ala Gly Leu His Lys Phe Met Ala Ile Phe
            20                  25                  30

Leu Val Phe Leu Ser Trp Ile Leu Val His Trp Ser Leu Arg Lys
        35                  40                  45

Gln Lys Gly Pro Arg Ser Trp Pro Val Ile Gly Ala Thr Leu Glu Gln
    50                  55                  60

Leu Arg Asn Tyr Tyr Arg Met His Asp Trp Leu Val Glu Tyr Leu Ser
65                  70                  75                  80

Lys His Arg Thr Val Thr Val Asp Met Pro Phe Thr Ser Tyr Thr Tyr
                85                  90                  95

Ile Ala Asp Pro Val Asn Val Glu His Val Leu Lys Thr Asn Phe Asn
            100                 105                 110

Asn Tyr Pro Lys Gly Glu Val Tyr Arg Ser Tyr Met Asp Val Leu Leu
        115                 120                 125

Gly Asp Gly Ile Phe Asn Ala Asp Gly Glu Leu Trp Arg Lys Gln Arg
    130                 135                 140

Lys Thr Ala Ser Phe Glu Phe Ala Ser Lys Asn Leu Arg Asp Phe Ser
145                 150                 155                 160

Thr Ile Val Phe Arg Glu Tyr Ser Leu Lys Leu Arg Ser Ile Leu Ser
                165                 170                 175

Gln Ala Cys Lys Ala Gly Lys Val Val Asp Met Gln Glu Leu Tyr Met
            180                 185                 190

Arg Met Thr Leu Asp Ser Ile Cys Lys Val Gly Phe Gly Val Glu Ile
        195                 200                 205

Gly Thr Leu Ser Pro Glu Leu Pro Glu Asn Ser Phe Ala Gln Ala Phe
    210                 215                 220

Asp Ala Ala Asn Ile Ile Val Thr Leu Arg Phe Ile Asp Pro Leu Trp
225                 230                 235                 240

Arg Val Lys Lys Phe Leu His Val Gly Ser Glu Ala Leu Leu Glu Gln
                245                 250                 255

Ser Ile Lys Leu Val Asp Glu Phe Thr Tyr Ser Val Ile Arg Arg Arg
            260                 265                 270

Lys Ala Glu Ile Val Gln Ala Arg Ala Ser Gly Lys Gln Glu Lys Ile
        275                 280                 285

Lys His Asp Ile Leu Ser Arg Phe Ile Glu Leu Gly Glu Ala Gly Gly
    290                 295                 300

Asp Asp Gly Gly Ser Leu Phe Gly Asp Lys Gly Leu Arg Asp Val
305                 310                 315                 320

Val Leu Asn Phe Val Ile Ala Gly Arg Asp Thr Thr Ala Thr Thr Leu
                325                 330                 335

Ser Trp Phe Thr Tyr Met Ala Met Thr His Pro Ala Val Ala Glu Lys
            340                 345                 350
```

```
Leu Arg Arg Glu Leu Ala Ala Phe Glu Ala Asp Arg Ala Arg Glu Asp
            355                 360                 365

Gly Val Ala Leu Val Pro Cys Ser Asp Ser Asp Gly Asp Gly Ser Asp
370                 375                 380

Glu Ala Phe Ala Ala Arg Val Ala Gln Phe Ala Gly Leu Leu Ser Tyr
385                 390                 395                 400

Asp Gly Leu Gly Lys Leu Val Tyr Leu His Ala Cys Val Thr Glu Thr
                405                 410                 415

Leu Arg Leu Tyr Pro Ala Val Pro Gln Asp Pro Lys Gly Ile Ala Glu
            420                 425                 430

Asp Asp Val Leu Pro Asp Gly Thr Lys Val Arg Ala Gly Gly Met Val
            435                 440                 445

Thr Tyr Val Pro Tyr Ser Met Gly Arg Met Glu Tyr Asn Trp Gly Pro
            450                 455                 460

Asp Ala Ala Ser Phe Arg Pro Glu Arg Trp Ile Gly Asp Asp Gly Ala
465                 470                 475                 480

Phe Arg Asn Ala Ser Pro Phe Lys Phe Thr Ala Phe Gln Ala Gly Pro
                485                 490                 495

Arg Ile Cys Leu Gly Lys Asp Ser Ala Tyr Leu Gln Met Lys Met Ala
            500                 505                 510

Leu Ala Ile Leu Cys Arg Phe Phe Arg Phe Glu Leu Val Glu Gly His
            515                 520                 525

Pro Val Lys Tyr Arg Met Met Thr Ile Leu Ser Met Ala His Gly Leu
            530                 535                 540

Lys Val Arg Val Ser Arg Ala Pro Leu Ala
545                 550

<210> SEQ ID NO 45
<211> LENGTH: 1920
<212> TYPE: DNA
<213> ORGANISM: Triticum aestivum

<400> SEQUENCE: 45
atgagcagcc ccatggagga agctcacctt ggcatgccgt cgacgacggc cttcttcccg     60
ctggcagggc tccacaagtt catggccgtc ttcctcgtgt tcctctcgtg gatcctggtc    120
cactggtgga gcctgaggaa gcagaagggg ccacggtcat ggccggtcat cggcgcgacg    180
ctggagcagc tgaggaacta ctaccggatg cacgactggc tcgtggagta cctgtccaag    240
caccggacgg tcaccgtcga catgcccttc acctcctaca cctacatcgc cgacccggtg    300
aacgtcgagc acgtgctcaa gaccaacttc aacaattacc ccaaggtgaa acaatcctcg    360
agatgtcagt caaggttcag tataatcggt actgacagtg ttacaaatgt ctgaaatctg    420
gaattgtgtg tgtaggggga ggtgtacagg tcctacatgg acgtgctgct cggcgacggc    480
atattcaacg ccgacggcga gctctggagg aagcagagga agacggcgag cttcgagttc    540
gcttccaaga acttgagaga cttcagcacg atcgtgttca gggagtactc cctgaagctg    600
tccagcatcc tgagccaggc ttgcaaggca ggcaaagttg tggacatgca ggtaactgaa    660
ctctttccct tggtcatatg aacgttgatt tcttggacaa atctcaaga ttctgacgcg    720 agcgagccaa ttcaggagct gtacatgagg atgacgctgg actcgatctg caaggtgggg    780
ttcggggtgg agatcggcac gctgtcgccg gagctgccgg agaacagctt cgcgcaggcc    840
ttcgacgccg ccaacatcat cgtgacgctg cggttcatcg acccgctgtg gcgcgtgaag    900
aaattcctgc acgtcggctc ggaggcgctg ctggagcaga gcatcaagct cgtcgacgag    960
```

```
ttcacctaca gcgtcatccg ccggcgcaag gccgagatcg tgcaagcccg ggccagcggc    1020
aagcaggaga aggtgcgtac gtggtcatcg tcattcgtca agctcccgat cgctggtttg    1080
tgcagatgcc actgatcact gacacattaa ctgggcgcgc agatcaagca cgacatactg    1140
tcgcggttca tcgagctggg cgaggccggc ggcgacgacg gcggcagcct gttcggggac    1200
gacaagggcc tccgcgacgt ggtgctcaac ttcgtcatcg ccgggcggga cacgacggcc    1260
acgacgctct cctggttcac ctacatggcc atgacgcacc cggccgtggc cgagaagctc    1320
cgccgcgagc tggccgcctt cgagtccgag cgcgcccgcg aggatggcgt cgctctggtc    1380
ccctgcagcg acggcgaggg ctccgacgag gccttcgccg cccgcgtggc gcagttcgcg    1440
ggactcctga gctacgacgg gctcgggaag ctggtgtacc tccacgcgtg cgtgacggag    1500 acgtccgcc tgtacccggc ggtgccgcag gaccccaagg gcatcgcgga ggacgacgtg    1560
ctcccggacg gcaccaaggt gcgcgccggc gggatggtga cgtacgtgcc ctactccatg    1620
gggcggatgg agtacaactg ggcccccgac gccgccagct tccggccaga gcggtggatc    1680
ggcgacgacg gcgccttccg caacgcgtcg ccgttcaagt tcacggcgtt ccaggcgggg    1740
ccgcggatct gcctgggcaa ggactcggcg tacctgcaga tgaagatggc gctgccatc     1800 ctgtgcaggt tcttcaggtt cgagctcgtg gagggccacc ccgtcaagta ccgcatgatg    1860
accatcctct ccatggcgca cggcctcaag gtccgcgtct ccagggtgcc gctcgcctga   1920

<210> SEQ ID NO 46
<211> LENGTH: 1000
<212> TYPE: DNA
<213> ORGANISM: Triticum aestivum

<400> SEQUENCE: 46
gttatcttca tcagatcatt gtcaaattta aagtgttctt catttatttt acatcatcca      60
caactcctac ggtagtacca acagaaaatg atcagcttga aagttttgaa tgcaatgtta     120
gggagtacta taaagtagag catatatgtg atagaagtgt tctgatctat ggaacatatt     180
tatttggcag cagtagatgc ttccacatat ttcaaggttt ttaatatttg tgattttttcc    240 ctgttacaag tttctaataa atatcctcgc aaaaaaaagt ttctaataaa tagaagatgg     300
ccactttctc aaaattttca tttgtcccaa agtggtcgga tccttccctt gaccctgcgc     360
aagcgggagc tacatgcacc gggctgccct ttagcttctg ctaaaaattt ctagcaagta     420
tagaagggcg gaactttcaa caaagatatg agaacatcag agcactcctt gacaccccctt    480 cattccaaat ttctcaactt gctctgcttt gacttcaaaa actgtctcac tgaaagatgc     540
actttgtatt ggttagtgcg ggttcattaa agatcagacg gaccataacc atggttccaa     600
ctgtgaagat gagaccatca caatgctaac tgtcatcaaa tgcatcacct acattccctg     660
caaaataaaa ataaaaatgc acgacctaca tgtgcagtaa aacagaagga aaatgcagaa     720 tccatgaccct agctcagcat caagcacata caaacatatc tagttatatg catataaaaa    780
tcagtatttt cttggtcagc agatcacaaa aaggacacaa acggtaggtt ccatctagtc     840 aggggggttag gttagggaca ccatgtggat gaggcaatct taattctcgg ccacaccaag    900
attgtttggt gctcggcagc actaatgccc aatatattac ctaaccgagc catccaaatg    960
ctacatagag ttaatcctcc tgtagacctg aaccccttc                          1000

<210> SEQ ID NO 47
<211> LENGTH: 1656
<212> TYPE: DNA
```

<213> ORGANISM: Triticum aestivum

<400> SEQUENCE: 47

```
atgagcagcc ccatggagga agctcacctt ggcatgccgt cgacgacggc cttcttcccg      60
ctggcagggc tccacaagtt catggccgtc ttcctcgtgt tcctctcgtg gatcctggtc     120
cactggtgga gcctgaggaa gcagaagggg ccacggtcat ggccggtcat cggcgcgacg     180
ctggagcagc tgaggaacta ctaccggatg cacgactggc tcgtggagta cctgtccaag     240
caccggacgg tcaccgtcga catgcccttc acctcctaca cctacatcgc cgacccggtg     300
aacgtcgagc acgtgctcaa gaccaacttc aacaattacc caaggggga ggtgtacagg      360
tcctacatgg acgtgctgct cggcgacggc atattcaacg ccgacggcga gctctggagg     420
aagcagagga gacggcgag cttcgagttc gcttccaaga acttgagaga cttcagcacg      480
atcgtgttca gggagtactc cctgaagctg tccagcatcc tgagccaggc ttgcaaggca     540
ggcaaagttg tggacatgca ggagctgtac atgaggatga cgctggactc gatctgcaag     600
gtggggttcg gggtggagat cggcacgctg tcgccggagc tgccgagaa cagcttcgcg      660
caggccttcg acgccgccaa catcatcgtg acgctgcggt tcatcgaccc gctgtggcgc     720
gtgaagaaat tcctgcacgt cggctcggag gcgctgctgg agcagagcat caagctcgtc     780
gacgagttca cctacagcgt catccgccgg cgcaaggccg agatcgtgca agcccgggcc     840
agcggcaagc aggagaagat caagcacgac atactgtcgc ggttcatcga gctgggcgag     900
gccggcggcg acgacggcgg cagcctgttc ggggacgaca agggcctccg cgacgtggtg     960
ctcaacttcg tcatcgccgg gcgggacacg acggccacga cgctctcctg gttcacctac    1020
atggccatga cgcacccggc cgtggccgag aagctccgcc gcgagctggc cgccttcgag    1080
tccgagcgcg cccgcgagga tggcgtcgct ctggtcccct gcagcgacgg cgagggctcc    1140
gacgaggcct cgccgcccg cgtggcgcag ttcgcgggac tcctgagcta cgacgggctc    1200
gggaagctgt tgtacctcca cgcgtgcgtg acggagacgc tccgcctgta cccggcggtg    1260
ccgcaggacc ccaagggcat cgcggaggac gacgtgctcc cggacggcac caaggtgcgc    1320
gccggcggga tggtgacgta cgtgccctac tccatggggc ggatggagta caactggggc    1380
cccgacgccg ccagcttccg ccagagcgg tggatcggcg acgacggcgc cttccgcaac    1440
gcgtcgccgt tcaagttcac ggcgttccag gcggggccgc ggatctgcct gggcaaggac    1500
tcggcgtacc tgcagatgaa gatggcgctg ccatcctgt gcaggttctt caggttcgag    1560
ctcgtggagg gccaccccgt caagtaccgc atgatgacca tcctctccat ggcgcacggc    1620
ctcaaggtcc gcgtctccag ggtgccgctc gcctga                             1656
```

<210> SEQ ID NO 48
<211> LENGTH: 551
<212> TYPE: PRT
<213> ORGANISM: Triticum aestivum

<400> SEQUENCE: 48

```
Met Ser Ser Pro Met Glu Glu Ala His Leu Gly Met Pro Ser Thr Thr
1               5                   10                  15

Ala Phe Phe Pro Leu Ala Gly Leu His Lys Phe Met Ala Val Phe Leu
            20                  25                  30

Val Phe Leu Ser Trp Ile Leu Val His Trp Trp Ser Leu Arg Lys Gln
        35                  40                  45

Lys Gly Pro Arg Ser Trp Pro Val Ile Gly Ala Thr Leu Glu Gln Leu
    50                  55                  60
```

```
Arg Asn Tyr Tyr Arg Met His Asp Trp Leu Val Glu Tyr Leu Ser Lys
 65                  70                  75                  80

His Arg Thr Val Thr Val Asp Met Pro Phe Thr Ser Tyr Thr Tyr Ile
                 85                  90                  95

Ala Asp Pro Val Asn Val Glu His Val Leu Lys Thr Asn Phe Asn Asn
            100                 105                 110

Tyr Pro Lys Gly Glu Val Tyr Arg Ser Tyr Met Asp Val Leu Leu Gly
        115                 120                 125

Asp Gly Ile Phe Asn Ala Asp Gly Glu Leu Trp Arg Lys Gln Arg Lys
    130                 135                 140

Thr Ala Ser Phe Glu Phe Ala Ser Lys Asn Leu Arg Asp Phe Ser Thr
145                 150                 155                 160

Ile Val Phe Arg Glu Tyr Ser Leu Lys Leu Ser Ser Ile Leu Ser Gln
                165                 170                 175

Ala Cys Lys Ala Gly Lys Val Val Asp Met Gln Glu Leu Tyr Met Arg
            180                 185                 190

Met Thr Leu Asp Ser Ile Cys Lys Val Gly Phe Gly Val Glu Ile Gly
        195                 200                 205

Thr Leu Ser Pro Glu Leu Pro Glu Asn Ser Phe Ala Gln Ala Phe Asp
    210                 215                 220

Ala Ala Asn Ile Ile Val Thr Leu Arg Phe Ile Asp Pro Leu Trp Arg
225                 230                 235                 240

Val Lys Lys Phe Leu His Val Gly Ser Glu Ala Leu Leu Glu Gln Ser
                245                 250                 255

Ile Lys Leu Val Asp Glu Phe Thr Tyr Ser Val Ile Arg Arg Arg Lys
            260                 265                 270

Ala Glu Ile Val Gln Ala Arg Ala Ser Gly Lys Gln Glu Lys Ile Lys
        275                 280                 285

His Asp Ile Leu Ser Arg Phe Ile Glu Leu Gly Glu Ala Gly Gly Asp
    290                 295                 300

Asp Gly Gly Ser Leu Phe Gly Asp Asp Lys Gly Leu Arg Asp Val Val
305                 310                 315                 320

Leu Asn Phe Val Ile Ala Gly Arg Asp Thr Thr Ala Thr Thr Leu Ser
                325                 330                 335

Trp Phe Thr Tyr Met Ala Met Thr His Pro Ala Val Ala Glu Lys Leu
            340                 345                 350

Arg Arg Glu Leu Ala Ala Phe Glu Ser Glu Arg Ala Arg Glu Asp Gly
        355                 360                 365

Val Ala Leu Val Pro Cys Ser Asp Gly Glu Gly Ser Asp Glu Ala Phe
    370                 375                 380

Ala Ala Arg Val Ala Gln Phe Ala Gly Leu Leu Ser Tyr Asp Gly Leu
385                 390                 395                 400

Gly Lys Leu Val Tyr Leu His Ala Cys Val Thr Glu Thr Leu Arg Leu
                405                 410                 415

Tyr Pro Ala Val Pro Gln Asp Pro Lys Gly Ile Ala Glu Asp Asp Val
            420                 425                 430

Leu Pro Asp Gly Thr Lys Val Arg Ala Gly Gly Met Val Thr Tyr Val
        435                 440                 445

Pro Tyr Ser Met Gly Arg Met Glu Tyr Asn Trp Gly Pro Asp Ala Ala
    450                 455                 460

Ser Phe Arg Pro Glu Arg Trp Ile Gly Asp Asp Gly Ala Phe Arg Asn
465                 470                 475                 480
```

```
Ala Ser Pro Phe Lys Phe Thr Ala Phe Gln Ala Gly Pro Arg Ile Cys
                485                 490                 495

Leu Gly Lys Asp Ser Ala Tyr Leu Gln Met Lys Met Ala Leu Ala Ile
            500                 505                 510

Leu Cys Arg Phe Phe Arg Phe Glu Leu Val Glu Gly His Pro Val Lys
        515                 520                 525

Tyr Arg Met Met Thr Ile Leu Ser Met Ala His Gly Leu Lys Val Arg
    530                 535                 540

Val Ser Arg Val Pro Leu Ala
545                 550

<210> SEQ ID NO 49
<211> LENGTH: 1920
<212> TYPE: DNA
<213> ORGANISM: Triticum aestivum

<400> SEQUENCE: 49
atgagcagcc ccatggagga agctcacggc ggcatgccgt cgacgacggc cttcttcccg      60
ctggcagggc tccacaagtt catggccatc ttcctcgtgt tcctctcgtg gatcttggtc     120
cactggtgga gcctgaggaa gcagaagggg ccgaggtcat ggccggtcat cggcgcgacg     180
ctggagcagc tgaggaacta ctaccggatg cacgactggc tcgtggagta cctgtccaag     240
caccggacgg tgaccgtcga catgcccttc acctcctaca cctacatcgc cgacccggtg     300
aacgtcgagc atgtgctcaa gaccaacttc aacaattacc ccaaggtgaa acaatcctcg     360
agatgtcagt aaaggttcag tataatcggt actgacagtg ttacaaatgt ctgaaatctg     420
aaattgtatg tgtaggggga ggtgtacagg tcctacatgg acgtgctgct cggcgacggc     480
atattcaacg ccgacggcga gctctggagg aagcagagga gacggcgag cttcgagttc      540 gcttccaaga acttgagaga cttcagcacg atcgtgttca gggagtactc cctgaagctg     600
tccagcatac tgagccaggc ttgcaaggcc ggcaaagttg tggacatgca ggtaactgaa     660
ctcattccct tggtcatctg aacgttgatt tcttggacaa aatttcaaga ttctgacgcg     720
agcgagcgaa ttcaggagct gtatatgagg atgacgctgg actcgatctg caaagtgggg     780
ttcggagtcg agatcggcac gctgtcgccg gagctgccgg agaacagctt cgcgcaggcg     840
ttcgacgccg ccaacatcat cgtgacgctg cggttcatcg acccgctgtg gcgcgtgaag     900
aagttcctgc acgtcggctc ggaggcgctg ctggagcaga gcatcaagct cgtcgacgag     960
ttcacctaca cgtcatccg ccggcgcaag gccgagatcg tgcaggcccg ggccagcggc    1020
aagcaggaga aggtgcgtgc gtggtcatcg tcattcgtca agctcccggt cgctggtttg    1080
tgtagatgcc atggatcact gacacactaa ctgggcgcgc agatcaagca cgacatactg    1140
tcgcggttca tcgagctggg cgaggccggc ggcgacgacg cggcagtct gttcggggac     1200 gacaagggcc tccgcgacgt ggtgctcaac ttcgtgatcg ccgggcggga caccacggcc    1260
acgacgctgt cctggttcac ctacatggcc atgacgcacc cggacgtggc cgagaagctc    1320
cgccgcgagc tggccgccct tcgaggcgga gcgcgcccgcg aggatggcgt cgctctggtc    1380
ccctgcggcg acggcgaggg ctccgacgag gccttcgctg cccgcgtggc gcagttcgcg    1440
gggttcctga gctacgacgg cctcgggaag ctggtgtacc tccacgcgtg cgtgacggag    1500
acgctgcgcc tgtacccggc ggtgccgcag accccaagg gcatcgcgga ggacgacgtg     1560
ctcccggacg gcaccaaggt gcgcgccggc gggatggtga cgtacgtgcc ctactccatg    1620
gggcggatgg agtacaactg ggcccccgac gccgccagct ccggccgga gcggtggatc     1680
```

```
ggcgacgacg gcgccttccg caacgcgtcg ccgttcaagt tcacggcgtt ccaggcgggg    1740
ccgcggattt gcctcggcaa ggactcggcg tacctgcaga tgaagatggc gctggcaatc    1800
ctgtgcaggt tcttcaggtt cgagctcgtg gagggccacc ccgtcaagta ccgcatgatg    1860
accatcctct ccatggcgca cggcctcaag gtccgcgtct ccagggcgcc gctcgcctga    1920
```

<210> SEQ ID NO 50
<211> LENGTH: 1000
<212> TYPE: DNA
<213> ORGANISM: Triticum aestivum

<400> SEQUENCE: 50

```
catgaattat cttcatctga cccttgtcaa atttgaagtg atcttcatta gttgtacatc      60
atccgcaact gctactgtag taccaacaga aaacggtcag cttgaaagtt tcggaatgca    120
atgttaggga gtactattaa gtagagcata tatggataga agtgttctga tctgcgcaac    180
atatttattt ggcagcatta gatgcttcca catatgctct gcaaggtttc caatgtttgt    240
gatttttttt cccctgttaca agtttctact ccctccgttc ctaaatataa gtctttgtag    300
agatttcact atgaaccaca tacggatgta tataaatgca ttttagaagt agattcactc    360
attttgctcc atatgtagtc catagtgaaa cctctacaaa gacttgtatt taggacggat    420
ggagcaataa atagaaggtg atcattttca tcaaaaattt catttgtttg gtcctgttaa    480
aaaattctaa ttaatataga aggggggaaac tttcaacaat attttccatc tttgtgattt    540
tcaggctttt tccatttagg gagaacatca gagcacccct tgacacccct tcattccaaa    600
tttctcaact tgctctgctt ttgacttcaa aaactattgg ttagtgcggg ttcattaaag    660
atcagatgga ccataaccat ggctccaact gtgaagatga atcatcaca gtgctaattg    720 tcaaaaaaat gcatccaccta catcccccgc aaaagaaaat aaaaatgcat cacctacatg    780
tacagtattt tcttggtcag cagatcacaa aaaggacaca aacggtaggt tccatctagt    840 caggggggtta ggttagggac accatgtgga tgaggcaatc ttaattctcg gccacaccaa    900
gattgtttgg tgctcggcag cactaatgcc caatatatta cctaaccgag ccatccaaat    960
gctacataca gttaatcctc ctgtagactg aaccccttc                           1000
```

<210> SEQ ID NO 51
<211> LENGTH: 1656
<212> TYPE: DNA
<213> ORGANISM: Triticum aestivum

<400> SEQUENCE: 51

```
atgagcagcc ccatggagga agctcacggc ggcatgccgt cgacgacggc cttcttcccg     60
ctggcagggc tccacaagtt catggccatc ttcctcgtgt tcctctcgtg gatcttggtc    120
cactggtgga gcctgaggaa gcagaagggg ccgaggtcat ggccggtcat cggcgcgacg    180
ctggagcagc tgaggaacta ctaccggatg cacgactggc tcgtggagta cctgtccaag    240
caccggacgg tgaccgtcga catgcccttc acctcctaca cctacatcgc cgacccggtg    300
aacgtcgagc atgtgctcaa gaccaacttc aacaattacc caagggggga ggtgtacagg    360
tcctacatgg acgtgctgct cggcgacggc atattcaacg ccgacggcga gctctggagg    420
aagcagagga agacggcgag cttcgagttc gcttccaaga acttgagaga cttcagcacg    480
atcgtgttca gggagtactc cctgaagctg tccagcatac tgagccaggc ttgcaaggcc    540
ggcaaagttg tggacatgca ggagctgtat atgaggatga cgctggactc gatctgcaaa    600
gtggggttcg gagtcgagat cggcacgctg tcgccggagc tgccggagaa cagcttcgcg    660
```

-continued

```
caggcgttcg acgccgccaa catcatcgtg acgctgcggt tcatcgaccc gctgtggcgc    720
gtgaagaagt tcctgcacgt cggctcggag gcgctgctgg agcagagcat caagctcgtc    780
gacgagttca cctacagcgt catccgccgg cgcaaggccg agatcgtgca ggcccgggcc    840
agcggcaagc aggagaagat caagcacgac atactgtcgc ggttcatcga gctgggcgag    900
gccggcggcg acgacggcgg cagtctgttc ggggacgaca agggcctccg cgacgtggtg    960
ctcaacttcg tgatcgccgg gcgggacacc acggccacga cgctgtcctg gttcacctac   1020
atggccatga cgcacccgga cgtggccgag aagctccgcc gcgagctggc cgccttcgag   1080
gcggagcgcg cccgcgagga tggcgtcgct ctggtcccct cgcggcgacgg cgagggctcc   1140 gacgaggcct tcgctgcccg cgtggcgcag ttcgcggggt cctgagcta cgacggcctc   1200 gggaagctgg tgtacctcca cgcgtgcgtg acggagacgc tgcgcctgta cccggcggtg   1260
ccgcaggacc ccaagggcat cgcggaggac gacgtgctcc cggacggcac caaggtgcgc   1320
gccggcggga tggtgacgta cgtgccctac tccatgggc ggatggagta caactggggc   1380
cccgacgccg ccagcttccg gccggagcgg tggatcggcg acgacggcgc cttccgcaac   1440
gcgtcgccgt tcaagttcac ggcgttccag gcggggccgc ggatttgcct cggcaaggac   1500
tcggcgtacc tgcagatgaa gatggcgctg gcaatcctgt gcaggttctt caggttcgag   1560
ctcgtggagg gccacccccgt caagtaccgc atgatgacca tcctctccat ggcgcacggc   1620
ctcaaggtcc gcgtctccag ggcgccgctc gcctga                              1656
```

<210> SEQ ID NO 52
<211> LENGTH: 551
<212> TYPE: PRT
<213> ORGANISM: Triticum aestivum

<400> SEQUENCE: 52

```
Met Ser Ser Pro Met Glu Glu Ala His Gly Gly Met Pro Ser Thr Thr
1               5                   10                  15

Ala Phe Phe Pro Leu Ala Gly Leu His Lys Phe Met Ala Ile Phe Leu
            20                  25                  30

Val Phe Leu Ser Trp Ile Leu Val His Trp Ser Leu Arg Lys Gln
        35                  40                  45

Lys Gly Pro Arg Ser Trp Pro Val Ile Gly Ala Thr Leu Glu Gln Leu
    50                  55                  60

Arg Asn Tyr Tyr Arg Met His Asp Trp Leu Val Glu Tyr Leu Ser Lys
65                  70                  75                  80

His Arg Thr Val Thr Val Asp Met Pro Phe Thr Ser Tyr Thr Tyr Ile
                85                  90                  95

Ala Asp Pro Val Asn Val Glu His Val Leu Lys Thr Asn Phe Asn Asn
            100                 105                 110

Tyr Pro Lys Gly Glu Val Tyr Arg Ser Tyr Met Asp Val Leu Leu Gly
        115                 120                 125

Asp Gly Ile Phe Asn Ala Asp Gly Glu Leu Trp Arg Lys Gln Arg Lys
    130                 135                 140

Thr Ala Ser Phe Glu Phe Ala Ser Lys Asn Leu Arg Asp Phe Ser Thr
145                 150                 155                 160

Ile Val Phe Arg Glu Tyr Ser Leu Lys Leu Ser Ser Ile Leu Ser Gln
                165                 170                 175

Ala Cys Lys Ala Gly Lys Val Val Asp Met Gln Glu Leu Tyr Met Arg
            180                 185                 190
```

Met Thr Leu Asp Ser Ile Cys Lys Val Gly Phe Gly Val Glu Ile Gly
            195                 200                 205

Thr Leu Ser Pro Glu Leu Pro Glu Asn Ser Phe Ala Gln Ala Phe Asp
        210                 215                 220

Ala Ala Asn Ile Ile Val Thr Leu Arg Phe Ile Asp Pro Leu Trp Arg
225                 230                 235                 240

Val Lys Lys Phe Leu His Val Gly Ser Glu Ala Leu Leu Glu Gln Ser
                245                 250                 255

Ile Lys Leu Val Asp Glu Phe Thr Tyr Ser Val Ile Arg Arg Arg Lys
            260                 265                 270

Ala Glu Ile Val Gln Ala Arg Ala Ser Gly Lys Gln Glu Lys Ile Lys
        275                 280                 285

His Asp Ile Leu Ser Arg Phe Ile Glu Leu Gly Glu Ala Gly Gly Asp
    290                 295                 300

Asp Gly Gly Ser Leu Phe Gly Asp Asp Lys Gly Leu Arg Asp Val Val
305                 310                 315                 320

Leu Asn Phe Val Ile Ala Gly Arg Asp Thr Thr Ala Thr Thr Leu Ser
                325                 330                 335

Trp Phe Thr Tyr Met Ala Met Thr His Pro Asp Val Ala Glu Lys Leu
            340                 345                 350

Arg Arg Glu Leu Ala Ala Phe Glu Ala Glu Arg Ala Arg Glu Asp Gly
        355                 360                 365

Val Ala Leu Val Pro Cys Gly Asp Gly Glu Gly Ser Asp Glu Ala Phe
    370                 375                 380

Ala Ala Arg Val Ala Gln Phe Ala Gly Phe Leu Ser Tyr Asp Gly Leu
385                 390                 395                 400

Gly Lys Leu Val Tyr Leu His Ala Cys Val Thr Glu Thr Leu Arg Leu
                405                 410                 415

Tyr Pro Ala Val Pro Gln Asp Pro Lys Gly Ile Ala Glu Asp Asp Val
            420                 425                 430

Leu Pro Asp Gly Thr Lys Val Arg Ala Gly Gly Met Val Thr Tyr Val
        435                 440                 445

Pro Tyr Ser Met Gly Arg Met Glu Tyr Asn Trp Gly Pro Asp Ala Ala
    450                 455                 460

Ser Phe Arg Pro Glu Arg Trp Ile Gly Asp Asp Gly Ala Phe Arg Asn
465                 470                 475                 480

Ala Ser Pro Phe Lys Phe Thr Ala Phe Gln Ala Gly Pro Arg Ile Cys
                485                 490                 495

Leu Gly Lys Asp Ser Ala Tyr Leu Gln Met Lys Met Ala Leu Ala Ile
            500                 505                 510

Leu Cys Arg Phe Phe Arg Phe Glu Leu Val Glu Gly His Pro Val Lys
        515                 520                 525

Tyr Arg Met Met Thr Ile Leu Ser Met Ala His Gly Leu Lys Val Arg
    530                 535                 540

Val Ser Arg Ala Pro Leu Ala
545                 550

<210> SEQ ID NO 53
<211> LENGTH: 2026
<212> TYPE: DNA
<213> ORGANISM: Zea mays

<400> SEQUENCE: 53
atggaggaag ctcacctcac gccggcgacg ccatcgccat tcttcccact agcagggcct     60

| | |
|---|---|
| cacaagtaca tcgcgctcct tctggttgtc ctctcatgga tcctggtcca gaggtggagc | 120 |
| ctgaggaagc agaaaggccc gagatcatgg ccagtcatcg gcgcaacggt ggagcagctg | 180 |
| aggaactacc accggatgca cgactggctt gtcgggtacc tgtcacggca caggacagtg | 240 |
| accgtcgaca tgccgttcac ttcctacacc tacatcgctg acccggtgaa tgtcgagcat | 300 |
| gtcctcaaga ctaacttcac caattacccc aaggtaaatg acctgaactc actgatgttc | 360 |
| agtcttcgga aatcagagct gaaagctgaa tcgaatgtgc ctgaacaccg tgtagggaat | 420 |
| cgtgtacaga tcctacatgg acgtgctcct cggtgacggc atcttcaacg ccgacggcga | 480 |
| gctgtggagg aagcagagga agacggcgag tttcgagttc gcctccaaga acctgaggga | 540 |
| tttcagcgcc attgtgttca gagagtactc cctgaagctg tcgggtatac tgagccaggc | 600 |
| atccaaggca ggcaaagttg tggacatgca ggtgagatat cactggtccc ttgccattgc | 660 |
| caacatgagc atttcaacct gagacacgag agctaccttg ccgattcagg aactttacat | 720 |
| gaggatgacg ctggactcca tctgcaaggt tgggttcggg gtcgagatcg gcacgctgtc | 780 |
| gccagatctc cccgagaaca gcttcgcgca ggcgttcgat gccgccaaca tcatcatcac | 840 |
| gctgcggttc atcgacccgc tgtggcgcat caagaggttc ttccacgtcg gtcagaggc | 900 |
| cctcctagcg cagagcatca agctcgtgga cgagttcacc tacagcgtga tccgccggag | 960 |
| gaaggccgag atcgtcgagg tccgggccag cggcaaacag gagaaggtac gtgcacatga | 1020 |
| ctgtttcgat tcttcagttc atcgtcttgg ccggatgga cctgatcctg attgattata | 1080 |
| tatccatgtg acttgtgagg gcaaattaaa atgggcagat gaagcacgac atcctgtcac | 1140 |
| ggttcatcga gctgggcgag gccggcgacg acggcggcgg cttcggggac gataagagcc | 1200 |
| tccgggacgt ggtgctcaac ttcgtgatcg ccggcggga cacgacggcg acgacgctgt | 1260 |
| cgtggttcac gcacatggcc atgtcccacc cggacgtggc cgagaagctg cgccgcgagc | 1320 |
| tgtgcgcgtt cgaggcggag cgcgcgcgcg aggagggcgt cacgctcgtg ctctgcggcg | 1380 |
| gcgctgacgc cgacgacaag gcgttcgccg ccgcgtggc gcagttcgcg ggcctcctca | 1440 |
| cctacgacag cctcggcaag ctggtctacc tccacgcctg cgtcaccgag acgctccgcc | 1500 |
| tgtaccccgc cgtccctcag gtgagcgcgc ccgtcacgtc acgacctccg gtccgcgatg | 1560 |
| caacgcatat gtggctgtcc gcagagcaca gcatgcagtg agtggacctg aatgcaatgc | 1620 |
| acatgcactt gcgcgcgcgc aggacccccaa ggggatcctg gaggacgacg tgctgccgga | 1680 |
| cgggacgaag gtgagggccg gcgggatggt gacgtacgtg ccctactcga tggggcggat | 1740 |
| ggagtacaac tggggccccg acgcggcgag cttccggccg gagcggtgga tcaacgagga | 1800 |
| tggcgcgttc cgcaacgcgt cgccgttcaa gttcacggcg ttccaggcgg ggccgaggat | 1860 |
| ctgcctgggc aaggactcgg cgtacctgca gatgaagatg gcgctggcca tcctcttccg | 1920 |
| cttctacagc ttccggctgc tggaggggca cccggtgcag taccgcatga tgaccatcct | 1980 |
| ctccatggcg cacggcctca aggtccgcgt ctctagggcc gtctga | 2026 |

<210> SEQ ID NO 54
<211> LENGTH: 1001
<212> TYPE: DNA
<213> ORGANISM: Zea mays

<400> SEQUENCE: 54

| | |
|---|---|
| ccagggatgg caatggctgt ggcaatcggc tagaggtgga ggacaaggtg gtgaggattg | 60 |
| ggagggcaac ctatggcaag ttggtgaaga ggcacgcaat gagagatctc ttcagactta | 120 |
| cactggatgc cgccaacaaa ttcaacccttt agattttgat actgtcactc ctactttatt | 180 |

```
ccttggttgg gcaacttcca ataggctcat gttaatcaat gattagtaat tattcagcaa      240
atattcttgt ttgtttgaca tttataagaa gtggggtgag acggattaaa tatcatccat      300
gagagcttta tcttcatgct ctcttgattt tggtttcaga tcattctttc agtgttcaca      360
ataattttct cagtttggtc catgtaattt ttgaagtgag gttccttaaa tttcattatg      420
cttcctttct tttctagact agcaattgca tgacttttca ctttggcttc acaaattgac      480
tcacaagaaa acaaattcac ttttgggttc acaaattcct cttcaggatg tacttttcac      540
ttgaacttca tgtataggaa caaggaatgg ctcagttttt aaggaacaat gtacagattt      600
catttcagaa ctctttctgg ttggttgagt ttcagacttt ttgtaccaag ctgatggatc      660
acaatacttg tttccaaagt ctaataacag aaactggcaa ctcctaattg ataatataaa      720
agaataaaat acagtatcag atgtctcatt ttcttggttg gcagatcaca aaaaggaaca      780
caaaggctaa gcctcctact tgttcgggag ttaggtcagg acaccatat gaatgaaaga       840 aatcttaatt tggggtcaca ccaagattgt ctctctcgag gttggggat ccctaaggtt       900 ggtagtagca atacccaata tatcacctaa caaacccaat ccatgctaca tacatacata      960
gcatccatca cttgtagact ggacccttca tcaagagcac c                         1001

<210> SEQ ID NO 55
<211> LENGTH: 1632
<212> TYPE: DNA
<213> ORGANISM: Zea mays

<400> SEQUENCE: 55
atggaggaag ctcacctcac gccggcgacg ccatcgccat tcttcccact agcagggcct       60
cacaagtaca tcgcgctcct tctggttgtc ctctcatgga tcctggtcca gaggtggagc      120
ctgaggaagc agaaaggccc gagatcatgg ccagtcatcg gcgcaacggt ggagcagctg      180
aggaactacc accggatgca cgactggctt gtcgggtacc tgtcacggca caggacagtg      240
accgtcgaca tgccgttcac ttcctacacc tacatcgctg acccggtgaa tgtcgagcat      300
gtcctcaaga ctaacttcac caattacccc aagggaatcg tgtacagatc ctacatggac      360
gtgctcctcg gtgacggcat cttcaacgcc gacggcgagc tgtggaggaa cagaggaag      420 acggcgagtt tcgagttcgc ctccaagaac ctgagggatt tcagcgccat tgtgttcaga      480
gagtactccc tgaagctgtc gggtatactg agccaggcat ccaaggcagg caaagttgtg      540
gacatgcagg aactttacat gaggatgacg ctggactcca tctgcaaggt tgggttcggg      600
gtcgagatcg gcacgctgtc gccagatctc cccgagaaca gcttcgcgca ggcgttcgat      660
gccgccaaca tcatcatcac gctgcggttc atcgacccgc tgtggcgcat caagaggttc      720
ttccacgtcg ggtcagaggc cctcctagcg cagagcatca agctcgtgga cgagttcacc      780
tacagcgtga tccgccggag gaaggccgag atcgtcgagg tccgggccag cggcaaacag      840
gagaagatga agcacgacat cctgtcacgg ttcatcgagc tgggcgaggc cggcgacgac      900
ggcggcggct cggggacga taagagcctc cgggacgtgg tgctcaactt cgtgatcgcc      960
gggcgggaca cgacggcgac gacgctgtcg tggttcacgc acatggccat gtcccacccg     1020
gacgtggccg agaagctgcg ccgcgagctg tgcgcgttcg aggcggagcg cgcgcgcgag     1080
gagggcgtca cgctcgtgct ctgcggcggc gctgacgccg acgacaaggc gttcgccgcc     1140
cgcgtggcgc agttcgcggg cctcctcacc tacgacagcc tcggcaagct ggtctacctc     1200
cacgcctgcg tcaccgagac gctccgcctg taccccgccg tccctcagga ccccaagggg     1260
```

```
atcctggagg acgacgtgct gccggacggg acgaaggtga gggccggcgg gatggtgacg    1320
tacgtgccct actcgatggg gcggatggag tacaactggg ccccgacgc ggcgagcttc     1380 cggccggagc ggtggatcaa cgaggatggc gcgttccgca acgcgtcgcc gttcaagttc    1440
acggcgttcc aggcggggcc gaggatctgc ctgggcaagg actcggcgta cctgcagatg    1500
aagatggcgc tggccatcct cttccgcttc tacagcttcc ggctgctgga ggggcacccg    1560
gtgcagtacc gcatgatgac catcctctcc atggcgcacg gcctcaaggt ccgcgtctct    1620
agggccgtct ga                                                        1632
```

<210> SEQ ID NO 56
<211> LENGTH: 543
<212> TYPE: PRT
<213> ORGANISM: Zea mays

<400> SEQUENCE: 56

```
Met Glu Glu Ala His Leu Thr Pro Ala Thr Pro Ser Pro Phe Phe Pro
1               5                  10                  15

Leu Ala Gly Pro His Lys Tyr Ile Ala Leu Leu Val Val Leu Ser
            20                  25                  30

Trp Ile Leu Val Gln Arg Trp Ser Leu Arg Lys Gln Lys Gly Pro Arg
        35                  40                  45

Ser Trp Pro Val Ile Gly Ala Thr Val Glu Gln Leu Arg Asn Tyr His
    50                  55                  60

Arg Met His Asp Trp Leu Val Gly Tyr Leu Ser Arg His Arg Thr Val
65                  70                  75                  80

Thr Val Asp Met Pro Phe Thr Ser Tyr Thr Tyr Ile Ala Asp Pro Val
                85                  90                  95

Asn Val Glu His Val Leu Lys Thr Asn Phe Thr Asn Tyr Pro Lys Gly
            100                 105                 110

Ile Val Tyr Arg Ser Tyr Met Asp Val Leu Leu Gly Asp Gly Ile Phe
        115                 120                 125

Asn Ala Asp Gly Glu Leu Trp Arg Lys Gln Arg Lys Thr Ala Ser Phe
    130                 135                 140

Glu Phe Ala Ser Lys Asn Leu Arg Asp Phe Ser Ala Ile Val Phe Arg
145                 150                 155                 160

Glu Tyr Ser Leu Lys Leu Ser Gly Ile Leu Ser Gln Ala Ser Lys Ala
                165                 170                 175

Gly Lys Val Val Asp Met Gln Glu Leu Tyr Met Arg Met Thr Leu Asp
            180                 185                 190

Ser Ile Cys Lys Val Gly Phe Gly Val Glu Ile Gly Thr Leu Ser Pro
        195                 200                 205

Asp Leu Pro Glu Asn Ser Phe Ala Gln Ala Phe Asp Ala Ala Asn Ile
    210                 215                 220

Ile Ile Thr Leu Arg Phe Ile Asp Pro Leu Trp Arg Ile Lys Arg Phe
225                 230                 235                 240

Phe His Val Gly Ser Glu Ala Leu Leu Ala Gln Ser Ile Lys Leu Val
                245                 250                 255

Asp Glu Phe Thr Tyr Ser Val Ile Arg Arg Lys Ala Glu Ile Val
            260                 265                 270

Glu Val Arg Ala Ser Gly Lys Gln Glu Lys Met Lys His Asp Ile Leu
        275                 280                 285

Ser Arg Phe Ile Glu Leu Gly Ala Gly Asp Asp Gly Gly Phe
    290                 295                 300
```

| | | | | | | | | | | | | | | |
|---|---|---|---|---|---|---|---|---|---|---|---|---|---|---|
| Gly | Asp | Asp | Lys | Ser | Leu | Arg | Asp | Val | Val | Leu | Asn | Phe | Val | Ile | Ala |
| 305 | | | | 310 | | | | 315 | | | | | 320 | | |

Gly Asp Asp Lys Ser Leu Arg Asp Val Val Leu Asn Phe Val Ile Ala
305                 310                 315                 320

Gly Arg Asp Thr Thr Ala Thr Thr Leu Ser Trp Phe Thr His Met Ala
                325                 330                 335

Met Ser His Pro Asp Val Ala Glu Lys Leu Arg Arg Glu Leu Cys Ala
            340                 345                 350

Phe Glu Ala Glu Arg Ala Arg Glu Glu Gly Val Thr Leu Val Leu Cys
        355                 360                 365

Gly Gly Ala Asp Ala Asp Lys Ala Phe Ala Ala Arg Val Ala Gln
370                 375                 380

Phe Ala Gly Leu Leu Thr Tyr Asp Ser Leu Gly Lys Leu Val Tyr Leu
385                 390                 395                 400

His Ala Cys Val Thr Glu Thr Leu Arg Leu Tyr Pro Ala Val Pro Gln
                405                 410                 415

Asp Pro Lys Gly Ile Leu Glu Asp Val Leu Pro Asp Gly Thr Lys
            420                 425                 430

Val Arg Ala Gly Gly Met Val Thr Tyr Val Pro Tyr Ser Met Gly Arg
        435                 440                 445

Met Glu Tyr Asn Trp Gly Pro Asp Ala Ala Ser Phe Arg Pro Glu Arg
450                 455                 460

Trp Ile Asn Glu Asp Gly Ala Phe Arg Asn Ala Ser Pro Phe Lys Phe
465                 470                 475                 480

Thr Ala Phe Gln Ala Gly Pro Arg Ile Cys Leu Gly Lys Asp Ser Ala
                485                 490                 495

Tyr Leu Gln Met Lys Met Ala Leu Ala Ile Leu Phe Arg Phe Tyr Ser
            500                 505                 510

Phe Arg Leu Leu Glu Gly His Pro Val Gln Tyr Arg Met Met Thr Ile
        515                 520                 525

Leu Ser Met Ala His Gly Leu Lys Val Arg Val Ser Arg Ala Val
530                 535                 540

```
<210> SEQ ID NO 57
<211> LENGTH: 1930
<212> TYPE: DNA
<213> ORGANISM: Oryza sativa

<400> SEQUENCE: 57
atgaagagcc ccatggagga agctcatgca atgccagtga catcattctt cccagtagca      60
ggaatccaca agctcatagc tatcttcctt gttgtcctct catggatctt ggtccacaag     120
tggagcctga ggaaccagaa agggccaaga tcatggccaa tcatcggcgc gacagtggag     180
caactgaaga actaccacag gatgcatgac tggcttgtcg agtacttgtc gaaggacagg     240
acggtgaccg tcgacatgcc tttcacctcc tacacctaca tgccgacccc ggtgaacgtc     300
gagcatgtcc tgaagaccaa cttcaccaat taccccaagg taaagaaacc ataggatctt     360
cagtgtactg taaaatgtgc cttgcacagt actaacactg acacaaaaaa tgtctgaaaa     420
tatgcagggt gaagtgtaca ggtcttacat ggatgtgctg ctcggtgatg gcatattcaa     480
tgccgacggc gagatgtgga ggaagcaaag gaagacggcg agcttcgagt ttgcctccaa     540
gaacttgaga gacttcagca ctgtggtgtt cagggagtac tccctgaagc tatcaagcat     600
tctgagccaa gcatgcaagg ccggcagagt tgtagacatg caggtaacca actgaattcc     660
ttgcctaata cctaaacatt tcttgagaaa ccaaattgtt cagaattctg atgcaagaac     720
taaccaaaat tcaggaattg ttcatgagga tgacactgga ctcgatctgc aaggtcgggt     780
```

```
ttggggttga gatcgggacg ctgtcacctg atctcccgga gaacagcttt gcccaggcat    840
tcgacgctgc caacatcatc gtcacgctgc ggttcatcga tcctctgtgg cgtctgaaga    900
agttcttgca cgtcggatca gaggctctcc tcgagcagag catgaagctg gttgatgact    960
tcacctacag cgtgatccgc cgccgcaagg ctgagatctt gcaggctcga gccagcggca   1020
agcaagagaa ggtgatcctt cctctcttgc tcaaagaatc agtagaactg aactgacatg   1080
gtaatggtga tgatcagatc ggaaaaggtt ttgtttcttg atatcgttga tttgtaatgg   1140
cgagcagatc aagcacgaca tactgtcgcg gttcatcgag ctcggggagg ccggcggcga   1200
cgaggggggc ggcagcttcg gggacgacaa gagcctccgc gacgtggtgc tcaacttcgt   1260
gatcgccggg cgtgacacga cggcgacgac gctgtcgtgg ttcacgtaca tggcgatgac   1320
gcacccggcc gtcgccgaca agctccggcg cgagctggcc gcgttcgagg atgagcgcgc   1380
gcgcgaggag ggcgtcgcgc tcgccgacgc cgccggcgag gcgtcgttcg cggcgcgcgt   1440
ggcgcagttc gcgtcgctgc tgagctacga cgcggtgggg aagctggtgt acctgcacgc   1500
gtgcgtgacg gagacgctcc gcctctaccc ggcggtgccg caggacccca aggggatcgt   1560
ggaggacgac gtgctccccg acggcaccaa ggtgcgcgcc ggcgggatgg tgacgtacgt   1620
gccctactcc atggggagga tggagtacaa ctggggcccc gacgcggcga gcttccggcc   1680
ggagcggtgg ctcagcggcg acggcggcgc gttccggaac gcgtcgccgt caagttcac    1740
cgcgttccag gccgggccgc ggatctgcct cggcaaggac tccgcctacc tccagatgaa   1800
gatggcgctc gccatcctct ccgcttcta caccttcgac ctcgtcgagg accaccccgt    1860
caagtaccgg atgatgacca tcctctccat ggctcacggc tcaaggtcc gcgtctccac    1920
ctccgtctga                                                          1930

<210> SEQ ID NO 58
<211> LENGTH: 946
<212> TYPE: DNA
<213> ORGANISM: Oryza sativa

<400> SEQUENCE: 58
ggtttcagac ttgtttcagt gttgacattg gttatttctc aattcattcg agtatttgtt     60
gttacatcac aaaggataag ttctatagaa aaaatcttcc ttttcaagtg atgttcttta    120
attttctgta gaattgtgcc ctgcaatttc tcaaatcttt gatagatggc ttatttgtat    180
tgactggaaa agaaattagt tgtcaataac tagaagcttt agagatgcaa agtattggat    240
atatcttggc aatagtattt tatattgctt gtttatgtga gaatgtttta actagatggc    300
aactgatttc tgggacaaaa tcgcttctac aatagcattt tatggaactc gtactcgtcg    360
atagcatttc ttggatttgg gtgtttgtaa atggcatttc ttggattttc tcttcattaa    420
aatagcctat tcagatgaag tagaattcag gtgaagtaga accaactac tttgggttca     480
caatttatat ttcttttgag gataccccat ttcattttag ttgtcatcaa agactagaca    540
atatcgacag aaaatggtaa gcctggtttc agttggtgac aatttaacag aattcagatg    600
gatatggttc tgatattaga aggtggcata cctttagtcg ctgcaaacgc ttcagttatc    660
tgaacaaaac aacgaacttg gctgagcagg ggaaaaaaat actgtagcat tcattttgtg    720
tttacatgag taacgattct tttctaggtg gacagatcac aaaaagaaaa ctaaagctaa    780
gatccaactc ctaagggtgt taggttaggg acaccatatg aatgagacaa tcttaattct    840
tggtcacaca aagattgtct caaggttggt agcatcagtg cccaatatat cacctaacta    900
tgccatccaa aatgctacat agcatctctt gtagactgaa cccttc                   946
```

<210> SEQ ID NO 59
<211> LENGTH: 1635
<212> TYPE: DNA
<213> ORGANISM: Oryza sativa

<400> SEQUENCE: 59

```
atgaagagcc ccatggagga agctcatgca atgccagtga catcattctt cccagtagca      60
ggaatccaca agctcatagc tatcttcctt gttgtcctct catggatctt ggtccacaag     120
tggagcctga ggaaccagaa agggccaaga tcatggccaa tcatcggcgc gacagtggag     180
caactgaaga actaccacag gatgcatgac tggcttgtcg agtacttgtc gaaggacagg     240
acggtgaccg tcgacatgcc tttcacctcc tacacctaca ttgccgaccc ggtgaacgtc     300
gagcatgtcc tgaagaccaa cttcaccaat taccccaagg gtgaagtgta caggtcttac     360
atggatgtgc tgctcggtga tggcatattc aatgccgacg gcgagatgtg gaggaagcaa     420
aggaagacgg cgagcttcga gtttgcctcc aagaacttga gagacttcag cactgtggtg     480
ttcagggagt actccctgaa gctatcaagc attctgagcc aagcatgcaa ggccggcaga     540
gttgtagaca tgcaggaatt gttcatgagg atgacactgg actcgatctg caaggtcggg     600
tttggggttg agatcgggac gctgtcacct gatctcccgg agaacagctt tgcccaggca     660
ttcgacgctg ccaacatcat cgtcacgctg cggttcatcg atcctctgtg gcgtctgaag     720
aagttcttgc acgtcggatc agaggctctc ctcgagcaga gcatgaagct ggttgatgac     780
ttcacctaca gcgtgatccg ccgccgcaag gctgagatct tgcaggctcg agccagcggc     840
aagcaagaga agatcaagca cgacatactg tcgcggttca tcgagctcgg ggaggccggc     900
ggcgacgagg gggcggcag cttcggggac gacaagagcc tccgcgacgt ggtgctcaac     960
tcgtgatcg ccgggcgtga cacgacggcg acgacgctgt cgtggttcac gtacatggcg    1020
atgacgcacc cggccgtcgc cgacaagctc cggcgcgagc tggccgcgtt cgaggatgag    1080
cgcgcgcgcg aggagggcgt cgcgctcgcc gacgccgccg cgaggcgtc gttcgcggcg    1140
cgcgtggcgc agttcgcgtc gctgctgagc tacgacgcgg tggggaagct ggtgtacctg    1200
cacgcgtgcg tgacggagac gctccgcctc taccggcgg tgccgcagga ccccaagggg    1260
atcgtggagg acgacgtgct cccccgacggc accaaggtgc gcgccggcgg gatggtgacg    1320
tacgtgccct actccatggg gaggatggag tacaactggg gccccgacgc ggcgagcttc    1380
cggccggagc ggtggctcag cggcgacggc ggcgcgttcc ggaacgcgtc gccgttcaag    1440
ttcaccgcgt tccaggccgg gccgcggatc tgcctcggca aggactccgc ctacctccag    1500
atgaagatgg cgctcgccat cctcttccgc ttctacacct cgacctcgt cgaggaccac    1560
cccgtcaagt accggatgat gaccatcctc tccatggctc acggcctcaa ggtccgcgtc    1620
tccacctccg tctga                                                     1635
```

<210> SEQ ID NO 60
<211> LENGTH: 544
<212> TYPE: PRT
<213> ORGANISM: Oryza sativa

<400> SEQUENCE: 60

```
Met Lys Ser Pro Met Glu Glu Ala His Ala Met Pro Val Thr Ser Phe
1               5                   10                  15

Phe Pro Val Ala Gly Ile His Lys Leu Ile Ala Ile Phe Leu Val Val
            20                  25                  30
```

```
Leu Ser Trp Ile Leu Val His Lys Trp Ser Leu Arg Asn Gln Lys Gly
         35                  40                  45

Pro Arg Ser Trp Pro Ile Ile Gly Ala Thr Val Glu Gln Leu Lys Asn
 50                  55                  60

Tyr His Arg Met His Asp Trp Leu Val Glu Tyr Leu Ser Lys Asp Arg
 65                  70                  75                  80

Thr Val Thr Val Asp Met Pro Phe Thr Ser Tyr Thr Tyr Ile Ala Asp
                 85                  90                  95

Pro Val Asn Val Glu His Val Leu Lys Thr Asn Phe Thr Asn Tyr Pro
                100                 105                 110

Lys Gly Glu Val Tyr Arg Ser Tyr Met Asp Val Leu Leu Gly Asp Gly
                115                 120                 125

Ile Phe Asn Ala Asp Gly Glu Met Trp Arg Lys Gln Arg Lys Thr Ala
        130                 135                 140

Ser Phe Glu Phe Ala Ser Lys Asn Leu Arg Asp Phe Ser Thr Val Val
145                 150                 155                 160

Phe Arg Glu Tyr Ser Leu Lys Leu Ser Ser Ile Leu Ser Gln Ala Cys
                165                 170                 175

Lys Ala Gly Arg Val Val Asp Met Gln Glu Leu Phe Met Arg Met Thr
                180                 185                 190

Leu Asp Ser Ile Cys Lys Val Gly Phe Gly Val Glu Ile Gly Thr Leu
        195                 200                 205

Ser Pro Asp Leu Pro Glu Asn Ser Phe Ala Gln Ala Phe Asp Ala Ala
        210                 215                 220

Asn Ile Ile Val Thr Leu Arg Phe Ile Asp Pro Leu Trp Arg Leu Lys
225                 230                 235                 240

Lys Phe Leu His Val Gly Ser Glu Ala Leu Leu Glu Gln Ser Met Lys
                245                 250                 255

Leu Val Asp Asp Phe Thr Tyr Ser Val Ile Arg Arg Lys Ala Glu
                260                 265                 270

Ile Leu Gln Ala Arg Ala Ser Gly Lys Gln Lys Ile Lys His Asp
        275                 280                 285

Ile Leu Ser Arg Phe Ile Glu Leu Gly Glu Ala Gly Gly Asp Glu Gly
        290                 295                 300

Gly Gly Ser Phe Gly Asp Asp Lys Ser Leu Arg Asp Val Val Leu Asn
305                 310                 315                 320

Phe Val Ile Ala Gly Arg Asp Thr Thr Ala Thr Thr Leu Ser Trp Phe
                325                 330                 335

Thr Tyr Met Ala Met Thr His Pro Ala Val Ala Asp Lys Leu Arg Arg
                340                 345                 350

Glu Leu Ala Ala Phe Glu Asp Glu Arg Ala Arg Glu Glu Gly Val Ala
                355                 360                 365

Leu Ala Asp Ala Ala Gly Glu Ala Ser Phe Ala Ala Arg Val Ala Gln
        370                 375                 380

Phe Ala Ser Leu Leu Ser Tyr Asp Ala Val Gly Lys Leu Val Tyr Leu
385                 390                 395                 400

His Ala Cys Val Thr Glu Thr Leu Arg Leu Tyr Pro Ala Val Pro Gln
                405                 410                 415

Asp Pro Lys Gly Ile Val Glu Asp Val Leu Pro Asp Gly Thr Lys
                420                 425                 430

Val Arg Ala Gly Gly Met Val Thr Tyr Val Pro Tyr Ser Met Gly Arg
                435                 440                 445

Met Glu Tyr Asn Trp Gly Pro Asp Ala Ala Ser Phe Arg Pro Glu Arg
```

```
                450             455             460
Trp Leu Ser Gly Asp Gly Gly Ala Phe Arg Asn Ala Ser Pro Phe Lys
465                 470                 475                 480

Phe Thr Ala Phe Gln Ala Gly Pro Arg Ile Cys Leu Gly Lys Asp Ser
                485                 490                 495

Ala Tyr Leu Gln Met Lys Met Ala Leu Ala Ile Leu Phe Arg Phe Tyr
            500                 505                 510

Thr Phe Asp Leu Val Glu Asp His Pro Val Lys Tyr Arg Met Met Thr
        515                 520                 525

Ile Leu Ser Met Ala His Gly Leu Lys Val Arg Val Ser Thr Ser Val
    530                 535                 540

<210> SEQ ID NO 61
<211> LENGTH: 1483
<212> TYPE: DNA
<213> ORGANISM: Triticum aestivum

<400> SEQUENCE: 61
atggaagaga agaagccgcg gcggcaggga gccgcaggac gcgatggcat cgtgcagtac        60
ccgcacctct tcatcgcggc cctggcgctg gccctggtcc tcatggaccc cttccacctc       120
ggcccgctgg ccgggatcga ctaccggccg gtgaagcacg agctggcgcc gtacagggag       180
gtcatgcagc gctggccgag ggacaacggc agccgcctca ggctcggcag gctcgagttc       240
gtcaacgagg tgttcgggcc agagtccatc gagttcgacc gccagggccg cgggccctac       300
gccgggctcg ccgacggccg cgtcgtgcgg tggatggggg acaaggccgg gtgggagacg       360
ttcgccgtca tgaatcctga ctggtattgg cttactgcag aaaaaccata gcttacctgt       420
gtgtgtgcaa actaaaatag ttttttcgga aaaaaaaagg tcggagaaag tttgtgctaa       480
cggagtggag tcgacgacga agaagcagca cgggaaggag aagtggtgcg gccggcctct       540
cgggctgagg ttccacaggg agaccggcga gctcttcatc gccgacgcgt actatgggct       600
catggccgtt ggcgaaagcg gcggcgtggc gacctccctg gcgagggagg ccggcgggga       660
cccggtccac ttcgccaacg acctcgacat ccacatgaac ggctcgatat tcttcaccga       720
cacgagcacg agatacagca gaaagtgagc ggagtactgc tgccgatctc ctttttctgt       780
tcttgagatt tgtgtttgac aaatgactga tcatgcaggg accatttgaa cattttgctg       840
gaaggagaag gcacggggag gctgctgaga tatgaccgag aaaccggtgc cgttcatgtc       900
gtgctcaacg ggctggtctt cccaaacggc gtgcagatct cacaggacca gcaatttctc       960
ctcttctccg agacaacaaa ctgcaggtga gataaactca ggttttcagt atgatccggc      1020
tcgagagatc caggaactga tgacgccttt attaatcggc tcatgcatgc acactaggat      1080
catgaggtac tggctggaag gtccaagagc gggccaggtg gaggtgttcg cgaacctgcc      1140
ggggttcccc gacaacgtgc gcttgaacag caaggggcag ttctgggtgg cgatcgactg      1200
ctgccggacg ccgacgcagg aggtgttcgc gcggtggccg tggctgcgga ccgcctactt      1260
caagatcccg gtgtcgatga gacgctgggg aagatggtg agcatgaaga tgtacacgct       1320
tctcgcgctc ctcgacggcg aggggaacgt ggtcgaggta ctcgaggacc ggggcggcga      1380
ggtgatgaag ctggtgagcg aggtgaggga ggtggaccgg aggctgtgga tcgggaccgt      1440
tgcgcacaac cacatcgcca cgatccctta tccgttggac tag                         1483

<210> SEQ ID NO 62
<211> LENGTH: 1000
<212> TYPE: DNA
```

<213> ORGANISM: Triticum aestivum

<400> SEQUENCE: 62

| | | | | | |
|---|---|---|---|---|---|
| tagtagagat | gcttgaagaa | ataaaccaga | cttttcttaa | gcatcagtgc | ttatttatac | 60 |
| atggcagacg | cttaattaga | cgtctctcct | ataaaaataa | gcaccggtgc | ttgagaaaaa | 120 |
| tccggtttat | ttttgtaagc | acctctccta | agcaccttgc | attgtacaag | gtcttggaga | 180 |
| aataaaccag | gctttcttta | agtatccgtg | cttatttata | caggacagac | gcttaattag | 240 |
| acgtttctcc | tgtagaaata | ggcacaaatg | cttcaaaaaa | atccgatttg | tttttataag | 300 |
| cacctagcat | tgtacgaggc | cttacgtatt | tgttgggtgc | ttaaaaagga | agagaaagaa | 360 |
| agaaagaaag | cgatctagaa | atttaaacac | tgaagggacc | catgtcgtca | ccctagggcc | 420 |
| ttccgaaacg | taggaccgac | cctacacgca | ccgcattacg | ccaattatct | ctccctctaa | 480 |
| tccccttata | attacctcta | taacatctgt | caataactaa | atcattatca | cgaatgatac | 540 |
| cgaattcttg | actgctccct | tgctcttctg | cttctttctc | ctccaaagtt | tgctcttctc | 600 |
| tccctgatcc | tgatcctcac | cagatcaggt | catgcatgat | aattggctcg | gtatatcctc | 660 |
| ctggatcact | ttatgcttgc | ttttttttgag | aatccacttt | atgcttgttg | acctgtacat | 720 |
| cttgcatcac | tatccaagca | acgaaggcat | gcaaatccca | aattccaaaa | gcgccatatc | 780 |
| cccttagctg | ttctgaaccg | aaatacacct | actcccaaac | gatcacaccg | acccatgcaa | 840 |
| cctccgtgcg | tgccgggata | atattgtcac | gctagctgac | tcatgcaact | cccgtgcatg | 900 |
| tcggtatata | ttttcggggc | aaatccatta | agaatttaag | atcacattgc | ccgcgctttt | 960 |
| ttcgtccgca | tgcaaactag | agccactgcc | ctctacctcc | | | 1000 |

<210> SEQ ID NO 63
<211> LENGTH: 1242
<212> TYPE: DNA
<213> ORGANISM: Triticum aestivum

<400> SEQUENCE: 63

| | | | | | |
|---|---|---|---|---|---|
| atggaagaga | agaagccgcg | gcggcaggga | gccgcaggac | gcgatggcat | cgtgcagtac | 60 |
| ccgcacctct | tcatcgcggc | cctggcgctg | gccctggtcc | tcatggaccc | cttccacctc | 120 |
| ggcccgctgg | ccgggatcga | ctaccggccg | gtgaagcacg | agctggcgcc | gtacagggag | 180 |
| gtcatgcagc | gctggccgag | ggacaacggc | agccgcctca | ggctcggcag | gctcgagttc | 240 |
| gtcaacgagg | tgttcgggcc | agagtccatc | gagttcgacc | gccagggccg | cgggccctac | 300 |
| gccgggctcg | ccgacggccg | cgtcgtgcgg | tggatggggg | acaaggccgg | gtgggagacg | 360 |
| ttcgccgtca | tgaatcctga | ctggtcggag | aaagtttgtg | ctaacggagt | ggagtcgacg | 420 |
| acgaagaagc | agcacgggaa | ggagaagtgg | tgcggccggc | ctctcgggct | gaggttccac | 480 |
| agggagaccg | gcgagctctt | catcgccgac | gcgtactatg | ggctcatggc | cgttggcgaa | 540 |
| agcggcggcg | tggcgacctc | cctggcgagg | gaggccggcg | gggacccggt | ccacttcgcc | 600 |
| aacgacctcg | acatccacat | gaacggctcg | atattcttca | ccgacacgag | cacgagatac | 660 |
| agcagaaagg | accatttgaa | cattttgctg | gaaggagaag | gcacggggag | gctgctgaga | 720 |
| tatgaccgag | aaaccggtgc | cgttcatgtc | gtgctcaacg | gctggtcttt | cccaaacggc | 780 |
| gtgcagatct | cacaggacca | gcaatttctc | ctcttctccg | agacaacaaa | ctgcaggatc | 840 |
| atgaggtact | ggctggaagg | tccaagagcg | ggccaggtgg | aggtgttcgc | gaacctgccg | 900 |
| gggttccccg | acaacgtgcg | cttgaacagc | aaggggcagt | tctgggtggc | gatcgactgc | 960 |
| tgccggacgc | cgacgcagga | ggtgttcgcg | cggtggccgt | ggctgcggac | cgcctacttc | 1020 |

```
aagatcccgg tgtcgatgaa gacgctgggg aagatggtga gcatgaagat gtacacgctt   1080
ctcgcgctcc tcgacggcga ggggaacgtg gtcgaggtac tcgaggaccg gggcggcgag   1140
gtgatgaagc tggtgagcga ggtgagggag gtggaccgga ggctgtggat cgggaccgtt   1200
gcgcacaacc acatcgccac gatcccttat ccgttggact ag                      1242

<210> SEQ ID NO 64
<211> LENGTH: 413
<212> TYPE: PRT
<213> ORGANISM: Triticum aestivum

<400> SEQUENCE: 64

Met Glu Glu Lys Lys Pro Arg Arg Gln Gly Ala Ala Gly Arg Asp Gly
1               5                   10                  15

Ile Val Gln Tyr Pro His Leu Phe Ile Ala Ala Leu Ala Leu Ala Leu
            20                  25                  30

Val Leu Met Asp Pro Phe His Leu Gly Pro Leu Ala Gly Ile Asp Tyr
        35                  40                  45

Arg Pro Val Lys His Glu Leu Ala Pro Tyr Arg Glu Val Met Gln Arg
    50                  55                  60

Trp Pro Arg Asp Asn Gly Ser Arg Leu Arg Leu Gly Arg Leu Glu Phe
65                  70                  75                  80

Val Asn Glu Val Phe Gly Pro Glu Ser Ile Glu Phe Asp Arg Gln Gly
                85                  90                  95

Arg Gly Pro Tyr Ala Gly Leu Ala Asp Gly Arg Val Val Arg Trp Met
            100                 105                 110

Gly Asp Lys Ala Gly Trp Glu Thr Phe Ala Val Met Asn Pro Asp Trp
        115                 120                 125

Ser Glu Lys Val Cys Ala Asn Gly Val Glu Ser Thr Thr Lys Lys Gln
    130                 135                 140

His Gly Lys Glu Lys Trp Cys Gly Arg Pro Leu Gly Leu Arg Phe His
145                 150                 155                 160

Arg Glu Thr Gly Glu Leu Phe Ile Ala Asp Ala Tyr Tyr Gly Leu Met
                165                 170                 175

Ala Val Gly Glu Ser Gly Gly Val Ala Thr Ser Leu Ala Arg Glu Ala
            180                 185                 190

Gly Gly Asp Pro Val His Phe Ala Asn Asp Leu Asp Ile His Met Asn
        195                 200                 205

Gly Ser Ile Phe Phe Thr Asp Thr Ser Thr Arg Tyr Ser Arg Lys Asp
    210                 215                 220

His Leu Asn Ile Leu Leu Glu Gly Glu Gly Thr Gly Arg Leu Leu Arg
225                 230                 235                 240

Tyr Asp Arg Glu Thr Gly Ala Val His Val Val Leu Asn Gly Leu Val
                245                 250                 255

Phe Pro Asn Gly Val Gln Ile Ser Gln Asp Gln Gln Phe Leu Leu Phe
            260                 265                 270

Ser Glu Thr Thr Asn Cys Arg Ile Met Arg Tyr Trp Leu Glu Gly Pro
        275                 280                 285

Arg Ala Gly Gln Val Glu Val Phe Ala Asn Leu Pro Gly Phe Pro Asp
    290                 295                 300

Asn Val Arg Leu Asn Ser Lys Gly Gln Phe Trp Val Ala Ile Asp Cys
305                 310                 315                 320

Cys Arg Thr Pro Thr Gln Glu Val Phe Ala Arg Trp Pro Trp Leu Arg
                325                 330                 335
```

```
            Thr Ala Tyr Phe Lys Ile Pro Val Ser Met Lys Thr Leu Gly Lys Met
                            340                 345                 350

Val Ser Met Lys Met Tyr Thr Leu Leu Ala Leu Leu Asp Gly Glu Gly
                        355                 360                 365

Asn Val Val Glu Val Leu Glu Asp Arg Gly Glu Val Met Lys Leu
            370                 375                 380

Val Ser Glu Val Arg Glu Val Asp Arg Arg Leu Trp Ile Gly Thr Val
            385                 390                 395                 400

Ala His Asn His Ile Ala Thr Ile Pro Tyr Pro Leu Asp
                            405                 410

<210> SEQ ID NO 65
<211> LENGTH: 1481
<212> TYPE: DNA
<213> ORGANISM: Triticum aestivum

<400> SEQUENCE: 65
atggaagaga agaagccgcg gcggcaggga gccgcagtac gcgatggcat cgtgcagtac      60
ccgcacctct tcatcgcggc cctggcgctg gccctggtcg tcatggaccc cttccacctc     120
ggcccgctgg ctgggatcga ctaccggccg gtgaagcacg agctggcgcc atacagggag     180
gtcatgcagc gctggccgag ggacaacggc agccgcctca ggctcggcag gctcgagttc     240
gtcaacgagt gtttcgggcc ggagtccatc gagttcgaca gccagggccg cgggccctac     300
gccgggctcg ccgacggccg cgtcgtgcgg tggatggggg acaagaccgg tgggagacg     360 ttcgccgtca tgaatcctga ctggtaattg gcttactgca gataaatcca tagcttacct     420
gtgtgtttgc aaactaaaat gatttcttgg gaaaaaaaa ggtcggagaa agtttgtgct     480
aacggagtgg agtcaacgac gaagaagcag cacgggaagg agaagtggtg cggccggcct     540
ctcgggctga ggttccacag ggagaccggc gagctcttca tcgccgacgc gtactatggg     600
ctcatggccg tcggcgaaag cggcggcgtg gcgacctccc tggcagggga ggtcggcggg     660 gaccccggtcc acttcgccaa cgacctcgac atccacatga acggctcgat attcttcacc     720
gacacgagca cgagatacag cagaaagtga gcggagtact gtcgctgatc tccatttttg     780
ttcttgagat gttgtgtttg agtgtctgac accatgactg atcatgcagg gatcatttga     840
acattttgct agaaggagaa ggcacgggga ggctgctgag atatgaccga gaaccggtg     900 ccgttcatgt cgtgctcaac gggctggtct tcccaaacgg cgtgcagatt tcacaggacc     960
agcaatttct cctcttctcc gagacaacca actgcaggtg agataaactc aggttttcag    1020
tatgatccgg ctcgagagat ccaggaactg atgacggatc atgcatgcac gctaggatca    1080
tgaggtactg gctggaaggt ccaagagcgg gccaggtgga ggtgttcgcg aacctgccgg    1140
ggttccccga caacgtgcgc ctgaacagca agggcagtt ctgggtggcg atcgactgct    1200
gccggacgcc gacgcaggag gtgttcgcga ggtggccgtg gctgcggacc gcctacttca    1260
agatcccggt gtcgatgaag acgctgggga agatggtgag catgaagatg tacacgcttc    1320
tcgcgctcct cgacggcgag gggaacgtgg tggaggtgct cgaggaccgg ggcggcgagg    1380
tgatgaagct ggtgagcgag gtgagggagg tggaccggag gctgtggatc gggaccgttg    1440
cgcacaacca catcgccacg atcccttacc cgctggacta g                         1481

<210> SEQ ID NO 66
<211> LENGTH: 1000
<212> TYPE: DNA
<213> ORGANISM: Triticum aestivum
```

<400> SEQUENCE: 66

```
gggattcagg atcaaggatg ccttgtttgt tgtcgccatt gcgtgtggca ggccagcaac      60
ctactgttgt gtcgtgtgcc cgtgccggcg acccagctat ccggcatccg atgggagcaa    120
gttcatccgt tctttcaaaa atcccagct  acctattcat ccatgatcca tcccccaatt    180
tcagtgtaca cgattagggt ttcgatgtat aaattttaat ttagtctgtc acaagtacgt    240
attcatccat cctaattttg tgtgtcctat tcatgcctag ggttctcatg tataaatttc    300
taattcttcg tgttctcttt tcttcataat tttaggatat tagcccgcct tacaatgttg    360
tctaagaccc gtaaagaaa  caatgttctc taagaagcat ttgccgggtg cttaaaaaag    420
aagaaaagaa agaaagaaag tgatctgaaa attcaaacac tgaaggggcc catgtcgtcg    480
acctagggcc ttccgaaacg tagaaccaaa cctacacgca ccgcattacg ccaattatct    540
ctccctctaa tcctctgaca atttccttta taatgactgt caataactaa atccttatca    600
cgaatgagac cgaattttgc tcttctctcc ctgtatcctg atcctcacca gatcaggtca    660
tgcatgataa ttggctcggt atatcctcct ggatcacttt atgcttgttg acctgtacat    720
cttgcatcac tttccaagca acaaaggcat gcaagtctca aattccaaaa aggccatatc    780
cccttagctg ttctgaaccg aaatacacct actcccaaac gatcacaccg acccatgcaa    840
cctccgtgca tgtcgggata tcttgtgac  gctagctaac tcatgcaact cccgtgcatg    900
tcggaatata ttttcggggc aaatccatta agaatttaag atcacgttgc ccgcgctttt    960
ttcgtctgca tgcaaacgag aaccactgcc ctctgcctcc                         1000
```

<210> SEQ ID NO 67
<211> LENGTH: 1242
<212> TYPE: DNA
<213> ORGANISM: Triticum aestivum

<400> SEQUENCE: 67

```
atggaagaga agaagccgcg gcggcaggga gccgcagtac gcgatggcat cgtgcagtac     60
ccgcacctct tcatcgcggc cctggcgctg gccctggtcg tcatggaccc cttccacctc    120
ggcccgctgg ctgggatcga ctaccggccg gtgaagcacg agctggcgcc atacagggag    180
gtcatgcagc gctggccgag ggacaacggc agccgcctca ggctcggcag gctcgagttc    240
gtcaacgagg tgttcgggcc ggagtccatc gagttcgaca gccagggccg cgggccctac    300
gccgggctcg ccgacggccg cgtcgtgcgg tggatggggg acaagaccgg gtgggagacg    360
ttcgccgtca tgaatcctga ctggtcggag aaagtttgtg ctaacggagt ggagtcaacg    420
acgaagaagc agcacgggaa ggagaagtgg tgcggccggc ctctcgggct gaggttccac    480
agggagaccg cgagctctt  catcgccgac gcgtactatg ggctcatggc cgtcggcgaa    540
agcggcggcg tggcgaccct cctggcaagg gaggtcggcg gggacccggt ccacttcgcc    600
aacgacctcg acatccacat gaacggctcg atattcttca ccgacacgag cacgagatac    660
agcagaaagg atcatttgaa cattttgcta gaaggagaag gcacggggag gctgctgaga    720
tatgaccgag aaaccggtgc cgttcatgtc gtgctcaacg ggctggtctt cccaaacggc    780
gtgcagattt cacaggacca gcaatttctc ctcttctccg agacaaccaa ctgcaggatc    840
atgaggtact ggctggaagg tccaagagcg ggccaggtgg aggtgttcgc gaacctgccg    900
gggttccccg acaacgtgcg cctgaacagc aaggggcagt tctgggtggc gatcgactgc    960
tgccggacgc cgacgcagga ggtgttcgcg aggtggccgt ggctgcggac cgcctacttc   1020
```

```
aagatcccgg tgtcgatgaa gacgctgggg aagatggtga gcatgaagat gtacacgctt    1080
ctcgcgctcc tcgacggcga ggggaacgtg gtggaggtgc tcgaggaccg gggcggcgag    1140
gtgatgaagc tggtgagcga ggtgagggag gtggaccgga ggctgtggat cgggaccgtt    1200
gcgcacaacc acatcgccac gatcccttac ccgctggact ag                      1242
```

<210> SEQ ID NO 68
<211> LENGTH: 413
<212> TYPE: PRT
<213> ORGANISM: Triticum aestivum

<400> SEQUENCE: 68

```
Met Glu Glu Lys Lys Pro Arg Arg Gln Gly Ala Ala Val Arg Asp Gly
1               5                   10                  15

Ile Val Gln Tyr Pro His Leu Phe Ile Ala Ala Leu Ala Leu Ala Leu
                20                  25                  30

Val Val Met Asp Pro Phe His Leu Gly Pro Leu Ala Gly Ile Asp Tyr
            35                  40                  45

Arg Pro Val Lys His Glu Leu Ala Pro Tyr Arg Glu Val Met Gln Arg
        50                  55                  60

Trp Pro Arg Asp Asn Gly Ser Arg Leu Arg Leu Gly Arg Leu Glu Phe
65                  70                  75                  80

Val Asn Glu Val Phe Gly Pro Glu Ser Ile Glu Phe Asp Ser Gln Gly
                85                  90                  95

Arg Gly Pro Tyr Ala Gly Leu Ala Asp Gly Arg Val Val Arg Trp Met
                100                 105                 110

Gly Asp Lys Thr Gly Trp Glu Thr Phe Ala Val Met Asn Pro Asp Trp
            115                 120                 125

Ser Glu Lys Val Cys Ala Asn Gly Val Glu Ser Thr Thr Lys Lys Gln
130                 135                 140

His Gly Lys Glu Lys Trp Cys Gly Arg Pro Leu Gly Leu Arg Phe His
145                 150                 155                 160

Arg Glu Thr Gly Glu Leu Phe Ile Ala Asp Ala Tyr Tyr Gly Leu Met
                165                 170                 175

Ala Val Gly Glu Ser Gly Val Ala Thr Ser Leu Ala Arg Glu Val
            180                 185                 190

Gly Gly Asp Pro Val His Phe Ala Asn Asp Leu Asp Ile His Met Asn
        195                 200                 205

Gly Ser Ile Phe Phe Thr Asp Thr Ser Thr Arg Tyr Ser Arg Lys Asp
    210                 215                 220

His Leu Asn Ile Leu Leu Glu Gly Glu Gly Thr Gly Arg Leu Leu Arg
225                 230                 235                 240

Tyr Asp Arg Glu Thr Gly Ala Val His Val Val Leu Asn Gly Leu Val
                245                 250                 255

Phe Pro Asn Gly Val Gln Ile Ser Gln Asp Gln Gln Phe Leu Leu Phe
            260                 265                 270

Ser Glu Thr Thr Asn Cys Arg Ile Met Arg Tyr Trp Leu Glu Gly Pro
        275                 280                 285

Arg Ala Gly Gln Val Glu Val Phe Ala Asn Leu Pro Gly Phe Pro Asp
    290                 295                 300

Asn Val Arg Leu Asn Ser Lys Gly Gln Phe Trp Val Ala Ile Asp Cys
305                 310                 315                 320

Cys Arg Thr Pro Thr Gln Glu Val Phe Ala Arg Trp Pro Trp Leu Arg
                325                 330                 335
```

| Thr | Ala | Tyr | Phe | Lys | Ile | Pro | Val | Ser | Met | Lys | Thr | Leu | Gly | Lys | Met |
|---|---|---|---|---|---|---|---|---|---|---|---|---|---|---|---|
| | | | 340 | | | | 345 | | | | 350 | | | | |

| Val | Ser | Met | Lys | Met | Tyr | Thr | Leu | Leu | Ala | Leu | Leu | Asp | Gly | Glu | Gly |
|---|---|---|---|---|---|---|---|---|---|---|---|---|---|---|---|
| 355 | | | | | 360 | | | | | 365 | | | | | |

| Asn | Val | Val | Glu | Val | Leu | Glu | Asp | Arg | Gly | Glu | Val | Met | Lys | Leu |
|---|---|---|---|---|---|---|---|---|---|---|---|---|---|---|
| | 370 | | | | | 375 | | | | | 380 | | | |

| Val | Ser | Glu | Val | Arg | Glu | Val | Asp | Arg | Arg | Leu | Trp | Ile | Gly | Thr | Val |
|---|---|---|---|---|---|---|---|---|---|---|---|---|---|---|---|
| 385 | | | | 390 | | | | | 395 | | | | | 400 | |

| Ala | His | Asn | His | Ile | Ala | Thr | Ile | Pro | Tyr | Pro | Leu | Asp |
|---|---|---|---|---|---|---|---|---|---|---|---|---|
| | | | 405 | | | | | 410 | | | | |

<210> SEQ ID NO 69
<211> LENGTH: 1471
<212> TYPE: DNA
<213> ORGANISM: Triticum aestivum

<400> SEQUENCE: 69

```
atggaagaga agaaaccgcg gcggcaggga gccgcagtac gcgatggcat cgtgcagtac      60
ccgcacctct tcatcgcggc cctggcgctg gccctggtcc tcatggaccc gttccacctc     120
ggcccgctgg ccgggatcga ctaccgaccg gtgaagcacg agctggcgcc gtacagggag     180
gtcatgcagc gctggccgag ggacaacggc agccgcctca ggctcggcag gctcgagttc     240
gtcaacgagg tgttcgggcc ggagtccatc gagttcgacc gccagggccg cgggccttac     300
gccgggctcg ccgacggccg cgtcgtgcgg tggatggggg acaaggccgg gtgggagacg     360
ttcgccgtca tgaatcctga ctggtactgg cttactgcag aaaaacccat agcttacctg     420
tgtgtgtgca gactaaaata gtttctttca taaaaaaaag gtcggagaaa gtttgtgcta     480
acggagtgga gtcgacgacg aagaagcagc acgggaagga gaagtggtgc ggccggcctc     540
tcggcctgag gttccacagg gagaccggcg agctcttcat cgccgacgcg tactatgggc     600
tcatggccgt cggcgaaagg ggcggcgtgg cgacctccct ggcgagggag gccggcgggg     660
acccggtcca cttcgccaac gaccttgaca tccacatgaa cggctcgata ttcttcaccg     720
acacgagcac gagatacagc agaaagtgag cggagtactg ctgccgatct ccttttctg     780
ttcttgagat ttgtgtttga caaatgactg atcatgcagg gaccatttga acattttgct     840
ggaaggagaa ggcacgggga ggctgctgag atatgaccga gaaaccggtg ccgttcatgt     900
cgtgctcaac gggctggtct tcccaaacgg cgtgcagata tcacaggacc agcaatttct     960
cctcttctcc gagacaacaa actgcaggtg agataaactc aggttttcag tatgatccgg    1020
ctcgagagat ccaggaactg atgacggctc atgcatgcac actaggatca tgaggtactg    1080
gctggaaggt ccaagagcgg ccaggtggag gtgttcgcg aacctgccgg ggttccccga    1140
caatgtgcgc ctgaacagca agggcagtt ctgggtggcc atcgactgct gccgtacgcc    1200
gacgcaggag gtgttcgcgc ggtggccgtg gctgcggacc gcctacttca agatcccggt    1260
gtcgatgaag acgctgggga agatggtgag catgaagatg tacacgcttc tcgcgctcct    1320
cgacggcgag gggaacgtcg tggaggtgct cgaggaccgg ggcggcgagg tgatgaagct    1380
ggtgagcgag gtgagggagg tggaccggag gctgtggatc gggaccgttg cgcacaacca    1440
catcgccacg atcccttacc cgctggacta g                                  1471
```

<210> SEQ ID NO 70
<211> LENGTH: 1000
<212> TYPE: DNA
<213> ORGANISM: Triticum aestivum

<400> SEQUENCE: 70

```
tctaaggctt tgtacaatgc aaggtgctta gtagagatgc ttggagaaat aaaccatact    60
tttcttaagc atcggtgctt atttatacat ggcagacgct taattagacg cctctcctgt   120
aaaaataagc acccgtgctt tagaaaaatc cggtttattt ttgtaagcac ctctcctaag   180
caccttgcat tgtacaaggc cttggagaaa taaagcaggc tttctttaag tatcggtgct   240
tatttgtaca ggtcagacgc ttaattaggc gtctctcctg tagaaatagg caccgatgct   300
tcaaaaaaaa acccgctcta tttttctaag cacataacat tgtacaagac cttaagcatt   360
tgtcgggtgc ttaaaagaaa gaaaagaaa  gaaagaatgc gatctgaaaa tttaaacact   420
gaagggaccc atgtcgtcgc cctagggcct tcctaaacgt aggaccgacc ctgcatgcac   480
cgcattacgc caattatctc tccctctaat cttcttacaa ttatctccat aacaactgct   540
aataactaaa tcattatcac gaatgaggct gaattcttga cttctccctt gctcttctgc   600
ttctttctcc tccaaagttt gctcttctct ccctgtatac tgatcctcac cagatcaggt   660
catgcatgaa aattggctcg gtatcctcct ggatcacttt atgcttgttg acctgtacat   720
cttgcatcac tatccaagca acgaaggcat gcaagtccca aattccaaaa gcgccatatc   780
cccttagctg ttctgaaccg aaatacacct actcccaaac gatcacaccg acccatgcaa   840
cctccgtgcg tgtcgggata atcttgtgac gctagctgac tcatgcaact cccgtgcgtg   900
tcggaatata ttttcggagc aaatccatta agaatttaag atcacattgc ccgcgctttt   960
ttcgtctgca tgcaaaacag agccactgcc ctctacctcc                        1000
```

<210> SEQ ID NO 71
<211> LENGTH: 1242
<212> TYPE: DNA
<213> ORGANISM: Triticum aestivum

<400> SEQUENCE: 71

```
atggaagaga agaaaccgcg gcggcaggga gccgcagtac gcgatggcat cgtgcagtac    60
ccgcacctct tcatcgcggc cctggcgctg gccctggtcc tcatggaccc gttccacctc   120
ggcccgctgg ccgggatcga ctaccgaccg gtgaagcacg agctggcgcc gtacagggag   180
gtcatgcagc gctggccgag ggacaacggc agccgcctca ggctcggcag gctcgagttc   240
gtcaacgagg tgttcgggcc ggagtccatc gagttcgacc gccagggccg cgggccttac   300
gccgggctcg ccgacggccg cgtcgtgcgg tggatggggg acaaggccgg gtgggagacg   360
ttcgccgtca tgaatcctga ctggtcgagg aaagtttgtg ctaacggagt ggagtcgacg   420
acgaagaagc agcacgggaa ggagaagtgg tgcggccggc ctctcggcct gaggttccac   480
agggagaccg cgagctctt  catcgccgac gcgtactatg ggctcatggc cgtcggcgaa   540
aggggcggcg tggcgacctc cctggcgagg gaggccggcg gggacccggt ccacttcgcc   600
aacgaccttg acatccacat gaacggctcg atattcttca ccgacacgag cacgagatac   660
agcagaaagg accatttgaa cattttgctg gaaggagaag gcacggggag gctgctgaga   720
tatgaccgag aaaccggtgc cgttcatgtc gtgctcaacg ggctggtctt cccaaacggc   780
gtgcagatat cacaggacca gcaatttctc ctcttctccg agacaacaaa ctgcaggatc   840
atgaggtact ggctggaagg tccaagagcg ggccaggtgg aggtgttcgc gaacctgccg   900
gggttccccg acaatgtgcg cctgaacagc aaggggcagt tctgggtggc catcgactgc   960
tgccgtacgc cgacgcagga ggtgttcgcg cggtggccgt ggctgcggac cgcctacttc  1020
aagatcccgg tgtcgatgaa gacgctgggg aagatggtga gcatgaagat gtacacgctt  1080
```

-continued

```
ctcgcgctcc tcgacggcga ggggaacgtc gtggaggtgc tcgaggaccg ggcggcgag    1140 gtgatgaagc tggtgagcga ggtgagggag gtggaccgga ggctgtggat cgggaccgtt    1200
gcgcacaacc acatcgccac gatcccttac ccgctggact ag                       1242
```

<210> SEQ ID NO 72
<211> LENGTH: 413
<212> TYPE: PRT
<213> ORGANISM: Triticum aestivum

<400> SEQUENCE: 72

```
Met Glu Glu Lys Lys Pro Arg Arg Gln Gly Ala Ala Val Arg Asp Gly
1               5                   10                  15

Ile Val Gln Tyr Pro His Leu Phe Ile Ala Ala Leu Ala Leu Ala Leu
            20                  25                  30

Val Leu Met Asp Pro Phe His Leu Gly Pro Leu Ala Gly Ile Asp Tyr
        35                  40                  45

Arg Pro Val Lys His Glu Leu Ala Pro Tyr Arg Glu Val Met Gln Arg
    50                  55                  60

Trp Pro Arg Asp Asn Gly Ser Arg Leu Arg Leu Gly Arg Leu Glu Phe
65                  70                  75                  80

Val Asn Glu Val Phe Gly Pro Glu Ser Ile Glu Phe Asp Arg Gln Gly
                85                  90                  95

Arg Gly Pro Tyr Ala Gly Leu Ala Asp Gly Arg Val Val Arg Trp Met
            100                 105                 110

Gly Asp Lys Ala Gly Trp Glu Thr Phe Ala Val Met Asn Pro Asp Trp
        115                 120                 125

Ser Glu Lys Val Cys Ala Asn Gly Val Glu Ser Thr Thr Lys Lys Gln
    130                 135                 140

His Gly Lys Glu Lys Trp Cys Gly Arg Pro Leu Gly Leu Arg Phe His
145                 150                 155                 160

Arg Glu Thr Gly Glu Leu Phe Ile Ala Asp Ala Tyr Tyr Gly Leu Met
                165                 170                 175

Ala Val Gly Glu Arg Gly Gly Val Ala Thr Ser Leu Ala Arg Glu Ala
            180                 185                 190

Gly Gly Asp Pro Val His Phe Ala Asn Asp Leu Asp Ile His Met Asn
        195                 200                 205

Gly Ser Ile Phe Phe Thr Asp Thr Ser Thr Arg Tyr Ser Arg Lys Asp
    210                 215                 220

His Leu Asn Ile Leu Leu Glu Gly Glu Gly Thr Gly Arg Leu Leu Arg
225                 230                 235                 240

Tyr Asp Arg Glu Thr Gly Ala Val His Val Val Leu Asn Gly Leu Val
                245                 250                 255

Phe Pro Asn Gly Val Gln Ile Ser Gln Asp Gln Phe Leu Leu Phe
            260                 265                 270

Ser Glu Thr Thr Asn Cys Arg Ile Met Arg Tyr Trp Leu Glu Gly Pro
    275                 280                 285

Arg Ala Gly Gln Val Glu Val Phe Ala Asn Leu Pro Gly Phe Pro Asp
290                 295                 300

Asn Val Arg Leu Asn Ser Lys Gly Gln Phe Trp Val Ala Ile Asp Cys
305                 310                 315                 320

Cys Arg Thr Pro Thr Gln Glu Val Phe Ala Arg Trp Pro Trp Leu Arg
                325                 330                 335

Thr Ala Tyr Phe Lys Ile Pro Val Ser Met Lys Thr Leu Gly Lys Met
```

```
                340             345             350
Val Ser Met Lys Met Tyr Thr Leu Leu Ala Leu Leu Asp Gly Glu Gly
            355                 360                 365

Asn Val Glu Val Leu Glu Asp Arg Gly Gly Glu Val Met Lys Leu
    370                 375                 380

Val Ser Glu Val Arg Glu Val Asp Arg Arg Leu Trp Ile Gly Thr Val
385                 390                 395                 400

Ala His Asn His Ile Ala Thr Ile Pro Tyr Pro Leu Asp
                405                 410

<210> SEQ ID NO 73
<211> LENGTH: 1551
<212> TYPE: DNA
<213> ORGANISM: Zea mays

<400> SEQUENCE: 73
atggagaaga ggaacctgca gtggcggcga gggcgtgatg gcatcgtgca gtaccctcac      60
ctcttcttcg cggccctggc gctggccctc ctagtcgcgg accgttcgg cctcagtccg     120 ctggccgagg tcgactaccg gccggtgaag cacgagctcg cgccgtacgg ggaggtcatg     180
ggcagctggc ccagagacaa tgccagccgg ctcaggcgcg ggaggctgga gttcgtcggc     240
gaggtgttcg gccggagtc tatcgagttc gatctccagg ccgcgggcc gtacgccggc     300 ctcgccgacg ccgcgtcgt gcggtggatg gcgaggagg ccgggtggga cgttcgcc     360 gtcatgaatc ctgactggta agtgctcgat atcgctccgg cgtccactcg ttacatgcta     420
taatatagta gtactaagat attttgatct gattttttgc attcttggga gaaacgtcat     480
gcaaaatttg ttgtttcttg gcaaaggtca aagaagtct gtgccaatgg agtgaactca     540
acgacgagga agcagcacga gaaggaggag ttctgcggcc ggccgctcgg cctgaggttc     600
cacggggaga ccggcgagct ctacgtcgcc gacgcgtact acggtctcat ggtcgttggc     660
cagagcggcg cgtggcgtc ctccgtcgcg agggaagccg acggggaccc catccggttc     720
gcgaacgacc tcgatgtgca caggaatgga tccgtattct tcactgacac gagcatgaga     780
tacagcagaa agtgagcaaa cgacgtaac aatccggctt ctcattttca aacgcctctg     840
tattctctgc tgaaagagta gctcaccaga caagagctga atttgcaggg accatctgaa     900
catcctgtta aaggagaag caccgggag gctgctcagg tatgatccag aaacaagcgg     960
tgtccatgtc gtgctcaagg ggctggtgtt cccaaacggc gtgcagatct cagaggacca    1020
tcagtttctt ctcttctccg agacaacaaa ctgcaggtaa caaaaatact atctgacgat    1080
gctcatgatt ctaccgtatc catagtcatg aacacaaacc acacgaatct ggccttgacc    1140
aggataatga ggtactggct ggaaggccca agagcgggcg aggtagaggt gttcgcgaac    1200
ctgccgggct tccccgacaa cgtgcgctcc aacggcaggg gccagttctg gtggcgatc    1260 gactgctgcc ggacgccggc gcaggaggtg ttcgccaaga ggccgtggct ccggaccctg    1320
tacttcaagt tcccgctgtc gctcaaggtg ctcacttgga aggccgccag gaggatgcac    1380
acggtgctcg cgctcctcga cggcgaaggg cgcgtcgtgg aggtgctcga ggaccggggc    1440
cacgaggtga tgaagctggt gagcgaggtg cgggaggtgg ccgcaagct gtggatcgga    1500 accgtggcgc acaaccacat cgccaccatc ccctaccctt tagaggacta a             1551

<210> SEQ ID NO 74
<211> LENGTH: 1001
<212> TYPE: DNA
<213> ORGANISM: Zea mays
```

<400> SEQUENCE: 74

```
cagaaatgcg aggaccagcc atgtctagtg tccactattg cactaccca gaacaagatt    60
taaaaaaata accaaagtaa ctaatccact cgaaagctat catgtaatgt ttaaagaaac   120
atctattaaa accacgatcc tcttaaaaaa caagcatatt tcgaaagaga caaattatgt   180
tacagtttac aaacatctaa gagcgacaaa ttatatcgaa aggtaagcta tgacgttcag   240
attttctttt tcattcttg ttattttgtt attgttttta tatacatttt cttctcttac   300
aatagagtga ttttcttccg attttataaa atgactataa agtcattttt atataagagc   360
acgcatgtcg tagattctcg ttcaaaaatc tttctgattt ttttaagagc tagtttggca   420
accctgtttc tttcaaagaa ttttgatttt tcaaaaaaa attagtttat tttctcttta    480
taaaatagaa aacacttaga aaatagagt tgccagacta gccctagaat gttttcccaa    540
taaattacaa tcactgtgta taattatttg gccagcccca taaattattt aaaccgaaac   600
tgaaatcgag cgaaaccaaa tctgagctat ttctctagat tagtaaaaag ggagagagag   660
aggaagaaat cagttttaag tcattgtccc tgagatgtgc ggtttggcaa cgatagccac   720
cgtaatcata gctcataggt gcctacgtca ggttcggcag ctctcgtgtc atctcacatg   780
gcatactaca tgcttgttca accgttcgtc ttgttccatc gtccaagcct tgcctattct   840
gaaccaagag gataccact cccaaacaat ccatcttact catgcaactt ccatgcaaac    900
acgcacatat gtttcctgaa ccaatccatt aaagatcaca acagctagcg ttctcccgct   960
agcttccctc tctcctctgc cgatcttttt cgtccaccag c                      1001
```

<210> SEQ ID NO 75
<211> LENGTH: 1239
<212> TYPE: DNA
<213> ORGANISM: Zea mays

<400> SEQUENCE: 75

```
atggagaaga ggaacctgca gtggcggcga gggcgtgatg gcatcgtgca gtaccctcac    60
ctcttcttcg cggccctggc gctggccctc ctagtcgcgg acccgttcgg cctcagtccg   120
ctggccgagt cgactaccg gccggtgaag cacgagctcg cgccgtacgg ggaggtcatg    180
ggcagctggc cagagacaa tgccagccgg ctcaggcgcg ggaggctgga gttcgtcggc    240
gaggtgttcg ggccggagtc tatcgagttc gatctccagg gccgcgggcc gtacgccggc   300
ctcgccgacg gccgcgtcgt gcggtggatg ggcgaggagg ccgggtggga gacgttcgcc   360
gtcatgaatc ctgactggtc agaagaagtc tgtgccaatg gagtgaactc aacgacgagg   420
aagcagcacg agaaggagga gttctgcggc cggccgctcg gcctgaggtt ccacggggag   480
accggcgagc tctacgtcgc cgacgcgtac tacggtctca tggtcgttgg ccagagcggc   540
ggcgtggcgt cctccgtcgc gagggaagcc gacgggggacc ccatccggtt cgcgaacgac   600
ctcgatgtgc acaggaatgg atccgtattc ttcactgaca cgagcatgag atacagcaga   660
aaggaccatc tgaacatcct gttagaagga gaaggcaccg ggaggctgct caggtatgat   720
ccagaaacaa gcggtgtcca tgtcgtgctc aaggggctgg tgttcccaaa cggcgtgcag   780
atctcagagg accatcagtt tcttctcttc tccgagacaa caaactgcag gataatgagg   840
tactggctgg aaggcccaag agcgggcgag gtagaggtgt tcgcgaacct gccgggcttc   900
cccgacaacg tgcgctccaa cggcaggggc cagttctggg tggcgatcga ctgctgccgg   960
acgccggcgc aggaggtgtt cgccaagagg ccgtggctcc ggaccctgta cttcaagttc  1020
```

```
ccgctgtcgc tcaaggtgct cacttggaag gccgccagga ggatgcacac ggtgctcgcg    1080
ctcctcgacg gcgaagggcg cgtcgtggag gtgctcgagg accggggcca cgaggtgatg    1140
aagctggtga gcgaggtgcg ggaggtgggc cgcaagctgt ggatcggaac cgtggcgcac    1200
aaccacatcg ccaccatccc ctacccttta gaggactaa                           1239

<210> SEQ ID NO 76
<211> LENGTH: 412
<212> TYPE: PRT
<213> ORGANISM: Zea mays

<400> SEQUENCE: 76

Met Glu Lys Arg Asn Leu Gln Trp Arg Arg Gly Arg Asp Gly Ile Val
1               5                   10                  15

Gln Tyr Pro His Leu Phe Phe Ala Ala Leu Ala Leu Ala Leu Leu Val
            20                  25                  30

Ala Asp Pro Phe Gly Leu Ser Pro Leu Ala Glu Val Asp Tyr Arg Pro
        35                  40                  45

Val Lys His Glu Leu Ala Pro Tyr Gly Glu Val Met Gly Ser Trp Pro
    50                  55                  60

Arg Asp Asn Ala Ser Arg Leu Arg Arg Gly Arg Leu Glu Phe Val Gly
65                  70                  75                  80

Glu Val Phe Gly Pro Glu Ser Ile Glu Phe Asp Leu Gln Gly Arg Gly
                85                  90                  95

Pro Tyr Ala Gly Leu Ala Asp Gly Arg Val Val Arg Trp Met Gly Glu
            100                 105                 110

Glu Ala Gly Trp Glu Thr Phe Ala Val Met Asn Pro Asp Trp Ser Glu
        115                 120                 125

Glu Val Cys Ala Asn Gly Val Asn Ser Thr Thr Arg Lys Gln His Glu
    130                 135                 140

Lys Glu Glu Phe Cys Gly Arg Pro Leu Gly Leu Arg Phe His Gly Glu
145                 150                 155                 160

Thr Gly Glu Leu Tyr Val Ala Asp Ala Tyr Tyr Gly Leu Met Val Val
                165                 170                 175

Gly Gln Ser Gly Gly Val Ala Ser Ser Val Ala Arg Glu Ala Asp Gly
            180                 185                 190

Asp Pro Ile Arg Phe Ala Asn Asp Leu Asp Val His Arg Asn Gly Ser
        195                 200                 205

Val Phe Phe Thr Asp Thr Ser Met Arg Tyr Ser Arg Lys Asp His Leu
    210                 215                 220

Asn Ile Leu Leu Glu Gly Gly Thr Gly Arg Leu Leu Arg Tyr Asp
225                 230                 235                 240

Pro Glu Thr Ser Gly Val His Val Val Leu Lys Gly Leu Val Phe Pro
                245                 250                 255

Asn Gly Val Gln Ile Ser Glu Asp His Gln Phe Leu Leu Phe Ser Glu
            260                 265                 270

Thr Thr Asn Cys Arg Ile Met Arg Tyr Trp Leu Glu Gly Pro Arg Ala
        275                 280                 285

Gly Glu Val Glu Val Phe Ala Asn Leu Pro Gly Phe Pro Asp Asn Val
    290                 295                 300

Arg Ser Asn Gly Arg Gly Gln Phe Trp Val Ala Ile Asp Cys Cys Arg
305                 310                 315                 320

Thr Pro Ala Gln Glu Val Phe Ala Lys Arg Pro Trp Leu Arg Thr Leu
                325                 330                 335
```

Tyr Phe Lys Phe Pro Leu Ser Leu Lys Val Leu Thr Trp Lys Ala Ala
                340                 345                 350

Arg Arg Met His Thr Val Leu Ala Leu Leu Asp Gly Glu Gly Arg Val
        355                 360                 365

Val Glu Val Leu Glu Asp Arg Gly His Glu Val Met Lys Leu Val Ser
370                 375                 380

Glu Val Arg Glu Val Gly Arg Lys Leu Trp Ile Gly Thr Val Ala His
385                 390                 395                 400

Asn His Ile Ala Thr Ile Pro Tyr Pro Leu Glu Asp
                405                 410

<210> SEQ ID NO 77
<211> LENGTH: 1561
<212> TYPE: DNA
<213> ORGANISM: Oryza sativa

<400> SEQUENCE: 77

| | | |
|---|---|---|
| atggaagaga agaagcagca gcagcagcgt ccacagagag ggcgcgatgg catcctgcag | 60 |
| tatccgcacc ttttcttcgc ggcgctggcg ctggccctgc tcctcaccga cccgttccac | 120 |
| ctcggcccgc tcgccggggt ggactaccgg ccggtgaggc acgagctggc gccgtaccgc | 180 |
| gaggtgatgg cgcggtggcc gcgggacaac ggcagccggc tcaggcacgg caggctggag | 240 |
| ttcgtcggag aggtgttcgg gccggagtcc atcgagttcg accgcacgg ccgcggcccc | 300 |
| tacgccggcc tcgccgacgg ccgcgtcgtg cggtggatgg gggaggacgc cggtggggag | 360 |
| acgttcgccg tcatgagccc tgactggtaa cgaacacctc gcctgcattt tgctctcgcc | 420 |
| ctccacgaaa acacctctcg tagcagtgta caattacgtg ttcttatatt gcaaaaaag | 480 |
| gtcggagaaa gtttgtgcca atggggtgga gtcgacgacg aagaagcagc acgagatgga | 540 |
| gcgacggtgc ggccggcctc tcgggctgag gtttcacggc gagaccggcg agctctacgt | 600 |
| cgccgacgcg tactacgggc tcatgtccgt cggtccgaac ggcggggtgg cgacctctct | 660 |
| cgcgagagaa gtcggcggga gcccggtcaa cttcgcgaac gacctcgaca tccaccgcaa | 720 |
| cggctccgtg ttcttcaccg acacgagcac gagatacaac agaaagtgtg cagctgcagt | 780 |
| atcactctct tcagttgtat cgattctcta tttccttcta tcgttcaaga ttttctgatt | 840 |
| agaatcagtt gtgcagggat catctgaacg ttctgctaga aggtgaaggc acagggaggc | 900 |
| tgctcagata tgacccagaa accaaagctg cccatgtcgt gctgagcggg ctggtcttcc | 960 |
| cgaatggcgt gcagatttct gacgaccagc agttcctcct cttctccgaa caacaaact | 1020 |
| gcaggtgaaa tggcacaagc tttcacaggt tctgaaaata ctaaaggtta aacaagattc | 1080 |
| agaattgatt aacattgcac gcatatgctg ttctaggata atgcggtact ggctggaagg | 1140 |
| gccaagagcc gggcaggtgg aggtgttcgc cgacctgccg ggttccggg acaacgtgcg | 1200 |
| actgagcagc ggcggcggcg gcggacggtt ctgggtggcg atcgactgct gcaggacggc | 1260 |
| ggcgcaggag gtgttcgcca gcggccgtg gctgcgaacg ctctacttca gctgccct | 1320 |
| gacgatgcgg acgctgggga agatggtcag catgcggatg cacaccctcg tcgcgctcct | 1380 |
| cgacggcgaa ggggacgtcg tcgaggtgct cgaggaccgg ggcggcgagg tgatgcggct | 1440 |
| ggtgagcgag gtgagggagg tggggcgcaa gctgtggatc ggcaccgtgg ctcataacca | 1500 |
| catcgccacg atcccttacc cgttggaaga gcagagtagc agcaacgtgc ttggtgattg | 1560 |
| a | 1561 |

<210> SEQ ID NO 78

<211> LENGTH: 930
<212> TYPE: DNA
<213> ORGANISM: Oryza sativa

<400> SEQUENCE: 78

| | | | | | |
|---|---|---|---|---|---|
| ttatcgaaac | catatataaa | tgacttttaa | gataatctcc | ggtttttttt | aatatgaaac | 60 |
| gtcattgatt | tttaagatat | atttgaccat | tttcaaacct | aagaggtggt | ttattttccc | 120 |
| tcaagagaac | gcgccgttat | tttttacgt | cacctaaaaa | acataatttt | ttggaaaaaa | 180 |
| atatatgaaa | agacagatga | atatatgatt | tttttaaaa | atacagattc | aaactttact | 240 |
| tacacaaata | gaaacaaaaa | acaataaatt | tgcttatgaa | tggtcaaatt | cattattttt | 300 |
| atttgtacct | atgtaagtca | aatttaaact | tcatggtcat | tgatatattt | ataaaaaata | 360 |
| gttttttagt | tgaattttaa | agtaacaaaa | aaaacaaagg | gacaaataga | cttccctata | 420 |
| acccaacgca | tgctcaacca | cagtaaatgt | tttagctaag | acttagagtt | agttttcttg | 480 |
| caacatcgac | acaccattgc | ctgtgtcttg | tgatttttcc | tgcacgttta | gaagggtggc | 540 |
| atcgattgaa | cttctggaca | cttggagttc | ttccttcttc | gtgatgcacc | ttttgcttta | 600 |
| cagcgctagc | aatggccatg | gtcagggccc | tcagccctgg | ccgggttcgg | ttacatgcat | 660 |
| cgtgatatgc | ttgttgacct | gtgcatcttg | caccgtcatc | ccagcaatgc | aaaacatgca | 720 |
| aatccccact | tcgaaagcac | aagattcctt | ggctattccg | aaccaacaga | acacctactc | 780 |
| ccaaacaatc | acgctgactc | atgcaacctc | catgcatcga | atatatattt | tcgctgcaaa | 840 |
| ggcattaaga | atttaagtta | agatcaccgt | ctccaccaat | tccgtctttc | ctctgcgtgc | 900 |
| aaattccgtc | ttccctcgct | cctgatctcc | | | | 930 |

<210> SEQ ID NO 79
<211> LENGTH: 1284
<212> TYPE: DNA
<213> ORGANISM: Oryza sativa

<400> SEQUENCE: 79

| | | | | | |
|---|---|---|---|---|---|
| atggaagaga | agaagcagca | gcagcagcgt | ccacagagag | ggcgcgatgg | catcctgcag | 60 |
| tatccgcacc | ttttcttcgc | ggcgctggcg | ctggccctgc | tcctcaccga | cccgttccac | 120 |
| ctcggcccgc | tcgccggggt | ggactaccgg | ccggtgaggc | acgagctggc | gccgtaccgc | 180 |
| gaggtgatgg | cgcggtggcc | gcgggacaac | ggcagccggc | tcaggcacgg | caggctggag | 240 |
| ttcgtcggag | aggtgttcgg | gccggagtcc | atcgagttcg | accgccacgg | ccgcggcccc | 300 |
| tacgccggcc | tcgccgacgg | ccgcgtcgtg | cggtggatgg | gggaggacgc | cgggtgggag | 360 |
| acgttcgccg | tcatgagccc | tgactggtcg | gagaaagttt | gtgccaatgg | ggtggagtcg | 420 |
| acgacgaaga | agcagcacga | gatggagcga | cggtgcggcc | ggcctctcgg | gctgaggttt | 480 |
| cacggcgaga | ccggcgagct | ctacgtcgcc | gacgcgtact | acgggctcat | gtccgtcggt | 540 |
| ccgaacggcg | gggtggcgac | ctctctcgcg | agagaagtcg | gcgggagccc | ggtcaacttc | 600 |
| gcgaacgacc | tcgacatcca | ccgcaacggc | tccgtgttct | tcaccgacac | gagcacgaga | 660 |
| tacaacagaa | aggatcatct | gaacgttctg | ctagaaggtg | aaggcacagg | gaggctgctc | 720 |
| agatatgacc | cagaaaccaa | agctgcccat | gtcgtgctga | gcgggctggt | cttcccgaat | 780 |
| ggcgtgcaga | tttctgacga | ccagcagttc | ctcctcttct | ccgaaacaac | aaactgcagg | 840 |
| ataatgcggt | actggctgga | agggccaaga | gccgggcagg | tggaggtgtt | cgccgacctg | 900 |
| ccggggttcc | cggacaacgt | gcgactgagc | agcggcggcg | gcggcggacg | gttctgggtg | 960 |
| gcgatcgact | gctgcaggac | ggcggcgcag | gaggtgttcg | ccaagcggcc | gtggctgcga | 1020 |

```
acgctctact tcaagctgcc cctgacgatg cggacgctgg ggaagatggt cagcatgcgg    1080
atgcacaccc tcgtcgcgct cctcgacggc gaagggacg tcgtcgaggt gctcgaggac    1140
cggggcggcg aggtgatgcg gctggtgagc gaggtgaggg aggtggggcg caagctgtgg    1200
atcggcaccg tggctcataa ccacatcgcc acgatcccttt acccgttgga agagcagagt    1260
agcagcaacg tgcttggtga ttga                                          1284
```

<210> SEQ ID NO 80
<211> LENGTH: 427
<212> TYPE: PRT
<213> ORGANISM: Oryza sativa

<400> SEQUENCE: 80

```
Met Glu Glu Lys Lys Gln Gln Gln Arg Pro Gln Arg Gly Arg Asp
1               5                   10                  15

Gly Ile Leu Gln Tyr Pro His Leu Phe Phe Ala Ala Leu Ala Leu Ala
                20                  25                  30

Leu Leu Leu Thr Asp Pro Phe His Leu Gly Pro Leu Ala Gly Val Asp
            35                  40                  45

Tyr Arg Pro Val Arg His Glu Leu Ala Pro Tyr Arg Glu Val Met Ala
    50                  55                  60

Arg Trp Pro Arg Asp Asn Gly Ser Arg Leu Arg His Gly Arg Leu Glu
65                  70                  75                  80

Phe Val Gly Glu Val Phe Gly Pro Glu Ser Ile Glu Phe Asp Arg His
                85                  90                  95

Gly Arg Gly Pro Tyr Ala Gly Leu Ala Asp Gly Arg Val Val Arg Trp
            100                 105                 110

Met Gly Glu Asp Ala Gly Trp Glu Thr Phe Ala Val Met Ser Pro Asp
        115                 120                 125

Trp Ser Glu Lys Val Cys Ala Asn Gly Val Glu Ser Thr Thr Lys Lys
    130                 135                 140

Gln His Glu Met Glu Arg Arg Cys Gly Arg Pro Leu Gly Leu Arg Phe
145                 150                 155                 160

His Gly Glu Thr Gly Glu Leu Tyr Val Ala Asp Ala Tyr Tyr Gly Leu
                165                 170                 175

Met Ser Val Gly Pro Asn Gly Gly Val Ala Thr Ser Leu Ala Arg Glu
            180                 185                 190

Val Gly Gly Ser Pro Val Asn Phe Ala Asn Asp Leu Asp Ile His Arg
        195                 200                 205

Asn Gly Ser Val Phe Phe Thr Asp Thr Ser Thr Arg Tyr Asn Arg Lys
    210                 215                 220

Asp His Leu Asn Val Leu Leu Glu Gly Glu Gly Thr Gly Arg Leu Leu
225                 230                 235                 240

Arg Tyr Asp Pro Glu Thr Lys Ala Ala His Val Val Leu Ser Gly Leu
                245                 250                 255

Val Phe Pro Asn Gly Val Gln Ile Ser Asp Asp Gln Gln Phe Leu Leu
            260                 265                 270

Phe Ser Glu Thr Thr Asn Cys Arg Ile Met Arg Tyr Trp Leu Glu Gly
        275                 280                 285

Pro Arg Ala Gly Gln Val Glu Val Phe Ala Asp Leu Pro Gly Phe Pro
    290                 295                 300

Asp Asn Val Arg Leu Ser Ser Gly Gly Gly Gly Arg Phe Trp Val
305                 310                 315                 320
```

```
Ala Ile Asp Cys Cys Arg Thr Ala Ala Gln Glu Val Phe Ala Lys Arg
            325                 330                 335

Pro Trp Leu Arg Thr Leu Tyr Phe Lys Leu Pro Leu Thr Met Arg Thr
        340                 345                 350

Leu Gly Lys Met Val Ser Met Arg Met His Thr Leu Val Ala Leu Leu
            355                 360                 365

Asp Gly Glu Gly Asp Val Val Glu Val Leu Glu Asp Arg Gly Gly Glu
        370                 375                 380

Val Met Arg Leu Val Ser Glu Val Arg Glu Val Gly Arg Lys Leu Trp
385                 390                 395                 400

Ile Gly Thr Val Ala His Asn His Ile Ala Thr Ile Pro Tyr Pro Leu
                405                 410                 415

Glu Glu Gln Ser Ser Ser Asn Val Leu Gly Asp
            420                 425

<210> SEQ ID NO 81
<211> LENGTH: 23
<212> TYPE: DNA
<213> ORGANISM: Triticum aestivum

<400> SEQUENCE: 81
gcggccgccg tgctgcgaca agg                                              23

<210> SEQ ID NO 82
<211> LENGTH: 23
<212> TYPE: DNA
<213> ORGANISM: Triticum aestivum

<400> SEQUENCE: 82
gcgtcctcct ccgccgtcca cgg                                              23

<210> SEQ ID NO 83
<211> LENGTH: 23
<212> TYPE: DNA
<213> ORGANISM: Triticum aestivum

<400> SEQUENCE: 83
gaagaagggg ccgtggacgg cgg                                              23

<210> SEQ ID NO 84
<211> LENGTH: 23
<212> TYPE: DNA
<213> ORGANISM: Triticum aestivum

<400> SEQUENCE: 84 gaagggccg tggacggcgg agg                                               23

<210> SEQ ID NO 85
<211> LENGTH: 23
<212> TYPE: DNA
<213> ORGANISM: Triticum aestivum

<400> SEQUENCE: 85
ggggccgtgg acggcggagg agg                                              23

<210> SEQ ID NO 86
<211> LENGTH: 23
<212> TYPE: DNA
<213> ORGANISM: Triticum aestivum

<400> SEQUENCE: 86
```

```
ggtgccatgg ttggaggtgt agg                                                  23

<210> SEQ ID NO 87
<211> LENGTH: 23
<212> TYPE: DNA
<213> ORGANISM: Triticum aestivum

<400> SEQUENCE: 87
gttgccggtg ccatggttgg agg                                                  23

<210> SEQ ID NO 88
<211> LENGTH: 23
<212> TYPE: DNA
<213> ORGANISM: Triticum aestivum

<400> SEQUENCE: 88
gggaacagag gtccagttgc cgg                                                  23

<210> SEQ ID NO 89
<211> LENGTH: 23
<212> TYPE: DNA
<213> ORGANISM: Triticum aestivum

<400> SEQUENCE: 89
gcacgagaac ttcacgcagg agg                                                  23

<210> SEQ ID NO 90
<211> LENGTH: 23
<212> TYPE: DNA
<213> ORGANISM: Triticum aestivum

<400> SEQUENCE: 90
gaacttcacg caggaggagg agg                                                  23

<210> SEQ ID NO 91
<211> LENGTH: 23
<212> TYPE: DNA
<213> ORGANISM: Triticum aestivum

<400> SEQUENCE: 91
gcttcccagc atggcatgga ggg                                                  23

<210> SEQ ID NO 92
<211> LENGTH: 23
<212> TYPE: DNA
<213> ORGANISM: Triticum aestivum

<400> SEQUENCE: 92
gtcaccctcc atgccatgct ggg                                                  23

<210> SEQ ID NO 93
<211> LENGTH: 23
<212> TYPE: DNA
<213> ORGANISM: Triticum aestivum

<400> SEQUENCE: 93
gaaccagctg ccggggcgga cgg                                                  23

<210> SEQ ID NO 94
<211> LENGTH: 23
<212> TYPE: DNA
<213> ORGANISM: Triticum aestivum

<400> SEQUENCE: 94
```
tgaggtacac caactacctg agg                                                    23

<210> SEQ ID NO 95
<211> LENGTH: 23
<212> TYPE: DNA
<213> ORGANISM: Triticum aestivum

<400> SEQUENCE: 95
gccaggggcg gcggcgtccc cgg                                                    23

<210> SEQ ID NO 96
<211> LENGTH: 23
<212> TYPE: DNA
<213> ORGANISM: Zea mays

<400> SEQUENCE: 96
ggtgccatgg gtggaggtgt agg                                                    23

<210> SEQ ID NO 97
<211> LENGTH: 23
<212> TYPE: DNA
<213> ORGANISM: Zea mays

<400> SEQUENCE: 97
gttgccggtg ccatgggtgg agg                                                    23

<210> SEQ ID NO 98
<211> LENGTH: 23
<212> TYPE: DNA
<213> ORGANISM: Zea mays

<400> SEQUENCE: 98
ggtccagttg ccggtgccat ggg                                                    23

<210> SEQ ID NO 99
<211> LENGTH: 23
<212> TYPE: DNA
<213> ORGANISM: Zea mays

<400> SEQUENCE: 99
gggcacgttg gtccagttgc cgg                                                    23

<210> SEQ ID NO 100
<211> LENGTH: 23
<212> TYPE: DNA
<213> ORGANISM: Zea mays

<400> SEQUENCE: 100
gcggcaagag ctgcaggctg agg                                                    23

<210> SEQ ID NO 101
<211> LENGTH: 23
<212> TYPE: DNA
<213> ORGANISM: Zea mays

<400> SEQUENCE: 101
gaagttctcg tgcttcaggt tgg                                                    23

<210> SEQ ID NO 102
<211> LENGTH: 23
<212> TYPE: DNA
<213> ORGANISM: Zea mays

<400> SEQUENCE: 102
gggtgaagtt ctcgtgcttc agg                                    23

<210> SEQ ID NO 103
<211> LENGTH: 23
<212> TYPE: DNA
<213> ORGANISM: Zea mays

<400> SEQUENCE: 103
gatgaggtct tcctcctcct ggg                                    23

<210> SEQ ID NO 104
<211> LENGTH: 23
<212> TYPE: DNA
<213> ORGANISM: Zea mays

<400> SEQUENCE: 104
gaagcacgag aacttcaccc agg                                    23

<210> SEQ ID NO 105
<211> LENGTH: 23
<212> TYPE: DNA
<213> ORGANISM: Zea mays

<400> SEQUENCE: 105
gcacgagaac ttcacccagg agg                                    23

<210> SEQ ID NO 106
<211> LENGTH: 23
<212> TYPE: DNA
<213> ORGANISM: Zea mays

<400> SEQUENCE: 106
gcttccgagc atggcgtgga ggg                                    23

<210> SEQ ID NO 107
<211> LENGTH: 23
<212> TYPE: DNA
<213> ORGANISM: Zea mays

<400> SEQUENCE: 107
gtcaccctcc acgccatgct cgg                                    23

<210> SEQ ID NO 108
<211> LENGTH: 23
<212> TYPE: DNA
<213> ORGANISM: Zea mays

<400> SEQUENCE: 108
gaaccagctg ccgggaagga cgg                                    23

<210> SEQ ID NO 109
<211> LENGTH: 23
<212> TYPE: DNA
<213> ORGANISM: Zea mays

<400> SEQUENCE: 109
gcaagaagct gcggcagcgc ggg                                    23

<210> SEQ ID NO 110
<211> LENGTH: 23
<212> TYPE: DNA
<213> ORGANISM: Zea mays

<400> SEQUENCE: 110
gcgatggggc ggtgggtgag ggg                                  23

<210> SEQ ID NO 111
<211> LENGTH: 27
<212> TYPE: DNA
<213> ORGANISM: Oryza sativa

<400> SEQUENCE: 111
gctgcgacaa ggcgaacgtg aagaagg                              27

<210> SEQ ID NO 112
<211> LENGTH: 28
<212> TYPE: DNA
<213> ORGANISM: Oryza sativa

<400> SEQUENCE: 112
gctgcgacaa ggcgaacgtg aagaaggg                             28

<210> SEQ ID NO 113
<211> LENGTH: 27
<212> TYPE: DNA
<213> ORGANISM: Oryza sativa

<400> SEQUENCE: 113
ggcgtacacc tccacccacg gcaccgg                              27

<210> SEQ ID NO 114
<211> LENGTH: 26
<212> TYPE: DNA
<213> ORGANISM: Oryza sativa

<400> SEQUENCE: 114
gcgccggcgc cgcaggctgc tctcgg                               26

<210> SEQ ID NO 115
<211> LENGTH: 26
<212> TYPE: DNA
<213> ORGANISM: Oryza sativa

<400> SEQUENCE: 115
gcaggctgct ctcggccagt atcagg                               26

<210> SEQ ID NO 116
<211> LENGTH: 26
<212> TYPE: DNA
<213> ORGANISM: Oryza sativa

<400> SEQUENCE: 116
ggctgaggta caccaactac ctgagg                               26

<210> SEQ ID NO 117
<211> LENGTH: 23
<212> TYPE: DNA
<213> ORGANISM: Oryza sativa

<400> SEQUENCE: 117
gaagcacgag aacttcacgc agg                                  23

<210> SEQ ID NO 118
<211> LENGTH: 26
<212> TYPE: DNA

```
<213> ORGANISM: Oryza sativa

<400> SEQUENCE: 118
gaagcacgag aacttcacgc aggagg                                          26

<210> SEQ ID NO 119
<211> LENGTH: 26
<212> TYPE: DNA
<213> ORGANISM: Oryza sativa

<400> SEQUENCE: 119
gcacgagaac ttcacgcagg aggagg                                          26

<210> SEQ ID NO 120
<211> LENGTH: 22
<212> TYPE: DNA
<213> ORGANISM: Oryza sativa

<400> SEQUENCE: 120
gtcaccctcc acgccatgct gg                                              22

<210> SEQ ID NO 121
<211> LENGTH: 23
<212> TYPE: DNA
<213> ORGANISM: Oryza sativa

<400> SEQUENCE: 121
gtcaccctcc acgccatgct ggg                                             23

<210> SEQ ID NO 122
<211> LENGTH: 26
<212> TYPE: DNA
<213> ORGANISM: Oryza sativa

<400> SEQUENCE: 122
ggctgctctc ggccagtatc aggagg                                          26

<210> SEQ ID NO 123
<211> LENGTH: 27
<212> TYPE: DNA
<213> ORGANISM: Oryza sativa

<400> SEQUENCE: 123
ggtcgctgat cgcgaaccag ctgccgg                                         27

<210> SEQ ID NO 124
<211> LENGTH: 27
<212> TYPE: DNA
<213> ORGANISM: Oryza sativa

<400> SEQUENCE: 124
gactcgcagc atctgcagct caactgg                                         27

<210> SEQ ID NO 125
<211> LENGTH: 23
<212> TYPE: DNA
<213> ORGANISM: Oryza sativa

<400> SEQUENCE: 125
gccgacctca tgcagagcat cgg                                             23

<210> SEQ ID NO 126
<211> LENGTH: 23
```

```
<212> TYPE: DNA
<213> ORGANISM: Triticum aestivum

<400> SEQUENCE: 126
gttgaggatg cagcagcagg tgg                                          23

<210> SEQ ID NO 127
<211> LENGTH: 23
<212> TYPE: DNA
<213> ORGANISM: Triticum aestivum

<400> SEQUENCE: 127
gaggatgcag cagcaggtgg agg                                          23

<210> SEQ ID NO 128
<211> LENGTH: 23
<212> TYPE: DNA
<213> ORGANISM: Triticum aestivum

<400> SEQUENCE: 128
gcagcagcag gtggagggcg tgg                                          23

<210> SEQ ID NO 129
<211> LENGTH: 23
<212> TYPE: DNA
<213> ORGANISM: Triticum aestivum

<400> SEQUENCE: 129
gcagcaggtg gagggcgtgg tgg                                          23

<210> SEQ ID NO 130
<211> LENGTH: 23
<212> TYPE: DNA
<213> ORGANISM: Triticum aestivum

<400> SEQUENCE: 130
gtggagggcg tggtgggcgg cgg                                          23

<210> SEQ ID NO 131
<211> LENGTH: 23
<212> TYPE: DNA
<213> ORGANISM: Triticum aestivum

<400> SEQUENCE: 131
gtggcacatg cagcagccgc tgg                                          23

<210> SEQ ID NO 132
<211> LENGTH: 23
<212> TYPE: DNA
<213> ORGANISM: Triticum aestivum

<400> SEQUENCE: 132
gtggtcgtct tcagcgccag cgg                                          23

<210> SEQ ID NO 133
<211> LENGTH: 23
<212> TYPE: DNA
<213> ORGANISM: Triticum aestivum

<400> SEQUENCE: 133
gcaggaggcg cttgacgacg tgg                                          23

<210> SEQ ID NO 134
```

```
<211> LENGTH: 23
<212> TYPE: DNA
<213> ORGANISM: Triticum aestivum

<400> SEQUENCE: 134
gtcgtcaagc gcctcctgct tgg                                              23

<210> SEQ ID NO 135
<211> LENGTH: 23
<212> TYPE: DNA
<213> ORGANISM: Triticum aestivum

<400> SEQUENCE: 135
gtggccggcg ccgggtccgg ggg                                              23

<210> SEQ ID NO 136
<211> LENGTH: 23
<212> TYPE: DNA
<213> ORGANISM: Triticum aestivum

<400> SEQUENCE: 136
ggtggccggc gccgggtccg ggg                                              23

<210> SEQ ID NO 137
<211> LENGTH: 23
<212> TYPE: DNA
<213> ORGANISM: Triticum aestivum

<400> SEQUENCE: 137
gtggtggccg gcgccgggtc cgg                                              23

<210> SEQ ID NO 138
<211> LENGTH: 23
<212> TYPE: DNA
<213> ORGANISM: Triticum aestivum

<400> SEQUENCE: 138
ggacgagcgt gccgttgatg tgg                                              23

<210> SEQ ID NO 139
<211> LENGTH: 23
<212> TYPE: DNA
<213> ORGANISM: Triticum aestivum

<400> SEQUENCE: 139
gtgatggcgt gccacatcaa cgg                                              23

<210> SEQ ID NO 140
<211> LENGTH: 23
<212> TYPE: DNA
<213> ORGANISM: Triticum aestivum

<400> SEQUENCE: 140
gcgccggcgt ccttgaggag cgg                                              23

<210> SEQ ID NO 141
<211> LENGTH: 23
<212> TYPE: DNA
<213> ORGANISM: Zea mays

<400> SEQUENCE: 141
gtcgggagtg agcggcggcg tgg                                              23
```

```
<210> SEQ ID NO 142
<211> LENGTH: 23
<212> TYPE: DNA
<213> ORGANISM: Zea mays

<400> SEQUENCE: 142
gggagtgagc ggcggcgtgg tgg                                          23

<210> SEQ ID NO 143
<211> LENGTH: 23
<212> TYPE: DNA
<213> ORGANISM: Zea mays

<400> SEQUENCE: 143
gcggacgcgg cggcggcatc cgg                                          23

<210> SEQ ID NO 144
<211> LENGTH: 23
<212> TYPE: DNA
<213> ORGANISM: Zea mays

<400> SEQUENCE: 144
ggacgcggcg gcggcatccg ggg                                          23

<210> SEQ ID NO 145
<211> LENGTH: 23
<212> TYPE: DNA
<213> ORGANISM: Zea mays

<400> SEQUENCE: 145
gccaccatcg tcgtcgtcgt cgg                                          23

<210> SEQ ID NO 146
<211> LENGTH: 23
<212> TYPE: DNA
<213> ORGANISM: Zea mays

<400> SEQUENCE: 146
gccgacgacg acgacgatgg tgg                                          23

<210> SEQ ID NO 147
<211> LENGTH: 23
<212> TYPE: DNA
<213> ORGANISM: Zea mays

<400> SEQUENCE: 147
gacgacgacg atggtggccg cgg                                          23

<210> SEQ ID NO 148
<211> LENGTH: 23
<212> TYPE: DNA
<213> ORGANISM: Zea mays

<400> SEQUENCE: 148
gccagcgccg acgccgagtg cgg                                          23

<210> SEQ ID NO 149
<211> LENGTH: 23
<212> TYPE: DNA
<213> ORGANISM: Zea mays

<400> SEQUENCE: 149
ggtggccgcg gcgccgcact cgg                                          23
```

```
<210> SEQ ID NO 150
<211> LENGTH: 23
<212> TYPE: DNA
<213> ORGANISM: Zea mays

<400> SEQUENCE: 150
gccgcactcg gcgtcggcgc tgg                                              23

<210> SEQ ID NO 151
<211> LENGTH: 23
<212> TYPE: DNA
<213> ORGANISM: Zea mays

<400> SEQUENCE: 151
gcactcggcg tcggcgctgg cgg                                              23

<210> SEQ ID NO 152
<211> LENGTH: 23
<212> TYPE: DNA
<213> ORGANISM: Zea mays

<400> SEQUENCE: 152
ggcgctggcg gtgtacgagc ggg                                              23

<210> SEQ ID NO 153
<211> LENGTH: 23
<212> TYPE: DNA
<213> ORGANISM: Zea mays

<400> SEQUENCE: 153
gctggcggtg tacgagcggg tgg                                              23

<210> SEQ ID NO 154
<211> LENGTH: 23
<212> TYPE: DNA
<213> ORGANISM: Zea mays

<400> SEQUENCE: 154
gtacgagcgg gtggcgcgca tgg                                              23

<210> SEQ ID NO 155
<211> LENGTH: 23
<212> TYPE: DNA
<213> ORGANISM: Zea mays

<400> SEQUENCE: 155
gagcgggtgg cgcgcatggc ggg                                              23

<210> SEQ ID NO 156
<211> LENGTH: 28
<212> TYPE: DNA
<213> ORGANISM: Oryza sativa

<400> SEQUENCE: 156
gcgatgatgt cggtgtacga gagggtgg                                         28

<210> SEQ ID NO 157
<211> LENGTH: 26
<212> TYPE: DNA
<213> ORGANISM: Oryza sativa

<400> SEQUENCE: 157
gcggtggtgg tgttcagcgc gagcgg                                           26
```

-continued

<210> SEQ ID NO 158
<211> LENGTH: 27
<212> TYPE: DNA
<213> ORGANISM: Oryza sativa

<400> SEQUENCE: 158
gcggtggtgg tgttcagcgc gagcggg                                          27

<210> SEQ ID NO 159
<211> LENGTH: 26
<212> TYPE: DNA
<213> ORGANISM: Oryza sativa

<400> SEQUENCE: 159
gctcgccgcc gccgccgaca tccagg                                           26

<210> SEQ ID NO 160
<211> LENGTH: 26
<212> TYPE: DNA
<213> ORGANISM: Oryza sativa

<400> SEQUENCE: 160
gcgctgtcgc agctcctccc gccggg                                           26

<210> SEQ ID NO 161
<211> LENGTH: 27
<212> TYPE: DNA
<213> ORGANISM: Oryza sativa

<400> SEQUENCE: 161
gttcgtcggc ggcaggctcc tcggcgg                                          27

<210> SEQ ID NO 162
<211> LENGTH: 27
<212> TYPE: DNA
<213> ORGANISM: Oryza sativa

<400> SEQUENCE: 162
gaaggtgatg gcgtgccaca tcaatgg                                          27

<210> SEQ ID NO 163
<211> LENGTH: 28
<212> TYPE: DNA
<213> ORGANISM: Oryza sativa

<400> SEQUENCE: 163
ggcaccctcg tccccctcct caagcagg                                         28

<210> SEQ ID NO 164
<211> LENGTH: 23
<212> TYPE: DNA
<213> ORGANISM: Oryza sativa

<400> SEQUENCE: 164
gtccccctcc tcaagcaggc cgg                                              23

<210> SEQ ID NO 165
<211> LENGTH: 20
<212> TYPE: DNA
<213> ORGANISM: Oryza sativa

<400> SEQUENCE: 165

```
gagggggtc aaaggagtgg                                              20

<210> SEQ ID NO 166
<211> LENGTH: 20
<212> TYPE: DNA
<213> ORGANISM: Oryza sativa

<400> SEQUENCE: 166
ggtgcgaggg gggtcaaagg                                             20

<210> SEQ ID NO 167
<211> LENGTH: 23
<212> TYPE: DNA
<213> ORGANISM: Oryza sativa

<400> SEQUENCE: 167
gaattggtgt ggtgcgaggg ggg                                         23

<210> SEQ ID NO 168
<211> LENGTH: 21
<212> TYPE: DNA
<213> ORGANISM: Oryza sativa

<400> SEQUENCE: 168
gaattggtgt ggtgcgaggg g                                           21

<210> SEQ ID NO 169
<211> LENGTH: 21
<212> TYPE: DNA
<213> ORGANISM: Oryza sativa

<400> SEQUENCE: 169
gtcgagctcg tagacggcgg g                                           21

<210> SEQ ID NO 170
<211> LENGTH: 20
<212> TYPE: DNA
<213> ORGANISM: Oryza sativa

<400> SEQUENCE: 170
gtcgagctcg tagacggcgg                                             20

<210> SEQ ID NO 171
<211> LENGTH: 23
<212> TYPE: DNA
<213> ORGANISM: Triticum aestivum

<400> SEQUENCE: 171
ggcagggctc cacaagttca tgg                                         23

<210> SEQ ID NO 172
<211> LENGTH: 23
<212> TYPE: DNA
<213> ORGANISM: Triticum aestivum

<400> SEQUENCE: 172
gcttcctcag gctccaccag tgg                                         23

<210> SEQ ID NO 173
<211> LENGTH: 23
<212> TYPE: DNA
<213> ORGANISM: Triticum aestivum

<400> SEQUENCE: 173
```

-continued gtggagcctg aggaagcaga agg                                              23

<210> SEQ ID NO 174
<211> LENGTH: 23
<212> TYPE: DNA
<213> ORGANISM: Triticum aestivum

<400> SEQUENCE: 174
ggagcctgag gaagcagaag ggg                                              23

<210> SEQ ID NO 175
<211> LENGTH: 23
<212> TYPE: DNA
<213> ORGANISM: Triticum aestivum

<400> SEQUENCE: 175
gccggtcatc ggcgcgacgc tgg                                              23

<210> SEQ ID NO 176
<211> LENGTH: 23
<212> TYPE: DNA
<213> ORGANISM: Triticum aestivum

<400> SEQUENCE: 176
gcgcgacgct ggagcagctg agg                                              23

<210> SEQ ID NO 177
<211> LENGTH: 23
<212> TYPE: DNA
<213> ORGANISM: Triticum aestivum

<400> SEQUENCE: 177
gtacctgtcc aagcaccgga cgg                                              23

<210> SEQ ID NO 178
<211> LENGTH: 23
<212> TYPE: DNA
<213> ORGANISM: Triticum aestivum

<400> SEQUENCE: 178
ggaggtgaag ggcatgtcga cgg                                              23

<210> SEQ ID NO 179
<211> LENGTH: 23
<212> TYPE: DNA
<213> ORGANISM: Triticum aestivum

<400> SEQUENCE: 179
gatgtaggtg taggaggtga agg                                              23

<210> SEQ ID NO 180
<211> LENGTH: 23
<212> TYPE: DNA
<213> ORGANISM: Triticum aestivum

<400> SEQUENCE: 180
gtcggcgatg taggtgtagg agg                                              23

<210> SEQ ID NO 181
<211> LENGTH: 23
<212> TYPE: DNA
<213> ORGANISM: Triticum aestivum

```
<400> SEQUENCE: 181
gttcaccggg tcggcgatgt agg                                          23

<210> SEQ ID NO 182
<211> LENGTH: 23
<212> TYPE: DNA
<213> ORGANISM: Triticum aestivum

<400> SEQUENCE: 182
gccgagcagc acgtccatgt agg                                          23

<210> SEQ ID NO 183
<211> LENGTH: 23
<212> TYPE: DNA
<213> ORGANISM: Triticum aestivum

<400> SEQUENCE: 183
ggaggtgtac aggtcctaca tgg                                          23

<210> SEQ ID NO 184
<211> LENGTH: 23
<212> TYPE: DNA
<213> ORGANISM: Triticum aestivum

<400> SEQUENCE: 184
gcgagctctg gaggaagcag agg                                          23

<210> SEQ ID NO 185
<211> LENGTH: 23
<212> TYPE: DNA
<213> ORGANISM: Triticum aestivum

<400> SEQUENCE: 185
gcctgcgcga agctgttctc cgg                                          23

<210> SEQ ID NO 186
<211> LENGTH: 23
<212> TYPE: DNA
<213> ORGANISM: Zea mays

<400> SEQUENCE: 186
gcgatggcgt cgccggcgtg agg                                          23

<210> SEQ ID NO 187
<211> LENGTH: 23
<212> TYPE: DNA
<213> ORGANISM: Zea mays

<400> SEQUENCE: 187
ggaggaagct cacctcacgc cgg                                          23

<210> SEQ ID NO 188
<211> LENGTH: 23
<212> TYPE: DNA
<213> ORGANISM: Zea mays

<400> SEQUENCE: 188
gctagtggga agaatggcga tgg                                          23

<210> SEQ ID NO 189
<211> LENGTH: 23
<212> TYPE: DNA
<213> ORGANISM: Zea mays
```

```
<400> SEQUENCE: 189
ggccctgcta gtgggaagaa tgg                                              23

<210> SEQ ID NO 190
<211> LENGTH: 23
<212> TYPE: DNA
<213> ORGANISM: Zea mays

<400> SEQUENCE: 190
ggttgtcctc tcatggatcc tgg                                              23

<210> SEQ ID NO 191
<211> LENGTH: 23
<212> TYPE: DNA
<213> ORGANISM: Zea mays

<400> SEQUENCE: 191
gcttcctcag gctccacctc tgg                                              23

<210> SEQ ID NO 192
<211> LENGTH: 23
<212> TYPE: DNA
<213> ORGANISM: Zea mays

<400> SEQUENCE: 192
gccagtcatc ggcgcaacgg tgg                                              23

<210> SEQ ID NO 193
<211> LENGTH: 23
<212> TYPE: DNA
<213> ORGANISM: Zea mays

<400> SEQUENCE: 193
gcgcaacggt ggagcagctg agg                                              23

<210> SEQ ID NO 194
<211> LENGTH: 23
<212> TYPE: DNA
<213> ORGANISM: Zea mays

<400> SEQUENCE: 194
ggatgcacga ctggcttgtc ggg                                              23

<210> SEQ ID NO 195
<211> LENGTH: 23
<212> TYPE: DNA
<213> ORGANISM: Zea mays

<400> SEQUENCE: 195
ggcttgtcgg gtacctgtca cgg                                              23

<210> SEQ ID NO 196
<211> LENGTH: 23
<212> TYPE: DNA
<213> ORGANISM: Zea mays

<400> SEQUENCE: 196
ggaagtgaac ggcatgtcga cgg                                              23

<210> SEQ ID NO 197
<211> LENGTH: 23
<212> TYPE: DNA
```

<213> ORGANISM: Zea mays

<400> SEQUENCE: 197
ggacatgctc gacattcacc ggg    23

<210> SEQ ID NO 198
<211> LENGTH: 23
<212> TYPE: DNA
<213> ORGANISM: Zea mays

<400> SEQUENCE: 198
gacggcatct tcaacgccga cgg    23

<210> SEQ ID NO 199
<211> LENGTH: 23
<212> TYPE: DNA
<213> ORGANISM: Zea mays

<400> SEQUENCE: 199
gcgagctgtg gaggaagcag agg    23

<210> SEQ ID NO 200
<211> LENGTH: 23
<212> TYPE: DNA
<213> ORGANISM: Zea mays

<400> SEQUENCE: 200
gtggaggaag cagaggaaga cgg    23

<210> SEQ ID NO 201
<211> LENGTH: 27
<212> TYPE: DNA
<213> ORGANISM: Zea mays

<400> SEQUENCE: 201
gtactccatc cgccccatcg agtaggg    27

<210> SEQ ID NO 202
<211> LENGTH: 24
<212> TYPE: DNA
<213> ORGANISM: Zea mays

<400> SEQUENCE: 202
gcacgtacgt caccatcccg ccgg    24

<210> SEQ ID NO 203
<211> LENGTH: 24
<212> TYPE: DNA
<213> ORGANISM: Zea mays

<400> SEQUENCE: 203
gacgtacgtg ccctactcga tggg    24

<210> SEQ ID NO 204
<211> LENGTH: 25
<212> TYPE: DNA
<213> ORGANISM: Oryza sativa

<400> SEQUENCE: 204
gtggattcct gctactggga agaat    25

<210> SEQ ID NO 205
<211> LENGTH: 24

```
<212> TYPE: DNA
<213> ORGANISM: Oryza sativa

<400> SEQUENCE: 205
ggccttgcat gcttggctca gaat                                          24

<210> SEQ ID NO 206
<211> LENGTH: 32
<212> TYPE: DNA
<213> ORGANISM: Oryza sativa

<400> SEQUENCE: 206
gtcctgaaga ccaacttcac caattacccc aa                                 32

<210> SEQ ID NO 207
<211> LENGTH: 31
<212> TYPE: DNA
<213> ORGANISM: Oryza sativa

<400> SEQUENCE: 207
ggaagacggc gagcttcgag tttgcctcca a                                  31

<210> SEQ ID NO 208
<211> LENGTH: 31
<212> TYPE: DNA
<213> ORGANISM: Oryza sativa

<400> SEQUENCE: 208
gcctctaccc ggcggtgccg caggacccca a                                  31

<210> SEQ ID NO 209
<211> LENGTH: 31
<212> TYPE: DNA
<213> ORGANISM: Oryza sativa

<400> SEQUENCE: 209
gacatcattc ttcccagtag caggaatcca c                                  31

<210> SEQ ID NO 210
<211> LENGTH: 27
<212> TYPE: DNA
<213> ORGANISM: Oryza sativa

<400> SEQUENCE: 210
gttgtcctct catggatctt ggtccac                                       27

<210> SEQ ID NO 211
<211> LENGTH: 32
<212> TYPE: DNA
<213> ORGANISM: Oryza sativa

<400> SEQUENCE: 211
gcgcgacagt ggagcaactg aagaactacc ac                                 32

<210> SEQ ID NO 212
<211> LENGTH: 32
<212> TYPE: DNA
<213> ORGANISM: Oryza sativa

<400> SEQUENCE: 212
ggcgggatgg tgacgtacgt gccctactcc at                                 32

<210> SEQ ID NO 213
```

```
<211> LENGTH: 32
<212> TYPE: DNA
<213> ORGANISM: Oryza sativa

<400> SEQUENCE: 213
gcctacctcc agatgaagat ggcgctcgcc at                                    32

<210> SEQ ID NO 214
<211> LENGTH: 32
<212> TYPE: DNA
<213> ORGANISM: Oryza sativa

<400> SEQUENCE: 214
gaccaccccg tcaagtaccg gatgatgacc at                                    32

<210> SEQ ID NO 215
<211> LENGTH: 20
<212> TYPE: DNA
<213> ORGANISM: Oryza sativa

<400> SEQUENCE: 215
acgtacgtgc cctactccat                                                  20

<210> SEQ ID NO 216
<211> LENGTH: 23
<212> TYPE: DNA
<213> ORGANISM: Triticum aestivum

<400> SEQUENCE: 216
gggccgcgat gaagaggtgc ggg                                              23

<210> SEQ ID NO 217
<211> LENGTH: 23
<212> TYPE: DNA
<213> ORGANISM: Triticum aestivum

<400> SEQUENCE: 217
gcgccagggc cgcgatgaag agg                                              23

<210> SEQ ID NO 218
<211> LENGTH: 23
<212> TYPE: DNA
<213> ORGANISM: Triticum aestivum

<400> SEQUENCE: 218
gtacccgcac ctcttcatcg cgg                                              23

<210> SEQ ID NO 219
<211> LENGTH: 23
<212> TYPE: DNA
<213> ORGANISM: Triticum aestivum

<400> SEQUENCE: 219
gcacctcttc atcgcggccc tgg                                              23

<210> SEQ ID NO 220
<211> LENGTH: 23
<212> TYPE: DNA
<213> ORGANISM: Triticum aestivum

<400> SEQUENCE: 220
gccagcgggc cgaggtggaa ggg                                              23
```

```
<210> SEQ ID NO 221
<211> LENGTH: 23
<212> TYPE: DNA
<213> ORGANISM: Triticum aestivum

<400> SEQUENCE: 221
ggcgccagct cgtgcttcac cgg                                              23

<210> SEQ ID NO 222
<211> LENGTH: 23
<212> TYPE: DNA
<213> ORGANISM: Triticum aestivum

<400> SEQUENCE: 222
ggtcatgcag cgctggccga ggg                                              23

<210> SEQ ID NO 223
<211> LENGTH: 24
<212> TYPE: DNA
<213> ORGANISM: Triticum aestivum

<400> SEQUENCE: 223
gcagcgctgg ccgagggaca acgg                                             24

<210> SEQ ID NO 224
<211> LENGTH: 23
<212> TYPE: DNA
<213> ORGANISM: Triticum aestivum

<400> SEQUENCE: 224
gggacaacgg cagccgcctc agg                                              23

<210> SEQ ID NO 225
<211> LENGTH: 23
<212> TYPE: DNA
<213> ORGANISM: Triticum aestivum

<400> SEQUENCE: 225
gcagccgcct caggctcggc agg                                              23

<210> SEQ ID NO 226
<211> LENGTH: 23
<212> TYPE: DNA
<213> ORGANISM: Triticum aestivum

<400> SEQUENCE: 226
gagttcgtca acgaggtgtt cgg                                              23

<210> SEQ ID NO 227
<211> LENGTH: 23
<212> TYPE: DNA
<213> ORGANISM: Triticum aestivum

<400> SEQUENCE: 227
gacgcggccg tcggcgagcc cgg                                              23

<210> SEQ ID NO 228
<211> LENGTH: 23
<212> TYPE: DNA
<213> ORGANISM: Triticum aestivum

<400> SEQUENCE: 228
ggccgcgtcg tgcggtggat ggg                                              23
```

```
<210> SEQ ID NO 229
<211> LENGTH: 23
<212> TYPE: DNA
<213> ORGANISM: Triticum aestivum

<400> SEQUENCE: 229
gccgcgtcgt gcggtggatg ggg                                           23

<210> SEQ ID NO 230
<211> LENGTH: 23
<212> TYPE: DNA
<213> ORGANISM: Triticum aestivum

<400> SEQUENCE: 230
gacggcgaac gtctcccacc cgg                                           23

<210> SEQ ID NO 231
<211> LENGTH: 23
<212> TYPE: DNA
<213> ORGANISM: Triticum aestivum

<400> SEQUENCE: 231
gaaagtttgt gctaacggag tgg                                           23

<210> SEQ ID NO 232
<211> LENGTH: 23
<212> TYPE: DNA
<213> ORGANISM: Zea mays

<400> SEQUENCE: 232
ggaacctgca gtggcggcga ggg                                           23

<210> SEQ ID NO 233
<211> LENGTH: 23
<212> TYPE: DNA
<213> ORGANISM: Zea mays

<400> SEQUENCE: 233
gggccgcgaa gaagaggtga ggg                                           23

<210> SEQ ID NO 234
<211> LENGTH: 23
<212> TYPE: DNA
<213> ORGANISM: Zea mays

<400> SEQUENCE: 234
gcgccagggc cgcgaagaag agg                                           23

<210> SEQ ID NO 235
<211> LENGTH: 23
<212> TYPE: DNA
<213> ORGANISM: Zea mays

<400> SEQUENCE: 235
gtaccctcac ctcttcttcg cgg                                           23

<210> SEQ ID NO 236
<211> LENGTH: 23
<212> TYPE: DNA
<213> ORGANISM: Zea mays

<400> SEQUENCE: 236
gactaggagg gccagcgcca ggg                                           23
```

```
<210> SEQ ID NO 237
<211> LENGTH: 23
<212> TYPE: DNA
<213> ORGANISM: Zea mays

<400> SEQUENCE: 237
gaacgggtcc gcgactagga ggg                                          23

<210> SEQ ID NO 238
<211> LENGTH: 23
<212> TYPE: DNA
<213> ORGANISM: Zea mays

<400> SEQUENCE: 238
ggccgaacgg gtccgcgact agg                                          23

<210> SEQ ID NO 239
<211> LENGTH: 23
<212> TYPE: DNA
<213> ORGANISM: Zea mays

<400> SEQUENCE: 239
ggcgctggcc ctcctagtcg cgg                                          23

<210> SEQ ID NO 240
<211> LENGTH: 23
<212> TYPE: DNA
<213> ORGANISM: Zea mays

<400> SEQUENCE: 240
gccagcggac tgaggccgaa cgg                                          23

<210> SEQ ID NO 241
<211> LENGTH: 23
<212> TYPE: DNA
<213> ORGANISM: Zea mays

<400> SEQUENCE: 241
ggcgcgagct cgtgcttcac cgg                                          23

<210> SEQ ID NO 242
<211> LENGTH: 23
<212> TYPE: DNA
<213> ORGANISM: Zea mays

<400> SEQUENCE: 242
ggccgaggtc gactaccggc cgg                                          23

<210> SEQ ID NO 243
<211> LENGTH: 23
<212> TYPE: DNA
<213> ORGANISM: Zea mays

<400> SEQUENCE: 243
gcacgagctc gcgccgtacg ggg                                          23

<210> SEQ ID NO 244
<211> LENGTH: 23
<212> TYPE: DNA
<213> ORGANISM: Zea mays

<400> SEQUENCE: 244
```

```
gcgccgtacg gggaggtcat ggg                                              23

<210> SEQ ID NO 245
<211> LENGTH: 23
<212> TYPE: DNA
<213> ORGANISM: Zea mays

<400> SEQUENCE: 245
gagccggctg gcattgtctc tgg                                              23

<210> SEQ ID NO 246
<211> LENGTH: 23
<212> TYPE: DNA
<213> ORGANISM: Zea mays

<400> SEQUENCE: 246
ggcccagaga caatgccagc cgg                                              23

<210> SEQ ID NO 247
<211> LENGTH: 22
<212> TYPE: DNA
<213> ORGANISM: Zea mays

<400> SEQUENCE: 247
gctggccgag gtcgactacc gg                                               22

<210> SEQ ID NO 248
<211> LENGTH: 23
<212> TYPE: DNA
<213> ORGANISM: Zea mays

<400> SEQUENCE: 248
ggccgaggtc gactaccggc cgg                                              23

<210> SEQ ID NO 249
<211> LENGTH: 23
<212> TYPE: DNA
<213> ORGANISM: Zea mays

<400> SEQUENCE: 249
ggcgcgagct cgtgcttcac cgg                                              23

<210> SEQ ID NO 250
<211> LENGTH: 32
<212> TYPE: DNA
<213> ORGANISM: Oryza sativa

<400> SEQUENCE: 250
gcgtactacg ggctcatgtc cgtcggtccg aa                                    32

<210> SEQ ID NO 251
<211> LENGTH: 33
<212> TYPE: DNA
<213> ORGANISM: Oryza sativa

<400> SEQUENCE: 251
gggaggctgc tcagatatga cccagaaacc aaa                                   33

<210> SEQ ID NO 252
<211> LENGTH: 29
<212> TYPE: DNA
<213> ORGANISM: Oryza sativa

<400> SEQUENCE: 252
```
gtcgtgctga gcgggctggt cttcccgaa                                          29

<210> SEQ ID NO 253
<211> LENGTH: 31
<212> TYPE: DNA
<213> ORGANISM: Oryza sativa

<400> SEQUENCE: 253
gctggccctg ctcctcaccg acccgttcca c                                       31

<210> SEQ ID NO 254
<211> LENGTH: 29
<212> TYPE: DNA
<213> ORGANISM: Oryza sativa

<400> SEQUENCE: 254
gtcggagagg tgttcgggcc ggagtccat                                          29

<210> SEQ ID NO 255
<211> LENGTH: 24
<212> TYPE: DNA
<213> ORGANISM: Oryza sativa

<400> SEQUENCE: 255
gtgcctcacc ggccggtagt ccac                                               24

<210> SEQ ID NO 256
<211> LENGTH: 26
<212> TYPE: DNA
<213> ORGANISM: Oryza sativa

<400> SEQUENCE: 256
gccggctgcc gttgtcccgc ggccac                                             26

<210> SEQ ID NO 257
<211> LENGTH: 26
<212> TYPE: DNA
<213> ORGANISM: Oryza sativa

<400> SEQUENCE: 257
gtctcccacc cggcgtcctc ccccat                                             26

<210> SEQ ID NO 258
<211> LENGTH: 25
<212> TYPE: DNA
<213> ORGANISM: Oryza sativa

<400> SEQUENCE: 258
gctcatgacg gcgaacgtct cccac                                              25

<210> SEQ ID NO 259
<211> LENGTH: 27
<212> TYPE: DNA
<213> ORGANISM: Oryza sativa

<400> SEQUENCE: 259
gcttcttcgt cgtcgactcc accccat                                            27

<210> SEQ ID NO 260
<211> LENGTH: 27
<212> TYPE: DNA
<213> ORGANISM: Oryza sativa

<400> SEQUENCE: 260
gacttctctc gcgagagagg tcgccac                                                27

<210> SEQ ID NO 261
<211> LENGTH: 24
<212> TYPE: DNA
<213> ORGANISM: Oryza sativa

<400> SEQUENCE: 261
ggtcgtcaga aatctgcacg ccat                                                  24

<210> SEQ ID NO 262
<211> LENGTH: 30
<212> TYPE: DNA
<213> ORGANISM: Oryza sativa

<400> SEQUENCE: 262
gaaccccggc aggtcggcga acacctccac                                            30

<210> SEQ ID NO 263
<211> LENGTH: 26
<212> TYPE: DNA
<213> ORGANISM: Oryza sativa

<400> SEQUENCE: 263
gcttgaagta gagcgttcgc agccac                                                26

<210> SEQ ID NO 264
<211> LENGTH: 24
<212> TYPE: DNA
<213> ORGANISM: Oryza sativa

<400> SEQUENCE: 264
ggtgtgcatc cgcatgctga ccat                                                  24

<210> SEQ ID NO 265
<211> LENGTH: 44
<212> TYPE: DNA
<213> ORGANISM: Triticum aestivum

<400> SEQUENCE: 265
tacagggagg tcatgcagcg ctggccgagg gacaacggca gccg                            44

<210> SEQ ID NO 266
<211> LENGTH: 37
<212> TYPE: DNA
<213> ORGANISM: Triticum aestivum

<400> SEQUENCE: 266
tacagggagg tcatgcagcg agggacaacg gcagccg                                    37

<210> SEQ ID NO 267
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 267
gcggccgccg tgctgcgaca                                                       20

<210> SEQ ID NO 268
<211> LENGTH: 20

```
<212> TYPE: DNA
<213> ORGANISM: Artificial
<220> FEATURE:
<223> OTHER INFORMATION: DNA version of guideRNA to target DNA target

<400> SEQUENCE: 268
gcgtcctcct ccgccgtcca                                               20

<210> SEQ ID NO 269
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 269
gaagaagggg ccgtggacgg                                               20

<210> SEQ ID NO 270
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 270
gaaggggccg tggacggcgg                                               20

<210> SEQ ID NO 271
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 271
ggggccgtgg acggcggagg                                               20

<210> SEQ ID NO 272
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 272
ggtgccatgg ttggaggtgt                                               20

<210> SEQ ID NO 273
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 273
gttgccggtg ccatggttgg                                               20

<210> SEQ ID NO 274
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 274
```
gggaacagag gtccagttgc                                                  20

<210> SEQ ID NO 275
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 275
gcacgagaac ttcacgcagg                                                  20

<210> SEQ ID NO 276
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 276
gaacttcacg caggaggagg                                                  20

<210> SEQ ID NO 277
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 277
gcttcccagc atggcatgga                                                  20

<210> SEQ ID NO 278
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 278
gtcaccctcc atgccatgct                                                  20

<210> SEQ ID NO 279
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 279
gaaccagctg ccggggcgga                                                  20

<210> SEQ ID NO 280
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 280
tgaggtacac caactacctg                                                  20

<210> SEQ ID NO 281
<211> LENGTH: 20
<212> TYPE: DNA
<213> ORGANISM: Artificial

```
<220> FEATURE:
<223> OTHER INFORMATION: DNA version of guideRNA to target DNA target

<400> SEQUENCE: 281
gccaggggcg gcggcgtccc                                                    20

<210> SEQ ID NO 282
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 282
ggtgccatgg gtggaggtgt                                                    20

<210> SEQ ID NO 283
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 283
gttgccggtg ccatgggtgg                                                    20

<210> SEQ ID NO 284
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 284
ggtccagttg ccggtgccat                                                    20

<210> SEQ ID NO 285
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 285
gggcacgttg gtccagttgc                                                    20

<210> SEQ ID NO 286
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 286
gcggcaagag ctgcaggctg                                                    20

<210> SEQ ID NO 287
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 287
gaagttctcg tgcttcaggt                                                    20
```

<210> SEQ ID NO 288
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 288
gggtgaagtt ctcgtgcttc                                           20

<210> SEQ ID NO 289
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 289
gatgaggtct tcctcctcct                                           20

<210> SEQ ID NO 290
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 290
gaagcacgag aacttcaccc                                           20

<210> SEQ ID NO 291
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 291
gcacgagaac ttcacccagg                                           20

<210> SEQ ID NO 292
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 292
gcttccgagc atggcgtgga                                           20

<210> SEQ ID NO 293
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 293
gtcaccctcc acgccatgct                                           20

<210> SEQ ID NO 294
<211> LENGTH: 20
<212> TYPE: DNA
<213> ORGANISM: Artificial
<220> FEATURE:
<223> OTHER INFORMATION: DNA version of guideRNA to target DNA target -continued

<400> SEQUENCE: 294
gaaccagctg ccgggaagga                                               20

<210> SEQ ID NO 295
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 295
gcaagaagct gcggcagcgc                                               20

<210> SEQ ID NO 296
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 296
gcgatggggc ggtgggtgag                                               20

<210> SEQ ID NO 297
<211> LENGTH: 24
<212> TYPE: DNA
<213> ORGANISM: Artificial
<220> FEATURE:
<223> OTHER INFORMATION: DNA version of guideRNA to target DNA target

<400> SEQUENCE: 297
gctgcgacaa ggcgaacgtg aaga                                          24

<210> SEQ ID NO 298
<211> LENGTH: 25
<212> TYPE: DNA
<213> ORGANISM: Artificial
<220> FEATURE:
<223> OTHER INFORMATION: DNA version of guideRNA to target DNA target

<400> SEQUENCE: 298
gctgcgacaa ggcgaacgtg aagaa                                         25

<210> SEQ ID NO 299
<211> LENGTH: 24
<212> TYPE: DNA
<213> ORGANISM: Artificial
<220> FEATURE:
<223> OTHER INFORMATION: DNA version of guideRNA to target DNA target

<400> SEQUENCE: 299
ggcgtacacc tccacccacg gcac                                          24

<210> SEQ ID NO 300
<211> LENGTH: 23
<212> TYPE: DNA
<213> ORGANISM: Artificial
<220> FEATURE:
<223> OTHER INFORMATION: DNA version of guideRNA to target DNA target

<400> SEQUENCE: 300
gcgccggcgc cgcaggctgc tct                                           23

<210> SEQ ID NO 301

```
<211> LENGTH: 23
<212> TYPE: DNA
<213> ORGANISM: Artificial
<220> FEATURE:
<223> OTHER INFORMATION: DNA version of guideRNA to target DNA target

<400> SEQUENCE: 301
gcaggctgct ctcggccagt atc                                           23

<210> SEQ ID NO 302
<211> LENGTH: 23
<212> TYPE: DNA
<213> ORGANISM: Artificial
<220> FEATURE:
<223> OTHER INFORMATION: DNA version of guideRNA to target DNA target

<400> SEQUENCE: 302
ggctgaggta caccaactac ctg                                           23

<210> SEQ ID NO 303
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 303
gaagcacgag aacttcacgc                                               20

<210> SEQ ID NO 304
<211> LENGTH: 23
<212> TYPE: DNA
<213> ORGANISM: Artificial
<220> FEATURE:
<223> OTHER INFORMATION: DNA version of guideRNA to target DNA target

<400> SEQUENCE: 304
gaagcacgag aacttcacgc agg                                           23

<210> SEQ ID NO 305
<211> LENGTH: 23
<212> TYPE: DNA
<213> ORGANISM: Artificial
<220> FEATURE:
<223> OTHER INFORMATION: DNA version of guideRNA to target DNA target

<400> SEQUENCE: 305
gcacgagaac ttcacgcagg agg                                           23

<210> SEQ ID NO 306
<211> LENGTH: 19
<212> TYPE: DNA
<213> ORGANISM: Artificial
<220> FEATURE:
<223> OTHER INFORMATION: DNA version of guideRNA to target DNA target

<400> SEQUENCE: 306
gtcaccctcc acgccatgc                                                19

<210> SEQ ID NO 307
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 307
```

```
gtcaccctcc acgccatgct                                          20
```

<210> SEQ ID NO 308
<211> LENGTH: 23
<212> TYPE: DNA
<213> ORGANISM: Artificial
<220> FEATURE:
<223> OTHER INFORMATION: DNA version of guideRNA to target DNA target

<400> SEQUENCE: 308

```
ggctgctctc ggccagtatc agg                                      23
```

<210> SEQ ID NO 309
<211> LENGTH: 24
<212> TYPE: DNA
<213> ORGANISM: Artificial
<220> FEATURE:
<223> OTHER INFORMATION: DNA version of guideRNA to target DNA target

<400> SEQUENCE: 309

```
ggtcgctgat cgcgaaccag ctgc                                     24
```

<210> SEQ ID NO 310
<211> LENGTH: 24
<212> TYPE: DNA
<213> ORGANISM: Artificial
<220> FEATURE:
<223> OTHER INFORMATION: DNA version of guideRNA to target DNA target

<400> SEQUENCE: 310

```
gactcgcagc atctgcagct caac                                     24
```

<210> SEQ ID NO 311
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 311

```
gccgacctca tgcagagcat                                          20
```

<210> SEQ ID NO 312
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 312

```
gttgaggatg cagcagcagg                                          20
```

<210> SEQ ID NO 313
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 313

```
gaggatgcag cagcaggtgg                                          20
```

<210> SEQ ID NO 314
<211> LENGTH: 20
<212> TYPE: DNA

```
<213> ORGANISM: Artificial
<220> FEATURE:
<223> OTHER INFORMATION: DNA version of guideRNA to target DNA target

<400> SEQUENCE: 314
gcagcagcag gtggagggcg                                          20

<210> SEQ ID NO 315
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 315
gcagcaggtg gagggcgtgg                                          20

<210> SEQ ID NO 316
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 316
gtggagggcg tggtgggcgg                                          20

<210> SEQ ID NO 317
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 317
gtggcacatg cagcagccgc                                          20

<210> SEQ ID NO 318
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 318
gtggtcgtct tcagcgccag                                          20

<210> SEQ ID NO 319
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 319
gcaggaggcg cttgacgacg                                          20

<210> SEQ ID NO 320
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 320
gtcgtcaagc gcctcctgct                                          20
```

<210> SEQ ID NO 321
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 321
gtggccggcg ccgggtccgg                                         20

<210> SEQ ID NO 322
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 322
ggtggccggc gccgggtccg                                         20

<210> SEQ ID NO 323
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 323
gtggtggccg gcgccgggtc                                         20

<210> SEQ ID NO 324
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 324
ggacgagcgt gccgttgatg                                         20

<210> SEQ ID NO 325
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 325
gtgatggcgt gccacatcaa                                         20

<210> SEQ ID NO 326
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 326
gcgccggcgt ccttgaggag                                         20

<210> SEQ ID NO 327
<211> LENGTH: 20
<212> TYPE: DNA
<213> ORGANISM: Artificial
<220> FEATURE:

<223> OTHER INFORMATION: DNA version of guideRNA to target DNA target

<400> SEQUENCE: 327
gtcgggagtg agcggcggcg                                           20

<210> SEQ ID NO 328
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 328
gggagtgagc ggcggcgtgg                                           20

<210> SEQ ID NO 329
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 329
gcggacgcgg cggcggcatc                                           20

<210> SEQ ID NO 330
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 330
ggacgcggcg gcggcatccg                                           20

<210> SEQ ID NO 331
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 331
gccaccatcg tcgtcgtcgt                                           20

<210> SEQ ID NO 332
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 332
gccgacgacg acgacgatgg                                           20

<210> SEQ ID NO 333
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 333
gacgacgacg atggtggccg                                           20

<210> SEQ ID NO 334
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 334
gccagcgccg acgccgagtg                                           20

<210> SEQ ID NO 335
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 335
ggtggccgcg gcgccgcact                                           20

<210> SEQ ID NO 336
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 336
gccgcactcg gcgtcggcgc                                           20

<210> SEQ ID NO 337
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 337
gcactcggcg tcggcgctgg                                           20

<210> SEQ ID NO 338
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 338
ggcgctggcg gtgtacgagc                                           20

<210> SEQ ID NO 339
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 339
gctggcggtg tacgagcggg                                           20

<210> SEQ ID NO 340
<211> LENGTH: 20
<212> TYPE: DNA
<213> ORGANISM: Artificial
<220> FEATURE:
<223> OTHER INFORMATION: DNA version of guideRNA to target DNA target

```
<400> SEQUENCE: 340
gtacgagcgg gtggcgcgca                                              20

<210> SEQ ID NO 341
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 341
gagcgggtgg cgcgcatggc                                              20

<210> SEQ ID NO 342
<211> LENGTH: 25
<212> TYPE: DNA
<213> ORGANISM: Artificial
<220> FEATURE:
<223> OTHER INFORMATION: DNA version of guideRNA to target DNA target

<400> SEQUENCE: 342
gcgatgatgt cggtgtacga gaggg                                        25

<210> SEQ ID NO 343
<211> LENGTH: 23
<212> TYPE: DNA
<213> ORGANISM: Artificial
<220> FEATURE:
<223> OTHER INFORMATION: DNA version of guideRNA to target DNA target

<400> SEQUENCE: 343
gcggtggtgg tgttcagcgc gag                                          23

<210> SEQ ID NO 344
<211> LENGTH: 24
<212> TYPE: DNA
<213> ORGANISM: Artificial
<220> FEATURE:
<223> OTHER INFORMATION: DNA version of guideRNA to target DNA target

<400> SEQUENCE: 344
gcggtggtgg tgttcagcgc gagc                                         24

<210> SEQ ID NO 345
<211> LENGTH: 23
<212> TYPE: DNA
<213> ORGANISM: Artificial
<220> FEATURE:
<223> OTHER INFORMATION: DNA version of guideRNA to target DNA target

<400> SEQUENCE: 345
gctcgccgcc gccgccgaca tcc                                          23

<210> SEQ ID NO 346
<211> LENGTH: 23
<212> TYPE: DNA
<213> ORGANISM: Artificial
<220> FEATURE:
<223> OTHER INFORMATION: DNA version of guideRNA to target DNA target

<400> SEQUENCE: 346
gcgctgtcgc agctcctccc gcc                                          23

<210> SEQ ID NO 347
<211> LENGTH: 24
```

```
<212> TYPE: DNA
<213> ORGANISM: Artificial
<220> FEATURE:
<223> OTHER INFORMATION: DNA version of guideRNA to target DNA target

<400> SEQUENCE: 347
gttcgtcggc ggcaggctcc tcgg                                          24

<210> SEQ ID NO 348
<211> LENGTH: 24
<212> TYPE: DNA
<213> ORGANISM: Artificial
<220> FEATURE:
<223> OTHER INFORMATION: DNA version of guideRNA to target DNA target

<400> SEQUENCE: 348
gaaggtgatg gcgtgccaca tcaa                                          24

<210> SEQ ID NO 349
<211> LENGTH: 25
<212> TYPE: DNA
<213> ORGANISM: Artificial
<220> FEATURE:
<223> OTHER INFORMATION: DNA version of guideRNA to target DNA target

<400> SEQUENCE: 349
ggcaccctcg tccccctcct caagc                                         25

<210> SEQ ID NO 350
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 350
gtcccsctcc tcaagcaggc                                               20

<210> SEQ ID NO 351
<211> LENGTH: 17
<212> TYPE: DNA
<213> ORGANISM: Artificial
<220> FEATURE:
<223> OTHER INFORMATION: DNA version of guideRNA to target DNA target

<400> SEQUENCE: 351 gagggggtc aaaggag                                                   17

<210> SEQ ID NO 352
<211> LENGTH: 17
<212> TYPE: DNA
<213> ORGANISM: Artificial
<220> FEATURE:
<223> OTHER INFORMATION: DNA version of guideRNA to target DNA target

<400> SEQUENCE: 352
ggtgcgaggg gggtcaa                                                  17

<210> SEQ ID NO 353
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 353
```

```
gaattggtgt ggtgcgaggg                                               20

<210> SEQ ID NO 354
<211> LENGTH: 18
<212> TYPE: DNA
<213> ORGANISM: Artificial
<220> FEATURE:
<223> OTHER INFORMATION: DNA version of guideRNA to target DNA target

<400> SEQUENCE: 354
gaattggtgt ggtgcgag                                                 18

<210> SEQ ID NO 355
<211> LENGTH: 18
<212> TYPE: DNA
<213> ORGANISM: Artificial
<220> FEATURE:
<223> OTHER INFORMATION: DNA version of guideRNA to target DNA target

<400> SEQUENCE: 355
gtcgagctcg tagacggc                                                 18

<210> SEQ ID NO 356
<211> LENGTH: 17
<212> TYPE: DNA
<213> ORGANISM: Artificial
<220> FEATURE:
<223> OTHER INFORMATION: DNA version of guideRNA to target DNA target

<400> SEQUENCE: 356
gtcgagctcg tagacgg                                                  17

<210> SEQ ID NO 357
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 357
ggcagggctc cacaagttca                                               20

<210> SEQ ID NO 358
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 358
gcttcctcag gctccaccag                                               20

<210> SEQ ID NO 359
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 359
gtggagcctg aggaagcaga                                               20

<210> SEQ ID NO 360
<211> LENGTH: 20
<212> TYPE: DNA
<213> ORGANISM: artificial
```

```
<220> FEATURE:
<223> OTHER INFORMATION: DNA version of guideRNA to target DNA target

<400> SEQUENCE: 360
ggagcctgag gaagcagaag                                                    20

<210> SEQ ID NO 361
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 361
gccggtcatc ggcgcgacgc                                                    20

<210> SEQ ID NO 362
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 362
gcgcgacgct ggagcagctg                                                    20

<210> SEQ ID NO 363
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 363
gtacctgtcc aagcaccgga                                                    20

<210> SEQ ID NO 364
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 364
ggaggtgaag ggcatgtcga                                                    20

<210> SEQ ID NO 365
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 365
gatgtaggtg taggaggtga                                                    20

<210> SEQ ID NO 366
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 366
gtcggcgatg taggtgtagg                                                    20
```

```
<210> SEQ ID NO 367
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 367
gttcaccggg tcggcgatgt                                          20

<210> SEQ ID NO 368
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 368
gccgagcagc acgtccatgt                                          20

<210> SEQ ID NO 369
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 369
ggaggtgtac aggtcctaca                                          20

<210> SEQ ID NO 370
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 370
gcgagctctg gaggaagcag                                          20

<210> SEQ ID NO 371
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 371
gcctgcgcga agctgttctc                                          20

<210> SEQ ID NO 372
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 372
gcgatggcgt cgccggcgtg                                          20

<210> SEQ ID NO 373
<211> LENGTH: 20
<212> TYPE: DNA
<213> ORGANISM: artificial
<220> FEATURE:
<223> OTHER INFORMATION: DNA version of guideRNA to target DNA target
```

<400> SEQUENCE: 373
ggaggaagct caccteacgc                                           20

<210> SEQ ID NO 374
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 374
gctagtggga agaatggcga                                           20

<210> SEQ ID NO 375
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 375
ggccctgcta gtgggaagaa                                           20

<210> SEQ ID NO 376
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 376
ggttgtcctc tcatggatcc                                           20

<210> SEQ ID NO 377
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 377
gcttcctcag gctccacctc                                           20

<210> SEQ ID NO 378
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 378
gccagtcatc ggcgcaacgg                                           20

<210> SEQ ID NO 379
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 379
gcgcaacggt ggagcagctg                                           20

<210> SEQ ID NO 380

```
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 380
ggatgcacga ctggcttgtc                                              20

<210> SEQ ID NO 381
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 381
ggcttgtcgg gtacctgtca                                              20

<210> SEQ ID NO 382
<211> LENGTH: 20
<212> TYPE: DNA
<213> ORGANISM: ARTIFICIAL
<220> FEATURE:
<223> OTHER INFORMATION: DNA version of guideRNA to target DNA target

<400> SEQUENCE: 382
ggaagtgaac ggcatgtcga                                              20

<210> SEQ ID NO 383
<211> LENGTH: 20
<212> TYPE: DNA
<213> ORGANISM: ARTIFICIAL
<220> FEATURE:
<223> OTHER INFORMATION: DNA version of guideRNA to target DNA target

<400> SEQUENCE: 383
ggacatgctc gacattcacc                                              20

<210> SEQ ID NO 384
<211> LENGTH: 20
<212> TYPE: DNA
<213> ORGANISM: ARTIFICIAL
<220> FEATURE:
<223> OTHER INFORMATION: DNA version of guideRNA to target DNA target

<400> SEQUENCE: 384
gacggcatct tcaacgccga                                              20

<210> SEQ ID NO 385
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 385
gcgagctgtg gaggaagcag                                              20

<210> SEQ ID NO 386
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 386
```
gtggaggaag cagaggaaga                                                    20

<210> SEQ ID NO 387
<211> LENGTH: 24
<212> TYPE: DNA
<213> ORGANISM: artificial
<220> FEATURE:
<223> OTHER INFORMATION: DNA version of guideRNA to target DNA target

<400> SEQUENCE: 387
gtactccatc cgccccatcg agta                                               24

<210> SEQ ID NO 388
<211> LENGTH: 21
<212> TYPE: DNA
<213> ORGANISM: artificial
<220> FEATURE:
<223> OTHER INFORMATION: DNA version of guideRNA to target DNA target

<400> SEQUENCE: 388
gcacgtacgt caccatcccg c                                                  21

<210> SEQ ID NO 389
<211> LENGTH: 21
<212> TYPE: DNA
<213> ORGANISM: Artificial
<220> FEATURE:
<223> OTHER INFORMATION: DNA version of guideRNA to target DNA target

<400> SEQUENCE: 389
gacgtacgtg ccctactcga t                                                  21

<210> SEQ ID NO 390
<211> LENGTH: 18
<212> TYPE: DNA
<213> ORGANISM: artificial
<220> FEATURE:
<223> OTHER INFORMATION: DNA version of guideRNA to target DNA target

<400> SEQUENCE: 390
gtggattcct gctactgg                                                      18

<210> SEQ ID NO 391
<211> LENGTH: 17
<212> TYPE: DNA
<213> ORGANISM: artificial
<220> FEATURE:
<223> OTHER INFORMATION: DNA version of guideRNA to target DNA target

<400> SEQUENCE: 391
ggccttgcat gcttggc                                                       17

<210> SEQ ID NO 392
<211> LENGTH: 24
<212> TYPE: DNA
<213> ORGANISM: artificial
<220> FEATURE:
<223> OTHER INFORMATION: DNA version of guideRNA to target DNA target

<400> SEQUENCE: 392
gtcctgaaga ccaacttcac caat                                               24

<210> SEQ ID NO 393
<211> LENGTH: 23
<212> TYPE: DNA

```
<213> ORGANISM: Artificial
<220> FEATURE:
<223> OTHER INFORMATION: DNA version of guideRNA to target DNA target

<400> SEQUENCE: 393
ggaagacggc gagcttcgag ttt                                           23

<210> SEQ ID NO 394
<211> LENGTH: 23
<212> TYPE: DNA
<213> ORGANISM: Artificial
<220> FEATURE:
<223> OTHER INFORMATION: DNA version of guideRNA to target DNA target

<400> SEQUENCE: 394
gcctctaccc ggcggtgccg cag                                           23

<210> SEQ ID NO 395
<211> LENGTH: 24
<212> TYPE: DNA
<213> ORGANISM: Artificial
<220> FEATURE:
<223> OTHER INFORMATION: DNA version of guideRNA to target DNA target

<400> SEQUENCE: 395
gacatcattc ttcccagtag cagg                                          24

<210> SEQ ID NO 396
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 396
gttgtcctct catggatctt                                               20

<210> SEQ ID NO 397
<211> LENGTH: 25
<212> TYPE: DNA
<213> ORGANISM: artificial
<220> FEATURE:
<223> OTHER INFORMATION: DNA version of guideRNA to target DNA target

<400> SEQUENCE: 397
gcgcgacagt ggagcaactg aagaa                                         25

<210> SEQ ID NO 398
<211> LENGTH: 25
<212> TYPE: DNA
<213> ORGANISM: artificial
<220> FEATURE:
<223> OTHER INFORMATION: DNA version of guideRNA to target DNA target

<400> SEQUENCE: 398
ggcgggatgg tgacgtacgt gccct                                         25

<210> SEQ ID NO 399
<211> LENGTH: 25
<212> TYPE: DNA
<213> ORGANISM: artificial
<220> FEATURE:
<223> OTHER INFORMATION: DNA version of guideRNA to target DNA target

<400> SEQUENCE: 399
gcctacctcc agatgaagat ggcgc                                         25
```

```
<210> SEQ ID NO 400
<211> LENGTH: 25
<212> TYPE: DNA
<213> ORGANISM: artificial
<220> FEATURE:
<223> OTHER INFORMATION: DNA version of guideRNA to target DNA target

<400> SEQUENCE: 400
gaccaccccg tcaagtaccg gatga                                         25

<210> SEQ ID NO 401
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 401
acgtacgtgc cctactccat                                               20

<210> SEQ ID NO 402
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 402
gggccgcgat gaagaggtgc                                               20

<210> SEQ ID NO 403
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 403
gcgccagggc cgcgatgaag                                               20

<210> SEQ ID NO 404
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 404
gtacccgcac ctcttcatcg                                               20

<210> SEQ ID NO 405
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 405
gcacctcttc atcgcggccc                                               20

<210> SEQ ID NO 406
<211> LENGTH: 20
<212> TYPE: DNA
<213> ORGANISM: artificial
<220> FEATURE:
```

```
<223> OTHER INFORMATION: DNA version of guideRNA to target DNA target

<400> SEQUENCE: 406
gccagcgggc cgaggtggaa                                                  20

<210> SEQ ID NO 407
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 407
ggcgccagct cgtgcttcac                                                  20

<210> SEQ ID NO 408
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 408
ggtcatgcag cgctggccga                                                  20

<210> SEQ ID NO 409
<211> LENGTH: 21
<212> TYPE: DNA
<213> ORGANISM: artificial
<220> FEATURE:
<223> OTHER INFORMATION: DNA version of guideRNA to target DNA target

<400> SEQUENCE: 409
gcagcgctgg ccgagggaca a                                                21

<210> SEQ ID NO 410
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 410
gggacaacgg cagccgcctc                                                  20

<210> SEQ ID NO 411
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 411
gcagccgcct caggctcggc                                                  20

<210> SEQ ID NO 412
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 412
gagttcgtca acgaggtgtt                                                  20
```

```
<210> SEQ ID NO 413
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 413
gacgcggccg tcggcgagcc                                              20

<210> SEQ ID NO 414
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 414
ggccgcgtcg tgcggtggat                                              20

<210> SEQ ID NO 415
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 415
gccgcgtcgt gcggtggatg                                              20

<210> SEQ ID NO 416
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 416
gacggcgaac gtctcccacc                                              20

<210> SEQ ID NO 417
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 417
gaaagtttgt gctaacggag                                              20

<210> SEQ ID NO 418
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 418
ggaacctgca gtggcggcga                                              20

<210> SEQ ID NO 419
<211> LENGTH: 20
<212> TYPE: DNA
<213> ORGANISM: artificial
<220> FEATURE:
<223> OTHER INFORMATION: DNA version of guideRNA to target DNA target
```

<400> SEQUENCE: 419
gggccgcgaa gaagaggtga                                              20

<210> SEQ ID NO 420
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 420
gcgccagggc cgcgaagaag                                              20

<210> SEQ ID NO 421
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 421
gtaccctcac ctcttcttcg                                              20

<210> SEQ ID NO 422
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 422
gactaggagg gccagcgcca                                              20

<210> SEQ ID NO 423
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 423
gaacgggtcc gcgactagga                                              20

<210> SEQ ID NO 424
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 424
ggccgaacgg gtccgcgact                                              20

<210> SEQ ID NO 425
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 425
ggcgctggcc ctcctagtcg                                              20

<210> SEQ ID NO 426
<211> LENGTH: 20

```
<212> TYPE: DNA
<213> ORGANISM: artificial
<220> FEATURE:
<223> OTHER INFORMATION: DNA version of guideRNA to target DNA target

<400> SEQUENCE: 426
gccagcggac tgaggccgaa                                              20

<210> SEQ ID NO 427
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 427
ggcgcgagct cgtgcttcac                                              20

<210> SEQ ID NO 428
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 428
ggccgaggtc gactaccggc                                              20

<210> SEQ ID NO 429
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 429
gcacgagctc gcgccgtacg                                              20

<210> SEQ ID NO 430
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 430
gcgccgtacg gggaggtcat                                              20

<210> SEQ ID NO 431
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 431
gagccggctg gcattgtctc                                              20

<210> SEQ ID NO 432
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 432
```

-continued

```
ggcccagaga caatgccagc                                                20

<210> SEQ ID NO 433
<211> LENGTH: 19
<212> TYPE: DNA
<213> ORGANISM: artificial
<220> FEATURE:
<223> OTHER INFORMATION: DNA version of guideRNA to target DNA target

<400> SEQUENCE: 433
gctggccgag gtcgactac                                                 19

<210> SEQ ID NO 434
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 434
ggccgaggtc gactaccggc                                                20

<210> SEQ ID NO 435
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 435
ggcgcgagct cgtgcttcac                                                20

<210> SEQ ID NO 436
<211> LENGTH: 24
<212> TYPE: DNA
<213> ORGANISM: artificial
<220> FEATURE:
<223> OTHER INFORMATION: DNA version of guideRNA to target DNA target

<400> SEQUENCE: 436
gcgtactacg ggctcatgtc cgtc                                           24

<210> SEQ ID NO 437
<211> LENGTH: 25
<212> TYPE: DNA
<213> ORGANISM: artificial
<220> FEATURE:
<223> OTHER INFORMATION: DNA version of guideRNA to target DNA target

<400> SEQUENCE: 437
gggaggctgc tcagatatga cccag                                          25

<210> SEQ ID NO 438
<211> LENGTH: 21
<212> TYPE: DNA
<213> ORGANISM: ARTIFICIAL
<220> FEATURE:
<223> OTHER INFORMATION: DNA version of guideRNA to target DNA target

<400> SEQUENCE: 438
gtcgtgctga gcgggctggt c                                              21

<210> SEQ ID NO 439
<211> LENGTH: 24
<212> TYPE: DNA
<213> ORGANISM: ARTIFICIAL
```

```
<220> FEATURE:
<223> OTHER INFORMATION: DNA version of guideRNA to target DNA target

<400> SEQUENCE: 439
gctggccctg ctcctcaccg accc                                              24

<210> SEQ ID NO 440
<211> LENGTH: 22
<212> TYPE: DNA
<213> ORGANISM: ARTIFICIAL
<220> FEATURE:
<223> OTHER INFORMATION: DNA version of guideRNA to target DNA target

<400> SEQUENCE: 440
gtcggagagg tgttcgggcc gg                                                22

<210> SEQ ID NO 441
<211> LENGTH: 17
<212> TYPE: DNA
<213> ORGANISM: artificial
<220> FEATURE:
<223> OTHER INFORMATION: DNA version of guideRNA to target DNA target

<400> SEQUENCE: 441
gtgcctcacc ggccggt                                                      17

<210> SEQ ID NO 442
<211> LENGTH: 19
<212> TYPE: DNA
<213> ORGANISM: artificial
<220> FEATURE:
<223> OTHER INFORMATION: DNA version of guideRNA to target DNA target

<400> SEQUENCE: 442
gccggctgcc gttgtcccg                                                    19

<210> SEQ ID NO 443
<211> LENGTH: 19
<212> TYPE: DNA
<213> ORGANISM: artificial
<220> FEATURE:
<223> OTHER INFORMATION: DNA version of guideRNA to target DNA target

<400> SEQUENCE: 443
gtctcccacc cggcgtcct                                                    19

<210> SEQ ID NO 444
<211> LENGTH: 18
<212> TYPE: DNA
<213> ORGANISM: artificial
<220> FEATURE:
<223> OTHER INFORMATION: DNA version of guideRNA to target DNA target

<400> SEQUENCE: 444
gctcatgacg gcgaacgt                                                     18

<210> SEQ ID NO 445
<211> LENGTH: 20
<212> TYPE: DNA
<213> ORGANISM: Artificial
<220> FEATURE:
<223> OTHER INFORMATION: DNA version of guideRNA to target DNA target

<400> SEQUENCE: 445
gcttcttcgt cgtcgactcc                                                   20
```

-continued

```
<210> SEQ ID NO 446
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 446
gacttctctc gcgagagagg                                                      20

<210> SEQ ID NO 447
<211> LENGTH: 17
<212> TYPE: DNA
<213> ORGANISM: artificial
<220> FEATURE:
<223> OTHER INFORMATION: DNA version of guideRNA to target DNA target

<400> SEQUENCE: 447
ggtcgtcaga aatctgc                                                         17

<210> SEQ ID NO 448
<211> LENGTH: 23
<212> TYPE: DNA
<213> ORGANISM: artificial
<220> FEATURE:
<223> OTHER INFORMATION: DNA version of guideRNA to target DNA target

<400> SEQUENCE: 448
gaaccccggc aggtcggcga aca                                                  23

<210> SEQ ID NO 449
<211> LENGTH: 19
<212> TYPE: DNA
<213> ORGANISM: Artificial
<220> FEATURE:
<223> OTHER INFORMATION: DNA version of guideRNA to target DNA target

<400> SEQUENCE: 449
gcttgaagta gagcgttcg                                                       19

<210> SEQ ID NO 450
<211> LENGTH: 17
<212> TYPE: DNA
<213> ORGANISM: Artificial
<220> FEATURE:
<223> OTHER INFORMATION: DNA version of guideRNA to target DNA target

<400> SEQUENCE: 450
ggtgtgcatc cgcatgc                                                         17

<210> SEQ ID NO 451
<211> LENGTH: 1000
<212> TYPE: DNA
<213> ORGANISM: Triticum aestivum

<400> SEQUENCE: 451
cacagtcaca gacatcattc cttcagtata taattgccag ataaagaaaa aattcctctc          60
atacacagat acactactac ggaaaagtaa aataaaacct gcgagttaaa acatgagatc         120
cagccattca ggtaaacaca atgtatcaca attcaaagta cattcaggaa agcaccgcca         180
tttctatcgt gaattccatt tatccatttg tcctgggcac aaagccctgg gcctctgcag         240
cagaaaggat cgaagcgcca tcaacacacg ctgaacgtag caaagaataa gtctgaatgt         300
aacagtcttg aagagaggaa gtataggcat ctcggactgc acaatgtgga ttgcaggtca         360
```

```
agtcagtgcc tactaaaacc tcactcctca caagaaagct ctcggactgt cttcatatta      420
tcttcgttgc cccaaagtaa catgtaaacc caattcaaaa ggtcttcaaa catcccaaat      480
gccatcatat cacacaagtc tttaccgaaa aaatcatatc acacaagtat tcagagctca      540
taactgaaca aagagcaaaa gaggacgtaa tacattggaa aatactactc gatcgatctt      600
tagtagccat aatcacactt aacatttgtg aatcttaagg aaccaagccc gttattctga      660
cagttctggt gctcaacaca tttatattta tcaaggagca cattgttact cactgctagg      720
agggaatcga actaggaata ttgatcagag gaactacgag agagctgaag ataactgccc      780
tctagctctc actgatctgg gcgcatagtg agatgcagcc cacgtgagtt cagcaacggt      840
ctagcgctgg gcttttaggc ccgcatgatc gggctttgtc gggtggtcga cgtgttcacg      900
attggggaga gcaacgcagc agttcctctt agtttagtcc cacctcgcct gtccagcaga      960
gttctgaccg gtttataaac tcgcttgctg catcagactt                           1000
```

```
<210> SEQ ID NO 452
<211> LENGTH: 1000
<212> TYPE: DNA
<213> ORGANISM: Triticum aestivum

<400> SEQUENCE: 452
accgtttaga ttattgtcag aaaaaaatat cttacgccct gcggctggtc aatgagcaat       60
gttttctggg taaatttcaa cgggagcttc tgtatctcgc ctgtggtgaa ggagacgctc      120
cctgttggct catactgttt tcttattttt agatacaatt ggctacaaca agtaaaaaac      180
tactgtagca tgaagcgaag gcaaaggaaa aaagcaagac cctcggcgtg cgtgctccgg      240
tcccatgctc gtcgtcgtta gttttacatg cattagagga aatatggcaa atcgtttcat      300
cgtttcagag aactactagg tatagtccca ttttgcggtg tttacggtat ctctgatcct      360
tttgtggata gttcatagct tcatcccaat gttatcggc tcaacctaga gaagattctt       420
gtaaagcctt gaggatctgt ccgttttgta caattcagtt gagaactctg ctatgatttg      480
ggatatctga tatggttagt aaatcattga tgtggatgat caatgatttg cagaactgcc      540
aactccgtct ccgtggatca tataatttat aatctctgaa gcgaaactct gcgaggactt      600
ctcttgtgaa aagctcgaaa taaatctaca tacacgtttta tgttaaaatg tgagaagaat     660
gtagaatgtc tagtataaaa acggagtcaa ataaccagcg ttctccccca cggtgaaaaa      720
agaacctatc acatcggtag accatttttt tataggcaaa tcatatcggc agactaacag      780
gaaggctcac tattccgtac tagcacgatg gcccattacg gtcttccact attttgggcc     840
acaccgagag atccagccta ctcgtagccc accgcacgtt ccgacggcgc ttccgtctgg      900
acaagcaacg gggggagcag aaggctcgtt tgtttagtcc cacatcggct agcgaaaggg      960
agaacgacca gtttataagc cacgcgctgc acacagactc                           1000
```

```
<210> SEQ ID NO 453
<211> LENGTH: 1000
<212> TYPE: DNA
<213> ORGANISM: Triticum aestivum

<400> SEQUENCE: 453
cagaggagcc gaaccccaaa aagagaaaaa gtgatccctg gtggtccgga tttggcattg       60
ccgactgccc aaacatgcct cgccattttc attctcccct tgcatatatg ttcgatttga     120
ggttcgcata tagtctagtc atatgcggac tatttctgag gtttggttgg acgacgtttc     180
```

```
tcctctctcc tattcatgat gccttatggg caagatattt gtttcactga tattttagtt     240
ttccccgttt cttaaaacat gcttattctc tttagcatgg ccaacaaatt tgtaagagac     300
ccaccgagag gtgaccgacc aaaatagaca actaagcatg aaaaaatctc accggcagaa     360
ggaaccgcgc ggcgcaagcg cgggtatccc tctagtacac tactacttgc ccatagagcc     420
agtggtgtac gagtacgacc gacgatgcct tagacttaga cttcccagtc cgtgcaccgg     480
aagcacagaa ccgtccacga ctccacggac agaattcgct ccatcaacac ccaccaccac     540
accagcagta gctttcttca cgtgaaaaac aaccacatat acatgcctgc cgtagacgac     600
acccatgtac tctaccatat atgtacggtc gagacgatac atcggcacat cgcgcctacg     660
tgcccccaaa gcatgaaatc aatcgacatg acacatgaac ctcacgtgag cacacctctt     720
tttgatttta tcttttttgc aaatcctctt ttttgatttc cggctcggct cctctagttg     780
ggcccgaagc agggcatatg gcaaatgctc cagctcgatt ccttaagtgg gccggctgag     840
gaggatcaag tatacacgag gatacagccc acttggccgt ttggtggcat cccgcggtcc     900
tggtgcttgc tgaacgcagc gaacgaccct ggtttagtcc cacctcgctc accggaagaa     960
gcatcgatcg gtttataagc cccgcgcttg caccctcgct                          1000

<210> SEQ ID NO 454
<211> LENGTH: 45
<212> TYPE: DNA
<213> ORGANISM: Triticum aestivum

<400> SEQUENCE: 454
tacagggagg tcatgcagcg ctggcacgag ggacaacggc agccg                      45

<210> SEQ ID NO 455
<211> LENGTH: 45
<212> TYPE: DNA
<213> ORGANISM: Triticum aestivum

<400> SEQUENCE: 455
tacagggagg tcatgcagcg ctggcacgag ggacaacggc agccg                      45

<210> SEQ ID NO 456
<211> LENGTH: 44
<212> TYPE: DNA
<213> ORGANISM: Triticum aestivum

<400> SEQUENCE: 456
tacagggagg tcatgcagcg ctggccgagg gacaacggca gccg                       44

<210> SEQ ID NO 457
<211> LENGTH: 46
<212> TYPE: DNA
<213> ORGANISM: Triticum aestivum

<400> SEQUENCE: 457
tacagggagg tcatgcagcg ctggcaacga gggacaacgg cagccg                     46

<210> SEQ ID NO 458
<211> LENGTH: 45
<212> TYPE: DNA
<213> ORGANISM: Triticum aestivum

<400> SEQUENCE: 458
tacagggagg tcatgcagcg ctggcacgag ggacaacggc agccg                      45
```

```
<210> SEQ ID NO 459
<211> LENGTH: 45
<212> TYPE: DNA
<213> ORGANISM: Triticum aestivum

<400> SEQUENCE: 459
tacagggagg tcatgcagcg ctggctcgag ggacaacggc agccg            45
```